United States Patent
Orton

(10) Patent No.: US 8,901,306 B2
(45) Date of Patent: Dec. 2, 2014

(54) METHODS AND COMPOSITIONS USEFUL IN TREATING CANCER AND REDUCING WNT MEDIATED EFFECTS IN A CELL

(75) Inventor: Darren Orton, Nashville, TN (US)

(73) Assignee: StemSynergy Therapeutics, Inc., Lauderdale by the Sea, FL (US)

( * ) Notice: Subject to any disclaimer, the term of this patent is extended or adjusted under 35 U.S.C. 154(b) by 468 days.

(21) Appl. No.: 13/254,427

(22) PCT Filed: Mar. 2, 2010

(86) PCT No.: PCT/US2010/025984
§ 371 (c)(1),
(2), (4) Date: Oct. 3, 2011

(87) PCT Pub. No.: WO2010/101964
PCT Pub. Date: Sep. 10, 2010

(65) Prior Publication Data
US 2012/0046250 A1    Feb. 23, 2012

Related U.S. Application Data

(60) Provisional application No. 61/156,741, filed on Mar. 2, 2009.

(51) Int. Cl.
| | | |
|---|---|---|
| A61K 31/04 | (2006.01) | |
| C07D 215/38 | (2006.01) | |
| A61K 31/428 | (2006.01) | |
| C07D 417/04 | (2006.01) | |
| A61K 31/4436 | (2006.01) | |
| A61K 31/4427 | (2006.01) | |
| C07D 417/14 | (2006.01) | |
| C07D 215/58 | (2006.01) | |
| C07D 417/12 | (2006.01) | |
| C07D 401/12 | (2006.01) | |

(52) U.S. Cl.
CPC ............ *A61K 31/428* (2013.01); *C07D 417/04* (2013.01); *A61K 31/4436* (2013.01); *A61K 31/4427* (2013.01); *C07D 417/14* (2013.01); *C07D 215/58* (2013.01); *C07D 417/12* (2013.01); *C07D 401/12* (2013.01)
USPC ........... 546/153; 548/182; 548/159; 548/146; 514/312; 514/365

(58) Field of Classification Search
USPC ........... 546/159, 153; 514/312, 365; 548/182, 548/146, 159
See application file for complete search history.

(56) References Cited

U.S. PATENT DOCUMENTS 8,093,245 B2 * 1/2012 Augeri et al. ............... 514/235.8
2006/0122222 A1 * 6/2006 Whitehouse et al. ......... 514/311

FOREIGN PATENT DOCUMENTS

| EP | 1932830 A1 | 6/2008 |
|---|---|---|
| WO | WO 2004/018414 A2 | 3/2004 |
| WO | WO 2004/078115 A2 | 9/2004 |
| WO | WO 2005/004810 A2 | 1/2005 |
| WO | 2007/008541 | * 1/2007 |
| WO | 2008/124000 | * 10/2008 |

OTHER PUBLICATIONS

Moore, J Med Chem, VOl 52, pp. 105-116, 2009.*
Sun, J Med Chem, VOl 51(13), pp. 3731-3741, 2008, abstract only CA149:44295.*
Berge, S.M. et al., "Pharmaceutical salts", Journal of Pharmaceutical Science, Jan. 1977, 66(1):1-19.
International Search Report and Written Opinion dated Nov. 16, 2010 for PCT International Application No. PCT/US2010/025984, 11 pages.
International Preliminary Report on Patentability dated Sep. 6, 2011 for PCT International Application No. PCT/US2010/025984, 6 pages.

* cited by examiner

*Primary Examiner* — D M Seaman
(74) *Attorney, Agent, or Firm* — Kilpatrick Townsend & Stockton LLP

(57) ABSTRACT

Provided herein are novel compounds, pharmaceutical compositions for use, inter alia, in methods of reducing Wnt-mediated effects and treating cancer.

19 Claims, No Drawings

METHODS AND COMPOSITIONS USEFUL IN TREATING CANCER AND REDUCING WNT MEDIATED EFFECTS IN A CELL

CROSS-REFERENCES TO RELATED APPLICATIONS

This application claims priority benefit of U.S. Provisional Application No. 61/156,741, filed Mar. 2, 2009, the content of which is incorporated herein by reference in its entirety and for all purposes.

BACKGROUND OF THE INVENTION

The Wnt pathway is an evolutionarily conserved growth pathway in multicellular organisms that regulates animal development and plays critical roles in human disease. Signaling through the Wnt pathway is regulated by secreted Wnt proteins, which act as morphogens to mediate 1) cell fate determination and differentiation required for establishing the body plan, neural patterning, and organogenesis, 2) cell motility and polarity, 3) cell proliferation and apoptosis, and 4) stem cell maintenance.

In Wnt signaling, the transcriptional coactivator, beta-catenin, is constitutively degraded in the absence of a Wnt signal thereby allowing a cell to maintain low cytoplasmic levels of beta-catenin and keeping the Wnt pathway in the "off" position. Degradation of beta-catenin requires its recruitment into a complex consisting primarily of Glycogen synthase kinase (Gsk3), Casein Kinase 1 (CK1), Protein phosphatase 2A (PP2A), Axin, and the tumor suppressor adenomatous polyposis coli (APC). Within this complex, beta-catenin is phosphorylated by CK1, which primes it for further phosphorylation by Gsk3. Phosphorylated beta-catenin is recognized by the SCF (Skip1, Cullen, F-box) ubiquitin ligase complex, of which the specificity F-box determinant is beta-TRCP, and targeted for polyubiquitination and subsequent degradation by the proteasome. The Wnt pathway is turned "on" upon binding of Wnt ligands to the Frizzled family of receptors and the coreceptor family members LDL receptor-related protein 5 or 6 (LRP5/6), which results in translocation of the beta-catenin destruction complex to the membrane through interaction of Axin with LRP5/6. The interaction between Axin and LRP5/6 is promoted by the phosphorylation of LRP5/6 by CK1 and Gsk3, and Axin-LRP5/6 interaction results in inhibition of beta-catenin phosphorylation and degradation. Because beta-catenin is continually synthesized in cells, its cytoplasmic concentration increases, and it enters the nucleus and forms a complex with the TCF/LEF1 family of transcriptional factors (as well as the nuclear proteins BCL9 and Pygopus) to regulate a Wnt-specific transcriptional program.

Our bodies are composed of numerous cell types specialized to perform specific functions. These specialized or differentiated cells are derived from a small group of stem and progenitor cells that have the capacity to divide asymmetrically, allowing them to regenerate themselves, and also giving rise to a daughter cell that can differentiate into cell types characteristic of various organs in our bodies. It is recognized that diseases like diabetes, Parkinson's disease, and heart disease are caused by death or dysfunction of differentiated cells in tissues where stem cells are limiting. These diseases may be caused by loss of stem cell activity and/or misregulation of critical signaling pathways in stem cells residing in tissues such as the pancreas, brain, and heart. The Wnt pathway is a key regulator of stem cell behavior and viability, and modulation of this pathway presents a method of treating diseases associated with dysfunctional stem cell activity. For example, activation of the Wnt pathway has been associated with heart failure, and inhibition of Wnt signaling has been shown to improve recovery after a heart attack in animal models. Thus, Wnt inhibitors could have broad applications in regenerative (stem cell) medicine for the treatment of major human diseases such as heart disease.

Cancer has been shown to be stem cell related disease, resulting from failure of cells to respond to normal cues to stop proliferating. Wnt signaling is also a critical pathway that drives the uncontrolled proliferation of many solid tumors in cancer stem cells (CSCs). Thus, therapies that down-regulate the activity of Wnt signaling, a fundamental pathway in CSCs, would be effective in the treatment of cancer. Such inhibitors would result in a long-term therapeutic benefit because the cells capable of repopulating the tumor would be killed. Most notably, there is clear evidence that colorectal cancer arises from mutations in the stem cell compartment, and it has been demonstrated that all major solid cancers in humans (e.g. melanoma, hepatocellular carcinoma, and breast cancer) have abnormal Wnt signaling. Thus, Wnt inhibitors may be useful in the treatment of most of the major solid cancers in humans.

BRIEF SUMMARY OF THE INVENTION

Provided herein, inter alia, are novel pharmaceutical compositions and methods of reducing Wnt-mediated effects and treating cancer.

In one aspect, a compound is provided having the structure of Formula (IA) or (IB):

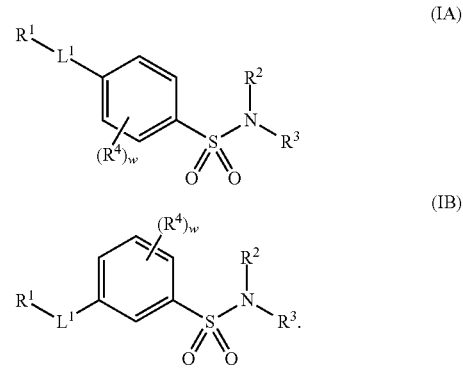

In Formulae (IA) and (IB), $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —CN, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is halogen, —CN, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently halogen, —CN, —CF$_3$, —NR$^{4A}$—C(O)R$^{4B}$, —NR$^{4A}$—C(O)—OR$^{4B}$, —C(O)NR$^{4A}$R$^{4B}$, —NR$^{4A}$S(O)$_2$R$^{4B}$, —S(O)$_2$N(R$^{4A}$)(R$^{4B}$), —SR$^{4A}$, —S(O)R$^{4B}$, —S(O)$_2$R$^{4B}$, —NR$^{4A}$R$^{4B}$, —OR$^{4A}$, —C(O)R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{4A}$ and $R^{4B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol w represents an integer from 0 to 4. $L^1$ is -$L^2$-N($R^{61}$)—C(O)—N($R^{62}$)-$L^3$-, -$L^2$-N($R^{61}$)—C(O)-$L^3$- or -$L^2$-C(O)—N($R^{61}$)-$L^3$-. $L^2$ and $L^3$ are independently a bond or substituted or unsubstituted alkylene. $R^{61}$ and $R^{62}$ are independently hydrogen, —CN, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, a compound is provided having the structure of Formula (XXIV):

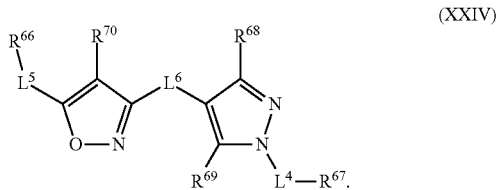

(XXIV)

In Formula (XXIV), $R^{66}$ and $R^{67}$ are independently substituted or unsubstituted aryl or substituted or unsubstituted heteroaryl. $R^{68}$, $R^{69}$ and $R^{70}$ are independently hydrogen, halogen, —CN, —CF$_3$, —NR$^{68A}$—C(O)R$^{68B}$, —NR$^{68A}$—C(O)—OR$^{68B}$, —C(O)NR$^{68A}$R$^{68B}$, —NR$^{68A}$S(O)$_2$R$^{68B}$, —S(O)$_2$N(R$^{68A}$)(R$^{68B}$), —SR$^{68A}$, —S(O)R$^{68B}$, —S(O)$_2$R$^{68B}$, —NR$^{68A}$R$^{68B}$, —OR$^{68A}$, —C(O)R$^{68B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{68A}$ and $R^{68B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^6$ is -$L^7$-N($R^{71}$)—C(O)—N($R^{72}$)-$L^8$-, -$L^7$-N($R^{61}$)—C(O)-$L^8$- or -$L^7$-C(O)—N($R^{71}$)-$L^8$-. $L^7$ and $L^8$ are independently a bond or substituted or unsubstituted alkylene. $L^4$ and $L^5$ are independently a bond or substituted or unsubstituted alkylene.

In another aspect, a method of reducing a Wnt-mediated effect on a cell is provided. The method includes contacting the cell with an effective amount of a compound provided herein (e.g. Formulae (IA) to (XXIIIA), (IB) to (XXIIIB) and (XXIV) and embodiments thereof), or pharmaceutically acceptable salt thereof.

In another aspect, a method of treating cancer in a subject in need thereof is provided. The method includes administering to the subject an effective amount of a compound provided herein (e.g. Formulae (IA) to (XXIIIA), (IB) to (XXIIIB) and (XXIV) and embodiments thereof), or pharmaceutically acceptable salt thereof.

In another aspect, the present invention provides a pharmaceutical composition including a pharmaceutically acceptable excipient and a compound provided herein (e.g. Formulae (IA) to (XXIIIA), (IB) to (XXIIIB) and (XXIV) and embodiments thereof).

DETAILED DESCRIPTION OF THE INVENTION

I. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, —Si and S, and wherein the nitrogen and sulfur atoms may optionally be oxidized and the nitrogen heteroatom may optionally be quaternized. The heteroatom(s) O, N, P, —S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively, which can be a single ring or multiple rings (preferably from 1 to 3 rings) which are fused together or linked covalently. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively.

The term "oxo" as used herein means an oxygen that is double bonded to a carbon atom.

Each of the above terms (e.g., "alkyl," "heteroalkyl," "aryl" and "heteroaryl"), unless otherwise noted, are meant to include both substituted and unsubstituted forms of the indicated radical. Where a substituent is R-substituted (e.g. an R$^{16}$-substituted alkyl), the substituent may be substituted with one or more R groups as allowed by chemical valency rules where each R group is optionally different (e.g. an R$^{16}$-substituted alkyl may include multiple R$^{16}$ groups wherein each R$^{16}$ group is optionally different). Certain examples of substituents for each type of radical are provided below.

Substituents for the alkyl and heteroalkyl radicals (including those groups often referred to as alkylenyl, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R'''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo (where allowed according to valency rules), —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo (where allowed according to valency rules, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo (where allowed according to valency rules, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

The symbol ⅀ denotes a point of attachment of a moiety to the remainder of a compound.

The phrase "effective amount" refers to an amount sufficient to attain the desired result. The phrase "therapeutically effective amount" means an amount sufficient to produce the desired therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, —Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

II. Compounds

In one aspect, compounds are provided for use in the methods disclosed herein and for incorporation into certain pharmaceutical compositions described herein.

In some embodiments, the compound has the structure of formula (IA) or (IB):

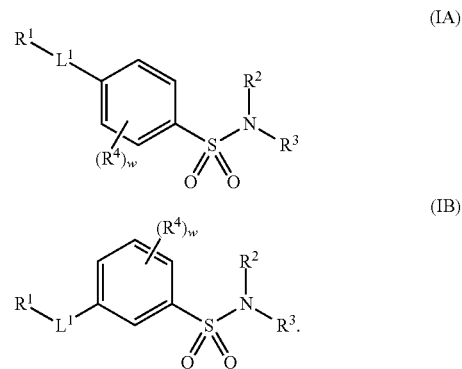

In Formulae (IA) and (IB), $R^1$ is substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^1$ is a substituted substituent, $R^1$ is substituted with $R^{16}$. For example, in some embodiments, $R^1$ is $R^{16}$-substituted or unsubstituted alkyl (e.g. substituted or unsubstituted $C_1$ to $C_{20}$ alkyl), $R^{16}$-substituted or unsubstituted heteroalkyl (e.g. substituted or unsubstituted 2 to 20 membered heteroalkyl), $R^{16}$-substituted or unsubstituted cycloalkyl (e.g. $C_3$ to $C_{14}$ cycloalkyl including fused ring structures), $R^{16}$-substituted or unsubstituted heterocycloalkyl (e.g. 3 to 14 membered heterocycloalkyl including fused ring structures), $R^{16}$-substituted or unsubstituted aryl (e.g. a $C_6$ to $C_{14}$ aryl including fused ring structures), or $R^{16}$-substituted or unsubstituted heteroaryl (e.g. 5 to 14 membered heteroaryl including fused rings structures).

$R^{16}$ is oxo (where permitted according to valency rules), halogen, —CN, —CF$_3$, —NR$^{16A}$—C(O)R$^{16B}$, —NR$^{16A}$—C(O)—OR$^{16B}$, —C(O)NR$^{16A}$R$^{16B}$, —NR$^{16A}$S(O)$_2$R$^{16B}$, —S(O)$_2$N(R$^{16A}$)(R$^{16B}$), —SR$^{16A}$, —S(O)R$^{16B}$, —S(O)$_2$R$^{16B}$, —NR$^{16A}$R$^{16B}$, —OR$^{16A}$, —C(O)R$^{16B}$, $R^{17}$-substituted or unsubstituted alkyl (e.g. substituted or unsubstituted $C_1$ to $C_{20}$ alkyl), $R^{17}$-substituted or unsubstituted heteroalkyl (e.g. substituted or unsubstituted 2 to 20 membered heteroalkyl), $R^{17}$-substituted or unsubstituted cycloalkyl (e.g. $C_3$ to $C_{14}$ cycloalkyl including fused ring structures), $R^{17}$-substituted or unsubstituted heterocycloalkyl (e.g. 3 to 14 membered heterocycloalkyl including fused ring structures), $R^{17}$-substituted or unsubstituted aryl (e.g. a $C_6$ to $C_{14}$ aryl including fused ring structures), or $R^{17}$-substituted or unsubstituted heteroaryl (e.g. 5 to 14 membered heteroaryl including fused rings structures).

$R^{16A}$ and $R^{16B}$ are independently hydrogen, $R^{17}$-substituted or unsubstituted alkyl (e.g. substituted or unsubstituted $C_1$ to $C_{20}$ alkyl), $R^{17}$-substituted or unsubstituted heteroalkyl (e.g. substituted or unsubstituted 2 to 20 membered heteroalkyl), $R^{17}$-substituted or unsubstituted cycloalkyl (e.g. $C_3$ to $C_{14}$ cycloalkyl including fused ring structures), $R^{17}$-substituted or unsubstituted heterocycloalkyl (e.g. 3 to 14 membered heterocycloalkyl including fused ring structures), $R^{17}$-substituted or unsubstituted aryl (e.g. a $C_6$ to $C_{14}$ aryl including fused ring structures), or $R^{17}$-substituted or unsubstituted heteroaryl (e.g. 5 to 14 membered heteroaryl including fused rings structures).

$R^{17}$ is independently oxo (where permitted according to valency rules), halogen, —CN, —CF$_3$, —NR$^{17A}$—C(O) R$^{17B}$, —NR$^{17A}$—C(O)—OR$^{17B}$, —C(O)NR$^{17A}$R$^{17B}$, —NR$^{17A}$S(O)$_2$R$^{17B}$, —S(O)$_2$N(R$^{17A}$)(R$^{17B}$), —SR$^{17A}$, —S(O)R$^{17B}$, —S(O)$_2$R$^{17B}$, —NR$^{17A}$R$^{17B}$, —OR$^{17A}$, —C(O)R$^{17B}$, R$^{18}$-substituted or unsubstituted alkyl (e.g. substituted or unsubstituted $C_1$ to $C_{20}$ alkyl), R$^{18}$-substituted or unsubstituted heteroalkyl (e.g. substituted or unsubstituted 2 to 20 membered heteroalkyl), R$^{18}$-substituted or unsubstituted cycloalkyl (e.g. $C_3$ to $C_{14}$ cycloalkyl including fused ring structures), R$^{18}$-substituted or unsubstituted heterocycloalkyl (e.g. 3 to 14 membered heterocycloalkyl including fused ring structures), R$^{18}$-substituted or unsubstituted aryl (e.g. a $C_6$ to $C_{14}$ aryl including fused ring structures), or R$^{18}$-substituted or unsubstituted heteroaryl (e.g. 5 to 14 membered heteroaryl including fused rings structures).

$R^{17A}$ and $R^{17B}$ are independently hydrogen, R$^{18}$-substituted or unsubstituted alkyl (e.g. substituted or unsubstituted $C_1$ to $C_{20}$ alkyl), R$^{18}$-substituted or unsubstituted heteroalkyl (e.g. substituted or unsubstituted 2 to 20 membered heteroalkyl), R$^{18}$-substituted or unsubstituted cycloalkyl (e.g. $C_3$ to $C_{14}$ cycloalkyl including fused ring structures), R$^{18}$-substituted or unsubstituted heterocycloalkyl (e.g. 3 to 14 membered heterocycloalkyl including fused ring structures), R$^{18}$-substituted or unsubstituted aryl (e.g. a $C_6$ to $C_{14}$ aryl including fused ring structures), or R$^{18}$-substituted or unsubstituted heteroaryl (e.g. 5 to 14 membered heteroaryl including fused rings structures).

$R^{18}$ is independently oxo (where permitted according to valency rules), halogen, —CN, —CF$_3$, —NR$^{18A}$—C(O) R$^{18B}$, —NR$^{18A}$—C(O)—OR$^{18B}$, —C(O)NR$^{18A}$R$^{18B}$, —NR$^{18A}$S(O)$_2$R$^{18B}$, —S(O)$_2$N(R$^{18A}$)(R$^{18B}$), —SR$^{18A}$, —S(O)R$^{18B}$, —S(O)$_2$R$^{18B}$, —NR$^{18A}$R$^{18B}$, —OR$^{18A}$, —C(O)R$^{18B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{18A}$ and $R^{18B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^2$ is hydrogen, halogen, —CN, —CF$_3$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures). In some embodiments, $R^2$ is methyl, ethyl, propyl, tertiary butyl, methylene cyclopropyl (—CH$_2$-cyclopropyl), methoxy, ethoxy, propoxy, butoxy or —CF$_3$.

In some embodiments, where $R^2$ is a substituted substituent, $R^2$ is substituted with $R^{19}$. For example, in some embodiments, $R^1$ is $R^{19}$-substituted or unsubstituted alkyl (e.g. substituted or unsubstituted $C_1$ to $C_{20}$ alkyl), R$^{19}$-substituted or unsubstituted heteroalkyl (e.g. substituted or unsubstituted 2 to 20 membered heteroalkyl), R$^{19}$-substituted or unsubstituted cycloalkyl (e.g. $C_3$ to $C_{14}$ cycloalkyl including fused ring structures), R$^{19}$-substituted or unsubstituted heterocycloalkyl (e.g. 3 to 14 membered heterocycloalkyl including fused ring structures), R$^{19}$-substituted or unsubstituted aryl (e.g. a $C_6$ to $C_{14}$ aryl including fused ring structures), or R$^{19}$-substituted or unsubstituted heteroaryl (e.g. 5 to 14 membered heteroaryl including fused rings structures).

$R^{19}$ is oxo (where permitted according to valency rules), halogen, —CN, —CF$_3$, —NR$^{19A}$—C(O)R$^{19B}$, —NR$^{19A}$—C(O)—OR$^{19B}$, —C(O)NR$^{19A}$R$^{19B}$, —NR$^{19A}$S(O)$_2$R$^{19B}$, —S(O)$_2$N(R$^{19A}$)(R$^{19B}$), —SR$^{19A}$, —S(O)R$^{19B}$, —S(O)$_2$R$^{19B}$, —NR$^{19A}$R$^{19B}$, —OR$^{19A}$, —C(O)R$^{19B}$, R$^{20}$-substituted or unsubstituted alkyl (e.g. substituted or unsubstituted $C_1$ to $C_{20}$ alkyl), R$^{20}$-substituted or unsubstituted heteroalkyl (e.g. substituted or unsubstituted 2 to 20 membered heteroalkyl), R$^{20}$-substituted or unsubstituted cycloalkyl (e.g. $C_3$ to $C_{14}$ cycloalkyl including fused ring structures), R$^{20}$-substituted or unsubstituted heterocycloalkyl (e.g. 3 to 14 membered heterocycloalkyl including fused ring structures), R$^{20}$-substituted or unsubstituted aryl (e.g. a $C_6$ to $C_{14}$ aryl including fused ring structures), or R$^{20}$-substituted or unsubstituted heteroaryl (e.g. 5 to 14 membered heteroaryl including fused rings structures).

$R^{19A}$ and $R^{19B}$ are independently hydrogen, R$^{20}$-substituted or unsubstituted alkyl (e.g. substituted or unsubstituted $C_1$ to $C_{20}$ alkyl), R$^{20}$-substituted or unsubstituted heteroalkyl (e.g. substituted or unsubstituted 2 to 20 membered heteroalkyl), R$^{20}$-substituted or unsubstituted cycloalkyl (e.g. $C_3$ to $C_{14}$ cycloalkyl including fused ring structures), R$^{20}$-substituted or unsubstituted heterocycloalkyl (e.g. 3 to 14 membered heterocycloalkyl including fused ring structures), R$^{20}$-substituted or unsubstituted aryl (e.g. a $C_6$ to $C_{14}$ aryl including fused ring structures), or R$^{20}$-substituted or unsubstituted heteroaryl (e.g. 5 to 14 membered heteroaryl including fused rings structures).

$R^{20}$ is independently oxo (where permitted according to valency rules), halogen, —CN, —CF$_3$, —NR$^{20A}$—C(O)R$^{20B}$, —NR$^{20A}$—C(O)—OR$^{20B}$, —C(O)NR$^{20A}$R$^{20B}$, —NR$^{20A}$S(O)$_2$R$^{20B}$, —S(O)$_2$N(R$^{20A}$)(R$^{20B}$), —SR$^{20A}$, —S(O)R$^{20B}$, —S(O)$_2$R$^{20B}$, —NR$^{20A}$R$^{20B}$, —OR$^{20A}$, —C(O)R$^{20B}$, R$^{21}$-substituted or unsubstituted alkyl (e.g. substituted or unsubstituted $C_1$ to $C_{20}$ alkyl), R$^{21}$-substituted or unsubstituted heteroalkyl (e.g. substituted or unsubstituted 2 to 20 membered heteroalkyl), R$^{21}$-substituted or unsubstituted cycloalkyl (e.g. $C_3$ to $C_{14}$ cycloalkyl including fused ring structures), R$^{21}$-substituted or unsubstituted heterocycloalkyl (e.g. 3 to 14 membered heterocycloalkyl including fused ring structures), R$^{21}$-substituted or unsubstituted aryl (e.g. a $C_6$ to $C_{14}$ aryl including fused ring structures), or R$^{21}$-substituted or unsubstituted heteroaryl (e.g. 5 to 14 membered heteroaryl including fused rings structures).

$R^{20A}$ and $R^{20B}$ are independently hydrogen, R$^{21}$-substituted or unsubstituted alkyl (e.g. substituted or unsubstituted $C_1$ to $C_{20}$ alkyl), R$^{21}$-substituted or unsubstituted heteroalkyl (e.g. substituted or unsubstituted 2 to 20 membered heteroalkyl), R$^{21}$-substituted or unsubstituted cycloalkyl (e.g. $C_3$ to $C_{14}$ cycloalkyl including fused ring structures), R$^{21}$-substituted or unsubstituted heterocycloalkyl (e.g. 3 to 14 membered heterocycloalkyl including fused ring structures), $R^{21}$-substituted or unsubstituted aryl (e.g. a $C_6$ to $C_{14}$ aryl including fused ring structures), or $R^{21}$-substituted or unsubstituted heteroaryl (e.g. 5 to 14 membered heteroaryl including fused rings structures).

$R^{21}$ is independently oxo (where permitted according to valency rules), halogen, —CN, —$CF_3$, —$NR^{21A}$—C(O)$R^{21B}$, —$NR^{21A}$—C(O)—$OR^{21B}$, —C(O)$NR^{21A}R^{21B}$, —$NR^{21A}S(O)_2R^{21B}$, —$S(O)_2N(R^{21A})(R^{21B})$, —$SR^{21A}$, —$S(O)R^{21B}$, —$S(O)_2R^{21B}$, —$NR^{21A}R^{21B}$, —$OR^{21A}$, —C(O)$R^{21B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{21A}$ and $R^{21B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^3$ is halogen, —CN, —$CF_3$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^3$ is a substituted substituent, $R^3$ is substituted with $R^{22}$. For example, in some embodiments, $R^3$ is $R^{22}$-substituted or unsubstituted alkyl (e.g. substituted or unsubstituted $C_1$ to $C_{20}$ alkyl), $R^{22}$-substituted or unsubstituted heteroalkyl (e.g. substituted or unsubstituted 2 to 20 membered heteroalkyl), $R^{22}$-substituted or unsubstituted cycloalkyl (e.g. $C_3$ to $C_{14}$ cycloalkyl including fused ring structures), $R^{22}$-substituted or unsubstituted heterocycloalkyl (e.g. 3 to 14 membered heterocycloalkyl including fused ring structures), $R^{22}$-substituted or unsubstituted aryl (e.g. a $C_6$ to $C_{14}$ aryl including fused ring structures), or $R^{22}$-substituted or unsubstituted heteroaryl (e.g. 5 to 14 membered heteroaryl including fused rings structures).

$R^{22}$ is oxo (where permitted according to valency rules), halogen, —CN, —$CF_3$, —$NR^{22A}$—C(O)$R^{22B}$, —$NR^{22A}$—C(O)—$OR^{22B}$, —C(O)$NR^{22A}R^{22B}$, —$NR^{22A}S(O)_2R^{22B}$, —$S(O)_2N(R^{22A})(R^{22B})$, —$SR^{22A}$, —$S(O)R^{22B}$, —$S(O)_2R^{22B}$, —$NR^{22A}R^{22B}$, —$OR^{22A}$, —C(O)$R^{22B}$, $R^{23}$-substituted or unsubstituted alkyl (e.g. substituted or unsubstituted $C_1$ to $C_{20}$ alkyl), $R^{23}$-substituted or unsubstituted heteroalkyl (e.g. substituted or unsubstituted 2 to 20 membered heteroalkyl), $R^{23}$-substituted or unsubstituted cycloalkyl (e.g. $C_3$ to $C_{14}$ cycloalkyl including fused ring structures), $R^{23}$-substituted or unsubstituted heterocycloalkyl (e.g. 3 to 14 membered heterocycloalkyl including fused ring structures), $R^{23}$-substituted or unsubstituted aryl (e.g. a $C_6$ to $C_{14}$ aryl including fused ring structures), or $R^{23}$-substituted or unsubstituted heteroaryl (e.g. 5 to 14 membered heteroaryl including fused rings structures).

$R^{22A}$ and $R^{22B}$ are independently hydrogen, $R^{23}$-substituted or unsubstituted alkyl (e.g. substituted or unsubstituted $C_1$ to $C_{20}$ alkyl), $R^{23}$-substituted or unsubstituted heteroalkyl (e.g. substituted or unsubstituted 2 to 20 membered heteroalkyl), $R^{23}$-substituted or unsubstituted cycloalkyl (e.g. $C_3$ to $C_{14}$ cycloalkyl including fused ring structures), $R^{23}$-substituted or unsubstituted heterocycloalkyl (e.g. 3 to 14 membered heterocycloalkyl including fused ring structures), $R^{23}$-substituted or unsubstituted aryl (e.g. a $C_6$ to $C_{14}$ aryl including fused ring structures), or $R^{23}$-substituted or unsubstituted heteroaryl (e.g. 5 to 14 membered heteroaryl including fused rings structures).

$R^{23}$ is independently oxo (where permitted according to valency rules), halogen, —CN, —$CF_3$, —$NR^{23A}$—C(O)$R^{23B}$, —$NR^{23A}$—C(O)—$OR^{23B}$, —C(O)$NR^{23A}R^{23B}$, —$NR^{23A}S(O)_2R^{23B}$, —$S(O)_2N(R^{23A})(R^{23B})$, —$SR^{23A}$, —$S(O)R^{23B}$, —$S(O)_2R^{23B}$, —$NR^{23A}R^{23B}$, —$OR^{23A}$, —C(O)$R^{23B}$, $R^{24}$-substituted or unsubstituted alkyl (e.g. substituted or unsubstituted $C_1$ to $C_{20}$ alkyl), $R^{24}$-substituted or unsubstituted heteroalkyl (e.g. substituted or unsubstituted 2 to 20 membered heteroalkyl), $R^{24}$-substituted or unsubstituted cycloalkyl (e.g. $C_3$ to $C_{14}$ cycloalkyl including fused ring structures), $R^{24}$-substituted or unsubstituted heterocycloalkyl (e.g. 3 to 14 membered heterocycloalkyl including fused ring structures), $R^{24}$-substituted or unsubstituted aryl (e.g. a $C_6$ to $C_{14}$ aryl including fused ring structures), or $R^{24}$-substituted or unsubstituted heteroaryl (e.g. 5 to 14 membered heteroaryl including fused rings structures).

$R^{23A}$ and $R^{23B}$ are independently hydrogen, $R^{24}$-substituted or unsubstituted alkyl (e.g. substituted or unsubstituted $C_1$ to $C_{20}$ alkyl), $R^{24}$-substituted or unsubstituted heteroalkyl (e.g. substituted or unsubstituted 2 to 20 membered heteroalkyl), $R^{24}$-substituted or unsubstituted cycloalkyl (e.g. $C_3$ to $C_{14}$ cycloalkyl including fused ring structures), $R^{24}$-substituted or unsubstituted heterocycloalkyl (e.g. 3 to 14 membered heterocycloalkyl including fused ring structures), $R^{24}$-substituted or unsubstituted aryl (e.g. a $C_6$ to $C_{14}$ aryl including fused ring structures), or $R^{24}$-substituted or unsubstituted heteroaryl (e.g. 5 to 14 membered heteroaryl including fused rings structures).

$R^{24}$ is independently oxo (where permitted according to valency rules), halogen, —CN, —$CF_3$, —$NR^{24A}$—C(O)$R^{24B}$, —$NR^{24A}$—C(O)—$OR^{24B}$, —C(O)$NR^{24A}R^{24B}$, —$NR^{24A}S(O)_2R^{24B}$, —$S(O)_2N(R^{24A})(R^{24B})$, —$SR^{24A}$, —$S(O)R^{24B}$, —$S(O)_2R^{24B}$, —$NR^{24A}R^{24B}$, —$OR^{24A}$, —C(O)$R^{24B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{24A}$ and $R^{24B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^4$ is independently halogen, —CN, —CF$_3$, —NR$^{4A}$—C(O)R$^{4B}$, —NR$^{4A}$—C(O)—OR$^{4B}$, —C(O)NR$^{4A}$R$^{4B}$, —NR$^{4A}$S(O)$_2$R$^{4B}$, —S(O)$_2$N(R$^{4A}$)(R$^{4B}$), —SR$^{4A}$, —S(O)R$^{4B}$, —S(O)$_2$R$^{4B}$, —NR$^{4A}$R$^{4B}$, —OR$^{4A}$, —C(O)R$^{4B}$, substituted or unsubstituted alkyl (e.g. substituted or unsubstituted C$_1$ to C$_{20}$ alkyl), substituted or unsubstituted heteroalkyl (e.g. substituted or unsubstituted 2 to 20 membered heteroalkyl), substituted or unsubstituted cycloalkyl (e.g. C$_3$ to C$_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a C$_6$ to C$_{14}$ aryl including fused ring structures), or substituted or unsubstituted heteroaryl (e.g. 5 to 14 membered heteroaryl including fused rings structures).

$R^{4A}$ and $R^{4B}$ are independently hydrogen, substituted or unsubstituted alkyl (e.g. substituted or unsubstituted C$_1$ to C$_{20}$ alkyl), substituted or unsubstituted heteroalkyl (e.g. substituted or unsubstituted 2 to 20 membered heteroalkyl), substituted or unsubstituted cycloalkyl (e.g. C$_3$ to C$_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a C$_6$ to C$_{14}$ aryl including fused ring structures), or substituted or unsubstituted heteroaryl (e.g. 5 to 14 membered heteroaryl including fused rings structures).

In some embodiments, where $R^4$, $R^{4A}$ and $R^{4B}$ are substituted substituents, $R^4$, $R^{4A}$ and $R^4$ are independently substituted with $R^{25}$. For example, in some embodiments, $R^4$, $R^{4A}$ and $R^4$ are independently $R^{25}$-substituted or unsubstituted alkyl (e.g. substituted or unsubstituted C$_1$ to C$_{20}$ alkyl), $R^{25}$-substituted or unsubstituted heteroalkyl (e.g. substituted or unsubstituted 2 to 20 membered heteroalkyl), $R^{25}$-substituted or unsubstituted cycloalkyl (e.g. C$_3$ to C$_{14}$ cycloalkyl including fused ring structures), $R^{25}$-substituted or unsubstituted heterocycloalkyl (e.g. 3 to 14 membered heterocycloalkyl including fused ring structures), $R^{25}$-substituted or unsubstituted aryl (e.g. a C$_6$ to C$_{14}$ aryl including fused ring structures), or $R^{25}$-substituted or unsubstituted heteroaryl (e.g. 5 to 14 membered heteroaryl including fused rings structures).

$R^{25}$ is independently oxo (where permitted according to valency rules), halogen, —CN, —CF$_3$, —NR$^{25A}$—C(O)R$^{25B}$, —NR$^{25A}$—C(O)—OR$^{25B}$, —C(O)NR$^{25A}$R$^{25B}$, —NR$^{25A}$S(O)$_2$R$^{25B}$, —S(O)$_2$N(R$^{25A}$)(R$^{25B}$), —SR$^{25A}$, —S(O)R$^{25B}$, —S(O)$_2$R$^{25B}$, —NR$^{25A}$R$^{25B}$, —OR$^{25A}$, —C(O)R$^{25B}$, R$^{26}$-substituted or unsubstituted alkyl (e.g. substituted or unsubstituted C$_1$ to C$_{20}$ alkyl), R$^{26}$-substituted or unsubstituted heteroalkyl (e.g. substituted or unsubstituted 2 to 20 membered heteroalkyl), R$^{26}$-substituted or unsubstituted cycloalkyl (e.g. C$_3$ to C$_{14}$ cycloalkyl including fused ring structures), R$^{26}$-substituted or unsubstituted heterocycloalkyl (e.g. 3 to 14 membered heterocycloalkyl including fused ring structures), R$^{26}$-substituted or unsubstituted aryl (e.g. a C$_6$ to C$_{14}$ aryl including fused ring structures), or R$^{26}$-substituted or unsubstituted heteroaryl (e.g. 5 to 14 membered heteroaryl including fused rings structures).

$R^{25A}$ and $R^{25B}$ are independently hydrogen, R$^{26}$-substituted or unsubstituted alkyl (e.g. substituted or unsubstituted C$_1$ to C$_{20}$ alkyl), R$^{26}$-substituted or unsubstituted heteroalkyl (e.g. substituted or unsubstituted 2 to 20 membered heteroalkyl), R$^{26}$-substituted or unsubstituted cycloalkyl (e.g. C$_3$ to C$_{14}$ cycloalkyl including fused ring structures), R$^{26}$-substituted or unsubstituted heterocycloalkyl (e.g. 3 to 14 membered heterocycloalkyl including fused ring structures), R$^{26}$-substituted or unsubstituted aryl (e.g. a C$_6$ to C$_{14}$ aryl including fused ring structures), or R$^{26}$-substituted or unsubstituted heteroaryl (e.g. 5 to 14 membered heteroaryl including fused rings structures).

$R^{26}$ is independently oxo (where permitted according to valency rules), halogen, —CN, —CF$_3$, —NR$^{26A}$—C(O)R$^{26B}$, —NR$^{26A}$—C(O)—OR$^{26B}$, —C(O)NR$^{26A}$R$^{26B}$, —NR$^{26A}$S(O)$_2$R$^{26B}$, —S(O)$_2$N(R$^{26A}$)(R$^{26B}$), —SR$^{26A}$, —S(O)R$^{26B}$, —S(O)$_2$R$^{26B}$, —NR$^{26A}$R$^{26B}$, —OR$^{26A}$, —C(O)R$^{26B}$, R$^{27}$-substituted or unsubstituted alkyl (e.g. substituted or unsubstituted C$_1$ to C$_{20}$ alkyl), R$^{27}$-substituted or unsubstituted heteroalkyl (e.g. substituted or unsubstituted 2 to 20 membered heteroalkyl), R$^{27}$-substituted or unsubstituted cycloalkyl (e.g. C$_3$ to C$_{14}$ cycloalkyl including fused ring structures), R$^{27}$-substituted or unsubstituted heterocycloalkyl (e.g. 3 to 14 membered heterocycloalkyl including fused ring structures), R$^{27}$-substituted or unsubstituted aryl (e.g. a C$_6$ to C$_{14}$ aryl including fused ring structures), or R$^{27}$-substituted or unsubstituted heteroaryl (e.g. 5 to 14 membered heteroaryl including fused rings structures).

$R^{26A}$ and $R^{26B}$ are independently hydrogen, R$^{27}$-substituted or unsubstituted alkyl (e.g. substituted or unsubstituted C$_1$ to C$_{20}$ alkyl), R$^{27}$-substituted or unsubstituted heteroalkyl (e.g. substituted or unsubstituted 2 to 20 membered heteroalkyl), R$^{27}$-substituted or unsubstituted cycloalkyl (e.g. C$_3$ to C$_{14}$ cycloalkyl including fused ring structures), R$^{27}$-substituted or unsubstituted heterocycloalkyl (e.g. 3 to 14 membered heterocycloalkyl including fused ring structures), R$^{27}$-substituted or unsubstituted aryl (e.g. a C$_6$ to C$_{14}$ aryl including fused ring structures), or R$^{27}$-substituted or unsubstituted heteroaryl (e.g. 5 to 14 membered heteroaryl including fused rings structures).

$R^{27}$ is independently oxo (where permitted according to valency rules), halogen, —CN, —CF$_3$, —NR$^{27A}$, —C(O)R$^{27B}$, —NR$^{27A}$—C(O)—OR$^{27B}$, —C(O)NR$^{27A}$R$^{27B}$, —NR$^{27A}$S(O)$_2$R$^{27B}$, —S(O)$_2$N(R$^{27A}$)(R$^{27B}$), —SR$^{27A}$, —S(O)R$^{27B}$, —S(O)$_2$R$^{27B}$, —NR$^{27A}$R$^{27B}$, —OR$^{27A}$, —C(O)R$^{27B}$, unsubstituted alkyl (e.g. substituted or unsubstituted C$_1$ to C$_{20}$ alkyl), unsubstituted heteroalkyl (e.g. substituted or unsubstituted 2 to 20 membered heteroalkyl), unsubstituted cycloalkyl (e.g. C$_3$ to C$_{14}$ cycloalkyl including fused ring structures), unsubstituted heterocycloalkyl (e.g. 3 to 14 membered heterocycloalkyl including fused ring structures), unsubstituted aryl (e.g. a C$_6$ to C$_{14}$ aryl including fused ring structures), or unsubstituted heteroaryl (e.g. 5 to 14 membered heteroaryl including fused rings structures).

$R^{27A}$ and $R^{27B}$ are independently hydrogen, unsubstituted alkyl (e.g. substituted or unsubstituted C$_1$ to C$_{20}$ alkyl), unsubstituted heteroalkyl (e.g. substituted or unsubstituted 2 to 20 membered heteroalkyl), unsubstituted cycloalkyl (e.g. C$_3$ to C$_{14}$ cycloalkyl including fused ring structures), unsubstituted heterocycloalkyl (e.g. 3 to 14 membered heterocycloalkyl including fused ring structures), unsubstituted aryl (e.g. a C$_6$ to C$_{14}$ aryl including fused ring structures), or unsubstituted heteroaryl (e.g. 5 to 14 membered heteroaryl including fused rings structures).

The symbol w is an integer from 0 to 4. In some embodiments, w is 0. In other embodiments, w is 1.

$L^1$ is -L$^2$-N(R$^{61}$)—C(O)—N(R$^{62}$)-L$^3$-, -L$^2$-N(R$^{61}$)—C(O)-L$^3$- or -L$^2$-C(O)—N(R$^{61}$-L$^3$-. $L^2$ and $L^3$ are independently a bond or substituted or unsubstituted alkylene (e.g. substituted or unsubstituted C$_1$ to C$_{20}$ alkylene). In some embodiments, $L^2$ and $L^3$ are independently a bond or substituted or unsubstituted C$_1$ to C$_{10}$ alkylene. In other embodiments, $L^2$ and $L^3$ are independently a bond or substituted or unsubstituted C$_1$ to C$_5$ alkylene. $L^2$ and $L^3$ may also independently be a bond or unsubstituted methylene. In some embodiments, $L^2$ and $L^3$ are a bond.

In some embodiments, where $L^2$ and $L^3$ are substituted, $L^2$ and $L^3$ are independently substituted with $R^{66}$. For example, in some embodiments, $L^2$ and $L^3$ are independently $R^{66}$- substituted or unsubstituted alkylene (e.g. substituted or unsubstituted $C_1$ to $C_{20}$ alkylene). $R^{66}$ is independently oxo (where permitted according to valency rules), halogen, —CN, —$CF_3$, —$NR^{66A}$—$C(O)R^{66B}$, —$NR^{66A}$—$C(O)$—$OR^{66B}$, —$C(O)NR^{66A}$, —$C(O)NR^{66A}R^{66B}$, —$NR^{66A}$—$S(O)_2R^{66B}$, —$S(O)_2N(R^{66A})(R^{66B})$, —$SR^{66A}$, —$S(O)R^{66B}$, —$S(O)_2R^{66B}$, —$NR^{66A}R^{66B}$, —$OR^{66A}$, —$C(O)R^{66B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures). $R^{66A}$ and $R^{66B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{61}$ and $R^{62}$ are independently hydrogen, —CN, —$CF_3$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{61}$ and $R^{62}$ are a substituted substituent, $R^{61}$ and $R^{62}$ are independently substituted with $R^{63}$. For example, in some embodiments, $R^{61}$ and $R^{63}$ are independently $R^{63}$-substituted or unsubstituted alkyl (e.g. substituted or unsubstituted $C_1$ to $C_{20}$ alkyl), $R^{63}$-substituted or unsubstituted heteroalkyl (e.g. substituted or unsubstituted 2 to 20 membered heteroalkyl), $R^{63}$-substituted or unsubstituted cycloalkyl (e.g. $C_3$ to $C_{14}$ cycloalkyl including fused ring structures), $R^{63}$-substituted or unsubstituted heterocycloalkyl (e.g. 3 to 14 membered heterocycloalkyl including fused ring structures), $R^{63}$-substituted or unsubstituted aryl (e.g. a $C_6$ to $C_{14}$ aryl including fused ring structures), or $R^{63}$-substituted or unsubstituted heteroaryl (e.g. 5 to 14 membered heteroaryl including fused rings structures).

$R^{63}$ is independently oxo (where permitted according to valency rules), halogen, —CN, —$CF_3$, —$NR^{63A}$—$C(O)R^{63B}$, —$NR^{63A}$—$C(O)$—$OR^{63B}$, —$C(O)NR^{63A}R^{63B}$, —$NR^{63A}S(O)_2R^{63B}$, —$S(O)_2N(R^{63A})(R^{63B})$, —$SR^{63A}$, —$S(O)R^{63B}$, —$S(O)_2R^{63B}$, —$NR^{63A}R^{63B}$, —$OR^{63A}$, —$C(O)R^{63B}$, $R^{64}$-substituted or unsubstituted alkyl (e.g. substituted or unsubstituted $C_1$ to $C_{20}$ alkyl), $R^{64}$-substituted or unsubstituted heteroalkyl (e.g. substituted or unsubstituted 2 to 20 membered heteroalkyl), $R^{64}$-substituted or unsubstituted cycloalkyl (e.g. $C_3$ to $C_{14}$ cycloalkyl including fused ring structures), $R^{64}$-substituted or unsubstituted heterocycloalkyl (e.g. 3 to 14 membered heterocycloalkyl including fused ring structures), $R^{64}$-substituted or unsubstituted aryl (e.g. a $C_6$ to $C_{14}$ aryl including fused ring structures), or $R^{64}$-substituted or unsubstituted heteroaryl (e.g. 5 to 14 membered heteroaryl including fused rings structures).

$R^{63A}$ and $R^{63B}$ are independently hydrogen, $R^{64}$-substituted or unsubstituted alkyl (e.g. substituted or unsubstituted $C_1$ to $C_{20}$ alkyl), $R^{64}$-substituted or unsubstituted heteroalkyl (e.g. substituted or unsubstituted 2 to 20 membered heteroalkyl), $R^{64}$-substituted or unsubstituted cycloalkyl (e.g. $C_3$ to $C_{14}$ cycloalkyl including fused ring structures), $R^{64}$-substituted or unsubstituted heterocycloalkyl (e.g. 3 to 14 membered heterocycloalkyl including fused ring structures), $R^{64}$-substituted or unsubstituted aryl (e.g. a $C_6$ to $C_{14}$ aryl including fused ring structures), or $R^{64}$-substituted or unsubstituted heteroaryl (e.g. 5 to 14 membered heteroaryl including fused rings structures).

$R^{64}$ is independently oxo (where permitted according to valency rules), halogen, —CN, —$CF_3$, —$NR^{64A}$—$C(O)R^{64B}$, —$NR^{64A}$—$C(O)$—$OR^{64B}$, —$C(O)NR^{64A}R^{64B}$, —$NR^{64A}S(O)R^{64B}$, —$S(O)_2N(R^{64A})(R^{64B})$, —$SR^{64A}$, —$S(O)R^{64B}$, —$S(O)_2R^{64B}$, —$NR^{64A}R^{64B}$, —$OR^{64A}$, —$C(O)R^{64B}$, $R^{65}$-substituted or unsubstituted alkyl (e.g. substituted or unsubstituted $C_1$ to $C_{20}$ alkyl), $R^{65}$-substituted or unsubstituted heteroalkyl (e.g. substituted or unsubstituted 2 to 20 membered heteroalkyl), $R^{65}$-substituted or unsubstituted cycloalkyl (e.g. $C_3$ to $C_{14}$ cycloalkyl including fused ring structures), $R^{65}$-substituted or unsubstituted heterocycloalkyl (e.g. 3 to 14 membered heterocycloalkyl including fused ring structures), $R^{65}$-substituted or unsubstituted aryl (e.g. a $C_6$ to $C_{14}$ aryl including fused ring structures), or $R^{65}$-substituted or unsubstituted heteroaryl (e.g. 5 to 14 membered heteroaryl including fused rings structures).

$R^{64A}$ and $R^{64B}$ are independently hydrogen, $R^{65}$-substituted or unsubstituted alkyl (e.g. substituted or unsubstituted $C_1$ to $C_{20}$ alkyl), $R^{65}$-substituted or unsubstituted heteroalkyl (e.g. substituted or unsubstituted 2 to 20 membered heteroalkyl), $R^{65}$-substituted or unsubstituted cycloalkyl (e.g. $C_3$ to $C_{14}$ cycloalkyl including fused ring structures), $R^{65}$-substituted or unsubstituted heterocycloalkyl (e.g. 3 to 14 membered heterocycloalkyl including fused ring structures), $R^{65}$-substituted or unsubstituted aryl (e.g. a $C_6$ to $C_{14}$ aryl including fused ring structures), or $R^{65}$-substituted or unsubstituted heteroaryl (e.g. 5 to 14 membered heteroaryl including fused rings structures).

$R^{65}$ is independently oxo (where permitted according to valency rules), halogen, —CN, —$CF_3$, —$NR^{65A}$—$C(O)R^{65B}$, —$NR^{65A}$—$C(O)$—$OR^{65B}$, —$C(O)NR^{65A}R^{65B}$, —$NR^{65A}S(O)_2R^{65B}$, —$S(O)_2N(R^{65A})(R^{65B})$, —$SR^{65A}$, —$S(O)R^{65B}$, —$S(O)_2R^{65B}$, —$NR^{65A}R^{65B}$, —$OR^{65A}$, —$C(O)R^{65B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{65A}$ and $R^{65B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{61}$ and $R^{62}$ are independently hydrogen, halogen, —CN, —$CF_3$, —OH, —$NH_2$, $R^{63}$-substituted or unsubstituted $C_1$ to $C_5$ alkyl, or $R^{63}$-substituted or unsubstituted 2 to 6 membered heteroalkyl, wherein $R^{63}$ is oxo, halogen, —CN, —CF$_3$, —OH, —NH$_2$, unsubstituted $C_1$ to $C_5$ alkyl, unsubstituted 2 to 6 membered heteroalkyl, or unsubstituted $C_3$ to $C_6$ cycloalkyl (e.g. cyclopropyl). In some embodiments, $R^{61}$ and $R^{62}$ are independently hydrogen, methyl, ethyl, propyl, tertiary butyl, or cyclopropyl methylene (—CH$_2$-cyclopropyl). In some embodiments, $R^{61}$ and $R^{62}$ are hydrogen.

In some embodiments, $L^1$ is —NH—C(O)—. Where $L^1$ is —NH—C(O)— as used herein (as opposed to a —C(O)—NH—), the orientation of the $L^1$ groups is as provided below:

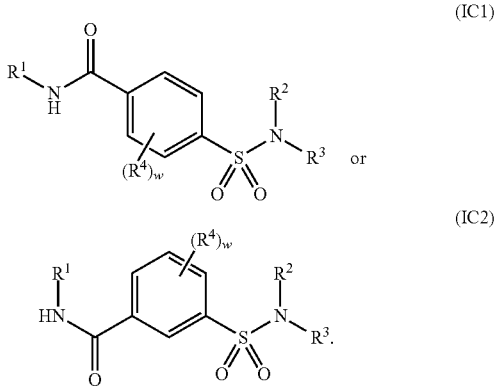

Thus, where $L^1$ is —NH—C(O)— for a formula provided herein, it is intended that the amide carbon is attached to the phenyl group and amide nitrogen is attached to the $R^1$ group.

In some embodiments, $R^1$ is a substituted (e.g. $R^{16}$-substituted) or unsubstituted heteroaryl (e.g. a 5 to 14 membered heteroaryl including fused ring heteroaryls) or a substituted (e.g. $R^{16}$-substituted) or unsubstituted aryl (e.g. a $C_6$ to $C_{14}$ aryl including fused ring structures). In some embodiments, $R^1$ is a substituted (e.g. $R^{16}$-substituted) or unsubstituted heteroaryl (e.g. a 5 to 14 membered heteroaryl including fused ring heteroaryls) or a substituted (e.g. $R^{16}$-substituted) or unsubstituted phenyl. $R^1$ may also be substituted (e.g. $R^{16}$-substituted) or unsubstituted pyridinyl, substituted (e.g. $R^{16}$-substituted) or unsubstituted thiazolyl, substituted (e.g. $R^{16}$-substituted) or unsubstituted benzothiazolyl, substituted (e.g. $R^{16}$-substituted) or unsubstituted oxazolyl, substituted (e.g. $R^{16}$-substituted) or unsubstituted phenyl, substituted (e.g. $R^{16}$-substituted) or unsubstituted 4,5-dihydro-1H-benzoindazolyl or substituted (e.g. $R^{16}$-substituted) or unsubstituted pyrazolyl. In certain embodiments, $R^1$ is substituted (e.g. $R^{16}$-substituted) or unsubstituted phenyl. In certain embodiments, $R^1$ is substituted (e.g. $R^{16}$-substituted) or unsubstituted thiazolyl. In certain embodiments, $R^1$ is substituted (e.g. $R^{16}$-substituted) or unsubstituted benzothiazolyl. In certain embodiments, $R^1$ is substituted (e.g. $R^{16}$-substituted) or unsubstituted 4,5-dihydro-1H-benzoindazolyl. In certain embodiments, $R^1$ is substituted (e.g. $R^{16}$-substituted) or unsubstituted pyrazolyl. In certain embodiments, $R^1$ is substituted (e.g. $R^{16}$-substituted) or unsubstituted pyridinyl.

In some embodiments, where $R^1$ is a $R^{16}$-substituted or unsubstituted heteroaryl (e.g. a 5 to 14 membered heteroaryl including fused ring heteroaryls) or a $R^{16}$-substituted or unsubstituted aryl (e.g. a $C_6$ to $C_{14}$ aryl including fused ring structures), $R^{16}$ is an $R^{17}$-substituted or unsubstituted heteroaryl (e.g. a 5 to 14 membered heteroaryl including fused ring heteroaryls) or $R^{17}$-substituted or unsubstituted aryl (e.g. a $C_6$ to $C_{14}$ aryl including fused ring structures). In some embodiments, where $R^1$ is $R^{16}$-substituted or unsubstituted thiazolyl, $R^{16}$ is an $R^{17}$-substituted or unsubstituted (e.g. a 5 to 14 membered heteroaryl including fused ring heteroaryls) or $R^{17}$-substituted or unsubstituted aryl (e.g. a $C_6$ to $C_{14}$ aryl including fused ring structures). In some embodiments, where $R^1$ is $R^{16}$-substituted or unsubstituted thiazolyl, $R^{16}$ is an $R^{17}$-substituted or unsubstituted pyridinyl or $R^{17}$-substituted or unsubstituted phenyl. $R^{17}$ may be halogen, —CN, —CF$_3$, —OH, —NH$_2$, $R^{18}$-substituted or unsubstituted $C_1$ to $C_5$ alkyl, $R^{18}$-substituted or unsubstituted 2 to 6 membered heteroalkyl, wherein $R^{18}$ is oxo, halogen, —CN, —CF$_3$, —OH, —NH$_2$, unsubstituted $C_1$ to $C_5$ alkyl, unsubstituted 2 to 6 membered heteroalkyl.

In some embodiments, where $R^1$ is $R^{16}$-substituted or unsubstituted thiazolyl, $R^{16}$ is an $R^{17}$-substituted or unsubstituted pyridinyl. In some embodiments, where $R^1$ is $R^{16}$-substituted or unsubstituted thiazolyl, $R^{16}$ is an $R^{17}$-substituted or unsubstituted pyridinyl. $R^{17}$ may be halogen, —CN, —CF$_3$, —OH, —NH$_2$, $R^{18}$-substituted or unsubstituted $C_1$ to $C_5$ alkyl, or $R^{18}$-substituted or unsubstituted 2 to 6 membered heteroalkyl, wherein $R^{18}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^1$ is $R^{16}$-substituted or unsubstituted thiazolyl and $R^{16}$ is unsubstituted pyridinyl.

In some embodiments, $R^2$ is hydrogen or unsubstituted alkyl (e.g. $C_1$ to $C_{10}$ alkyl). In some embodiments, $R^2$ is hydrogen. In some embodiments, $R^2$ is unsubstituted $C_1$ to $C_5$ alkyl. In some embodiments, $R^2$ is methyl. In some embodiments, $R^2$ is methyl, ethyl, propyl, tertiary butyl, methylene cyclopropyl (—CH$_2$-cyclopropyl), methoxy, ethoxy, propoxy, butoxy or —CF$_3$. These embodiments are applicable to all appropriate formulae as set forth herein.

$R^3$ may be substituted (e.g. $R^{22}$-substituted) or unsubstituted phenyl. In some embodiments, $R^{22}$ is joined together with $R^2$ to form a substituted (e.g. $R^6$-substituted as defined below) or unsubstituted heteroaryl or substituted (e.g. $R^6$-substituted) or unsubstituted heterocycloalkyl. In other embodiments, $R^2$ and $R^3$ are joined together to form a substituted (e.g. $R^6$-substituted) or unsubstituted heteroaryl. $R^2$ and $R^3$ may be joined together to form a substituted (e.g. $R^6$-substituted) or unsubstituted indolin-1-yl or a substituted (e.g. $R^6$-substituted) or unsubstituted tetrahydroquinolinyl. In some embodiments, $R^6$ is halogen, —CN, —CF$_3$, —OH, —NH$_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted $C_1$ to $C_5$ alkyl, unsubstituted 2 to 6 membered heteroalkyl.

In some embodiments, where $R^3$ is $R^{22}$-substituted or unsubstituted phenyl, $R^{22}$ is halogen, —CN, —CF$_3$, —OH, —NH$_2$, $R^{23}$-substituted or unsubstituted $C_1$ to $C_5$ alkyl, or $R^{23}$-substituted or unsubstituted 2 to 6 membered heteroalkyl, wherein $R^{23}$ is oxo, halogen, —CN, —CF$_3$, —OH, —NH$_2$, unsubstituted $C_1$ to $C_5$ alkyl, or unsubstituted 2 to 6 membered heteroalkyl.

$R^4$ may be halogen, —CN, —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is —CF$_3$, —OH, —NH$_2$, unsubstituted $C_1$ to $C_5$ alkyl, or unsubstituted 2 to 6 membered heteroalkyl. In some embodiments, $R^4$ is methyl, methoxy, —$CF_3$, or —OH.

In some embodiments, the compound has the structure of formula (IIA) or (IIB):

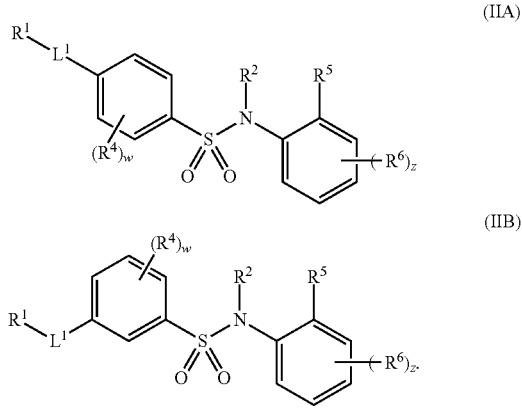

(IIA)

(IIB)

In formulae (IIA) and (IIB), $L^1$, $R^1$, $R^2$, $R^4$ and w are as defined above. In some embodiments, $R^1$ is substituted (e.g. $R^{16}$-substituted) or unsubstituted aryl (e.g. $C_6$ to $C_{14}$ aryl including fused ring aryls) or substituted (e.g. $R^{16}$-substituted) or unsubstituted heteroaryl (e.g. 5 to 14 membered heteroaryl including fused rings structures). In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH.

$R^2$ is as defined above, and may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments, $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. $C_1$ to $C_{10}$ alkyl). In some embodiments, $R^2$ is hydrogen. In some embodiments, $R^2$ is unsubstituted $C_1$ to $C_5$ alkyl. In some embodiments, $R^2$ is methyl. In some embodiments, $R^2$ is methyl, ethyl, propyl, tertiary butyl, methylene cyclopropyl (—$CH_2$-cyclopropyl), methoxy, ethoxy, propoxy, butoxy or —$CF_3$.

$R^5$ is hydrogen, halogen, —CN, —$CF_3$, —$NR^{5A}$—C(O)$R^{5B}$, —$NR^{5A}$—C(O)—$OR^{5B}$, —C(O)$NR^{5A}R^{5B}$, —$NR^{5A}$S(O)$_2R^{5B}$, —S(O)$_2$N($R^{5A}$)($R^{5B}$), —$SR^A$, —S(O)$R^{5B}$, —S(O)$_2R^{5B}$, —$NR^{5A}R^{5B}$, —$OR^{5A}$, —C(O)$R^{5B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{5A}$, $R^{5B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^5$, $R^{5A}$ and $R^{5B}$ are substituted substituents, $R^5$, $R^{5A}$ and $R^5$ are independently substituted with $R^{28}$. For example, in some embodiments, $R^5$, $R^{5A}$ and $R^5$ are independently $R^{28}$-substituted or unsubstituted alkyl (e.g. substituted or unsubstituted $C_1$ to $C_{20}$ alkyl), $R^{28}$-substituted or unsubstituted heteroalkyl (e.g. substituted or unsubstituted 2 to 20 membered heteroalkyl), $R^{28}$-substituted or unsubstituted cycloalkyl (e.g. $C_3$ to $C_{14}$ cycloalkyl including fused ring structures), $R^{28}$-substituted or unsubstituted heterocycloalkyl (e.g. 3 to 14 membered heterocycloalkyl including fused ring structures), $R^{28}$-substituted or unsubstituted aryl (e.g. a $C_6$ to $C_{14}$ aryl including fused ring structures), or $R^{28}$-substituted or unsubstituted heteroaryl (e.g. 5 to 14 membered heteroaryl including fused rings structures).

$R^{28}$ is independently oxo (where permitted according to valency rules), halogen, —CN, —$CF_3$, —$NR^{28A}$—C(O)$R^{28B}$, —$NR^{28A}$—C(O)—$OR^{28B}$, —C(O)$NR^{28A}R^{28B}$, —$NR^{28A}$S(O)$R^{28B}$, —S(O)$_2$N($R^{28A}$)($R^{28B}$), —$SR^{28A}$, —S(O)$R^{28B}$, —S(O)$_2R^{28B}$, —$NR^{28A}R^{28B}$, —$OR^{28A}$, —C(O)$R^{28B}$, $R^{29}$-substituted or unsubstituted alkyl (e.g. substituted or unsubstituted $C_1$ to $C_{20}$ alkyl), $R^{29}$-substituted or unsubstituted heteroalkyl (e.g. substituted or unsubstituted 2 to 20 membered heteroalkyl), $R^{29}$-substituted or unsubstituted cycloalkyl (e.g. $C_3$ to $C_{14}$ cycloalkyl including fused ring structures), $R^{29}$-substituted or unsubstituted heterocycloalkyl (e.g. 3 to 14 membered heterocycloalkyl including fused ring structures), $R^{29}$-substituted or unsubstituted aryl (e.g. a $C_6$ to $C_{14}$ aryl including fused ring structures), or $R^{29}$-substituted or unsubstituted heteroaryl (e.g. 5 to 14 membered heteroaryl including fused rings structures).

$R^{28A}$ and $R^{28B}$ are independently hydrogen, $R^{29}$-substituted or unsubstituted alkyl (e.g. substituted or unsubstituted $C_1$ to $C_{20}$ alkyl), $R^{29}$-substituted or unsubstituted heteroalkyl (e.g. substituted or unsubstituted 2 to 20 membered heteroalkyl), $R^{29}$-substituted or unsubstituted cycloalkyl (e.g. $C_3$ to $C_{14}$ cycloalkyl including fused ring structures), $R^{29}$-substituted or unsubstituted heterocycloalkyl (e.g. 3 to 14 membered heterocycloalkyl including fused ring structures), $R^{29}$-substituted or unsubstituted aryl (e.g. a $C_6$ to $C_{14}$ aryl including fused ring structures), or $R^{29}$-substituted or unsubstituted heteroaryl (e.g. 5 to 14 membered heteroaryl including fused rings structures).

$R^{29}$ is independently oxo (where permitted according to valency rules), halogen, —CN, —$CF_3$, —$NR^{29A}$—C(O)$R^{29B}$, —$NR^{29A}$—C(O)—$OR^{29B}$, —C(O)$NR^{29A}R^{29B}$, —$NR^{29A}$S(O)$_2R^{29B}$, —S(O)$_2$N($R^{29A}$)($R^{29B}$), —$SR^{29A}$, —S(O)$R^{29B}$, —S(O)$_2R^{29B}$, —$NR^{29A}R^{29B}$, —$OR^{29A}$, —C(O)$R^{29B}$, $R^{30}$-substituted or unsubstituted alkyl (e.g. substituted or unsubstituted $C_1$ to $C_{20}$ alkyl), $R^{30}$-substituted or unsubstituted heteroalkyl (e.g. substituted or unsubstituted 2 to 20 membered heteroalkyl), $R^{30}$-substituted or unsubstituted cycloalkyl (e.g. $C_3$ to $C_{14}$ cycloalkyl including fused ring structures), $R^{30}$-substituted or unsubstituted heterocycloalkyl (e.g. 3 to 14 membered heterocycloalkyl including fused ring structures), $R^{30}$-substituted or unsubstituted aryl (e.g. a $C_6$ to $C_{14}$ aryl including fused ring structures), or $R^{30}$-substituted or unsubstituted heteroaryl (e.g. 5 to 14 membered heteroaryl including fused rings structures).

$R^{29A}$ and $R^{29B}$ are independently hydrogen, $R^{30}$-substituted or unsubstituted alkyl (e.g. substituted or unsubstituted $C_1$ to $C_{20}$ alkyl), $R^{30}$-substituted or unsubstituted heteroalkyl (e.g. substituted or unsubstituted 2 to 20 membered heteroalkyl), $R^{30}$-substituted or unsubstituted cycloalkyl (e.g. $C_3$ to $C_{14}$ cycloalkyl including fused ring structures), $R^{30}$-substituted or unsubstituted heterocycloalkyl (e.g. 3 to 14 membered heterocycloalkyl including fused ring structures), $R^{30}$-substituted or unsubstituted aryl (e.g. a $C_6$ to $C_{14}$ aryl including fused ring structures), or $R^{30}$-substituted or unsubstituted heteroaryl (e.g. 5 to 14 membered heteroaryl including fused rings structures).

$R^{30}$ is independently oxo (where permitted according to valency rules), halogen, —CN, —$CF_3$, —$NR^{30A}$—C(O)$R^{30B}$, —$NR^{30A}$—C(O)—$OR^{30B}$, —C(O)$NR^{30A}R^{30B}$, —$NR^{30A}S(O)_2R^{30B}$, —$S(O)_2N(R^{30A})(R^{30B})$, —$SR^{30A}$, —$S(O)R^{30B}$, —$S(O)_2R^{30B}$, —$NR^{30A}R^{30B}$, —$OR^{30A}$, —C(O)$R^{30B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{30A}$ and $R^{30B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^5$ is hydrogen, halogen, —CN, —$CF_3$, —OH, —$NH_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^5$ is methoxy, ethoxy, propoxy, Cl, F or $CF_3$. In some embodiments, $R^5$ is methoxy, ethoxy, or propoxy. In some embodiments, $R^5$ is methoxy.

$R^6$ is independently halogen, —CN, —$CF_3$, —$NR^{6A}$—C(O)$R^{6B}$, —$NR^{6A}$—C(O)—$OR^{6B}$, —C(O)$NR^{6A}R^{6B}$, —$NR^{6A}S(O)_2R^{6B}$, —$S(O)_2N(R^{6A})(R^{6B})$, —$SR^{6A}$, —S(O)$R^{6B}$, —$S(O)_2R^{6B}$, —$NR^{6A}R^{6B}$, —$OR^{6A}$, —C(O)$R^{6B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{6A}$ and $R^{6B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^6$, $R^{6A}$ and $R^{6B}$ are substituted substituents, $R^6$, $R^{6A}$ and $R^6$ are independently substituted with $R^{31}$. For example, in some embodiments, $R^6$, $R^{6A}$ and $R^6$ are independently $R^{31}$-substituted or unsubstituted alkyl (e.g. substituted or unsubstituted $C_1$ to $C_{20}$ alkyl), $R^{31}$-substituted or unsubstituted heteroalkyl (e.g. substituted or unsubstituted 2 to 20 membered heteroalkyl), $R^{31}$-substituted or unsubstituted cycloalkyl (e.g. $C_3$ to $C_{14}$ cycloalkyl including fused ring structures), $R^{31}$-substituted or unsubstituted heterocycloalkyl (e.g. 3 to 14 membered heterocycloalkyl including fused ring structures), $R^{31}$-substituted or unsubstituted aryl (e.g. a $C_6$ to $C_{14}$ aryl including fused ring structures), or $R^{31}$-substituted or unsubstituted heteroaryl (e.g. 5 to 14 membered heteroaryl including fused rings structures).

$R^{31}$ is independently oxo (where permitted according to valency rules), halogen, —CN, —$CF_3$, —$NR^{31A}$—C(O)$R^{31B}$, —$NR^{31A}$—C(O)—$OR^{31B}$, —C(O)$NR^{31A}R^{31B}$, —$NR^{31A}S(O)_2R^{31B}$, —$S(O)_2N(R^{31A})(R^{31B})$, —$SR^{31A}$, —S(O)$R^{31B}$, —$S(O)_2R^{31B}$, —$NR^{31A}R^{31B}$, —$OR^{31A}$, —C(O)$R^{31B}$, $R^{32}$-substituted or unsubstituted alkyl (e.g. substituted or unsubstituted $C_1$ to $C_{20}$ alkyl), $R^{32}$-substituted or unsubstituted heteroalkyl (e.g. substituted or unsubstituted 2 to 20 membered heteroalkyl), $R^{32}$-substituted or unsubstituted cycloalkyl (e.g. $C_3$ to $C_{14}$ cycloalkyl including fused ring structures), $R^{32}$-substituted or unsubstituted heterocycloalkyl (e.g. 3 to 14 membered heterocycloalkyl including fused ring structures), $R^{32}$-substituted or unsubstituted aryl (e.g. a $C_6$ to $C_{14}$ aryl including fused ring structures), or $R^{32}$-substituted or unsubstituted heteroaryl (e.g. 5 to 14 membered heteroaryl including fused rings structures).

$R^{31A}$ and $R^{31B}$ are independently hydrogen, $R^{32}$-substituted or unsubstituted alkyl (e.g. substituted or unsubstituted $C_1$ to $C_{20}$ alkyl), $R^{32}$-substituted or unsubstituted heteroalkyl (e.g. substituted or unsubstituted 2 to 20 membered heteroalkyl), $R^{32}$-substituted or unsubstituted cycloalkyl (e.g. $C_3$ to $C_{14}$ cycloalkyl including fused ring structures), $R^{32}$-substituted or unsubstituted heterocycloalkyl (e.g. 3 to 14 membered heterocycloalkyl including fused ring structures), $R^{32}$-substituted or unsubstituted aryl (e.g. a $C_6$ to $C_{14}$ aryl including fused ring structures), or $R^{32}$-substituted or unsubstituted heteroaryl (e.g. 5 to 14 membered heteroaryl including fused rings structures).

$R^{32}$ is independently oxo (where permitted according to valency rules), halogen, —CN, —$CF_3$, —$NR^{32A}$—C(O)$R^{32B}$, —$NR^{32A}$—C(O)—$OR^{32B}$, —C(O)$NR^{32A}R^{32B}$, —$NR^{32A}S(O)_2R^{32B}$, —$S(O)_2N(R^{32A})(R^{32B})$, —$SR^{32A}$, —S(O)$R^{32B}$, —$S(O)_2R^{32B}$, —$NR^{32A}R^{32B}$, —$OR^{32A}$, —C(O)$R^{32B}$, $R^{33}$-substituted or unsubstituted alkyl (e.g. substituted or unsubstituted $C_1$ to $C_{20}$ alkyl), $R^{33}$-substituted or unsubstituted heteroalkyl (e.g. substituted or unsubstituted 2 to 20 membered heteroalkyl), $R^{33}$-substituted or unsubstituted cycloalkyl (e.g. $C_3$ to $C_{14}$ cycloalkyl including fused ring structures), $R^{33}$-substituted or unsubstituted heterocycloalkyl (e.g. 3 to 14 membered heterocycloalkyl including fused ring structures), $R^{33}$-substituted or unsubstituted aryl (e.g. a $C_6$ to $C_{14}$ aryl including fused ring structures), or $R^{33}$-substituted or unsubstituted heteroaryl (e.g. 5 to 14 membered heteroaryl including fused rings structures).

$R^{32A}$ and $R^{32B}$ are independently hydrogen, $R^{33}$-substituted or unsubstituted alkyl (e.g. substituted or unsubstituted $C_1$ to $C_{20}$ alkyl), $R^{33}$-substituted or unsubstituted heteroalkyl (e.g. substituted or unsubstituted 2 to 20 membered heteroalkyl), $R^{33}$-substituted or unsubstituted cycloalkyl (e.g. $C_3$ to $C_{14}$ cycloalkyl including fused ring structures), $R^{33}$-substituted or unsubstituted heterocycloalkyl (e.g. 3 to 14 membered heterocycloalkyl including fused ring structures), $R^{33}$-substituted or unsubstituted aryl (e.g. a $C_6$ to $C_{14}$ aryl including fused ring structures), or $R^{33}$-substituted or unsubstituted heteroaryl (e.g. 5 to 14 membered heteroaryl including fused rings structures).

$R^{33}$ is independently oxo (where permitted according to valency rules), halogen, —CN, —$CF_3$, —$NR^{33A}$—C(O)$R^{33B}$, —$NR^{33A}$—C(O)—$OR^{33B}$, —C(O)$NR^{33A}R^{33B}$, —$NR^{33A}S(O)_2R^{33B}$, —$S(O)_2N(R^{33A})(R^{33B})$, —$SR^{33A}$, —$S(O)R^{33B}$, —$S(O)_2R^{33B}$, —$NR^{33A}R^{33B}$, —$OR^{33A}$, —C(O)$R^{33B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{33A}$ and $R^{33B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, the compound has the formula:

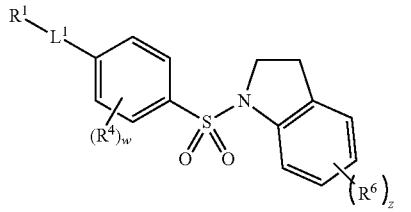

(IIIA)

or

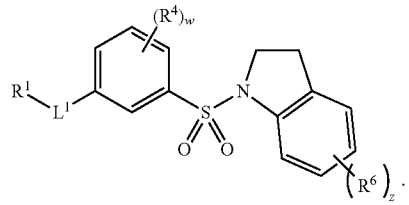

(IIIB)

In Formulae (IIIA) and (IIIB), $R^1$, $L^1$, $R^4$, $R^6$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH.

In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, the compound has the formula:

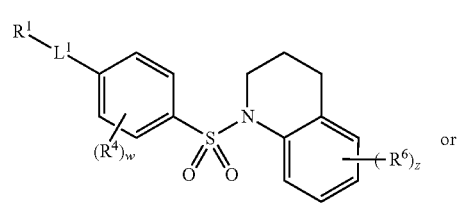

(IVA)

or

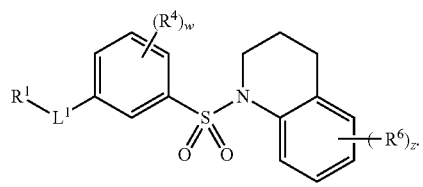

(IVB)

In Formulae (IVA) and (IVB), $R^1$, $L^1$, $R^4$, $R^6$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_{25}$ $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, the compound has the formula:

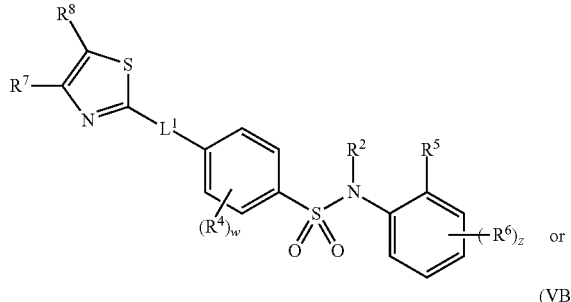

(VA)

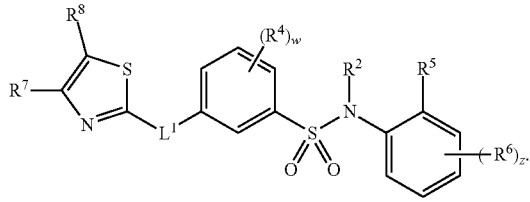

(VB)

In Formulae (VA) and (VB), $R^2$, $R^4$, $R^5$, $R^6$, $L^1$, w and z are as defined above. In some embodiments, w is 0. In other embodiments, w is 1. In some embodiments, $L^1$ is —NH—C(O)— as illustrated in Formula (IC1) or (IC2). As set forth above in Formulae (IIA) and (IIB), $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (VA) and (VB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. $C_1$ to $C_{10}$ alkyl). In some embodiments, $R^2$ is hydrogen. In some embodiments, $R^2$ is unsubstituted $C_1$ to $C_5$ alkyl. In some embodiments, $R^2$ is methyl. In some embodiments, $R^2$ is methyl, ethyl, propyl, tertiary butyl, methylene cyclopropyl (—$CH_2$-cyclopropyl), methoxy, ethoxy, propoxy, butoxy or —$CF_3$.

$R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

$R^7$ is hydrogen, halogen, —CN, —$CF_3$, —$NR^{7A}$—C(O) $R^{7B}$, —$NR^{7A}$—C(O)—$OR^{7B}$, —C(O)$NR^{7A}R^{7B}$, —$NR^{7A}$S(O)$_2R^{7B}$, —S(O)$_2$N($R^{7A}$)($R^{7B}$), —$SR^{7A}$—S(O)$R^{7B}$, —S(O)$_2$ $R^{7B}$, —$NR^{7A}R^{7B}$, —$OR^{7A}$, —C(O)$R^{7B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{7A}$ and $R^{7B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^7$, $R^{7A}$ and $R^{7B}$ are substituted substituents, $R^7$, $R^{7A}$ and $R^7$ are independently substituted with $R^{34}$. For example, in some embodiments, $R^7$, $R^{7A}$ and $R^7$ are independently $R^{34}$-substituted or unsubstituted alkyl (e.g. substituted or unsubstituted $C_1$ to $C_{20}$ alkyl), $R^{34}$-substituted or unsubstituted heteroalkyl (e.g. substituted or unsubstituted 2 to 20 membered heteroalkyl), $R^{34}$-substituted or unsubstituted cycloalkyl (e.g. $C_3$ to $C_{14}$ cycloalkyl including fused ring structures), $R^{34}$-substituted or unsubstituted heterocycloalkyl (e.g. 3 to 14 membered heterocycloalkyl including fused ring structures), $R^{34}$-substituted or unsubstituted aryl (e.g. a $C_6$ to $C_{14}$ aryl including fused ring structures), or $R^{34}$-substituted or unsubstituted heteroaryl (e.g. 5 to 14 membered heteroaryl including fused rings structures).

$R^{34}$ is independently oxo (where permitted according to valency rules), halogen, —CN, —CF$_3$, —NR$^{34A}$—C(O)R$^{34B}$, —NR$^{34A}$—C(O)—OR$^{34B}$, —C(O)NR$^{34A}$R$^{34B}$, —NR$^{34A}$S(O)$_2$R$^{34B}$, —S(O)$_2$N(R$^{34A}$)(R$^{34B}$), —SR$^{34A}$, —S(O)R$^{34B}$, —S(O)$_2$R$^{34B}$, —NR$^{34A}$R$^{34B}$, —OR$^{34A}$, —C(O)R$^{34B}$, $R^{35}$-substituted or unsubstituted alkyl (e.g. substituted or unsubstituted C$_1$ to C$_{20}$ alkyl), $R^{35}$-substituted or unsubstituted heteroalkyl (e.g. substituted or unsubstituted 2 to 20 membered heteroalkyl), $R^{35}$-substituted or unsubstituted cycloalkyl (e.g. C$_3$ to C$_{14}$ cycloalkyl including fused ring structures), $R^{35}$-substituted or unsubstituted heterocycloalkyl (e.g. 3 to 14 membered heterocycloalkyl including fused ring structures), $R^{35}$-substituted or unsubstituted aryl (e.g. a C$_6$ to C$_{14}$ aryl including fused ring structures), or $R^{35}$-substituted or unsubstituted heteroaryl (e.g. 5 to 14 membered heteroaryl including fused rings structures).

$R^{34A}$ and $R^{34B}$ are independently hydrogen, $R^{35}$-substituted or unsubstituted alkyl (e.g. substituted or unsubstituted C$_1$ to C$_{20}$ alkyl), $R^{35}$-substituted or unsubstituted heteroalkyl (e.g. substituted or unsubstituted 2 to 20 membered heteroalkyl), $R^{35}$-substituted or unsubstituted cycloalkyl (e.g. C$_3$ to C$_{14}$ cycloalkyl including fused ring structures), $R^{35}$-substituted or unsubstituted heterocycloalkyl (e.g. 3 to 14 membered heterocycloalkyl including fused ring structures), $R^{35}$-substituted or unsubstituted aryl (e.g. a C$_6$ to C$_{14}$ aryl including fused ring structures), or $R^{35}$-substituted or unsubstituted heteroaryl (e.g. 5 to 14 membered heteroaryl including fused rings structures).

$R^{35}$ is independently oxo (where permitted according to valency rules), halogen, —CN, —CF$_3$, —NR$^{35A}$—C(O)R$^{35B}$, —NR$^{35A}$—C(O)—OR$^{35B}$, —C(O)NR$^{35A}$R$^{35B}$, —NR$^{35A}$S(O)R$^{35B}$, —S(O)$_2$N(R$^{35A}$)(R$^{35B}$), —SR$^{35A}$, —S(O)R$^{35B}$, —S(O)$_2$R$^{35B}$, —NR$^{35A}$R$^{35B}$, —OR$^{35A}$, —C(O)R$^{35B}$, $R^{36}$-substituted or unsubstituted alkyl (e.g. substituted or unsubstituted C$_1$ to C$_{20}$ alkyl), $R^{36}$-substituted or unsubstituted heteroalkyl (e.g. substituted or unsubstituted 2 to 20 membered heteroalkyl), $R^{36}$-substituted or unsubstituted cycloalkyl (e.g. C$_3$ to C$_{14}$ cycloalkyl including fused ring structures), $R^{36}$-substituted or unsubstituted heterocycloalkyl (e.g. 3 to 14 membered heterocycloalkyl including fused ring structures), $R^{36}$-substituted or unsubstituted aryl (e.g. a C$_6$ to C$_{14}$ aryl including fused ring structures), or $R^{36}$-substituted or unsubstituted heteroaryl (e.g. 5 to 14 membered heteroaryl including fused rings structures).

$R^{35A}$ and $R^{35B}$ are independently hydrogen, $R^{36}$-substituted or unsubstituted alkyl (e.g. substituted or unsubstituted C$_1$ to C$_{20}$ alkyl), $R^{36}$-substituted or unsubstituted heteroalkyl (e.g. substituted or unsubstituted 2 to 20 membered heteroalkyl), $R^{36}$-substituted or unsubstituted cycloalkyl (e.g. C$_3$ to C$_{14}$ cycloalkyl including fused ring structures), $R^{36}$-substituted or unsubstituted heterocycloalkyl (e.g. 3 to 14 membered heterocycloalkyl including fused ring structures), $R^{36}$-substituted or unsubstituted aryl (e.g. a C$_6$ to C$_{14}$ aryl including fused ring structures), or $R^{36}$-substituted or unsubstituted heteroaryl (e.g. 5 to 14 membered heteroaryl including fused rings structures).

$R^{36}$ is independently oxo (where permitted according to valency rules), halogen, —CN, —CF$_3$, —NR$^{36A}$, —C(O)R$^{36B}$, —NR$^{36A}$—C(O)—OR$^{36B}$, —C(O) NR$^{36A}$R$^{36B}$, —NR$^{36A}$S(O)$_2$R$^{36B}$, —S(O)$_2$N(R$^{36A}$)(R$^{36B}$), —SR$^{36A}$, —S(O)R$^{36B}$, —S(O)$_2$R$^{36B}$, —NR$^{36A}$R$^{36B}$, —OR$^{36A}$, —C(O)R$^{36B}$, unsubstituted alkyl (e.g. substituted or unsubstituted C$_1$ to C$_{20}$ alkyl), unsubstituted heteroalkyl (e.g. substituted or unsubstituted 2 to 20 membered heteroalkyl), unsubstituted cycloalkyl (e.g. C$_3$ to C$_{14}$ cycloalkyl including fused ring structures), unsubstituted heterocycloalkyl (e.g. 3 to 14 membered heterocycloalkyl including fused ring structures), unsubstituted aryl (e.g. a C$_6$ to C$_{14}$ aryl including fused ring structures), or unsubstituted heteroaryl (e.g. 5 to 14 membered heteroaryl including fused rings structures).

$R^{36A}$ and $R^{36B}$ are independently hydrogen, unsubstituted alkyl (e.g. substituted or unsubstituted C$_1$ to C$_{20}$ alkyl), unsubstituted heteroalkyl (e.g. substituted or unsubstituted 2 to 20 membered heteroalkyl), unsubstituted cycloalkyl (e.g. C$_3$ to C$_{14}$ cycloalkyl including fused ring structures), unsubstituted heterocycloalkyl (e.g. 3 to 14 membered heterocycloalkyl including fused ring structures), unsubstituted aryl (e.g. a C$_6$ to C$_{14}$ aryl including fused ring structures), or unsubstituted heteroaryl (e.g. 5 to 14 membered heteroaryl including fused rings structures).

$R^8$ is hydrogen, halogen, —CN, —CF$_3$, —NR$^{8A}$—C(O)R$^{8B}$, —NR$^{8A}$—C(O)—OR$^{8B}$, —C(O)NR$^{8A}$R$^{8B}$, —NR$^{8A}$S(O)$_2$R$^{8B}$, —S(O)$_2$N(R$^{8A}$)(R$^{8B}$), —SR$^{8A}$, —S(O)R$^{8B}$, —S(O)$_2$R$^{8B}$, —NR$^{8A}$R$^{8B}$, —OR$^{8A}$, —C(O)R$^{8B}$, substituted or unsubstituted alkyl (e.g. substituted or unsubstituted C$_1$ to C$_{20}$ alkyl), substituted or unsubstituted heteroalkyl (e.g. substituted or unsubstituted 2 to 20 membered heteroalkyl), substituted or unsubstituted cycloalkyl (e.g. C$_3$ to C$_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a C$_6$ to C$_{14}$ aryl including fused ring structures), or substituted or unsubstituted heteroaryl (e.g. 5 to 14 membered heteroaryl including fused rings structures).

$R^7$ and $R^8$ are optionally joined together to form a substituted (e.g. $R^{15}$-substituted as defined below) or unsubstituted cycloalkyl (e.g. C$_3$ to C$_{14}$ cycloalkyl including fused ring structures), substituted (e.g. $R^{15}$-substituted as defined below) or unsubstituted heterocycloalkyl (e.g. 3 to 14 membered heterocycloalkyl including fused ring structures), substituted (e.g. $R^{15}$-substituted as defined below) or unsubstituted aryl (e.g. a C$_6$ to C$_{14}$ aryl including fused ring structures), or substituted (e.g. $R^{15}$-substituted as defined below) or unsubstituted heteroaryl (e.g. 5 to 14 membered heteroaryl including fused rings structures).

$R^{8A}$ and $R^{8B}$ are independently hydrogen, substituted or unsubstituted alkyl (e.g. substituted or unsubstituted C$_1$ to C$_{20}$ alkyl), substituted or unsubstituted heteroalkyl (e.g. substituted or unsubstituted 2 to 20 membered heteroalkyl), substituted or unsubstituted cycloalkyl (e.g. C$_3$ to C$_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a C$_6$ to C$_{14}$ aryl including fused ring structures), or substituted or unsubstituted heteroaryl (e.g. 5 to 14 membered heteroaryl including fused rings structures).

In some embodiments, where $R^8$, $R^{8A}$ and $R^{8B}$ are substituted substituents, $R^8$, $R^{8A}$ and $R^8$ are independently substituted with $R^{37}$. For example, in some embodiments, $R^8$, $R^{8A}$ and $R^8$ are independently $R^{37}$-substituted or unsubstituted alkyl (e.g. substituted or unsubstituted C$_1$ to C$_{20}$ alkyl), $R^{37}$-substituted or unsubstituted heteroalkyl (e.g. substituted or unsubstituted 2 to 20 membered heteroalkyl), $R^{37}$-substituted or unsubstituted cycloalkyl (e.g. C$_3$ to C$_{14}$ cycloalkyl including fused ring structures), $R^{37}$-substituted or unsubstituted heterocycloalkyl (e.g. 3 to 14 membered heterocycloalkyl including fused ring structures), $R^{37}$-substituted or unsubstituted aryl (e.g. a C$_6$ to C$_{14}$ aryl including fused ring structures), or $R^{37}$-substituted or unsubstituted heteroaryl (e.g. 5 to 14 membered heteroaryl including fused rings structures).

$R^{37}$ is independently oxo (where permitted according to valency rules), halogen, —CN, —CF$_3$, —NR$^{37A}$—C(O)

$R^{37B}$, —$NR^{37A}$—C(O)—$OR^{37B}$, —C(O)$NR^{37A}R^{37B}$, —$NR^{37A}$S(O)$_2R^{37B}$, —S(O)$_2$N($R^{37A}$)($R^{37B}$), —$SR^{37A}$, —S(O)$R^{37B}$, —S(O)$_2R^{37B}$, —$NR^{37A}R^{37B}$, —$OR^{37A}$, —C(O) $R^{37B}$, $R^{38}$-substituted or unsubstituted alkyl (e.g. substituted or unsubstituted $C_1$ to $C_{20}$ alkyl), $R^{38}$-substituted or unsubstituted heteroalkyl (e.g. substituted or unsubstituted 2 to 20 membered heteroalkyl), $R^{38}$-substituted or unsubstituted cycloalkyl (e.g. $C_3$ to $C_{14}$ cycloalkyl including fused ring structures), $R^{38}$-substituted or unsubstituted heterocycloalkyl (e.g. 3 to 14 membered heterocycloalkyl including fused ring structures), $R^{38}$-substituted or unsubstituted aryl (e.g. a $C_6$ to $C_{14}$ aryl including fused ring structures), or $R^{38}$-substituted or unsubstituted heteroaryl (e.g. 5 to 14 membered heteroaryl including fused rings structures).

$R^{37A}$ and $R^{37B}$ are independently hydrogen, $R^{38}$-substituted or unsubstituted alkyl (e.g. substituted or unsubstituted $C_1$ to $C_{20}$ alkyl), $R^{38}$-substituted or unsubstituted heteroalkyl (e.g. substituted or unsubstituted 2 to 20 membered heteroalkyl), $R^{38}$-substituted or unsubstituted cycloalkyl (e.g. $C_3$ to $C_{14}$ cycloalkyl including fused ring structures), $R^{38}$-substituted or unsubstituted heterocycloalkyl (e.g. 3 to 14 membered heterocycloalkyl including fused ring structures), $R^{38}$-substituted or unsubstituted aryl (e.g. a $C_6$ to $C_{14}$ aryl including fused ring structures), or $R^{38}$-substituted or unsubstituted heteroaryl (e.g. 5 to 14 membered heteroaryl including fused rings structures).

$R^{38}$ is independently oxo (where permitted according to valency rules), halogen, —CN, —$CF_3$, —$NR^{38A}$—C(O) $R^{38B}$, —$NR^{38A}$—C(O)—$OR^{38B}$, —C(O)$NR^{38A}R^{38B}$, —$NR^{38A}$S(O)$_2R^{38B}$, —S(O)$_2$N($R^{38A}$)($R^{38B}$), —$SR^{38A}$, —S(O)$R^{38B}$, —S(O)$_2R^{38B}$, —$NR^{38A}R^{38B}$, —$OR^{38A}$, —C(O) $R^{38B}$, $R^{39}$-substituted or unsubstituted alkyl (e.g. substituted or unsubstituted $C_1$ to $C_{20}$ alkyl), $R^{39}$-substituted or unsubstituted heteroalkyl (e.g. substituted or unsubstituted 2 to 20 membered heteroalkyl), $R^{39}$-substituted or unsubstituted cycloalkyl (e.g. $C_3$ to $C_{14}$ cycloalkyl including fused ring structures), $R^{39}$-substituted or unsubstituted heterocycloalkyl (e.g. 3 to 14 membered heterocycloalkyl including fused ring structures), $R^{39}$-substituted or unsubstituted aryl (e.g. a $C_6$ to $C_{14}$ aryl including fused ring structures), or $R^{39}$-substituted or unsubstituted heteroaryl (e.g. 5 to 14 membered heteroaryl including fused rings structures).

$R^{38A}$ and $R^{38B}$ are independently hydrogen, $R^{39}$-substituted or unsubstituted alkyl (e.g. substituted or unsubstituted $C_1$ to $C_{20}$ alkyl), $R^{39}$-substituted or unsubstituted heteroalkyl (e.g. substituted or unsubstituted 2 to 20 membered heteroalkyl), $R^{39}$-substituted or unsubstituted cycloalkyl (e.g. $C_3$ to $C_{14}$ cycloalkyl including fused ring structures), $R^{39}$-substituted or unsubstituted heterocycloalkyl (e.g. 3 to 14 membered heterocycloalkyl including fused ring structures), $R^{39}$-substituted or unsubstituted aryl (e.g. a $C_6$ to $C_{14}$ aryl including fused ring structures), or $R^{39}$-substituted or unsubstituted heteroaryl (e.g. 5 to 14 membered heteroaryl including fused rings structures).

$R^{39}$ is independently oxo (where permitted according to valency rules), halogen, —CN, —$CF_3$, —$NR^{39A}$—C(O) $R^{39B}$, —$NR^{39A}$—C(O)—$OR^{39B}$, —C(O)$NR^{39A}R^{39B}$, —$NR^{39A}$S(O)$R^{39B}$, —S(O)$_2$N($R^{39A}$)($R^{39B}$), —$SR^{39A}$, —S(O)$R^{39B}$, —S(O)$_2R^{39B}$, —$NR^{39A}R^{39B}$, —$OR^{39A}$, —C(O) $R^{39B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{39A}$ and $R^{39B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^5$ is hydrogen, halogen, —CN, —$CF_3$, —OH, —$NH_2$ $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^5$ is methoxy, ethoxy, propoxy, Cl, F or $CF_3$. In some embodiments, $R^5$ is methoxy, ethoxy, or propoxy. In some embodiments, $R^5$ is methoxy.

In some embodiments, $R^8$ is hydrogen, halogen, —CN, —$CF_3$, —OH, —$NH_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —$CF_3$, methoxy, ethoxy, propoxy. In some embodiments, $R^8$ is hydrogen, —F, methyl or methoxy. In some embodiments, $R^8$ is hydrogen.

In some embodiments, the compound has the formula:

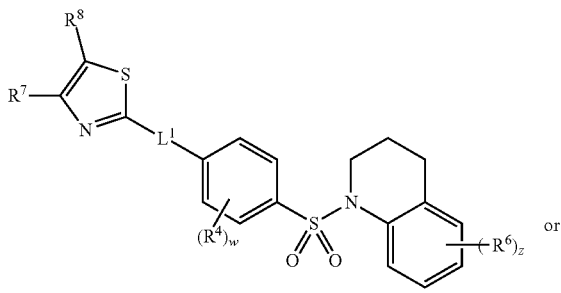

(VIA)

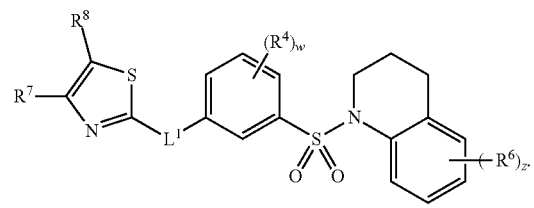

(VIB)

In Formulae (VIA) and (VIB), $R^4$, $R^6$, $R^7$, $R^8$, $L^1$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^8$ is hydrogen, halogen, —CN, —$CF_3$, —OH, —$NH_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —$CF_3$, methoxy, ethoxy, propoxy. In some embodiments, $R^8$ is hydrogen, —F, methyl or methoxy. In some embodiments, $R^8$ is hydrogen.

In some embodiments, the compound has the formula:

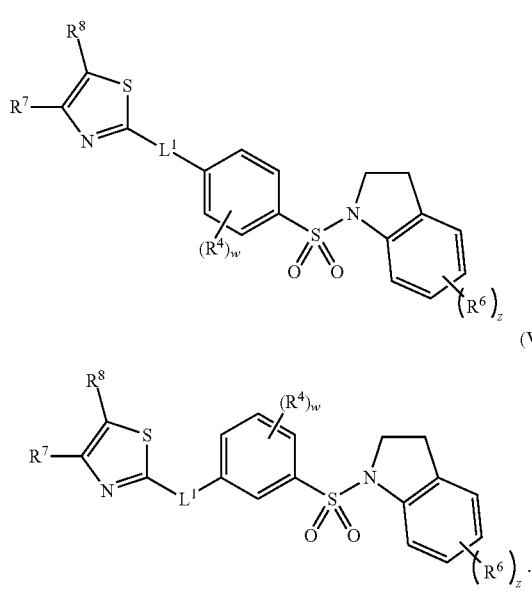

(VIIA)

or (VIIB)

In Formulae (VIIA) and (VIIB), $R^4$, $R^6$, $R^7$, $R^8$, $L^1$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety. In some embodiments, $R^8$ is hydrogen, halogen, —CN, —$CF_3$, —OH, —$NH_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —$CF_3$, methoxy, ethoxy, propoxy. In some embodiments, $R^8$ is hydrogen, —F, methyl or methoxy. In some embodiments, $R^8$ is hydrogen.

In some embodiments, the compound has the formula:

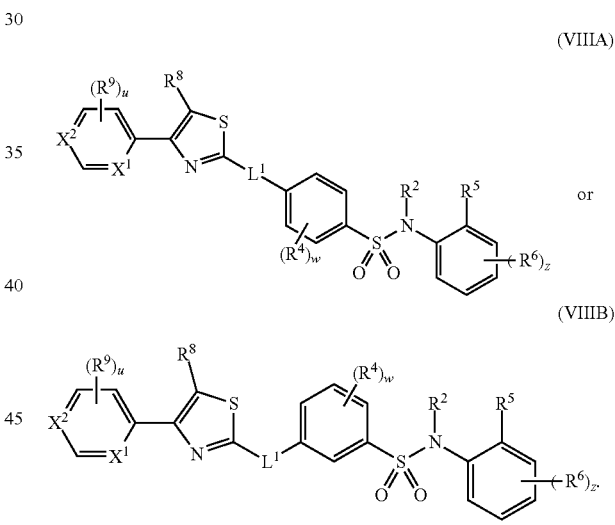

(VIIIA)

or (VIIIB)

In Formulae (VIIIA) and (VIIIB), $R^2$, $R^4$, $R^5$, $R^6$, $R^8$, $L^1$, w and z are as defined above. In some embodiments, w is 0. In other embodiments, w is 1. In some embodiments, $L^1$ is —NH—C(O)— as illustrated in Formula (IC1) or (IC2). $X^1$ and $X^2$ are independently carbon or nitrogen. A person having ordinary skill in the art will immediately recognize that when carbon, $X^1$ and/or $X^2$ may optionally be attached to substituent $R^9$.

As set forth above in Formulae (IIA), (IIB), (VA) and (VB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (VIIIA) and (VIIIB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. $C_1$ to $C_{10}$ alkyl). In some embodiments, $R^2$ is hydrogen. In some embodiments, $R^2$ is unsubstituted $C_1$ to $C_5$ alkyl. In some embodiments, $R^2$ is methyl. In some embodiments, $R^2$ is methyl, ethyl, propyl, tertiary butyl, methylene cyclopropyl (—CH$_2$-cyclopropyl), methoxy, ethoxy, propoxy, butoxy or —CF$_3$.

$R^4$ may be halogen, —CN, —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is —CF$_3$, —OH, —NH$_2$, unsubstituted $C_1$ to $C_5$ alkyl, or unsubstituted 2 to 6 membered heteroalkyl. In some embodiments, $R^4$ is methyl, methoxy, —CF$_3$, or —OH. In some embodiments, $R^6$ is halogen, —CN, —CF$_3$, —OH, —NH$_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^6$ is methoxy, ethoxy, propoxy, Cl, F or CF$_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^8$ is hydrogen, halogen, —CN, —CF$_3$, —OH, —NH$_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —CF$_3$, methoxy, ethoxy, propoxy. In some embodiments, $R^8$ is hydrogen, —F, methyl or methoxy. In some embodiments, $R^8$ is hydrogen.

$R^9$ is independently halogen, —CN, —CF$_3$, —NR$^{9A}$—C(O)R$^{9B}$, —NR$^{9A}$—C(O)—OR$^{9B}$, —C(O)NR$^{9A}$R$^{9B}$, —NR$^{9A}$S(O)$_2$R$^{9B}$, —S(O)$_2$N(R$^{9A}$)(R$^{9B}$), —SR$^{9A}$, —S(O)R$^{9B}$, —S(O)$_2$R$^{9B}$, —NR$^{9A}$R$^{9B}$, —OR$^{9A}$, —C(O)R$^{9B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{9A}$ and $R^{9B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^9$, $R^{9A}$ and $R^{9B}$ are substituted substituents, $R^9$, $R^{9A}$ and $R^9$ are independently substituted with $R^{40}$. For example, in some embodiments, $R^9$, $R^{9A}$ and $R^9$ are independently $R^{40}$-substituted or unsubstituted alkyl (e.g. substituted or unsubstituted $C_1$ to $C_{20}$ alkyl), $R^{40}$-substituted or unsubstituted heteroalkyl (e.g. substituted or unsubstituted 2 to 20 membered heteroalkyl), $R^{40}$-substituted or unsubstituted cycloalkyl (e.g. $C_3$ to $C_{14}$ cycloalkyl including fused ring structures), $R^{40}$-substituted or unsubstituted heterocycloalkyl (e.g. 3 to 14 membered heterocycloalkyl including fused ring structures), $R^{40}$-substituted or unsubstituted aryl (e.g. a $C_6$ to $C_{14}$ aryl including fused ring structures), or $R^{40}$-substituted or unsubstituted heteroaryl (e.g. 5 to 14 membered heteroaryl including fused rings structures).

$R^{40}$ is independently oxo (where permitted according to valency rules), halogen, —CN, —CF$_3$, —NR$^{40A}$—C(O)R$^{40B}$, —NR$^{40A}$—C(O)—OR$^{40B}$, —S(O)$_2$N(R$^{40A}$)(R$^{40B}$), —SR$^{40A}$, —S(O)R$^{40B}$, —S(O)$_2$R$^{40B}$, —NR$^{40A}$R$^{40B}$, —OR$^{40A}$, —C(O)R$^{40B}$, $R^{41}$-substituted or unsubstituted alkyl (e.g. substituted or unsubstituted $C_1$ to $C_{20}$ alkyl), $R^{41}$-substituted or unsubstituted heteroalkyl (e.g. substituted or unsubstituted 2 to 20 membered heteroalkyl), $R^{41}$-substituted or unsubstituted cycloalkyl (e.g. $C_3$ to $C_{14}$ cycloalkyl including fused ring structures), $R^{41}$-substituted or unsubstituted heterocycloalkyl (e.g. 3 to 14 membered heterocycloalkyl including fused ring structures), $R^{41}$-substituted or unsubstituted aryl (e.g. a $C_6$ to $C_{14}$ aryl including fused ring structures), or $R^{41}$-substituted or unsubstituted heteroaryl (e.g. 5 to 14 membered heteroaryl including fused rings structures).

$R^{40A}$ and $R^{40B}$ are independently hydrogen, $R^{41}$-substituted or unsubstituted alkyl (e.g. substituted or unsubstituted $C_1$ to $C_{20}$ alkyl), $R^{41}$-substituted or unsubstituted heteroalkyl (e.g. substituted or unsubstituted 2 to 20 membered heteroalkyl), $R^{41}$-substituted or unsubstituted cycloalkyl (e.g. $C_3$ to $C_{14}$ cycloalkyl including fused ring structures), $R^{41}$-substituted or unsubstituted heterocycloalkyl (e.g. 3 to 14 membered heterocycloalkyl including fused ring structures), $R^{41}$-substituted or unsubstituted aryl (e.g. a $C_6$ to $C_{14}$ aryl including fused ring structures), or $R^{41}$-substituted or unsubstituted heteroaryl (e.g. 5 to 14 membered heteroaryl including fused rings structures).

$R^{41}$ is independently oxo (where permitted according to valency rules), halogen, —CN, —CF$_3$, —NR$^{41A}$—C(O)R$^{41B}$, —NR$^{41A}$—C(O)—OR$^{41B}$, —C(O)NR$^{41A}$R$^{41B}$, —NR$^{41A}$S(O)$_2$R$^{41B}$, —S(O)$_2$N(R$^{41A}$)(R$^{41B}$), —SR$^{41A}$, —S(O)R$^{41B}$, —S(O)$_2$R$^{41B}$, —NR$^{41A}$R$^{41B}$, —OR$^{41A}$, —C(O)R$^{41B}$, $R^{42}$-substituted or unsubstituted alkyl (e.g. substituted or unsubstituted $C_1$ to $C_{20}$ alkyl), $R^{42}$-substituted or unsubstituted heteroalkyl (e.g. substituted or unsubstituted 2 to 20 membered heteroalkyl), $R^{42}$-substituted or unsubstituted cycloalkyl (e.g. $C_3$ to $C_{14}$ cycloalkyl including fused ring structures), $R^{42}$-substituted or unsubstituted heterocycloalkyl (e.g. 3 to 14 membered heterocycloalkyl including fused ring structures), $R^{42}$-substituted or unsubstituted aryl (e.g. a $C_6$ to $C_{14}$ aryl including fused ring structures), or $R^{42}$-substituted or unsubstituted heteroaryl (e.g. 5 to 14 membered heteroaryl including fused rings structures).

$R^{41A}$ and $R^{41B}$ are independently hydrogen, $R^{42}$-substituted or unsubstituted alkyl (e.g. substituted or unsubstituted $C_1$ to $C_{20}$ alkyl), $R^{42}$-substituted or unsubstituted heteroalkyl (e.g. substituted or unsubstituted 2 to 20 membered heteroalkyl), $R^{42}$-substituted or unsubstituted cycloalkyl (e.g. $C_3$ to $C_{14}$ cycloalkyl including fused ring structures), $R^{42}$-substituted or unsubstituted heterocycloalkyl (e.g. 3 to 14 membered heterocycloalkyl including fused ring structures), $R^{42}$-substituted or unsubstituted aryl (e.g. a $C_6$ to $C_{14}$ aryl including fused ring structures), or $R^{42}$-substituted or unsubstituted heteroaryl (e.g. 5 to 14 membered heteroaryl including fused rings structures).

$R^{42}$ is independently oxo (where permitted according to valency rules), halogen, —CN, —$CF_3$, —$NR^{42A}$—C(O) $R^{42B}$, —$NR^{42A}$—C(O)—$OR^{42B}$, —C(O)$NR^{42A}R^{42B}$, —$NR^{42A}S(O)_2R^{42B}$, —$S(O)_2N(R^{42A})(R^{42B})$, —$SR^{42A}$, —$S(O)R^{42B}$, —$S(O)_2R^{42B}$, —$NR^{42A}R^{42B}$, —$OR^{42A}$, —C(O)$R^{42B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{42A}$ and $R^{42B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^5$ is hydrogen, halogen, —CN, —$CF_3$, —OH, —$NH_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^5$ is methoxy, ethoxy, propoxy, Cl, F or $CF_3$. In some embodiments, $R^5$ is methoxy, ethoxy, or propoxy. In some embodiments, $R^5$ is methoxy.

In some embodiments, $R^9$ is halogen, —CN, —$CF_3$, —OH, —$NH_2$, $R^{40}$-substituted or unsubstituted $C_1$ to $C_5$ alkyl, or $R^{40}$-substituted or unsubstituted 2 to 6 membered heteroalkyl, wherein $R^{40}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^9$ is methyl, ethyl, propyl, —Cl, —F, —$CF_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

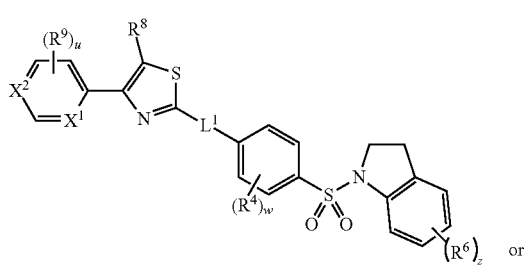

(IXA)

or

-continued

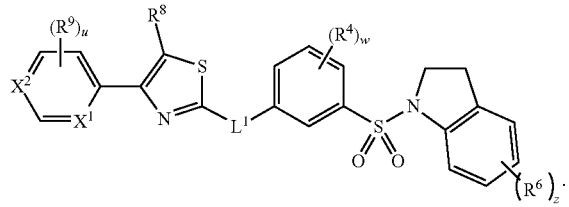

(IXB)

In Formulae (IXA) and (IXB), $R^4$, $R^6$, $R^8$, $R^9$, $L^1$, u, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^8$ is hydrogen, halogen, —CN, —$CF_3$, —OH, —$NH_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —$CF_3$, methoxy, ethoxy, propoxy. In some embodiments, $R^8$ is hydrogen, —F, methyl or methoxy. In some embodiments, $R^8$ is hydrogen.

In some embodiments, $R^9$ is halogen, —CN, —$CF_3$, —OH, —$NH_2$, $R^{40}$-substituted or unsubstituted $C_1$ to $C_5$ alkyl, or $R^{40}$-substituted or unsubstituted 2 to 6 membered heteroalkyl, wherein $R^{40}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^9$ is methyl, ethyl, propyl, —Cl, —F, —$CF_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

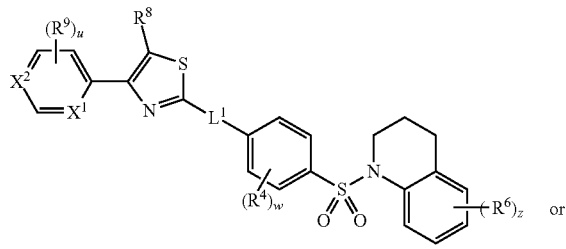

(XA)

or

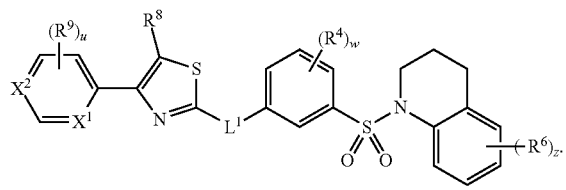

(XB)

In Formulae (XA) and (XB), $R^4$, $R^6$, $R^8$, $R^9$, $L^1$, u, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is —CF$_3$, —OH, —NH$_2$, unsubstituted $C_1$ to $C_5$ alkyl, or unsubstituted 2 to 6 membered heteroalkyl. In some embodiments, $R^4$ is methyl, methoxy, —CF$_3$, or —OH. In some embodiments, $R^6$ is halogen, —CN, —CF$_3$, —OH, —NH$_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^6$ is methoxy, ethoxy, propoxy, Cl, F or CF$_3$. In some embodiments, $R^6$ is methoxy, ethoxy, or propoxy.

In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^8$ is hydrogen, halogen, —CN, —CF$_3$, —OH, —NH$_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —CF$_3$, methoxy, ethoxy, propoxy. In some embodiments, $R^8$ is hydrogen, —F, methyl or methoxy. In some embodiments, $R^8$ is hydrogen.

In some embodiments, $R^9$ is halogen, —CN, —CF$_3$, —OH, —NH$_2$, $R^{40}$-substituted or unsubstituted $C_1$ to $C_5$ alkyl, or $R^{40}$-substituted or unsubstituted 2 to 6 membered heteroalkyl, wherein $R^{40}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^9$ is methyl, ethyl, propyl, —Cl, —F, —CF$_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

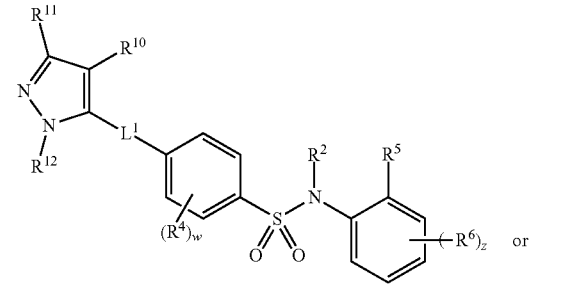

(XIA)

or

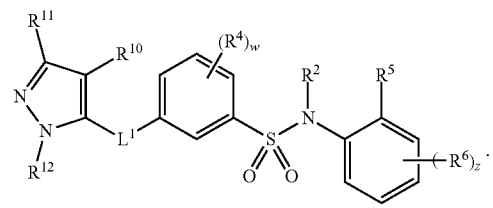

(XIB)

In Formulae (XIA) and (XIB), $R^2$, $R^4$, $R^5$, $R^6$, $L^1$, z and w are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is —CF$_3$, —OH, —NH$_2$, unsubstituted $C_1$ to $C_5$ alkyl, or unsubstituted 2 to 6 membered heteroalkyl. In some embodiments, $R^4$ is methyl, methoxy, —CF$_3$, or —OH. In some embodiments, $R^6$ is halogen, —CN, —CF$_3$, —OH, —NH$_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^6$ is methoxy, ethoxy, propoxy, Cl, F or CF$_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

As set forth above in Formulae (IIA), (IIB), (VA), (VB), (VIIIA) and (VIIIB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (XIA) and (XIB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. $C_1$ to $C_{10}$ alkyl). In some embodiments, $R^2$ is hydrogen. In some embodiments, $R^2$ is unsubstituted $C_1$ to $C_5$ alkyl. In some embodiments, $R^2$ is methyl. In some embodiments, $R^2$ is methyl, ethyl, propyl, tertiary butyl, methylene cyclopropyl (—$CH_2$-cyclopropyl), methoxy, ethoxy, propoxy, butoxy or —$CF_3$.

$R^{10}$ is hydrogen, halogen, —CN, —$CF_3$, —$NR^{10A}$—C(O)$R^{10B}$, —$NR^{10A}$—C(O)—$OR^{10B}$, —C(O)$NR^{10A}R^{10B}$, —$NR^{10A}S(O)_2R^{10B}$, —$S(O)_2N(R^{10A})(R^{10B})$, —$SR^{10A}$, —S(O)$R^{10B}$, —$S(O)_2R^{10B}$, —$NR^{10A}R^{10B}$, —$OR^{10A}$, —C(O)$R^{10B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{10A}$ and $R^{10B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{10A}$ and $R^{10B}$ are substituted substituents, $R^{10}$, $R^{10A}$ and $R^{10}$ are independently substituted with $R^{43}$. For example, in some embodiments, $R^{10}$, $R^{10A}$ and $R^{10B}$ are independently $R^{43}$-substituted or unsubstituted alkyl (e.g. substituted or unsubstituted $C_1$ to $C_{20}$ alkyl), $R^{43}$-substituted or unsubstituted heteroalkyl (e.g. substituted or unsubstituted 2 to 20 membered heteroalkyl), $R^{43}$-substituted or unsubstituted cycloalkyl (e.g. $C_3$ to $C_{14}$ cycloalkyl including fused ring structures), $R^{43}$-substituted or unsubstituted heterocycloalkyl (e.g. 3 to 14 membered heterocycloalkyl including fused ring structures), $R^{43}$-substituted or unsubstituted aryl (e.g. a $C_6$ to $C_{14}$ aryl including fused ring structures), or $R^{43}$-substituted or unsubstituted heteroaryl (e.g. 5 to 14 membered heteroaryl including fused rings structures).

$R^{43}$ is independently oxo (where permitted according to valency rules), halogen, —CN, —$CF_3$, —$NR^{43A}$—C(O)$R^{43B}$, —$NR^{43A}$—C(O)—$OR^{43B}$, —C(O)$NR^{43A}R^{43B}$, —$NR^{43A}S(O)_2R^{43B}$, —$S(O)_2N(R^{43A})(R^{43B})$, —$SR^{43A}$, —S(O)$R^{43B}$, —$S(O)_2R^{43B}$, —$NR^{43A}R^{43B}$, —$OR^{43A}$, —C(O)$R^{43B}$, $R^{44}$-substituted or unsubstituted alkyl (e.g. substituted or unsubstituted $C_1$ to $C_{20}$ alkyl), $R^{44}$-substituted or unsubstituted heteroalkyl (e.g. substituted or unsubstituted 2 to 20 membered heteroalkyl), $R^{44}$-substituted or unsubstituted cycloalkyl (e.g. $C_3$ to $C_{14}$ cycloalkyl including fused ring structures), $R^{44}$-substituted or unsubstituted heterocycloalkyl (e.g. 3 to 14 membered heterocycloalkyl including fused ring structures), $R^{44}$-substituted or unsubstituted aryl (e.g. a $C_6$ to $C_{14}$ aryl including fused ring structures), or $R^{44}$-substituted or unsubstituted heteroaryl (e.g. 5 to 14 membered heteroaryl including fused rings structures).

$R^{43A}$ and $R^{43B}$ are independently hydrogen, $R^{44}$-substituted or unsubstituted alkyl (e.g. substituted or unsubstituted $C_1$ to $C_{20}$ alkyl), $R^{44}$-substituted or unsubstituted heteroalkyl (e.g. substituted or unsubstituted 2 to 20 membered heteroalkyl), $R^{44}$-substituted or unsubstituted cycloalkyl (e.g. $C_3$ to $C_{14}$ cycloalkyl including fused ring structures), $R^{44}$-substituted or unsubstituted heterocycloalkyl (e.g. 3 to 14 membered heterocycloalkyl including fused ring structures), $R^{44}$-substituted or unsubstituted aryl (e.g. a $C_6$ to $C_{14}$ aryl including fused ring structures), or $R^{44}$-substituted or unsubstituted heteroaryl (e.g. 5 to 14 membered heteroaryl including fused rings structures).

$R^{44}$ is independently oxo (where permitted according to valency rules), halogen, —CN, —$CF_3$, —$NR^{44A}$—C(O)$R^{44B}$, —$NR^{44A}$—C(O)—$OR^{44B}$, —C(O)$NR^{44A}R^{44B}$, —$NR^{44A}S(O)_2R^{44B}$, —$S(O)_2N(R^{44A})(R^{44B})$, —$SR^{44A}$, —S(O)$R^{44B}$, —$S(O)_2R^{44B}$, —$NR^{44A}R^{44B}$, —$OR^{44A}$, —C(O)$R^{44B}$, $R^{45}$-substituted or unsubstituted alkyl (e.g. substituted or unsubstituted $C_1$ to $C_{20}$ alkyl), $R^{45}$-substituted or unsubstituted heteroalkyl (e.g. substituted or unsubstituted 2 to 20 membered heteroalkyl), $R^{45}$-substituted or unsubstituted cycloalkyl (e.g. $C_3$ to $C_{14}$ cycloalkyl including fused ring structures), $R^{45}$-substituted or unsubstituted heterocycloalkyl (e.g. 3 to 14 membered heterocycloalkyl including fused ring structures), $R^{45}$-substituted or unsubstituted aryl (e.g. a $C_6$ to $C_{14}$ aryl including fused ring structures), or $R^{45}$-substituted or unsubstituted heteroaryl (e.g. 5 to 14 membered heteroaryl including fused rings structures).

$R^{44A}$ and $R^{44B}$ are independently hydrogen, $R^{45}$-substituted or unsubstituted alkyl (e.g. substituted or unsubstituted $C_1$ to $C_{20}$ alkyl), $R^{45}$-substituted or unsubstituted heteroalkyl (e.g. substituted or unsubstituted 2 to 20 membered heteroalkyl), $R^{45}$-substituted or unsubstituted cycloalkyl (e.g. $C_3$ to $C_{14}$ cycloalkyl including fused ring structures), $R^{45}$-substituted or unsubstituted heterocycloalkyl (e.g. 3 to 14 membered heterocycloalkyl including fused ring structures), $R^{45}$-substituted or unsubstituted aryl (e.g. a $C_6$ to $C_{14}$ aryl including fused ring structures), or $R^{45}$-substituted or unsubstituted heteroaryl (e.g. 5 to 14 membered heteroaryl including fused rings structures).

$R^{45}$ is independently oxo (where permitted according to valency rules), halogen, —CN, —$CF_3$, —$NR^{45A}$—C(O)$R^{45B}$, —$NR^{45A}$—C(O)—$OR^{45B}$, —C(O) $NR^{45A}R^{45B}$, —$NR^{45A}S(O)_2R^{45B}$, —$S(O)_2N(R^{45A})(R^{45B})$, —$SR^{45A}$, —S(O)$R^{45B}$, —$S(O)_2R^{45B}$, —$NR^{45A}R^{45B}$, —$OR^{45A}$, —C(O)$R^{45B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{45A}$ and $R^{45B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^5$ is hydrogen, halogen, —CN, —CF$_3$, —OH, —NH$_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^5$ is methoxy, ethoxy, propoxy, Cl, F or CF$_3$. In some embodiments, $R^5$ is methoxy, ethoxy, or propoxy. In some embodiments, $R^5$ is methoxy.

In some embodiments, $R^{10}$ is hydrogen, halogen, —CN, —CF$_3$, —OH, —NH$_2$, $R^{43}$-substituted or unsubstituted $C_1$ to $C_5$ alkyl, or $R^{43}$-substituted or unsubstituted 2 to 6 membered heteroalkyl, wherein $R^{43}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^{10}$ is hydrogen, methyl, ethyl, propyl, —Cl, —F, —CF$_3$, methoxy, ethoxy, propoxy. In some embodiments, $R^{10}$ is hydrogen, —F, methyl or methoxy. In some embodiments, $R^{10}$ is hydrogen.

$R^{11}$ is hydrogen, halogen, —CN, —CF$_3$, —NR$^{11A}$—C(O)R$^{11B}$, —NR$^{11A}$—C(O)R$^{11B}$, —C(O)NR$^{11A}$R$^{11B}$, —NR$^{11A}$S(O)$_2$R$^{11B}$, —S(O)$_2$N(R$^{11A}$)(R$^{11B}$), —SR$^{11A}$, —S(O)R$^{11B}$, —S(O)$_2$R$^{11B}$, —NR$^{11A}$R$^{11B}$, —OR$^{11A}$, —C(O)R$^{11B}$, substituted or unsubstituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{11A}$ and $R^{11B}$ independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{11}$, $R^{11A}$ and $R^{11B}$ are substituted substituents, $R^{11}$, $R^{11A}$ and $R^{11B}$ are independently substituted with $R^{46}$. For example, in some embodiments, $R^{11}$, $R^{11A}$ and $R^{11B}$ are independently $R^{46}$-substituted or unsubstituted alkyl (e.g. substituted or unsubstituted $C_1$ to $C_{20}$ alkyl), $R^{46}$-substituted or unsubstituted heteroalkyl (e.g. substituted or unsubstituted 2 to 20 membered heteroalkyl), $R^{46}$-substituted or unsubstituted cycloalkyl (e.g. $C_3$ to $C_{14}$ cycloalkyl including fused ring structures), $R^{46}$-substituted or unsubstituted heterocycloalkyl (e.g. 3 to 14 membered heterocycloalkyl including fused ring structures), $R^{46}$-substituted or unsubstituted aryl (e.g. a $C_6$ to $C_{14}$ aryl including fused ring structures), or $R^{46}$-substituted or unsubstituted heteroaryl (e.g. 5 to 14 membered heteroaryl including fused rings structures).

$R^{46}$ is independently oxo (where permitted according to valency rules), halogen, —CN, —CF$_3$, —NR$^{46A}$—C(O)R$^{46B}$, —NR$^{46A}$—C(O)—OR$^{46B}$, —C(O)NR$^{46A}$R$^{46B}$, —NR$^{46A}$S(O)$_2$R$^{46B}$, —S(O)$_2$N(R$^{46A}$)(R$^{46B}$), —SR$^{46A}$, —S(O)R$^{46B}$, —S(O)$_2$R$^{46B}$, —NR$^{46A}$R$^{46B}$, —OR$^{46A}$, —C(O)R$^{46B}$, $R^{47}$-substituted or unsubstituted alkyl (e.g. substituted or unsubstituted $C_1$ to $C_{20}$ alkyl), $R^{47}$-substituted or unsubstituted heteroalkyl (e.g. substituted or unsubstituted 2 to 20 membered heteroalkyl), $R^{47}$-substituted or unsubstituted cycloalkyl (e.g. $C_3$ to $C_{14}$ cycloalkyl including fused ring structures), $R^{47}$-substituted or unsubstituted heterocycloalkyl (e.g. 3 to 14 membered heterocycloalkyl including fused ring structures), $R^{47}$-substituted or unsubstituted aryl (e.g. a $C_6$ to $C_{14}$ aryl including fused ring structures), or $R^{47}$-substituted or unsubstituted heteroaryl (e.g. 5 to 14 membered heteroaryl including fused rings structures).

$R^{46A}$ and $R^{46B}$ are independently hydrogen, $R^{47}$-substituted or unsubstituted alkyl (e.g. substituted or unsubstituted $C_1$ to $C_{20}$ alkyl), $R^{47}$-substituted or unsubstituted heteroalkyl (e.g. substituted or unsubstituted 2 to 20 membered heteroalkyl), $R^{47}$-substituted or unsubstituted cycloalkyl (e.g. $C_3$ to $C_{14}$ cycloalkyl including fused ring structures), $R^{47}$-substituted or unsubstituted heterocycloalkyl (e.g. 3 to 14 membered heterocycloalkyl including fused ring structures), $R^{47}$-substituted or unsubstituted aryl (e.g. a $C_6$ to $C_{14}$ aryl including fused ring structures), or $R^{47}$-substituted or unsubstituted heteroaryl (e.g. 5 to 14 membered heteroaryl including fused rings structures).

$R^{47}$ is independently oxo (where permitted according to valency rules), halogen, —CN, —CF$_3$, —NR$^{47A}$—C(O)R$^{47B}$, —NR$^{47A}$—C(O)—OR$^{47B}$, —C(O)NR$^{47A}$R$^{47B}$, —NR$^{47A}$S(O)$_2$R$^{47B}$, —S(O)$_2$N(R$^{47A}$)(R$^{47B}$), —SR$^{47A}$, —S(O)R$^{47B}$, —S(O)$_2$R$^{47B}$, —NR$^{47A}$R$^{47B}$, —OR$^{47A}$, —C(O)R$^{47B}$, $R^{48}$-substituted or unsubstituted alkyl (e.g. substituted or unsubstituted $C_1$ to $C_{20}$ alkyl), $R^{48}$-substituted or unsubstituted heteroalkyl (e.g. substituted or unsubstituted 2 to 20 membered heteroalkyl), $R^{48}$-substituted or unsubstituted cycloalkyl (e.g. $C_3$ to $C_{14}$ cycloalkyl including fused ring structures), $R^{48}$-substituted or unsubstituted heterocycloalkyl (e.g. 3 to 14 membered heterocycloalkyl including fused ring structures), $R^{48}$-substituted or unsubstituted aryl (e.g. a $C_6$ to $C_{14}$ aryl including fused ring structures), or $R^{48}$-substituted or unsubstituted heteroaryl (e.g. 5 to 14 membered heteroaryl including fused rings structures).

$R^{47A}$ and $R^{47B}$ are independently hydrogen, $R^{48}$-substituted or unsubstituted alkyl (e.g. substituted or unsubstituted $C_1$ to $C_{20}$ alkyl), $R^{48}$-substituted or unsubstituted heteroalkyl (e.g. substituted or unsubstituted 2 to 20 membered heteroalkyl), $R^{48}$-substituted or unsubstituted cycloalkyl (e.g. $C_3$ to $C_{14}$ cycloalkyl including fused ring structures), $R^{48}$-substituted or unsubstituted heterocycloalkyl (e.g. 3 to 14 membered heterocycloalkyl including fused ring structures), $R^{48}$-substituted or unsubstituted aryl (e.g. a $C_6$ to $C_{14}$ aryl including fused ring structures), or $R^{48}$-substituted or unsubstituted heteroaryl (e.g. 5 to 14 membered heteroaryl including fused rings structures).

$R^{48}$ is independently oxo (where permitted according to valency rules), halogen, —CN, —CF$_3$, —NR$^{48A}$—C(O)R$^{48B}$, —NR$^{48A}$—C(O)—OR$^{48B}$, —C(O)NR$^{48A}$R$^{48B}$, —NR$^{48A}$S(O)$_2$R$^{48B}$, —S(O)$_2$N(R$^{48A}$)(R$^{48B}$), —SR$^{48A}$, —S(O)R$^{48B}$, —S(O)$_2$R$^{48B}$, —NR$^{48A}$R$^{48B}$, —OR$^{48A}$, —C(O)R$^{48B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{48A}$ and $R^{48B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{11}$ is hydrogen, halogen, —CN, —$CF_3$, —OH, —$NH_2$, $R^{46}$-substituted or unsubstituted $C_1$ to $C_5$ alkyl, or $R^{46}$-substituted or unsubstituted 2 to 6 membered heteroalkyl, wherein $R^{46}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{11}$ is hydrogen, methyl, ethyl, propyl, —Cl, —F, —$CF_3$, methoxy, ethoxy, propoxy. In some embodiments, $R^{11}$ is hydrogen, —F, methyl or methoxy. In some embodiments, $R^{11}$ is hydrogen.

$R^{12}$ is hydrogen, halogen, —CN, —$CF_3$, —$NR^{12A}$—C(O)$R^{12B}$, —$NR^{12A}$—C(O)—$OR^{12B}$, —C(O)$NR^{12A}R^{12B}$, —$NR^{12A}S(O)_2R^{12B}$, —$S(O)_2N(R^{12A})(R^{12B})$, —$SR^{12A}$, —$S(O)R^{12B}$, —$S(O)_2R^{12B}$, —$NR^{12A}R^{12B}$, —$OR^{12A}$, —C(O)$R^{12B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{12A}$ and $R^{12B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{12}$, $R^{12A}$ and $R^{12B}$ are substituted substituents, $R^{12}$, $R^{12A}$ and $R^{12}$ are independently substituted with $R^{49}$. For example, in some embodiments, $R^{12}$, $R^{12A}$, and $R^{12B}$ are independently $R^{49}$-substituted or unsubstituted alkyl (e.g. substituted or unsubstituted $C_1$ to $C_{20}$ alkyl), $R^{49}$-substituted or unsubstituted heteroalkyl (e.g. substituted or unsubstituted 2 to 20 membered heteroalkyl), $R^{49}$-substituted or unsubstituted cycloalkyl (e.g. $C_3$ to $C_{14}$ cycloalkyl including fused ring structures), $R^{49}$-substituted or unsubstituted heterocycloalkyl (e.g. 3 to 14 membered heterocycloalkyl including fused ring structures), $R^{49}$-substituted or unsubstituted aryl (e.g. a $C_6$ to $C_{14}$ aryl including fused ring structures), or $R^{49}$-substituted or unsubstituted heteroaryl (e.g. 5 to 14 membered heteroaryl including fused rings structures).

$R^{49}$ is independently oxo (where permitted according to valency rules), halogen, —CN, —$CF_3$, —$NR^{49A}$—C(O)$R^{49B}$, —$NR^{49A}$—C(O)—$OR^{49B}$, —C(O)$NR^{49A}R^{49B}$, —$NR^{49A}S(O)_2R^{49B}$, —$S(O)_2N(R^{49A})(R^{49B})$, —$SR^{49A}$, —$S(O)R^{49B}$, —$S(O)_2R^{49B}$, —$NR^{49A}R^{49B}$, —$OR^{49A}$, —C(O)$R^{49B}$, $R^{50}$-substituted or unsubstituted alkyl (e.g. substituted or unsubstituted $C_1$ to $C_{20}$ alkyl), $R^{50}$-substituted or unsubstituted heteroalkyl (e.g. substituted or unsubstituted 2 to 20 membered heteroalkyl), $R^{50}$-substituted or unsubstituted cycloalkyl (e.g. $C_3$ to $C_{14}$ cycloalkyl including fused ring structures), $R^{50}$-substituted or unsubstituted heterocycloalkyl (e.g. 3 to 14 membered heterocycloalkyl including fused ring structures), $R^{50}$-substituted or unsubstituted aryl (e.g. a $C_6$ to $C_{14}$ aryl including fused ring structures), or $R^{50}$-substituted or unsubstituted heteroaryl (e.g. 5 to 14 membered heteroaryl including fused rings structures).

$R^{49A}$ and $R^{49B}$ are independently hydrogen, $R^{50}$-substituted or unsubstituted alkyl (e.g. substituted or unsubstituted $C_1$ to $C_{20}$ alkyl), $R^{50}$-substituted or unsubstituted heteroalkyl (e.g. substituted or unsubstituted 2 to 20 membered heteroalkyl), $R^{50}$-substituted or unsubstituted cycloalkyl (e.g. $C_3$ to $C_{14}$ cycloalkyl including fused ring structures), $R^{50}$-substituted or unsubstituted heterocycloalkyl (e.g. 3 to 14 membered heterocycloalkyl including fused ring structures), $R^{50}$-substituted or unsubstituted aryl (e.g. a $C_6$ to $C_{14}$ aryl including fused ring structures), or $R^{50}$-substituted or unsubstituted heteroaryl (e.g. 5 to 14 membered heteroaryl including fused rings structures).

$R^{50}$ is independently oxo (where permitted according to valency rules), halogen, —CN, —$CF_3$, —$NR^{50A}$—C(O)$R^{50B}$, —$NR^{50A}$—C(O)—$OR^{50B}$, —C(O)$NR^{50A}R^{50B}$, —$NR^{50A}S(O)_2R^{50B}$, —$S(O)_2N(R^{50A})(R^{50B})$, —$SR^{50A}$, —$S(O)R^{50B}$, —$S(O)_2R^{50B}$, —$NR^{50A}R^{50B}$, —$OR^{50A}$, —C(O)$R^{50B}$, $R^{51}$-substituted or unsubstituted alkyl (e.g. substituted or unsubstituted $C_1$ to $C_{20}$ alkyl), $R^{51}$-substituted or unsubstituted heteroalkyl (e.g. substituted or unsubstituted 2 to 20 membered heteroalkyl), $R^{51}$-substituted or unsubstituted cycloalkyl (e.g. $C_3$ to $C_{14}$ cycloalkyl including fused ring structures), $R^{51}$-substituted or unsubstituted heterocycloalkyl (e.g. 3 to 14 membered heterocycloalkyl including fused ring structures), $R^{51}$-substituted or unsubstituted aryl (e.g. a $C_6$ to $C_{14}$ aryl including fused ring structures), or $R^{51}$-substituted or unsubstituted heteroaryl (e.g. 5 to 14 membered heteroaryl including fused rings structures).

$R^{50A}$ and $R^{50B}$ are independently hydrogen, $R^{51}$-substituted or unsubstituted alkyl (e.g. substituted or unsubstituted $C_1$ to $C_{20}$ alkyl), $R^{51}$-substituted or unsubstituted heteroalkyl (e.g. substituted or unsubstituted 2 to 20 membered heteroalkyl), $R^{51}$-substituted or unsubstituted cycloalkyl (e.g. $C_3$ to $C_{14}$ cycloalkyl including fused ring structures), $R^{51}$-substituted or unsubstituted heterocycloalkyl (e.g. 3 to 14 membered heterocycloalkyl including fused ring structures), $R^{51}$-substituted or unsubstituted aryl (e.g. a $C_6$ to $C_{14}$ aryl including fused ring structures), or $R^{51}$-substituted or unsubstituted heteroaryl (e.g. 5 to 14 membered heteroaryl including fused rings structures).

$R^{51}$ is independently oxo (where permitted according to valency rules), halogen, —CN, —$CF_3$, —$NR^{51A}$—C(O)$R^{51B}$, —$NR^{51A}$—C(O)—$OR^{51B}$, —$NR^{51A}S(O)_2R^{51B}$, —$S(O)_2N(R^{51A})(R^{51B})$, —$SR^{51A}$, —$S(O)R^{51B}$, —$S(O)_2R^{51B}$, —$NR^{51A}R^{51B}$, —$OR^{51A}$, —C(O)$R^{51B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{51A}$ and $R^{51B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{12}$ is hydrogen, halogen, —CN, —$CF_3$, —OH, —$NH_2$, $R^{49}$-substituted or unsubstituted $C_1$ to $C_5$ alkyl, or $R^{49}$-substituted or unsubstituted 2 to 6 membered heteroalkyl, wherein $R^{49}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{12}$ is hydrogen, methyl, ethyl, propyl, —Cl, —F, —$CF_3$, methoxy, ethoxy, propoxy. In some embodiments, $R^{12}$ is hydrogen, —F, methyl or methoxy. In some embodiments, $R^{12}$ is hydrogen.

In some embodiment, the compound has the formula:

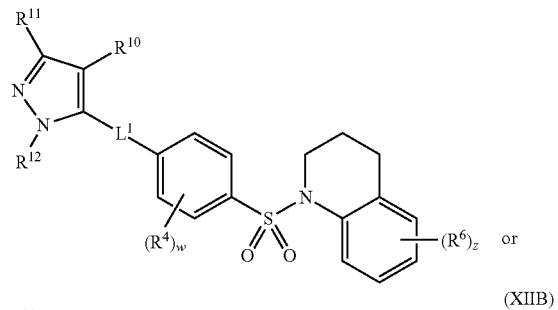

(XIIA)

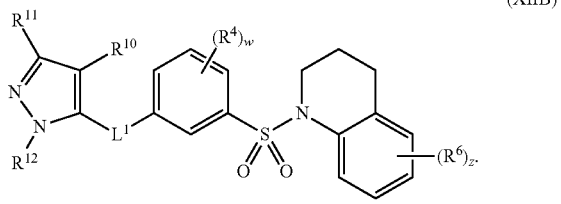

(XIIB)

In Formulae (XIIA) and (XIIB), $R^4$, $R^6$, $R^{10}$, $R^{11}$, $R^{12}$, $L^1$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_{25}$ unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_{25}$ unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^{10}$ is hydrogen, halogen, —CN, —$CF_3$, —OH, —$NH_2$, $R^{43}$-substituted or unsubstituted $C_1$ to $C_5$ alkyl, or $R^{43}$-substituted or unsubstituted 2 to 6 membered heteroalkyl, wherein $R^{43}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{10}$ is hydrogen, methyl, ethyl, propyl, —Cl, —F, —$CF_3$, methoxy, ethoxy, propoxy. In some embodiments, $R^{10}$ is hydrogen, —F, methyl or methoxy. In some embodiments, $R^{10}$ is hydrogen.

In some embodiments, $R^{11}$ is hydrogen, halogen, —CN, —$CF_3$, —OH, —$NH_2$, $R^{46}$-substituted or unsubstituted $C_1$ to $C_5$ alkyl, or $R^{46}$-substituted or unsubstituted 2 to 6 membered heteroalkyl, wherein $R^{46}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{11}$ is hydrogen, methyl, ethyl, propyl, —Cl, —F, —$CF_3$, methoxy, ethoxy, propoxy. In some embodiments, $R^{11}$ is hydrogen, —F, methyl or methoxy. In some embodiments, $R^{11}$ is hydrogen.

In some embodiments, $R^{12}$ is hydrogen, halogen, —CN, —$CF_3$, —OH, —$NH_2$, $R^{49}$-substituted or unsubstituted $C_1$ to $C_5$ alkyl, or $R^{49}$-substituted or unsubstituted 2 to 6 membered heteroalkyl, wherein $R^{49}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{12}$ is hydrogen, methyl, ethyl, propyl, —Cl, —F, —$CF_3$, methoxy, ethoxy, propoxy. In some embodiments, $R^{12}$ is hydrogen, —F, methyl or methoxy. In some embodiments, $R^{11}$ is hydrogen.

In some embodiment, the compound has the formula:

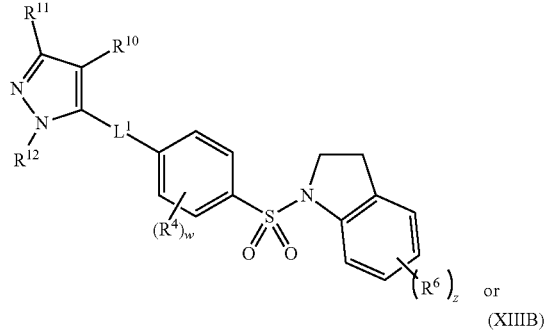

(XIIIA)

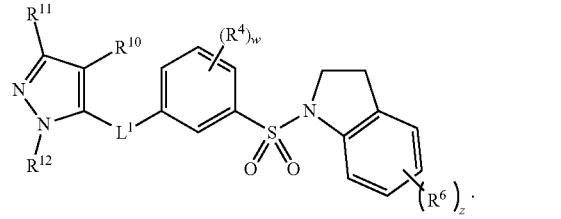

(XIIIB)

In Formulae (XIIIA) and (XIIIB), $R^4$, $R^6$, $R^{10}$, $R^{11}$, $R^{12}$, $L^1$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_{25}$ unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^{10}$ is hydrogen, halogen, —CN, —$CF_3$, —OH, —$NH_2$, $R^{43}$-substituted or unsubstituted $C_1$ to $C_5$ alkyl, or $R^{43}$-substituted or unsubstituted 2 to 6 membered heteroalkyl, wherein $R^{43}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{10}$ is hydrogen, methyl, ethyl, propyl, —Cl, —F, —$CF_3$, methoxy, ethoxy, propoxy. In some embodiments, $R^{10}$ is hydrogen, —F, methyl or methoxy. In some embodiments, $R^{10}$ is hydrogen.

In some embodiments, $R^{11}$ is hydrogen, halogen, —CN, —$CF_3$, —OH, —$NH_2$, $R^{46}$-substituted or unsubstituted $C_1$ to $C_5$ alkyl, or $R^{46}$-substituted or unsubstituted 2 to 6 membered heteroalkyl, wherein $R^{46}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{11}$ is hydrogen, methyl, ethyl, propyl, —Cl, —F, —$CF_3$, methoxy, ethoxy, propoxy. In some embodiments, $R^{11}$ is hydrogen, —F, methyl or methoxy. In some embodiments, $R^{11}$ is hydrogen.

In some embodiments, $R^{12}$ is hydrogen, halogen, —CN, —$CF_3$, —OH, —$NH_2$, $R^{49}$-substituted or unsubstituted $C_1$ to $C_5$ alkyl, or $R^{49}$-substituted or unsubstituted 2 to 6 membered heteroalkyl, wherein $R^{49}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{12}$ is hydrogen, methyl, ethyl, propyl, —Cl, —F, —$CF_3$, methoxy, ethoxy, propoxy. In some embodiments, $R^{12}$ is hydrogen, —F, methyl or methoxy. In some embodiments, $R^{11}$ is hydrogen.

In some embodiments, the compound has the formula:

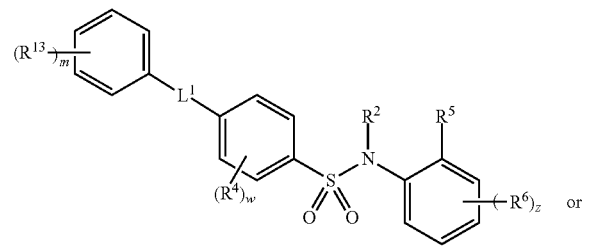

(XIVA)

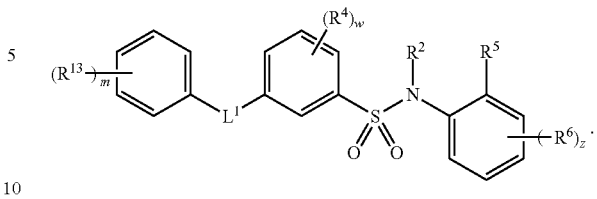

(XIVB)

In Formulae (XIVA) and (XIVB), $R^2$, $R^4$, $R^5$, $R^6$, $L^1$, w and z are as defined above. The symbol m is an integer from 0 to 5. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

As set forth above in Formulae (IIA), (IIB), (VA), (VB), (VIIIA), (VIIIB), (XIA) and (XIB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (XIVA) and (XIVB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. $C_1$ to $C_{10}$ alkyl). In some embodiments, $R^2$ is hydrogen. In some embodiments, $R^2$ is unsubstituted $C_1$ to $C_5$ alkyl. In some embodiments, $R^2$ is methyl. In some embodiments, $R^2$ is methyl, ethyl, propyl, tertiary butyl, methylene cyclopropyl (—$CH_2$-cyclopropyl), methoxy, ethoxy, propoxy, butoxy or —$CF_3$.

$R^{13}$ is independently halogen, —CN, —$CF_3$, —$NR^{13A}$—C(O)$R^{13B}$, —$NR^{13A}$—C(O)—$OR^{13B}$, —C(O)$NR^{13A}R^{13B}$, —$NR^{13A}$S(O)$_2R^{13B}$, —S(O)$_2$N($R^{13A}$)($R^{13B}$), —$SR^{13A}$, —S(O)$R^{13B}$, —S(O)$_2R^{13B}$, —$NR^{13A}R^{13B}$, —$OR^{13A}$, —C(O)$R^{13B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{13A}$ and $R^{13B}$ independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{13}$, $R^{13A}$ and $R^{13B}$ are substituted substituents, $R^{13}$, $R^{13A}$ and $R^{13}$ are independently substituted with $R^{52}$. For example, in some embodiments, $R^{13}$, $R^{13A}$ and $R^{13B}$ are independently $R^{52}$-substituted or unsubstituted alkyl (e.g. substituted or unsubstituted $C_1$ to $C_{20}$ alkyl), $R^{52}$-substituted or unsubstituted heteroalkyl (e.g. substituted or unsubstituted 2 to 20 membered heteroalkyl), $R^{52}$-substituted or unsubstituted cycloalkyl (e.g. $C_3$ to $C_{14}$ cycloalkyl including fused ring structures), $R^{52}$-substituted or unsubstituted heterocycloalkyl (e.g. 3 to 14 membered heterocycloalkyl including fused ring structures), $R^{52}$-substituted or unsubstituted aryl (e.g. a $C_6$ to $C_{14}$ aryl including fused ring structures), or $R^{52}$-substituted or unsubstituted heteroaryl (e.g. 5 to 14 membered heteroaryl including fused rings structures).

$R^{52}$ is independently oxo (where permitted according to valency rules), halogen, —CN, —$CF_3$, —$NR^{52A}$—C(O)$R^{52B}$, —$NR^{52A}$—C(O)—$OR^{52B}$, —C(O)$NR^{52A}R^{52B}$, —$NR^{52A}S(O)_2R^{52B}$, —$S(O)_2N(R^{52A})(R^{52B})$, —$SR^{52A}$, —$S(O)R^{52B}$, —$S(O)_2R^{52B}$, —$NR^{52A}R^{52B}$, —$OR^{52A}$, —$C(O)R^{52B}$, $R^{53}$-substituted or unsubstituted alkyl (e.g. substituted or unsubstituted $C_1$ to $C_{20}$ alkyl), $R^{53}$-substituted or unsubstituted heteroalkyl (e.g. substituted or unsubstituted 2 to 20 membered heteroalkyl), $R^{53}$-substituted or unsubstituted cycloalkyl (e.g. $C_3$ to $C_{14}$ cycloalkyl including fused ring structures), $R^{53}$-substituted or unsubstituted heterocycloalkyl (e.g. 3 to 14 membered heterocycloalkyl including fused ring structures), $R^{53}$-substituted or unsubstituted aryl (e.g. a $C_6$ to $C_{14}$ aryl including fused ring structures), or $R^{53}$-substituted or unsubstituted heteroaryl (e.g. 5 to 14 membered heteroaryl including fused rings structures).

$R^{52A}$ and $R^{52B}$ are independently hydrogen, $R^{53}$-substituted or unsubstituted alkyl (e.g. substituted or unsubstituted $C_1$ to $C_{20}$ alkyl), $R^{53}$-substituted or unsubstituted heteroalkyl (e.g. substituted or unsubstituted 2 to 20 membered heteroalkyl), $R^{53}$-substituted or unsubstituted cycloalkyl (e.g. $C_3$ to $C_{14}$ cycloalkyl including fused ring structures), $R^{53}$-substituted or unsubstituted heterocycloalkyl (e.g. 3 to 14 membered heterocycloalkyl including fused ring structures), $R^{53}$-substituted or unsubstituted aryl (e.g. a $C_6$ to $C_{14}$ aryl including fused ring structures), or $R^{53}$-substituted or unsubstituted heteroaryl (e.g. 5 to 14 membered heteroaryl including fused rings structures).

$R^{53}$ is independently oxo (where permitted according to valency rules), halogen, —CN, —$CF_3$, —$NR^{53A}$—C(O)$R^{53B}$, —$NR^{53A}$—C(O)—$OR^{53B}$, —C(O)$NR^{53A}R^{53B}$, —$NR^{53A}S(O)_2R^{53B}$, —$S(O)_2N(R^{53A})(R^{53B})$, —$SR^{53A}$, —$S(O)R^{53B}$, —$S(O)_2R^{53B}$, —$NR^{53A}R^{53B}$, —$OR^{53A}$, —$C(O)R^{53B}$, $R^{54}$-substituted or unsubstituted alkyl (e.g. substituted or unsubstituted $C_1$ to $C_{20}$ alkyl), $R^{54}$-substituted or unsubstituted heteroalkyl (e.g. substituted or unsubstituted 2 to 20 membered heteroalkyl), $R^{54}$-substituted or unsubstituted cycloalkyl (e.g. $C_3$ to $C_{14}$ cycloalkyl including fused ring structures), $R^{54}$-substituted or unsubstituted heterocycloalkyl (e.g. 3 to 14 membered heterocycloalkyl including fused ring structures), $R^{54}$-substituted or unsubstituted aryl (e.g. a $C_6$ to $C_{14}$ aryl including fused ring structures), or $R^{54}$-substituted or unsubstituted heteroaryl (e.g. 5 to 14 membered heteroaryl including fused rings structures).

$R^{53A}$ and $R^{53B}$ are independently hydrogen, $R^{54}$-substituted or unsubstituted alkyl (e.g. substituted or unsubstituted $C_1$ to $C_{20}$ alkyl), $R^{54}$-substituted or unsubstituted heteroalkyl (e.g. substituted or unsubstituted 2 to 20 membered heteroalkyl), $R^{54}$-substituted or unsubstituted cycloalkyl (e.g. $C_3$ to $C_{14}$ cycloalkyl including fused ring structures), $R^{54}$-substituted or unsubstituted heterocycloalkyl (e.g. 3 to 14 membered heterocycloalkyl including fused ring structures), $R^{54}$-substituted or unsubstituted aryl (e.g. a $C_6$ to $C_{14}$ aryl including fused ring structures), or $R^{54}$-substituted or unsubstituted heteroaryl (e.g. 5 to 14 membered heteroaryl including fused rings structures).

$R^{54}$ is independently oxo (where permitted according to valency rules), halogen, —CN, —$CF_3$, —$NR^{54A}$—C(O)$R^{54B}$, —$NR^{54A}$—C(O)—$OR^{54B}$, —C(O)$NR^{54A}R^{54B}$, —$NR^{54A}S(O)_2R^{54B}$, —$S(O)_2N(R^{54A})(R^{54B})$, —$SR^{54A}$, —$S(O)R^{54B}$, —$S(O)_2R^{54B}$, —$NR^{54A}R^{54B}$, —$OR^{54A}$, —$C(O)R^{54B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{54A}$ and $R^{54B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^5$ is hydrogen, halogen, —CN, —$CF_3$, —OH, —$NH_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^5$ is methoxy, ethoxy, propoxy, Cl, F or $CF_3$. In some embodiments, $R^5$ is methoxy, ethoxy, or propoxy. In some embodiments, $R^5$ is methoxy.

In some embodiments, $R^{13}$ is halogen, —CN, —$CF_3$, —OH, —$NH_2$, $R^{52}$-substituted or unsubstituted $C_1$ to $C_5$ alkyl, or $R^{52}$-substituted or unsubstituted 2 to 6 membered heteroalkyl, wherein $R^{52}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{13}$ is methyl, ethyl, propyl, —Cl, —F, —$CF_3$, methoxy, ethoxy, propoxy. In some embodiments, $R^{13}$ is —F, methyl or methoxy. In some embodiments, m is 0. In other embodiments, m is one.

In some embodiments, the compound has the formula:

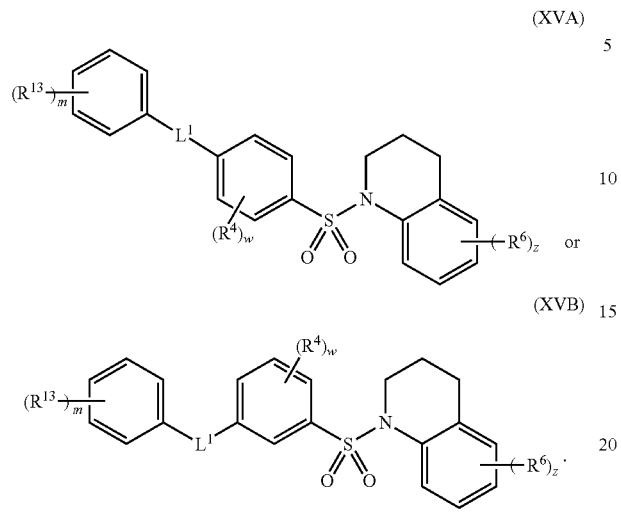

(XVA)

or (XVB)

In some embodiments, the compound has the formula:

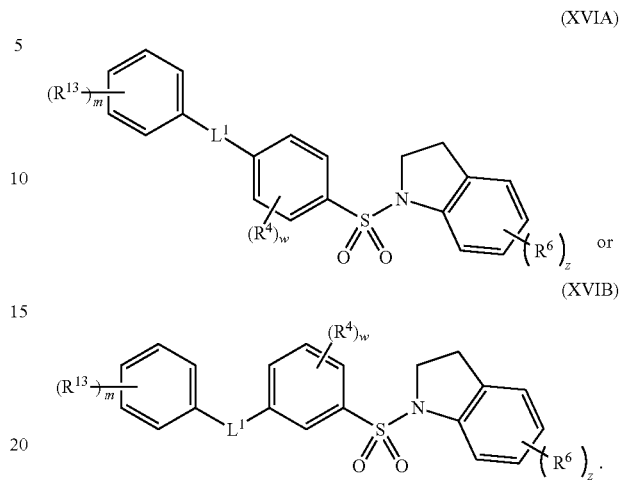

(XVIA)

or (XVIB)

In Formulae (XVA) and (XVB), $R^4$, $R^6$, $R^{13}$, $L^1$, w, z and m are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^{13}$ is halogen, —CN, —$CF_3$, —OH, —$NH_2$, $R^{52}$-substituted or unsubstituted $C_1$ to $C_5$ alkyl, or $R^{52}$-substituted or unsubstituted 2 to 6 membered heteroalkyl, wherein $R^{52}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{13}$ is methyl, ethyl, propyl, —Cl, —F, —$CF_3$, methoxy, ethoxy, propoxy. In some embodiments, $R^{13}$ is —F, methyl or methoxy. In some embodiments, m is 0. In other embodiments, m is one.

In Formulae (XVIA) and (XVIB), $R^4$, $R^6$, $R^{13}$, $L^1$, w, z and m are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^{13}$ is halogen, —CN, —$CF_3$, —OH, —$NH_2$, $R^{52}$-substituted or unsubstituted $C_1$ to $C_5$ alkyl, or $R^{52}$-substituted or unsubstituted 2 to 6 membered heteroalkyl, wherein $R^{52}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{13}$ is methyl, ethyl, propyl, —Cl, —F, —$CF_3$, methoxy, ethoxy, propoxy. In some embodiments, $R^{13}$ is —F, methyl or methoxy. In some embodiments, m is 0. In other embodiments, m is one.

In some embodiments, the compound has the formula:

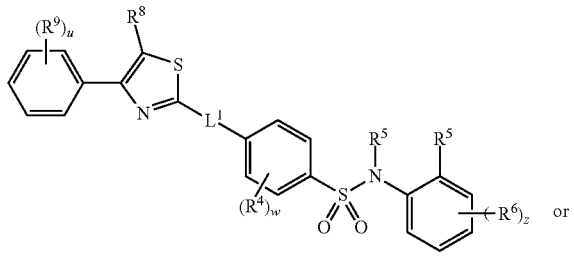

(XVIIA)

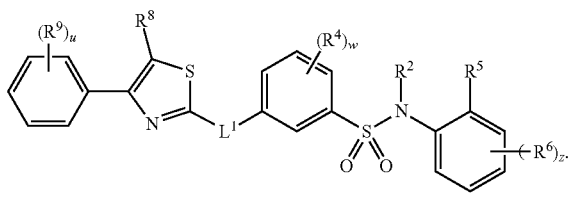

(XVIIB)

In Formulae (XVIIA) and (XVIIB), $L^1$, $R^2$, $R^4$, $R^5$, $R^6$, $R^8$, $R^9$, z, w and u are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —CF$_3$, —OH, —NH$_2$, $R^{25}$-substituted or unsubstituted C$_1$ to C$_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted C$_1$ to C$_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted C$_1$ to C$_5$ alkyl, or $R^{25}$-substituted or unsubstituted 2 to 6 membered heteroalkyl, wherein $R^{25}$ is —CF$_3$, —OH, —NH$_2$, unsubstituted C$_1$ to C$_5$ alkyl, or unsubstituted 2 to 6 membered heteroalkyl. In some embodiments, $R^4$ is methyl, methoxy, —CF$_3$, or —OH. As set forth above in Formulae (IIA), (IIB), (VA), (VB), (VIIIA), (VIIIB), (XIA), (XIB), (XIVA) and (XIVB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (XVIIA) or (XVIIB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. C$_1$ to C$_{10}$ alkyl). In some embodiments, $R^2$ is hydrogen. In some embodiments, $R^2$ is unsubstituted C$_1$ to C$_5$ alkyl. In some embodiments, $R^2$ is methyl. In some embodiments, $R^2$ is methyl, ethyl, propyl, tertiary butyl, methylene cyclopropyl (—CH$_2$-cyclopropyl), methoxy, ethoxy, propoxy, butoxy or —CF$_3$. In some embodiments, $R^6$ is halogen, —CN, —CF$_3$, —OH, —NH$_2$, $R^{31}$-substituted or unsubstituted C$_1$ to C$_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted C$_1$ to C$_5$ alkyl, unsubstituted 2 to 6 membered heteroalkyl. In some embodiments, $R^6$ is methoxy, ethoxy, propoxy, Cl, F or CF$_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^5$ is hydrogen, halogen, —CN, —CF$_3$, —OH, —NH$_2$, $R^{28}$-substituted or unsubstituted C$_1$ to C$_5$ alkyl, or $R^{28}$-substituted or unsubstituted 2 to 6 membered heteroalkyl, wherein $R^{28}$ is oxo, halogen, —CN, —CF$_3$, —OH, —NH$_2$, unsubstituted C$_1$ to C$_5$ alkyl, unsubstituted 2 to 6 membered heteroalkyl. In some embodiments, $R^5$ is methoxy, ethoxy, propoxy, Cl, F or CF$_3$. In some embodiments, $R^5$ is methoxy, ethoxy, or propoxy. In some embodiments, $R^5$ is methoxy.

In some embodiments, $R^8$ is hydrogen, halogen, —CN, —CF$_3$, —OH, —NH$_2$, $R^{37}$-substituted or unsubstituted C$_1$ to C$_5$ alkyl, or $R^{37}$-substituted or unsubstituted 2 to 6 membered heteroalkyl, wherein $R^{37}$ is oxo, halogen, —CN, —CF$_3$, —OH, —NH$_2$, unsubstituted C$_1$ to C$_5$ alkyl, unsubstituted 2 to 6 membered heteroalkyl. In some embodiments, $R^8$ is hydrogen, methyl, ethyl, propyl, —Cl, —F, —CF$_3$, methoxy, ethoxy, propoxy. In some embodiments, $R^8$ is hydrogen, —F, methyl or methoxy. In some embodiments, $R^8$ is hydrogen.

In some embodiments, $R^9$ is halogen, —CN, —CF$_3$, —OH, —NH$_2$, $R^{40}$-substituted or unsubstituted C$_1$ to C$_5$ alkyl, or $R^{40}$-substituted or unsubstituted 2 to 6 membered heteroalkyl, wherein $R^{40}$ is oxo, halogen, —CN, —CF$_3$, —OH, —NH$_2$, unsubstituted C$_1$ to C$_5$ alkyl, unsubstituted 2 to 6 membered heteroalkyl. In some embodiments, $R^9$ is methyl, ethyl, propyl, —Cl, —F, —CF$_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

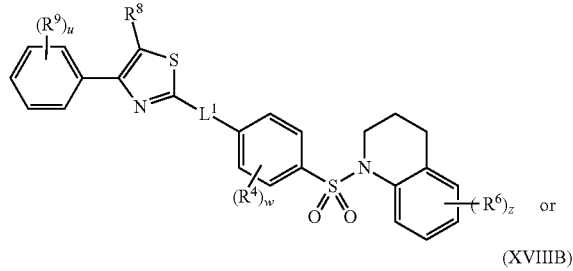

(XVIIIA)

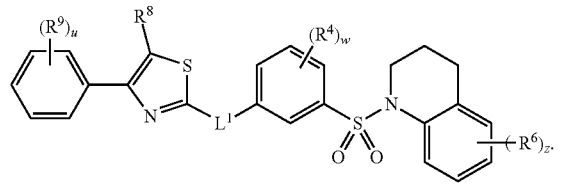

(XVIIIB)

In Formulae (XVIIIA) and (XVIIIB), $L^1$, $R^4$, $R^8$, $R^9$, z, w and u are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —CF$_3$, —OH, —NH$_2$, $R^{25}$-substituted or unsubstituted C$_1$ to C$_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted C$_1$ to C$_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^8$ is hydrogen, halogen, —CN, —$CF_3$, —OH, —$NH_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —$CF_3$, methoxy, ethoxy, propoxy. In some embodiments, $R^8$ is hydrogen, —F, methyl or methoxy. In some embodiments, $R^8$ is hydrogen.

In some embodiments, $R^9$ is halogen, —CN, —$CF_3$, —OH, —$NH_2$, $R^{40}$-substituted or unsubstituted $C_1$ to $C_5$ alkyl, or $R^{40}$-substituted or unsubstituted 2 to 6 membered heteroalkyl, wherein $R^{40}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^9$ is methyl, ethyl, propyl, —Cl, —F, —$CF_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

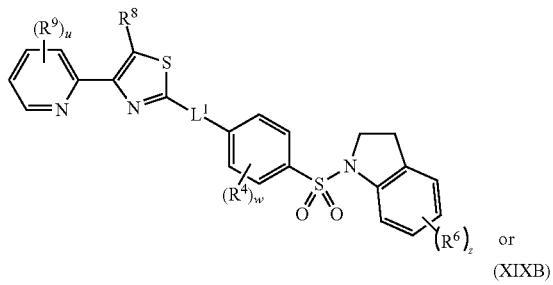

(XIXA)

or (XIXB)

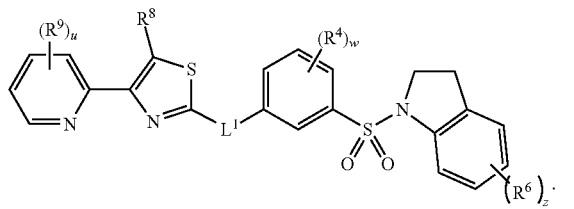

In Formulae (XIXA) and (XIXB), $L^1$, $R^4$, $R^6$, $R^8$, $R^9$, z, w and u are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^8$ is hydrogen, halogen, —CN, —$CF_3$, —OH, —$NH_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —$CF_3$, methoxy, ethoxy, propoxy. In some embodiments, $R^8$ is hydrogen, —F, methyl or methoxy. In some embodiments, $R^8$ is hydrogen.

In some embodiments, $R^9$ is halogen, —CN, —$CF_3$, —OH, —$NH_2$, $R^{40}$-substituted or unsubstituted $C_1$ to $C_5$ alkyl, or $R^{40}$-substituted or unsubstituted 2 to 6 membered heteroalkyl, wherein $R^{40}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^9$ is methyl, ethyl, propyl, —Cl, —F, —$CF_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

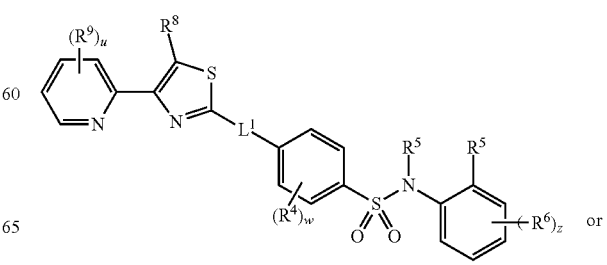

(XXA)

or

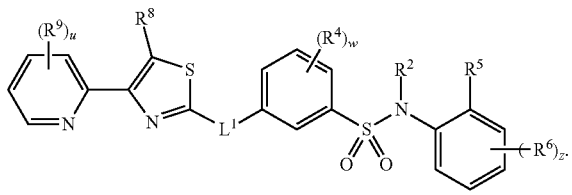

(XXB)

In Formulae (XXA) and (XXB), $L^1$, $R^2$, $R^4$, $R^5$, $R^6$, $R^8$, $R^9$, z, w and u are as defined above. In some embodiments, w is 0. In other embodiments, w is 1. $R^4$ may be halogen, —CN, —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is —CF$_3$, —OH, —NH$_2$, unsubstituted $C_1$ to $C_5$ alkyl, or unsubstituted 2 to 6 membered heteroalkyl. In some embodiments, $R^4$ is methyl, methoxy, —CF$_3$, or —OH. As set forth above in Formulae (IIA), (IIB), (VA), (VB), (VIIIA), (VIIIB), (XIA), (XIB), (XIVA), (XIVB), (XVIIA) and (XVIIB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (XXA) and (XXB), $R^2$ and $R^5$ are not joined together to form a substituted or unsubstituted heterocycloalkyl or substituted or unsubstituted heteroaryl. In some embodiments, $R^6$ is halogen, —CN, —CF$_3$, —OH, —NH$_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted $C_1$ to $C_5$ alkyl, unsubstituted 2 to 6 membered heteroalkyl.

In some embodiments, $R^6$ is methoxy, ethoxy, propoxy, Cl, F or CF$_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^5$ is hydrogen, halogen, —CN, —CF$_3$, —OH, —NH$_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^5$ is methoxy, ethoxy, propoxy, Cl, F or CF$_3$. In some embodiments, $R^5$ is methoxy, ethoxy, or propoxy. In some embodiments, $R^5$ is methoxy.

In some embodiments, $R^8$ is hydrogen, halogen, —CN, —CF$_3$, —OH, —NH$_2$, $R^{37}$-substituted or unsubstituted $C_1$ to $C_5$ alkyl, or $R^{37}$-substituted or unsubstituted 2 to 6 membered heteroalkyl, wherein $R^{37}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^8$ is hydrogen, methyl, ethyl, propyl, —Cl, —F, —CF$_3$, methoxy, ethoxy, propoxy. In some embodiments, $R^8$ is hydrogen, —F, methyl or methoxy. In some embodiments, $R^8$ is hydrogen.

In some embodiments, $R^9$ is halogen, —CN, —CF$_3$, —OH, —NH$_2$, $R^{40}$-substituted or unsubstituted $C_1$ to $C_5$ alkyl, or $R^{40}$-substituted or unsubstituted 2 to 6 membered heteroalkyl, wherein $R^{40}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^9$ is methyl, ethyl, propyl, —Cl, —F, —CF$_3$, methoxy, ethoxy, propoxy. In some embodiments, $R^9$ is —F, methyl or methoxy. The symbol u is an integer from 0 to 5. In some embodiments, u is 0. In other embodiments, u is 1. In some embodiments, $X^1$ and $X^2$ are carbon. In other embodiments, $X^1$ is carbon and $X^2$ is nitrogen.

In some embodiments, the compound has the formula:

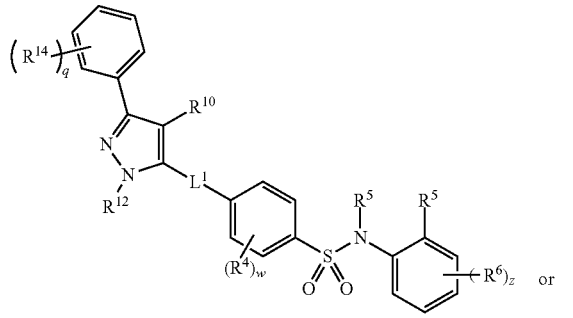

(XXIA)

or

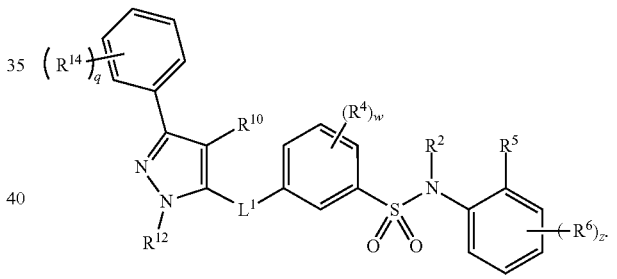

(XXIB)

In Formulae (XXIA) and (XXIB), $L^1$, $R^2$, $R^4$, $R^5$, $R^6$, $R^{10}$, $R^{12}$, z and w are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —CF$_3$, —OH, —NH$_{25}$ unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted $C_1$ to $C_5$ alkyl, or $R^{25}$-substituted or unsubstituted 2 to 6 membered heteroalkyl, wherein $R^{25}$ is —CF$_3$, —OH, —NH$_2$, unsubstituted $C_1$ to $C_5$ alkyl, or unsubstituted 2 to 6 membered heteroalkyl. In some embodiments, $R^4$ is methyl, methoxy, —CF$_3$, or —OH.

The symbol q is an integer from 0 to 5. As set forth above in Formulae (IIA), (IIB), (VA), (VB), (VIIIA), (VIIIB), (XIA), (XIB), (XIVA), (XIVB), (XVIIA), (XVIIB), (XXA) and (XXB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (XXIA) and (XXIB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. $C_1$ to $C_{10}$ alkyl). In some embodiments, $R^2$ is hydrogen. In some embodiments, $R^2$ is methyl, ethyl, propyl, tertiary butyl, methylene cyclopropyl ($-CH_2$-cyclopropyl), methoxy, ethoxy, propoxy, butoxy or $-CF_3$. In some embodiments, $R^2$ is unsubstituted $C_1$ to $C_5$ alkyl. In some embodiments, $R^2$ is methyl. In some embodiments, $R^6$ is halogen, $-CN$, $-CF_3$, $-OH$, $-NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, $-CN$, $-CF_3$, $-OH$, $-NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^5$ is hydrogen, halogen, $-CN$, $-CF_3$, $-OH$, $-NH_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, $-CN$, $-CF_3$, $-OH$, $-NH_2$, unsubstituted $C_1$ to $C_5$ alkyl, unsubstituted 2 to 6 membered heteroalkyl. In some embodiments, $R^5$ is methoxy, ethoxy, propoxy, Cl, F or $CF_3$. In some embodiments, $R^5$ is methoxy, ethoxy, or propoxy. In some embodiments, $R^5$ is methoxy.

In some embodiments, $R^{10}$ is hydrogen, halogen, $-CN$, $-CF_3$, $-OH$, $-NH_2$, $R^{43}$-substituted or unsubstituted $C_1$ to $C_5$ alkyl, or $R^{43}$-substituted or unsubstituted 2 to 6 membered heteroalkyl, wherein $R^{43}$ is oxo, halogen, $-CN$, $-CF_3$, $-OH$, $-NH_2$, unsubstituted $C_1$ to $C_5$ alkyl, unsubstituted 2 to 6 membered heteroalkyl. In some embodiments, $R^{10}$ is hydrogen, methyl, ethyl, propyl, $-Cl$, $-F$, $-CF_3$, methoxy, ethoxy, propoxy. In some embodiments, $R^{10}$ is hydrogen, $-F$, methyl or methoxy. In some embodiments, $R^{10}$ is hydrogen.

In some embodiments, $R^{12}$ is hydrogen, halogen, $-CN$, $-CF_3$, $-OH$, $-NH_2$, $R^{49}$-substituted or unsubstituted $C_1$ to $C_5$ alkyl, or $R^{49}$-substituted or unsubstituted 2 to 6 membered heteroalkyl, wherein $R^{49}$ is oxo, halogen, $-CN$, $-CF_3$, $-OH$, $-NH_2$, unsubstituted $C_1$ to $C_5$ alkyl, unsubstituted 2 to 6 membered heteroalkyl. In some embodiments, $R^{12}$ is hydrogen, methyl, ethyl, propyl, $-Cl$, $-F$, $-CF_3$, methoxy, ethoxy, propoxy. In some embodiments, $R^{12}$ is hydrogen, $-F$, methyl or methoxy. In some embodiments, $R^{11}$ is hydrogen.

$R^{14}$ is independently halogen, $-CN$, $-CF_3$, $-NR^{14A}-C(O)R^{14B}$, $-NR^{14A}-C(O)-OR^{14B}$, $-C(O)NR^{14A}R^{14B}$, $-NR^{14A}S(O)_2R^{14B}$, $-S(O)_2N(R^{14A})(R^{14B})$, $-SR^{14A}$, $-S(O)R^{14B}$, $-S(O)_2R^{14B}$, $-NR^{14A}R^{14B}$, $-OR^{14A}$, $-C(O)R^{14B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{14A}$ and $R^{14B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{14}$, $R^{14A}$ and $R^{14B}$ are substituted substituents, $R^{14}$, $R^{14A}$ and $R^{14}$ are independently substituted with $R^{55}$. For example, in some embodiments, $R^{14}$, $R^{14A}$ and $R^{14B}$ are independently $R^{55}$-substituted or unsubstituted alkyl (e.g. substituted or unsubstituted $C_1$ to $C_{20}$ alkyl), $R^{55}$-substituted or unsubstituted heteroalkyl (e.g. substituted or unsubstituted 2 to 20 membered heteroalkyl), $R^{55}$-substituted or unsubstituted cycloalkyl (e.g. $C_3$ to $C_{14}$ cycloalkyl including fused ring structures), $R^{55}$-substituted or unsubstituted heterocycloalkyl (e.g. 3 to 14 membered heterocycloalkyl including fused ring structures), $R^{55}$-substituted or unsubstituted aryl (e.g. a $C_6$ to $C_{14}$ aryl including fused ring structures), or $R^{55}$-substituted or unsubstituted heteroaryl (e.g. 5 to 14 membered heteroaryl including fused rings structures).

$R^{55}$ is independently oxo (where permitted according to valency rules), halogen, $-CN$, $-CF_3$, $-NR^{55A}-C(O)R^{55B}$, $-NR^{55A}-C(O)-OR^{55B}$, $-C(O)NR^{55A}R^{55B}$, $-NR^{55A}S(O)_2R^{55B}$, $-S(O)_2N(R^{55A})(R^{55B})$, $-SR^{55A}$, $-S(O)R^{55B}$, $-S(O)_2R^{55B}$, $-NR^{55A}R^{55B}$, $-OR^{55A}$, $-C(O)R^{55B}$, $R^{56}$-substituted or unsubstituted alkyl (e.g. substituted or unsubstituted $C_1$ to $C_{20}$ alkyl), $R^{56}$-substituted or unsubstituted heteroalkyl (e.g. substituted or unsubstituted 2 to 20 membered heteroalkyl), $R^{56}$-substituted or unsubstituted cycloalkyl (e.g. $C_3$ to $C_{14}$ cycloalkyl including fused ring structures), $R^{56}$-substituted or unsubstituted heterocycloalkyl (e.g. 3 to 14 membered heterocycloalkyl including fused ring structures), $R^{56}$-substituted or unsubstituted aryl (e.g. a $C_6$ to $C_{14}$ aryl including fused ring structures), or $R^{56}$-substituted or unsubstituted heteroaryl (e.g. 5 to 14 membered heteroaryl including fused rings structures).

$R^{55A}$ and $R^{55B}$ are independently hydrogen, $R^{56}$-substituted or unsubstituted alkyl (e.g. substituted or unsubstituted $C_1$ to $C_{20}$ alkyl), $R^{56}$-substituted or unsubstituted heteroalkyl (e.g. substituted or unsubstituted 2 to 20 membered heteroalkyl), $R^{56}$-substituted or unsubstituted cycloalkyl (e.g. $C_3$ to $C_{14}$ cycloalkyl including fused ring structures), $R^{56}$-substituted or unsubstituted heterocycloalkyl (e.g. 3 to 14 membered heterocycloalkyl including fused ring structures), $R^{56}$-substituted or unsubstituted aryl (e.g. a $C_6$ to $C_{14}$ aryl including fused ring structures), or $R^{56}$-substituted or unsubstituted heteroaryl (e.g. 5 to 14 membered heteroaryl including fused rings structures).

$R^{56}$ is independently oxo (where permitted according to valency rules), halogen, $-CN$, $-CF_3$, $-NR^{56A}-C(O)R^{56B}$, $-NR^{56A}-C(O)-OR^{56B}$, $-C(O)NR^{56A}R^{56B}$, $-NR^{56A}S(O)_2R^{56B}$, $-S(O)_2N(R^{56A})(R^{56B})$, $-SR^{56A}$, $-S(O)R^{56B}$, $-S(O)_2R^{56B}$, $-NR^{56A}R^{56B}$, $-OR^{56A}$, $-C(O)R^{56B}$, $R^{57}$-substituted or unsubstituted alkyl (e.g. substituted or unsubstituted $C_1$ to $C_{20}$ alkyl), $R^{57}$-substituted or unsubstituted heteroalkyl (e.g. substituted or unsubstituted 2 to 20 membered heteroalkyl), $R^{57}$-substituted or unsubstituted cycloalkyl (e.g. $C_3$ to $C_{14}$ cycloalkyl including fused ring structures), $R^{57}$-substituted or unsubstituted heterocycloalkyl (e.g. 3 to 14 membered heterocycloalkyl including fused ring structures), $R^{57}$-substituted or unsubstituted aryl (e.g. a $C_6$ to $C_{14}$ aryl including fused ring structures), or $R^{57}$-substituted or unsubstituted heteroaryl (e.g. 5 to 14 membered heteroaryl including fused rings structures).

$R^{56A}$ and $R^{56B}$ are independently hydrogen, $R^{57}$-substituted or unsubstituted alkyl (e.g. substituted or unsubstituted $C_1$ to $C_{20}$ alkyl), $R^{57}$-substituted or unsubstituted heteroalkyl (e.g. substituted or unsubstituted 2 to 20 membered heteroalkyl), $R^{57}$-substituted or unsubstituted cycloalkyl (e.g. $C_3$ to $C_{14}$ cycloalkyl including fused ring structures), $R^{57}$-substituted or unsubstituted heterocycloalkyl (e.g. 3 to 14 membered heterocycloalkyl including fused ring structures), $R^{57}$-substituted or unsubstituted aryl (e.g. a $C_6$ to $C_{14}$ aryl including fused ring structures), or $R^{57}$-substituted or unsubstituted heteroaryl (e.g. 5 to 14 membered heteroaryl including fused rings structures).

$R^{57}$ is independently oxo (where permitted according to valency rules), halogen, —CN, —$CF_3$, —$NR^{57A}$—C(O)$R^{57B}$, —$NR^{57A}$—C(O)—O$R^{57B}$, —C(O)$NR^{57A}R^{57B}$, —$NR^{57A}S(O)_2R^{57B}$, —S(O)$_2$N($R^{57A}$)($R^{57B}$), —S$R^{57A}$, —S(O)$R^{57B}$, —S(O)$_2R^{57B}$, —$NR^{57A}R^{57B}$, —O$R^{57A}$, —C(O)$R^{57B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{57A}$ and $R^{57B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{14}$ is halogen, —CN, —$CF_3$, —OH, —$NH_2$, $R^{55}$-substituted or unsubstituted $C_1$ to $C_5$ alkyl, or $R^{55}$-substituted or unsubstituted 2 to 6 membered heteroalkyl, wherein $R^{55}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{14}$ is methyl, ethyl, propyl, —Cl, —F, —$CF_3$, methoxy, ethoxy, propoxy. In some embodiments, $R^{14}$ is —F, methyl or methoxy. In some embodiments, q is 0. In other embodiments, q is one.

In some embodiments, the compound has the formula:

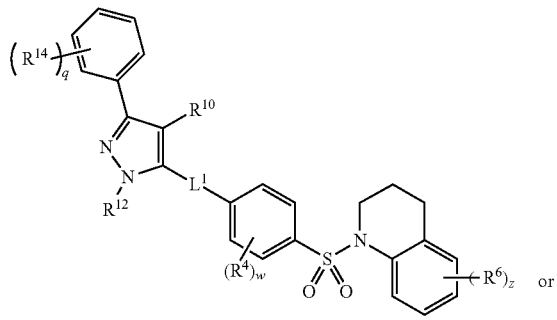

(XXIIA)

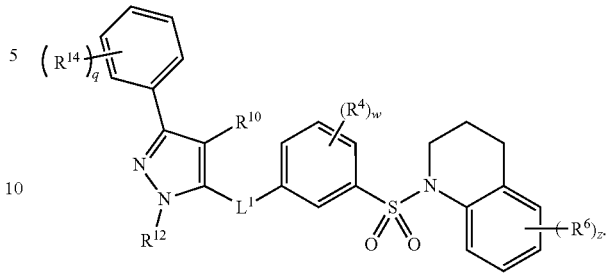

(XXIIB)

In Formulae (XXIIA) and (XXIIB), $R^4$, $R^6$, $R^{10}$, $R^{12}$, $R^{14}$, $L^1$, q, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is oxo, halogen, —CN, —$CF_3$, —OH, —$NH_2$, unsubstituted $C_1$ to $C_5$ alkyl, or unsubstituted 2 to 6 membered heteroalkyl. In some embodiments, $R^4$ is not F. In some embodiments, $R^4$ is not halogen. In some embodiments, $R^4$ is —$CF_3$, —OH, —$NH_2$, $R^{25}$-substituted or unsubstituted $C_1$ to $C_5$ alkyl, or $R^{25}$-substituted or unsubstituted 2 to 6 membered heteroalkyl, wherein $R^{25}$ is —$CF_3$, —OH, —$NH_2$, unsubstituted $C_1$ to $C_5$ alkyl, or unsubstituted 2 to 6 membered heteroalkyl. In some embodiments, $R^4$ is methyl, methoxy, —$CF_3$, or —OH. In some embodiments, $R^6$ is halogen, —CN, —$CF_3$, —OH, —$NH_2$, $R^{31}$-substituted or unsubstituted $C_1$ to $C_5$ alkyl, or $R^{31}$-substituted or unsubstituted 2 to 6 membered heteroalkyl, wherein $R^{31}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^6$ is methoxy, ethoxy, propoxy, Cl, F or $CF_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

In some embodiments, $R^{10}$ is hydrogen, halogen, —CN, —$CF_3$, —OH, —$NH_2$, $R^{43}$-substituted or unsubstituted $C_1$ to $C_5$ alkyl, or $R^{43}$-substituted or unsubstituted 2 to 6 membered heteroalkyl, wherein $R^{43}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{10}$ is hydrogen, methyl, ethyl, propyl, —Cl, —F, —$CF_3$, methoxy, ethoxy, propoxy. In some embodiments, $R^{10}$ is hydrogen, —F, methyl or methoxy. In some embodiments, $R^{10}$ is hydrogen.

In some embodiments, $R^{12}$ is hydrogen, halogen, —CN, —$CF_3$, —OH, —$NH_2$, $R^{49}$-substituted or unsubstituted $C_1$ to $C_5$ alkyl, or $R^{49}$-substituted or unsubstituted 2 to 6 membered heteroalkyl, wherein $R^{49}$ is oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{12}$ is hydrogen, methyl, ethyl, propyl, —Cl, —F, —$CF_3$, methoxy, ethoxy, propoxy. In some embodiments, $R^{12}$ is hydrogen, —F, methyl or methoxy. In some embodiments, $R^{11}$ is hydrogen.

In some embodiments, $R^{14}$ is halogen, —CN, —$CF_3$, —OH, —$NH_2$, $R^{55}$-substituted or unsubstituted $C_1$ to $C_5$ alkyl, or $R^{55}$-substituted or unsubstituted 2 to 6 membered heteroalkyl, wherein $R^{55}$ is oxo, halogen, —CN, —CF$_3$, —OH, —NH$_2$, unsubstituted C$_1$ to C$_5$ alkyl, unsubstituted 2 to 6 membered heteroalkyl. In some embodiments, $R^{14}$ is methyl, ethyl, propyl, —Cl, —F, —CF$_3$, methoxy, ethoxy, propoxy. In some embodiments, $R^{14}$ is —F, methyl or methoxy. In some embodiments, q is 0. In other embodiments, q is one.

In some embodiments, the compound has the formula:

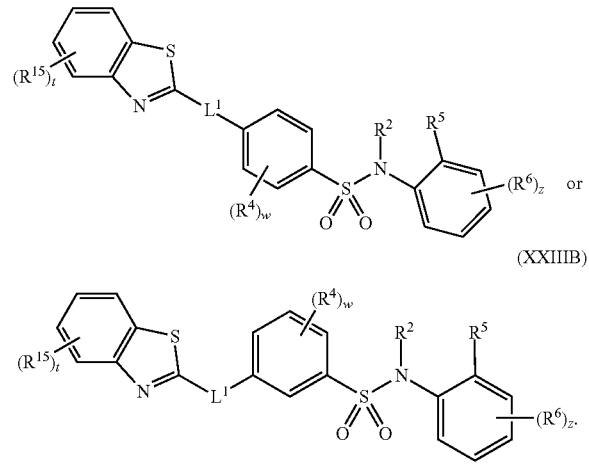

(XXIIIA)

(XXIIIB)

In Formulae (XXIIIA) and (XXIIIB), $R^2$, $R^4$, $R^5$, $R^6$, w and z are as defined above. In some embodiments, w is 0. In other embodiments, w is 1. In some embodiments, $L^1$ is —NH—C(O)— as illustrated in Formula (IC1) or (IC2). $R^4$ may be halogen, —CN, —CF$_3$, —OH, —NH$_2$, $R^{25}$-substituted or unsubstituted C$_1$ to C$_5$ alkyl, or $R^{25}$-substituted or unsubstituted 2 to 6 membered heteroalkyl, wherein $R^{25}$ is oxo, halogen, —CN, —CF$_3$, —OH, —NH$_2$, unsubstituted C$_1$ to C$_5$ alkyl, or unsubstituted 2 to 6 membered heteroalkyl. In some embodiments, $R^4$ is not F. In some embodiments, $R^4$ is not halogen. In some embodiments, $R^4$ is —CF$_3$, —OH, —NH$_2$, $R^{25}$-substituted or unsubstituted C$_1$ to C$_5$ alkyl, or $R^{25}$-substituted or unsubstituted 2 to 6 membered heteroalkyl, wherein $R^{25}$ is —CF$_3$, —OH, —NH$_2$, unsubstituted C$_1$ to C$_5$ alkyl, or unsubstituted 2 to 6 membered heteroalkyl. In some embodiments, $R^4$ is methyl, methoxy, —CF$_3$, or —OH.

The symbol t is an integer from 0 to 4. As set forth above in Formulae (IIA), (IIB), (VA), (VB), (VIIIA), (VIIIB), (XIA), (XIB), (XIVA), (XIVB), (XVIIA), (XVIIB), (XXA), (XXB), (XXIA) and (XXIB) above, $R^2$ may be joined together with $R^5$ to form a substituted or unsubstituted (e.g. $R^6$-substituted) heterocycloalkyl (e.g. 3 to 14 membered heterocycloalkyl including fused ring structures) or substituted (e.g. $R^{16}$-substituted) or unsubstituted heteroaryl (e.g. 5 to 14 membered heteroaryl including fused rings structures). In some embodiments of Formulae (XXIIIA) and (XXIIIB), $R^2$ and $R^5$ are not joined together to form a substituted or unsubstituted heterocycloalkyl or substituted or unsubstituted heteroaryl. In some embodiments, $R^2$ is hydrogen or unsubstituted alkyl (e.g. C$_1$ to C$_{10}$ alkyl). In some embodiments, $R^2$ is hydrogen. In some embodiments, $R^2$ is unsubstituted C$_1$ to C$_5$ alkyl. In some embodiments, $R^2$ is methyl. In some embodiments, $R^2$ is methyl, ethyl, propyl, tertiary butyl, methylene cyclopropyl (—CH$_2$-cyclopropyl), methoxy, ethoxy, propoxy, butoxy or —CF$_3$. In some embodiments, $R^6$ is halogen, —CN, —CF$_3$, —OH, —NH$_2$, $R^{31}$-substituted or unsubstituted C$_1$ to C$_5$ alkyl, or $R^{31}$-substituted or unsubstituted 2 to 6 membered heteroalkyl, wherein $R^{31}$ is oxo, halogen, —CN, —CF$_3$, —OH, —NH$_2$, unsubstituted C$_1$ to C$_5$ alkyl, unsubstituted 2 to 6 membered heteroalkyl. In some embodiments, $R^6$ is methoxy, ethoxy, propoxy, Cl, F or CF$_3$. In some embodiments, $R^6$ is methoxy, ethoxy, or propoxy. In some embodiments, $R^6$ is methoxy. The symbol z is an integer from 0 to 4. In some embodiments, z is 0. In other embodiments z is one. Where z is one, $R^6$ may be attached to the phenyl ring para to the sulfonamide moiety. In other embodiments where z is one, $R^6$ is attached to the phenyl ring meta to the sulfonamide moiety.

$R^{15}$ is independently halogen, —CN, —CF$_3$, —NR$^{15A}$—C(O)R$^{15B}$, —NR$^{15A}$—C(O)—OR$^{15B}$, —C(O)NR$^{15A}$R$^{15B}$, —NR$^{15A}$S(O)$_2$R$^{15B}$, —S(O)$_2$N(R$^{15A}$)(R$^{15B}$), —SR$^{15A}$, —S(O)R$^{15B}$, —S(O)$_2$R$^{15B}$, —NR$^{15A}$R$^{15B}$, —OR$^{15A}$, —C(O)R$^{15B}$, substituted or unsubstituted alkyl (e.g. substituted or unsubstituted C$_1$ to C$_{20}$ alkyl), substituted or unsubstituted heteroalkyl (e.g. substituted or unsubstituted 2 to 20 membered heteroalkyl), substituted or unsubstituted cycloalkyl (e.g. C$_3$ to C$_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a C$_6$ to C$_{14}$ aryl including fused ring structures), or substituted or unsubstituted heteroaryl (e.g. 5 to 14 membered heteroaryl including fused rings structures).

$R^{15A}$ and $R^{15B}$ are independently hydrogen, substituted or unsubstituted alkyl (e.g. substituted or unsubstituted C$_1$ to C$_{20}$ alkyl), substituted or unsubstituted heteroalkyl (e.g. substituted or unsubstituted 2 to 20 membered heteroalkyl), substituted or unsubstituted cycloalkyl (e.g. C$_3$ to C$_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a C$_6$ to C$_{14}$ aryl including fused ring structures), or substituted or unsubstituted heteroaryl (e.g. 5 to 14 membered heteroaryl including fused rings structures).

In some embodiments, where $R^{15}$, $R^{15A}$ and $R^{15B}$ are substituted substituents, $R^{15}$, $R^{15A}$ and $R^{15}$ are independently substituted with $R^{58}$. For example, in some embodiments, $R^{15}$, $R^{15A}$ and $R^{15B}$ are independently $R^{58}$-substituted or unsubstituted alkyl (e.g. substituted or unsubstituted C$_1$ to C$_{20}$ alkyl), $R^{58}$-substituted or unsubstituted heteroalkyl (e.g. substituted or unsubstituted 2 to 20 membered heteroalkyl), $R^{58}$-substituted or unsubstituted cycloalkyl (e.g. C$_3$ to C$_{14}$ cycloalkyl including fused ring structures), $R^{58}$-substituted or unsubstituted heterocycloalkyl (e.g. 3 to 14 membered heterocycloalkyl including fused ring structures), $R^{58}$-substituted or unsubstituted aryl (e.g. a C$_6$ to C$_{14}$ aryl including fused ring structures), or $R^{58}$-substituted or unsubstituted heteroaryl (e.g. 5 to 14 membered heteroaryl including fused rings structures).

$R^{58}$ is independently oxo (where permitted according to valency rules), halogen, —CN, —CF$_3$, —NR$^{58A}$—C(O)R$^{58B}$, —NR$^{58A}$—C(O)—OR$^{58B}$, —C(O)NR$^{58A}$R$^{58B}$, —NR$^{58A}$S(O)$_2$R$^{58B}$, —S(O)$_2$N(R$^{58A}$)(R$^{58B}$), —SR$^{58A}$, —S(O)R$^{58B}$, —S(O)$_2$R$^{58B}$, —NR$^{58A}$R$^{58B}$, —OR$^{58A}$, —C(O)R$^{58B}$, $R^{59}$-substituted or unsubstituted alkyl (e.g. substituted or unsubstituted C$_1$ to C$_{20}$ alkyl), $R^{59}$-substituted or unsubstituted heteroalkyl (e.g. substituted or unsubstituted 2 to 20 membered heteroalkyl), $R^{59}$-substituted or unsubstituted cycloalkyl (e.g. C$_3$ to C$_{14}$ cycloalkyl including fused ring structures), $R^{59}$-substituted or unsubstituted heterocycloalkyl (e.g. 3 to 14 membered heterocycloalkyl including fused ring structures), $R^{59}$-substituted or unsubstituted aryl (e.g. a C$_6$ to $C_{14}$ aryl including fused ring structures), or $R^{59}$-substituted or unsubstituted heteroaryl (e.g. 5 to 14 membered heteroaryl including fused ring structures).

$R^{58A}$ and $R^{58B}$ are independently hydrogen, $R^{59}$-substituted or unsubstituted alkyl (e.g. substituted or unsubstituted $C_1$ to $C_{20}$ alkyl), $R^{59}$-substituted or unsubstituted heteroalkyl (e.g. substituted or unsubstituted 2 to 20 membered heteroalkyl), $R^{59}$-substituted or unsubstituted cycloalkyl (e.g. $C_3$ to $C_{14}$ cycloalkyl including fused ring structures), $R^{59}$-substituted or unsubstituted heterocycloalkyl (e.g. 3 to 14 membered heterocycloalkyl including fused ring structures), $R^{59}$-substituted or unsubstituted aryl (e.g. a $C_6$ to $C_{14}$ aryl including fused ring structures), or $R^{59}$-substituted or unsubstituted heteroaryl (e.g. 5 to 14 membered heteroaryl including fused rings structures).

$R^{59}$ is independently oxo (where permitted according to valency rules), halogen, —CN, —CF$_3$, —NR$^{59A}$—C(O) R$^{59B}$, —NR$^{59A}$—C(O)—OR$^{59B}$, —C(O)NR$^{59A}$R$^{59B}$, —NR$^{59A}$S(O)$_2$R$^{59B}$, —S(O)$_2$N(R$^{59A}$)(R$^{59B}$), —SR$^{59A}$, —S(O)R$^{59B}$, —S(O)$_2$R$^{59B}$, —NR$^{59A}$R$^{59B}$, —OR$^{59A}$, —C(O) R$^{59B}$, $R^{60}$-substituted or unsubstituted alkyl (e.g. substituted or unsubstituted $C_1$ to $C_{20}$ alkyl), $R^{60}$-substituted or unsubstituted heteroalkyl (e.g. substituted or unsubstituted 2 to 20 membered heteroalkyl), $R^{60}$-substituted or unsubstituted cycloalkyl (e.g. $C_3$ to $C_{14}$ cycloalkyl including fused ring structures), $R^{60}$-substituted or unsubstituted heterocycloalkyl (e.g. 3 to 14 membered heterocycloalkyl including fused ring structures), $R^{60}$-substituted or unsubstituted aryl (e.g. a $C_6$ to $C_{14}$ aryl including fused ring structures), or $R^{60}$-substituted or unsubstituted heteroaryl (e.g. 5 to 14 membered heteroaryl including fused rings structures).

$R^{59A}$ and $R^{59B}$ are independently hydrogen, $R^{60}$-substituted or unsubstituted alkyl (e.g. substituted or unsubstituted $C_1$ to $C_{20}$ alkyl), $R^{60}$-substituted or unsubstituted heteroalkyl (e.g. substituted or unsubstituted 2 to 20 membered heteroalkyl), $R^{60}$-substituted or unsubstituted cycloalkyl (e.g. $C_3$ to $C_{14}$ cycloalkyl including fused ring structures), $R^{60}$-substituted or unsubstituted heterocycloalkyl (e.g. 3 to 14 membered heterocycloalkyl including fused ring structures), $R^{60}$-substituted or unsubstituted aryl (e.g. a $C_6$ to $C_{14}$ aryl including fused ring structures), or $R^{60}$-substituted or unsubstituted heteroaryl (e.g. 5 to 14 membered heteroaryl including fused rings structures).

$R^{60}$ is independently oxo (where permitted according to valency rules), halogen, —CN, —CF$_3$, —NR$^{60A}$—C(O) R$^{60B}$, —NR$^{60A}$—C(O)—OR$^{60B}$, —C(O)NR$^{60A}$R$^{60B}$, —NR$^{60A}$S(O)$_2$R$^{60B}$, —S(O)$_2$N(R$^{60A}$)(R$^{60B}$), —SR$^{60A}$, —S(O)R$^{60B}$, —S(O)$_2$R$^{60B}$, —NR$^{60A}$R$^{60B}$, —OR$^{60A}$, —C(O) R$^{60B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{60A}$ and $R^{60B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^5$ is hydrogen, halogen, —CN, —CF$_3$, —OH, —NH$_2$, $R^{28}$-substituted or unsubstituted $C_1$ to $C_5$ alkyl, or $R^{28}$-substituted or unsubstituted 2 to 6 membered heteroalkyl, wherein $R^{28}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^5$ is methoxy, ethoxy, propoxy, Cl, F or CF$_3$. In some embodiments, $R^5$ is methoxy, ethoxy, or propoxy. In some embodiments, $R^5$ is methoxy.

In some embodiments, $R^{15}$ is halogen, —CN, —CF$_3$, —OH, —NH$_2$, $R^{58}$-substituted or unsubstituted $C_1$ to $C_5$ alkyl, or $R^{58}$-substituted or unsubstituted 2 to 6 membered heteroalkyl, wherein $R^{58}$ is oxo, halogen, —CN, —CF$_3$, —OH, —NH$_2$, unsubstituted $C_1$ to $C_5$ alkyl, unsubstituted 2 to 6 membered heteroalkyl. In some embodiments, $R^{15}$ is methyl, ethyl, propyl, —Cl, —F, —CF$_3$, methoxy, ethoxy, propoxy. In some embodiments, $R^{15}$ is —F, methyl or methoxy. In some embodiments, t is 0. In other embodiments, t is one.

In another aspect, the compound has the formula:

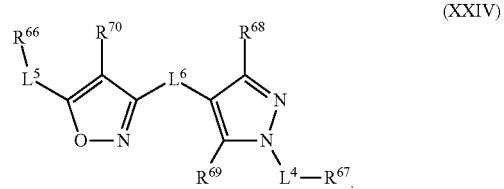

(XXIV)

In Formula (XXIV), $R^{66}$ and $R^{67}$ are independently substituted or unsubstituted aryl (e.g. a $C_6$ to $C_{14}$ aryl including fused ring structures), or substituted or unsubstituted heteroaryl (e.g. 5 to 14 membered heteroaryl including fused rings structures). In some embodiments, $R^{66}$ and $R^{67}$ are independently substituted or unsubstituted heteroaryl (e.g. 5 to 14 membered heteroaryl including fused rings structures). In some embodiments, $R^{66}$ and $R^{67}$ are independently substituted or unsubstituted phenyl.

In some embodiments, where $R^{66}$ and $R^{67}$ are substituted substituents, $R^{66}$ and $R^{67}$ are independently substituted with $R^{74}$. For example, in some embodiments, $R^{66}$ and $R^{67}$ are independently $R^{74}$-substituted or unsubstituted aryl (e.g. a $C_6$ to $C_{14}$ aryl including fused ring structures) or $R^{74}$-substituted or unsubstituted heteroaryl (e.g. 5 to 14 membered heteroaryl including fused rings structures).

$R^{74}$ is independently oxo (where permitted according to valency rules), halogen, —CN, —CF$_3$, —NR$^{74A}$—C(O) R$^{74B}$, —NR$^{74A}$—C(O)—OR$^{74B}$, —C(O)NR$^{74A}$R$^{74B}$, —NR$^{74A}$S(O)$_2$R$^{74B}$, —S(O)$_2$N(R$^{74A}$)(R$^{74B}$), —SR$^{74A}$, —S(O)R$^{74B}$, —S(O)$_2$R$^{74B}$, —NR$^{74A}$R$^{74B}$, —OR$^{74A}$, —C(O) R$^{74B}$, $R^{75}$-substituted or unsubstituted alkyl (e.g. substituted or unsubstituted $C_1$ to $C_{20}$ alkyl), $R^{75}$-substituted or unsubstituted heteroalkyl (e.g. substituted or unsubstituted 2 to 20 membered heteroalkyl), $R^{75}$-substituted or unsubstituted cycloalkyl (e.g. $C_3$ to $C_{14}$ cycloalkyl including fused ring structures), $R^{75}$-substituted or unsubstituted heterocycloalkyl (e.g. 3 to 14 membered heterocycloalkyl including fused ring structures), $R^{75}$-substituted or unsubstituted aryl (e.g. a $C_6$ to $C_{14}$ aryl including fused ring structures), or $R^{75}$-substituted or unsubstituted heteroaryl (e.g. 5 to 14 membered heteroaryl including fused rings structures).

$R^{74A}$ and $R^{74B}$ are independently hydrogen, $R^{75}$-substituted or unsubstituted alkyl (e.g. substituted or unsubstituted $C_1$ to $C_{20}$ alkyl), $R^{75}$-substituted or unsubstituted heteroalkyl (e.g. substituted or unsubstituted 2 to 20 membered heteroalkyl), $R^{75}$-substituted or unsubstituted cycloalkyl (e.g. $C_3$ to $C_{14}$ cycloalkyl including fused ring structures), $R^{75}$-substituted or unsubstituted heterocycloalkyl (e.g. 3 to 14 membered heterocycloalkyl including fused ring structures), $R^{75}$-substituted or unsubstituted aryl (e.g. a $C_6$ to $C_{14}$ aryl including fused ring structures), or $R^{75}$-substituted or unsubstituted heteroaryl (e.g. 5 to 14 membered heteroaryl including fused rings structures).

$R^{75}$ is independently oxo (where permitted according to valency rules), halogen, —CN, —$CF_3$, —$NR^{75A}$—C(O)$R^{75B}$, —$NR^{75A}$—C(O)—$OR^{75B}$, —C(O)$NR^{75A}R^{75B}$, —$NR^{75A}S(O)_2R^{75B}$, —$S(O)_2N(R^{75A})(R^{75B})$, —$SR^{75A}$, —$S(O)R^{75B}$, —$S(O)_2R^{75B}$, —$NR^{75A}R^{75B}$, —$OR^{75A}$, —C(O)$R^{75B}$, $R^{76}$-substituted or unsubstituted alkyl (e.g. substituted or unsubstituted $C_1$ to $C_{20}$ alkyl), $R^{76}$-substituted or unsubstituted heteroalkyl (e.g. substituted or unsubstituted 2 to 20 membered heteroalkyl), $R^{76}$-substituted or unsubstituted cycloalkyl (e.g. $C_3$ to $C_{14}$ cycloalkyl including fused ring structures), $R^{76}$-substituted or unsubstituted heterocycloalkyl (e.g. 3 to 14 membered heterocycloalkyl including fused ring structures), $R^{76}$-substituted or unsubstituted aryl (e.g. a $C_6$ to $C_{14}$ aryl including fused ring structures), or $R^{76}$-substituted or unsubstituted heteroaryl (e.g. 5 to 14 membered heteroaryl including fused rings structures).

$R^{75A}$ and $R^{75B}$ are independently hydrogen, $R^{76}$-substituted or unsubstituted alkyl (e.g. substituted or unsubstituted $C_1$ to $C_{20}$ alkyl), $R^{76}$-substituted or unsubstituted heteroalkyl (e.g. substituted or unsubstituted 2 to 20 membered heteroalkyl), $R^{76}$-substituted or unsubstituted cycloalkyl (e.g. $C_3$ to $C_{14}$ cycloalkyl including fused ring structures), $R^{76}$-substituted or unsubstituted heterocycloalkyl (e.g. 3 to 14 membered heterocycloalkyl including fused ring structures), $R^{76}$-substituted or unsubstituted aryl (e.g. a $C_6$ to $C_{14}$ aryl including fused ring structures), or $R^{76}$-substituted or unsubstituted heteroaryl (e.g. 5 to 14 membered heteroaryl including fused rings structures).

$R^{76}$ is independently oxo (where permitted according to valency rules), halogen, —CN, —$CF_3$, —$NR^{76A}$—C(O)$R^{76B}$, —$NR^{76A}$—C(O)—$OR^{76B}$, —C(O)$NR^{76A}R^{76B}$, —$NR^{76A}S(O)_2R^{76B}$, —$S(O)_2N(R^{76A})(R^{76B})$, —$SR^{76A}$, —$S(O)R^{76B}$, —$S(O)_2R^{76B}$, —$NR^{76A}R^{76B}$, —$OR^{76A}$, —C(O)$R^{76B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{76A}$ and $R^{76B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{66}$ and $R^{67}$ are independently $R^{74}$-substituted or unsubstituted phenyl. In some embodiments, $R^{66}$ and $R^{67}$ are independently $R^{74}$-substituted or unsubstituted phenyl, wherein $R^{74}$ is independently hydrogen, halogen, —CN, —$CF_3$, —OH, —$NH_2$, $R^{75}$-substituted or unsubstituted $C_1$ to $C_5$ alkyl, or $R^{75}$-substituted or unsubstituted 2 to 6 membered heteroalkyl, wherein $R^{75}$ is independently oxo, halogen, —CN, —$CF_3$, —OH, —$NH_2$, unsubstituted $C_1$ to $C_5$ alkyl, unsubstituted 2 to 6 membered heteroalkyl. In some embodiments, $R^{74}$ is independently hydrogen, methyl, ethyl, propyl, tertiary butyl, —Cl, —F, —$CF_3$, methoxy, ethoxy, propoxy. In some embodiments, $R^{74}$ is independently hydrogen, —F, methyl or methoxy. In some embodiments, $R^{74}$ is hydrogen.

$R^{68}$, $R^{69}$ and $R^{70}$ are independently hydrogen, halogen, —CN, —$CF_3$, —$NR^{68A}$—C(O)$R^{68B}$, —$NR^{68A}$—C(O)—$OR^{68B}$, —C(O)$NR^{68A}R^{68B}$, —$NR^{68A}S(O)_2R^{68B}$, —$S(O)_2N(R^{68A})(R^{68B})$, —$SR^{68A}$, —$S(O)R^{68B}$, —$S(O)_2R^{68B}$, —$NR^{68A}R^{68B}$, —$OR^{68A}$, —C(O)$R^{68B}$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

$R^{68A}$ and $R^{68B}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, $R^{68}$, $R^{69}$, and $R^{70}$ are independently hydrogen, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures). In some embodiments, $R^{68}$, $R^{69}$, and $R^{70}$ are independently hydrogen, substituted or unsubstituted alkyl (e.g. substituted or unsubstituted $C_1$ to $C_{20}$ alkyl), or substituted or unsubstituted heteroalkyl (e.g. substituted or unsubstituted 2 to 20 membered heteroalkyl). In some embodiments, $R^{70}$ is hydrogen, substituted or unsubstituted alkyl (e.g. substituted or unsubstituted $C_1$ to $C_{20}$ alkyl), or substituted or unsubstituted heteroalkyl (e.g. substituted or unsubstituted 2 to 20 membered heteroalkyl) and $R^{68}$ and $R^{69}$ are independently substituted or unsubstituted alkyl (e.g. substituted or unsubstituted $C_1$ to $C_{20}$ alkyl), or substituted or unsubstituted heteroalkyl (e.g. substituted or unsubstituted 2 to 20 membered heteroalkyl). In some embodiments, $R^{70}$ is hydrogen. In some embodiments, $R^{68}$ and $R^{69}$ are independently substituted or unsubstituted alkyl (e.g. substituted or unsubstituted $C_1$ to $C_{20}$ alkyl). In some embodiments, $R^{68}$ and $R^{69}$ are independently substituted or unsubstituted $C_1$ to $C_{10}$ alkyl. In some embodiments, $R^{68}$ and $R^{69}$ are independently substituted or unsubstituted $C_1$ to $C_5$ alkyl. In some embodiments, $R^{68}$ and $R^{69}$ are independently methyl, ethyl, propyl, or tertiary butyl.

In some embodiments, where $R^{68}$, $R^{69}$, $R^{70}$, $R^4$, $R^{68A}$ and $R^{68B}$ are substituted substituents, $R^{68}$, $R^{69}$, $R^{70}$, $R^4$, $R^{68A}$ and $R^{68B}$ are independently substituted with $R^{77}$. For example, in some embodiments, $R^{68}$, $R^{69}$, $R^{70}$, $R^4$, $R^{68A}$ and $R^{68B}$ are independently $R^{77}$-substituted or unsubstituted alkyl (e.g. substituted or unsubstituted $C_1$ to $C_{20}$ alkyl), $R^{77}$-substituted or unsubstituted heteroalkyl (e.g. substituted or unsubstituted 2 to 20 membered heteroalkyl), $R^{77}$-substituted or unsubstituted cycloalkyl (e.g. $C_3$ to $C_{14}$ cycloalkyl including fused ring structures), $R^{77}$-substituted or unsubstituted heterocycloalkyl (e.g. 3 to 14 membered heterocycloalkyl including fused ring structures), $R^{77}$-substituted or unsubstituted aryl (e.g. a $C_6$ to $C_{14}$ aryl including fused ring structures), or $R^{77}$-substituted or unsubstituted heteroaryl (e.g. 5 to 14 membered heteroaryl including fused rings structures).

$R^{77}$ is independently oxo (where permitted according to valency rules), halogen, —CN, —CF$_3$, —NR$^{77A}$—C(O)R$^{77B}$, —NR$^{77A}$—C(O)—OR$^{77B}$, —C(O)NR$^{77A}$R$^{77B}$, —NR$^{77A}$S(O)$_2$R$^{77B}$, —S(O)$_2$N(R$^{77A}$)(R$^{77B}$), —SR$^{77A}$, —S(O)R$^{77B}$, —S(O)$_2$R$^{77B}$, —NR$^{77A}$R$^{77B}$, —OR$^{77A}$, —C(O)R$^{77B}$, $R^{78}$-substituted or unsubstituted alkyl (e.g. substituted or unsubstituted $C_1$ to $C_{20}$ alkyl), $R^{78}$-substituted or unsubstituted heteroalkyl (e.g. substituted or unsubstituted 2 to 20 membered heteroalkyl), $R^{78}$-substituted or unsubstituted cycloalkyl (e.g. $C_3$ to $C_{14}$ cycloalkyl including fused ring structures), $R^{78}$-substituted or unsubstituted heterocycloalkyl (e.g. 3 to 14 membered heterocycloalkyl including fused ring structures), $R^{78}$-substituted or unsubstituted aryl (e.g. a $C_6$ to $C_{14}$ aryl including fused ring structures), or $R^{78}$-substituted or unsubstituted heteroaryl (e.g. 5 to 14 membered heteroaryl including fused rings structures).

$R^{77A}$ and $R^{77B}$ are independently hydrogen, $R^{78}$-substituted or unsubstituted alkyl (e.g. substituted or unsubstituted $C_1$ to $C_{20}$ alkyl), $R^{78}$-substituted or unsubstituted heteroalkyl (e.g. substituted or unsubstituted 2 to 20 membered heteroalkyl), $R^{78}$-substituted or unsubstituted cycloalkyl (e.g. $C_3$ to $C_{14}$ cycloalkyl including fused ring structures), $R^{78}$-substituted or unsubstituted heterocycloalkyl (e.g. 3 to 14 membered heterocycloalkyl including fused ring structures), $R^{78}$-substituted or unsubstituted aryl (e.g. a $C_6$ to $C_{14}$ aryl including fused ring structures), or $R^{78}$-substituted or unsubstituted heteroaryl (e.g. 5 to 14 membered heteroaryl including fused rings structures).

$R^{78}$ is independently oxo (where permitted according to valency rules), halogen, —CN, —CF$_3$, —NR$^{78A}$—C(O)R$^{78B}$, —NR$^{78A}$—C(O)—OR$^{78B}$, —C(O)NR$^{78A}$R$^{78B}$, —NR$^{78A}$S(O)$_2$R$^{78B}$, —S(O)$_2$N(R$^{78A}$)(R$^{78B}$), —SR$^{78A}$, —S(O)R$^{78B}$, —S(O)$_2$R$^{78B}$, —NR$^{78A}$R$^{78B}$, —OR$^{78A}$, —C(O)R$^{78B}$, $R^{79}$-substituted or unsubstituted alkyl (e.g. substituted or unsubstituted $C_1$ to $C_{20}$ alkyl), $R^{79}$-substituted or unsubstituted heteroalkyl (e.g. substituted or unsubstituted 2 to 20 membered heteroalkyl), $R^{79}$-substituted or unsubstituted cycloalkyl (e.g. $C_3$ to $C_{14}$ cycloalkyl including fused ring structures), $R^{79}$-substituted or unsubstituted heterocycloalkyl (e.g. 3 to 14 membered heterocycloalkyl including fused ring structures), $R^{79}$-substituted or unsubstituted aryl (e.g. a $C_6$ to $C_{14}$ aryl including fused ring structures), or $R^{79}$-substituted or unsubstituted heteroaryl (e.g. 5 to 14 membered heteroaryl including fused rings structures).

$R^{78A}$ and $R^{78B}$ are independently hydrogen, $R^{79}$-substituted or unsubstituted alkyl (e.g. substituted or unsubstituted $C_1$ to $C_{20}$ alkyl), $R^{79}$-substituted or unsubstituted heteroalkyl (e.g. substituted or unsubstituted 2 to 20 membered heteroalkyl), $R^{79}$-substituted or unsubstituted cycloalkyl (e.g. $C_3$ to $C_{14}$ cycloalkyl including fused ring structures), $R^{79}$-substituted or unsubstituted heterocycloalkyl (e.g. 3 to 14 membered heterocycloalkyl including fused ring structures), $R^{79}$-substituted or unsubstituted aryl (e.g. a $C_6$ to $C_{14}$ aryl including fused ring structures), or $R^{79}$-substituted or unsubstituted heteroaryl (e.g. 5 to 14 membered heteroaryl including fused rings structures).

$R^{79}$ is independently oxo (where permitted according to valency rules), halogen, —CN, —CF$_3$, —NR$^{79A}$—C(O)R$^{79B}$, —NR$^{79A}$—C(O)—OR$^{79B}$, —C(O)NR$^{79A}$R$^{79B}$, —NR$^{79A}$S(O)$_2$R$^{79B}$, —S(O)$_2$N(R$^{79A}$)(R$^{79B}$), —SR$^{79A}$, —S(O)R$^{79B}$, —S(O)$_2$R$^{79B}$, —NR$^{79A}$R$^{79B}$, —OR$^{79A}$, —C(O)R$^{79B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{79A}$ and $R^{79B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{68}$ and $R^{69}$ are independently halogen, —CN, —CF$_3$, —OH, —NH$_2$, $R^{77}$-substituted or unsubstituted alkyl (e.g. substituted or unsubstituted $C_1$ to $C_{20}$ alkyl) or $R^{77}$-substituted or unsubstituted heteroalkyl (e.g. substituted or unsubstituted 2 to 20 membered heteroalkyl). $R^{68}$ and $R^{69}$ may also independently be $R^{77}$-substituted or unsubstituted $C_1$ to $C_{10}$ alkyl. $R^{68}$ and $R^{69}$ may also independently be $R^{77}$-substituted or unsubstituted $C_1$ to $C_5$ alkyl.

In some embodiments, $R^{70}$ are independently hydrogen, halogen, —CN, —CF$_3$, —OH, —NH$_2$, $R^{77}$-substituted or unsubstituted alkyl (e.g. substituted or unsubstituted $C_1$ to $C_{20}$ alkyl) or $R^{77}$-substituted or unsubstituted heteroalkyl (e.g. substituted or unsubstituted 2 to 20 membered heteroalkyl). $R^{70}$ may also independently be hydrogen, $R^{77}$-substituted or unsubstituted $C_1$ to $C_{10}$ alkyl. $R^{70}$ may also independently be hydrogen or $R^{77}$-substituted or unsubstituted $C_1$ to $C_5$ alkyl.

$L^6$ is -L$^7$-N(R$^{71}$)—C(O)—N(R$^{72}$)-L$^8$-, -L$^7$-N(R$^{61}$)—C(O)-L$^8$- or -L$^7$-C(O)—N(R$^{71}$)-L$^8$-. $L^7$ and $L^8$ are independently a bond or substituted or unsubstituted alkylene (e.g. substituted or unsubstituted $C_1$ to $C_{20}$ alkylene). In some embodiments, $L^7$ and $L^8$ are independently a bond or substituted or unsubstituted $C_1$ to $C_{10}$ alkylene. In other embodiments, $L^7$ and $L^8$ are independently a bond or substituted or unsubstituted $C_1$ to $C_5$ alkylene. $L^7$ and $L^8$ may also independently be a bond or unsubstituted methylene. In some embodiments, $L^7$ and $L^8$ are a bond.

In some embodiments, where $L^7$ and $L^8$ are substituted, $L^7$ and $L^8$ are independently substituted with $R^{73}$. For example, in some embodiments, $L^7$ and $L^8$ are independently $R^{73}$-substituted or unsubstituted alkyl (e.g. substituted or unsubstituted $C_1$ to $C_{20}$ alkyl). $R^{73}$ is independently oxo (where permitted according to valency rules), halogen, —CN, —CF$_3$, —NR$^{73A}$—C(O)R$^{73B}$, —NR$^{73A}$—C(O)—OR$^{73B}$, —C(O)NR$^{73A}$R$^{73B}$, —NR$^{73A}$S(O)$_2$R$^{73B}$, —S(O)$_2$N(R$^{73A}$)(R$^{73B}$), —SR$^{73A}$, —S(O)R$^{73B}$, —S(O)$_2$R$^{73B}$, —NR$^{73A}$, —NR$^{73A}$R$^{73B}$, —OR$^{73A}$, —C(O)R$^{73B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures). $R^{73A}$ and $R^{73B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{71}$ and $R^{72}$ are independently hydrogen, —CN, —$CF_3$, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused ring structures), substituted or unsubstituted aryl (e.g. a $C_6$ to $C_{14}$ aryl including fused ring structures), or substituted or unsubstituted heteroaryl (e.g. 5 to 14 membered heteroaryl including fused rings structures).

In some embodiments, where $R^{71}$ and $R^{72}$ are a substituted substituent, $R^{71}$ and $R^{72}$ are independently substituted with $R^{80}$. For example, in some embodiments, $R^{71}$ and $R^{72}$ are independently $R^{80}$-substituted or unsubstituted alkyl (e.g. substituted or unsubstituted $C_1$ to $C_{20}$ alkyl), $R^{80}$-substituted or unsubstituted heteroalkyl (e.g. substituted or unsubstituted 2 to 20 membered heteroalkyl), $R^{80}$-substituted or unsubstituted cycloalkyl (e.g. $C_3$ to $C_{14}$ cycloalkyl including fused ring structures), $R^{80}$-substituted or unsubstituted heterocycloalkyl (e.g. 3 to 14 membered heterocycloalkyl including fused ring structures), $R^{80}$-substituted or unsubstituted aryl (e.g. a $C_6$ to $C_{14}$ aryl including fused ring structures), or $R^{80}$-substituted or unsubstituted heteroaryl (e.g. 5 to 14 membered heteroaryl including fused rings structures).

$R^{80}$ is oxo (where permitted according to valency rules), halogen, —CN, —$CF_3$, —$NR^{80A}$—C(O)$R^{80B}$, —$NR^{80A}$—C(O)—$OR^{80B}$, —C(O)$NR^{80A}R^{80B}$, —$NR^{80A}S(O)_2R^{80B}$, —$S(O)_2N(R^{80A})(R^{80B})$, —$SR^{80A}$, —$S(O)R^{80B}$, —$S(O)_2R^{80B}$, —$NR^{80A}R^{80B}$, —$OR^{80A}$, —C(O)$R^{80B}$, $R^{81}$-substituted or unsubstituted alkyl (e.g. substituted or unsubstituted $C_1$ to $C_{20}$ alkyl), $R^{81}$-substituted or unsubstituted heteroalkyl (e.g. substituted or unsubstituted 2 to 20 membered heteroalkyl), $R^{81}$-substituted or unsubstituted cycloalkyl (e.g. $C_3$ to $C_{14}$ cycloalkyl including fused ring structures), $R^{41}$-substituted or unsubstituted heterocycloalkyl (e.g. 3 to 14 membered heterocycloalkyl including fused ring structures), $R^{81}$-substituted or unsubstituted aryl (e.g. a $C_6$ to $C_{14}$ aryl including fused ring structures), or $R^{81}$-substituted or unsubstituted heteroaryl (e.g. 5 to 14 membered heteroaryl including fused rings structures).

$R^{80A}$ and $R^{80B}$ are independently hydrogen, $R^{81}$-substituted or unsubstituted alkyl (e.g. substituted or unsubstituted $C_1$ to $C_{20}$ alkyl), $R^{81}$-substituted or unsubstituted heteroalkyl (e.g. substituted or unsubstituted 2 to 20 membered heteroalkyl), $R^{81}$-substituted or unsubstituted cycloalkyl (e.g. $C_3$ to $C_{14}$ cycloalkyl including fused ring structures), $R^{81}$-substituted or unsubstituted heterocycloalkyl (e.g. 3 to 14 membered heterocycloalkyl including fused ring structures), $R^{81}$-substituted or unsubstituted aryl (e.g. a $C_6$ to $C_{14}$ aryl including fused ring structures), or $R^{81}$-substituted or unsubstituted heteroaryl (e.g. 5 to 14 membered heteroaryl including fused rings structures).

$R^{81}$ is independently oxo (where permitted according to valency rules), halogen, —CN, —$CF_3$, —$NR^{81A}$, —C(O)$R^{81B}$, —$NR^{81A}$—C(O)—$OR^{81B}$, —C(O)$NR^{81A}R^{81B}$, —$NR^{81A}S(O)_2R^{81B}$, —$S(O)_2N(R^{81A})(R^{82B})$, —$SR^{81A}$, —$S(O)R^{81B}$, —$S(O)_2R^{81B}$, —$NR^{81A}R^{81B}$, —$OR^{81A}$, —C(O)$R^{81B}$, $R^{82}$-substituted or unsubstituted alkyl (e.g. substituted or unsubstituted $C_1$ to $C_{20}$ alkyl), $R^{82}$-substituted or unsubstituted heteroalkyl (e.g. substituted or unsubstituted 2 to 20 membered heteroalkyl), $R^{82}$-substituted or unsubstituted cycloalkyl (e.g. $C_3$ to $C_{14}$ cycloalkyl including fused ring structures), $R^{82}$-substituted or unsubstituted heterocycloalkyl (e.g. 3 to 14 membered heterocycloalkyl including fused ring structures), $R^{82}$-substituted or unsubstituted aryl (e.g. a $C_6$ to $C_{14}$ aryl including fused ring structures), or $R^{82}$-substituted or unsubstituted heteroaryl (e.g. 5 to 14 membered heteroaryl including fused rings structures).

$R^{81A}$ and $R^{81B}$ are independently hydrogen, $R^{82}$-substituted or unsubstituted alkyl (e.g. substituted or unsubstituted $C_1$ to $C_{20}$ alkyl), $R^{82}$-substituted or unsubstituted heteroalkyl (e.g. substituted or unsubstituted 2 to 20 membered heteroalkyl), $R^{82}$-substituted or unsubstituted cycloalkyl (e.g. $C_3$ to $C_{14}$ cycloalkyl including fused ring structures), $R^{82}$-substituted or unsubstituted heterocycloalkyl (e.g. 3 to 14 membered heterocycloalkyl including fused ring structures), $R^{82}$-substituted or unsubstituted aryl (e.g. a $C_6$ to $C_{14}$ aryl including fused ring structures), or $R^{82}$-substituted or unsubstituted heteroaryl (e.g. 5 to 14 membered heteroaryl including fused rings structures).

$R^{82}$ is independently oxo (where permitted according to valency rules), halogen, —CN, —$CF_3$, —$NR^{82A}$—C(O)$R^{82B}$, —$NR^{82A}$—C(O)—$OR^{82B}$, —C(O)$NR^{82A}R^{82B}$, —$NR^{82A}S(O)_2R^{82B}$, —$S(O)_2N(R^{82A})(R^{82B})$, —$SR^{82A}$, —$S(O)R^{82B}$, —$S(O)_2R^{82B}$, —$NR^{82A}R^{82B}$, —$OR^{82A}$, —C(O)$R^{82B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

$R^{82A}$ and $R^{82B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, $R^{71}$ and $R^{72}$ are independently hydrogen, halogen, —CN, —$CF_3$, —OH, —$NH_2$, $R^{80}$-substituted or unsubstituted $C_1$ to $C_5$ alkyl, or $R^{80}$-substituted or unsubstituted 2 to 6 membered heteroalkyl, wherein $R^{80}$ is oxo, halogen, —CN, —$CF_3$, —OH, —$NH_2$, unsubstituted $C_1$ to $C_5$ alkyl, unsubstituted 2 to 6 membered heteroalkyl, or unsubstituted $C_3$ to $C_6$ cycloalkyl (e.g. cyclopropyl). In some embodiments, $R^{71}$ and $R^{72}$ are independently hydrogen, methyl, ethyl, propyl, tertiary butyl, or cyclopropyl methylene (—$CH_2$-cyclopropyl). In some embodiments, $R^{61}$ and $R^{62}$ are hydrogen.

L⁴ and L⁵ are independently a bond or substituted or unsubstituted alkylene (e.g. substituted or unsubstituted $C_1$ to $C_{20}$ alkylene). In some embodiments, L⁴ and L⁵ are independently a bond or substituted or unsubstituted $C_1$ to $C_{10}$ alkylene. In other embodiments, L⁴ and L⁵ are independently a bond or unsubstituted $C_1$ to $C_5$ alkylene. L⁴ and L⁵ may also independently be a bond or unsubstituted methylene. In some embodiments, L⁵ is a bond and L⁴ is substituted or unsubstituted alkylene (e.g. substituted or unsubstituted $C_1$ to $C_{20}$ alkylene). In some embodiments, L⁵ is a bond and L⁴ is unsubstituted $C_1$ to $C_5$ alkylene. In some embodiments, L⁵ is a bond and L⁴ is unsubstituted methylene.

In some embodiments, where L⁴ and L⁵ are substituted, L⁴ and L⁵ are independently substituted with $R^{83}$. For example, in some embodiments, L⁴ and L⁵ are independently $R^{83}$-substituted or unsubstituted alkyl (e.g. substituted or unsubstituted $C_1$ to $C_{20}$ alkyl). $R^{83}$ is independently oxo (where permitted according to valency rules), halogen, —CN, —CF₃, —NR$^{83A}$—C(O)R$^{83B}$, —NR$^{83A}$—C(O)—OR$^{83B}$, —C(O)NR$^{83A}$R$^{83B}$, —NR$^{83A}$S(O)₂R$^{83B}$, —S(O)₂N(R$^{83A}$)(R$^{83B}$), —SR$^{83A}$, —S(O)R$^{83B}$, —S(O)₂R$^{83B}$, —NR$^{83A}$R$^{83B}$, —OR$^{83A}$, —C(O)R$^{83B}$, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures). $R^{83A}$ and $R^{83B}$ are independently hydrogen, unsubstituted alkyl (e.g. substituted or unsubstituted $C_1$ to $C_{20}$ alkyl), unsubstituted heteroalkyl (e.g. substituted or unsubstituted 2 to 20 membered heteroalkyl), unsubstituted cycloalkyl (e.g. $C_3$ to $C_{14}$ cycloalkyl including fused ring structures), unsubstituted heterocycloalkyl (e.g. 3 to 14 membered heterocycloalkyl including fused ring structures), unsubstituted aryl (e.g. a $C_6$ to $C_{14}$ aryl including fused ring structures), or unsubstituted heteroaryl (e.g. 5 to 14 membered heteroaryl including fused rings structures).

In some embodiments, each substituted group described above in the compounds of Formulae (IA) to (XXIIIA), (IB) to (XXIIIB) and (XXIV) is substituted with at least one substituent group. More specifically, in some embodiments, each substituted alkyl, substituted heteroalkyl, substituted cycloalkyl, substituted heterocycloalkyl, substituted aryl, and/or substituted heteroaryl described above in the compounds of Formulae (IA) to (XXIIIA), (IB) to (XXIIIB) and (XXIV) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (IA) to (XXIIIA), (IB) to (XXIIIB) and (XXIV), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and/or each substituted or unsubstituted heterocycloalkyl is a substituted or unsubstituted 5 to 7 membered heterocycloalkyl.

In another embodiment, the compounds useful in the methods and pharmaceutical compositions disclosed herein include any one or all of the compounds set forth in Table 1 and Table 2. In another embodiment, the compounds useful in the methods and pharmaceutical compositions disclosed herein include any one or all of the compounds set forth in Table 1. In another embodiment, the compounds useful in the methods and pharmaceutical compositions disclosed herein include any one or all of the compounds set forth in Table 2. In another embodiment, the compounds useful in the methods and pharmaceutical compositions disclosed herein include any one or all of the compounds set forth in Examples 2 to 61. In some related embodiments, the compounds useful in the methods and pharmaceutical compositions disclosed herein do not include the compounds set forth in Example 62. In some related embodiments, the compounds useful in the methods and pharmaceutical compositions disclosed herein do not include the following compound:

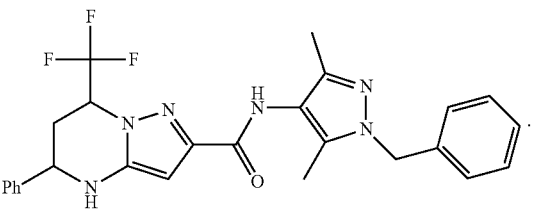 [SMILES: Cc1nn(Cc2ccccc2)c(C)c1NC(=O)c1cc2n(n1)C(C(F)(F)F)CC(c1ccccc1)N2]

III. Methods

In one aspect, a method of reducing a Wnt-mediated effect on a cell is provided. The method includes contacting the cell with an effective amount of a compound as set forth herein (e.g., —Section II above or Examples below, such as Formulae (IA) to (XXIIIA), (IB) to (XXIIIB) and (XXIV) and embodiments thereof). For example, the method of reducing a Wnt-mediated effect on a cell may include contacting the cell with an effective amount of a compound of Formula (IA) or (IB) as defined above, including embodiments thereof. Thus, any of the Formulae or embodiments thereof set forth above may be applicable to the method of reducing a Wnt-mediated effect on a cell. The Wnt-mediated effect on a cell is reduced relative the amount of Wnt-medatiated effect on the cell in the absence of the compound.

In one embodiment, the Wnt-mediated effect is an increase in degradation of Pygopus (relative to the degradation of Pygopus in the absence of the compound), an increase in degradation of non-oncogenic beta-Catenin (relative to the degradation of beta-Catenin in the absence of the compound), a decrease in degradation of Axin (relative to the degradation of Axin in the absence of the compound), a decrease in activity of Myc (relative to the activity of Myc in the absence of the compound), a decrease in activity of CD44 (relative to the activity of CD44 in the absence of the compound), a decrease in activity of Axin2 (relative to the activity of Axin 2 in the absence of the compound), a decrease in activity of Bcl-9 (relative to the activity of Bcl-9 in the absence of the compound), and/or a decrease in activity of cyclin D (relative to the activity of cyclin D in the absence of the compound). These Wnt-mediated effects may be assessed using standard assays known in the art.

In another aspect, a method of treating cancer in a subject in need thereof is provided. The method includes administering to the subject an effective amount of a compound as set forth hereinin (e.g., —Section II above or Examples below, such as. Formulae (IA) to (XXIIIA), (IB) to (XXIIIB) and (XXIV) and embodiments thereof), or pharmaceutically acceptable salt thereof. The compound may optionally be administered with a pharmaceutically acceptable excipient. Therefore, the compound may be administered as a pharmaceutical composition as set forth below. For example, the method of treating cancer may include administering to the subject an effective amount of a compound of Formula (IB) or (IA) as defined above, including embodiments thereof. Thus, any of the Formulae or embodiments thereof set forth above may be applicable to the method of treating cancer.

In some embodiments, the cancer is colon cancer, breast cancer, gastric cancer, brain cancer, head and neck cancer, liver cancer, lung cancer, lymphoma, melanoma, pancreatic cancer or prostate cancer. In some embodiment, the subject is a mammalian subject. In certain embodiments, the subject is a human subject (e.g. a cancer patient). Moreover, the compound may be administered in conjunction with other known cancer therapies, including known chemotherapeutic compounds.

IV. Pharmaceutical Compositions

In another aspect, the present invention provides a pharmaceutical composition including a pharmaceutically acceptable excipient and a compound as set forth herein (e.g., Section II above or Examples below, such as Formulae (IA) to (XXIIIA), Formulae (IB) to (XXIIIB) and (XXIV)). In some embodiments, the pharmaceutical composition includes a therapeutically effective amount of the compound. Desired therapeutic results are described above in the Methods section.

For example, in some embodiments, the pharmaceutical composition includes a pharmaceutically acceptable excipient and a compound of Formula (IIA) or (IIB) or embodiments thereof. In other embodiments, the pharmaceutical composition includes a pharmaceutically acceptable excipient and a compound of Formula (IIIA) or (IIIB) or embodiments thereof. In other embodiments, the pharmaceutical composition includes a pharmaceutically acceptable excipient and a compound of Formula (IVA) or (IVB) or embodiments thereof. In other embodiments, the pharmaceutical composition includes a pharmaceutically acceptable excipient and a compound of Formula (VA) or (VB) or embodiments thereof. In other embodiments, the pharmaceutical composition includes a pharmaceutically acceptable excipient and a compound of Formula (VIA) or (VIB) or embodiments thereof. In other embodiments, the pharmaceutical composition includes a pharmaceutically acceptable excipient and a compound of Formula (VIIA) or (VIIB) or embodiments thereof. In other embodiments, the pharmaceutical composition includes a pharmaceutically acceptable excipient and a compound of Formula (VIIIA) or (VIIIB) or embodiments thereof. In other embodiments, the pharmaceutical composition includes a pharmaceutically acceptable excipient and a compound of Formula (IXA) or (IXB) or embodiments thereof. In other embodiments, the pharmaceutical composition includes a pharmaceutically acceptable excipient and a compound of Formula (XA) or (XB) or embodiments thereof. In other embodiments, the pharmaceutical composition includes a pharmaceutically acceptable excipient and a compound of Formula (XIA) or (XIB) or embodiments thereof. In other embodiments, the pharmaceutical composition includes a pharmaceutically acceptable excipient and a compound of Formula (XIIA) or (XIIB) or embodiments thereof. In other embodiments, the pharmaceutical composition includes a pharmaceutically acceptable excipient and a compound of Formula (XIIIA) or (XIIIB) or embodiments thereof. In other embodiments, the pharmaceutical composition includes a pharmaceutically acceptable excipient and a compound of Formula (XIVA) or (XIVB) or embodiments thereof. In other embodiments, the pharmaceutical composition includes a pharmaceutically acceptable excipient and a compound of Formula (XVA) or (XVB) or embodiments thereof. In other embodiments, the pharmaceutical composition includes a pharmaceutically acceptable excipient and a compound of Formula (XVIA) or (XVIB) or embodiments thereof. In other embodiments, the pharmaceutical composition includes a pharmaceutically acceptable excipient and a compound of Formula (XXIV) or embodiments thereof.

As described above, pharmaceutical compositions are provided that include the compound and pharmaceutically acceptable excipient, for example, in admixture with a pharmaceutically acceptable excipient. One of skill in the art will recognize that the pharmaceutical compositions may include the pharmaceutically acceptable salts of the compounds described herein (e.g. in Section II).

In therapeutic and/or diagnostic applications, the compounds of the invention can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds disclosed herein are effective over a wide dosage range. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the composition. Alternatively, these agents may be part of a single dosage form, mixed together with the compound in a single composition.

Dosage forms (compositions) suitable for internal administration contain from about 1.0 milligram to about 5000 milligrams of active ingredient per unit. In these pharmaceutical compositions, the active ingredient may be present in an amount of about 0.5 to about 95% by weight based on the total weight of the composition. Another convention for denoting the dosage form is in mg per meter squared (mg/m$^2$) of body surface area (BSA). Typically, an adult will have approximately 1.75 m$^2$ of BSA. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one tablet or capsule will provide a dose of 25 mg per kg for that patient. It will provide a dose of only 12.5 mg/kg for a 80 kg patient.

By way of general guidance, for humans a dosage of as little as about 1 milligrams (mg) per kilogram (kg) of body weight and up to about 10000 mg per kg of body weight is suitable as a therapeutically effective dose. Preferably, from about 5 mg/kg to about 2500 mg/kg of body weight is used. Other preferred doses range between 25 mg/kg to about 1000 mg/kg of body weight. However, a dosage of between about 2 milligrams (mg) per kilogram (kg) of body weight to about 400 mg per kg of body weight is also suitable for treating some cancers.

Intravenously, the most preferred rates of administration can range from about 1 to about 1000 mg/kg/minute during a constant rate infusion. A pharmaceutical composition of the present invention can be administered in a single daily dose, or the total daily dosage may be administered in divided doses of two, three, or four times daily. The composition is generally given in one or more doses on a daily basis or from one to three times a week.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the compounds described above are equally applicable to the methods and pharmaceutical compositions described herein. References cited throughout this application are incorporated by reference herein in their entirety for all purposes, whether previously specifically incorporated or not.

V. EXAMPLES

The following examples are intended to illustrate certain embodiments of the invention and not to limit the scope of the invention.

Exemplary Syntheses. Synthesis of compounds useful for the methods described herein generally followed synthetic routes known in the art and/or described herein. Using chemical techniques known in the art and the teaching provided herein, a person having ordinary skill in the art will immediately understand appropriate synthesis routes to the compounds disclosed herein (e.g. the Formulae and embodiments disclosed in Section II). An exemplary synthetic is shown below in Scheme 1.

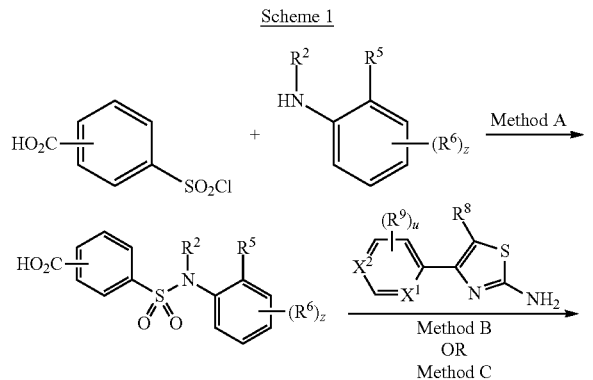

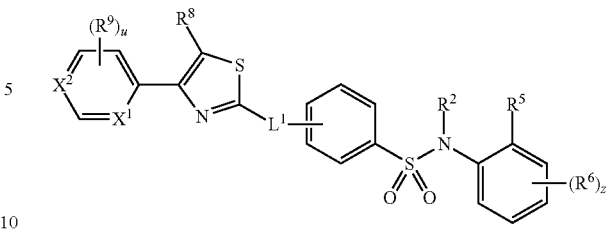

Scheme 1 (Method A). A solution of the acid (1 equiv) in MeOH (10 vol) was cooled to 0° C. and the amine (3 equiv) was added. The reaction mixture was stirred at 0° C. for 1 hour and 14 hours at room temperature. The reaction mixture was concentrated and partitioned between EtOAc and 0.5 M HCl solution. The organics were separated and dried over $MgSO_4$. The resulting dark solid was partitioned between $Et_2O$ and 0.5 M NaOH solution. The aqueous layer was separated and acidified to pH=1 with conc. HCl. The resulting suspension was extracted with EtOAc. The organic layers were combined, dried over $MgSO_4$ and concentrated. The resulting solid was triturated with diethyl ether to provide the desired acid.

Scheme 1 (Method B). To a solution of the acid (1.2 equiv), the amine (1 equiv), and HOBt (1.5 equiv) in DMF (5 vol) was added DIPEA (2.5 equiv) and EDC (1.5 equiv). The reaction mixture was stirred at room temperature for 48 hours. The reaction mixture was concentrated, partitioned between EtOAc and 5% lithium chloride solution. The organic layers were combined, dried over $MgSO_4$ and concentrated. The resulting dark oil was purified by column chromatography.

Scheme 1 (Method C). To a solution of the acid (1.2 equiv) and the amine (1 equiv) in DMF (5 vol) was added DIPEA (3 equiv) and pybop (1.5 equiv). The reaction mixture was stirred at room temperature or 40° C. for 48-96 hours. The reaction mixture was concentrated and partitioned between EtOAc and 5% lithium chloride solution. The organic layers were combined, dried over $MgSO_4$ and concentrated. The resulting dark oil was purified by column chromatography.

Acids useful in the synthesis of compounds described herein are exemplified, but not limited to, the acids shown below.

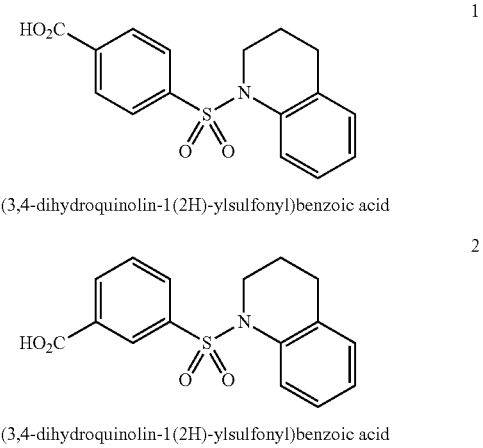

4-(3,4-dihydroquinolin-1(2H)-ylsulfonyl)benzoic acid 3-(3,4-dihydroquinolin-1(2H)-ylsulfonyl)benzoic acid

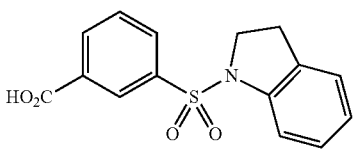
3-(indolin-1-ylsulfonyl)benzoic acid

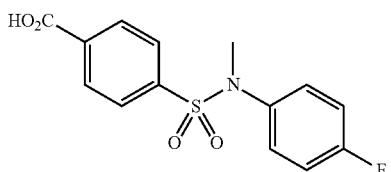
4-(N-(4-fluorophenyl)-N-methylsulfamoy)benzoic acid

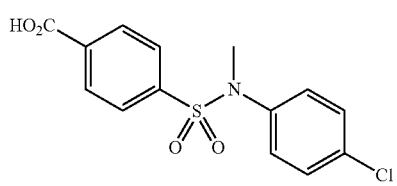
4-(N-(4-chlorophenyl)-N-methylsulfamoy)benzoic acid

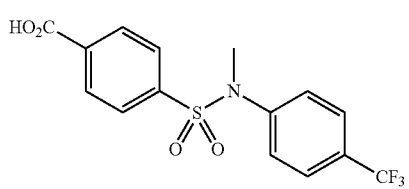
4-(N-methyl-N-(4-(trifluoromethyl)phenyl)sulfamoyl)benzoic acid

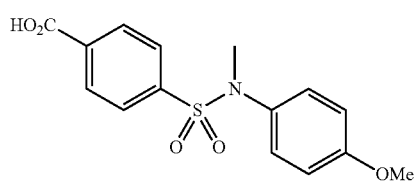
4-(N-(4-methoxphenyl)-N-methylsulfamoyl)benzoic acid

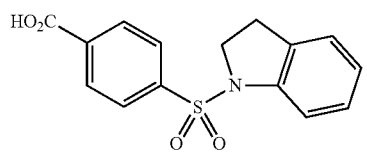
4-(indolin-1-ylsulfonyl)benzoic acid

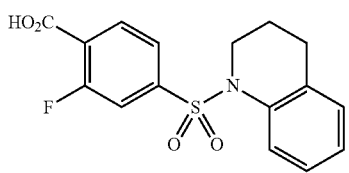
4-(3,4-dihydroquinolin-1(2H)-ylsulfonyl)-2-fluorobenzoic acid

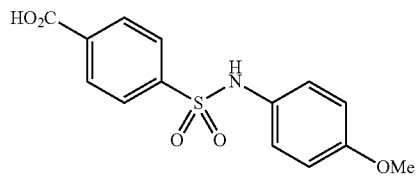
4-(N-(4-methoxyphenyl)sulfamonyl)benzoic acid

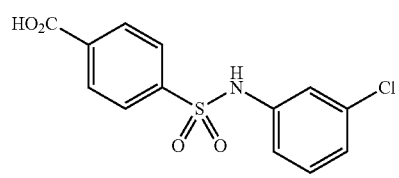
4-(N-(3-chlorophenyl)sulfamonyl)benzoic acid

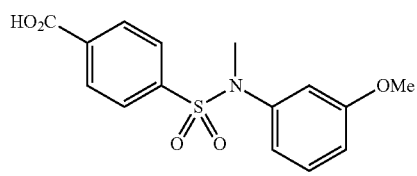
4-(N-(3-methoxyphenyl)-N-methylsulfamonyl)benzoic acid

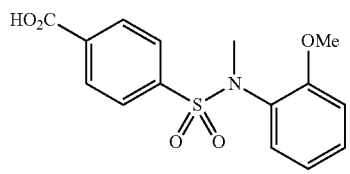
4-(N-(2-methoxyphenyl)-N-methylsulfamonyl)benzoic acid

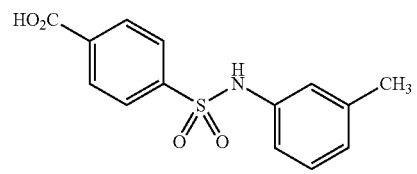
4-(N-m-tolylsulfamoyl)benzoic acid

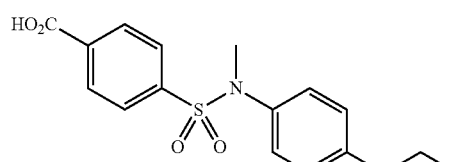
4-(N-(4-(benzyloxy)phenyl)-N-methylsulfamoyl)benzoic acid

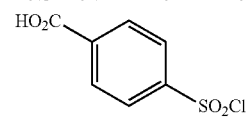
4-(chlorosulfonyl)benzoic acid

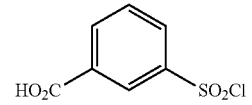
3-(chlorosulfonyl)benzoic acid

Amines useful in the synthesis of compounds described herein are exemplified by the compounds shown following.
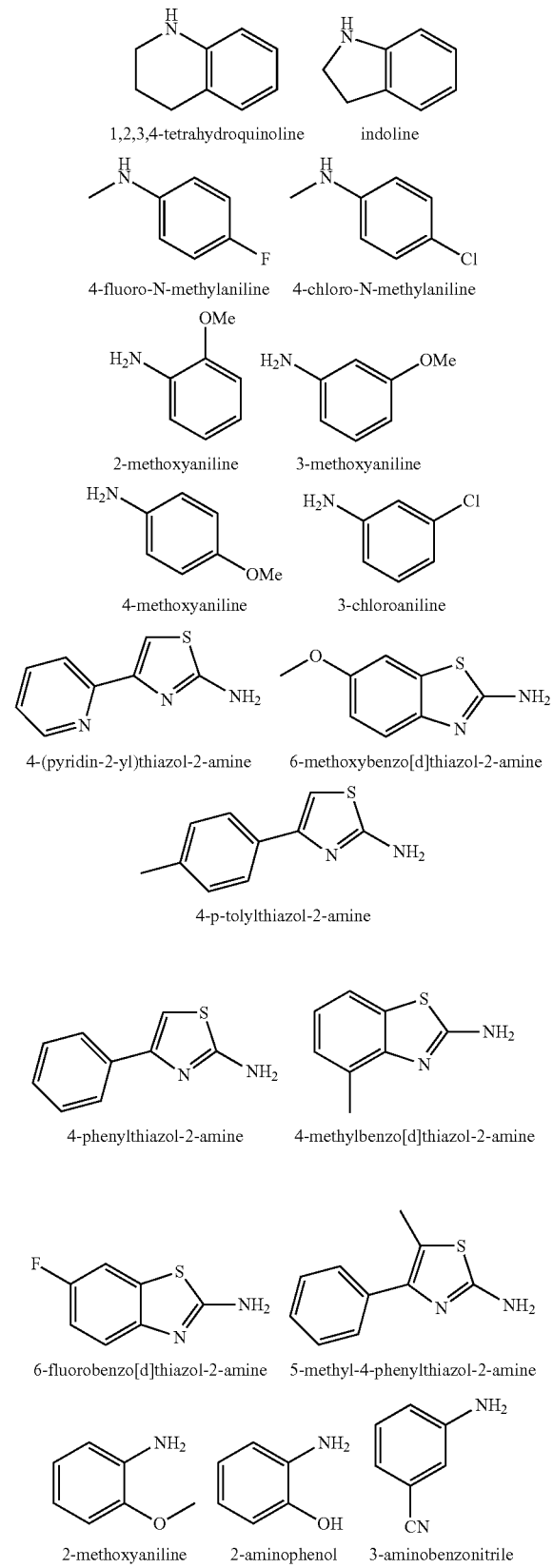
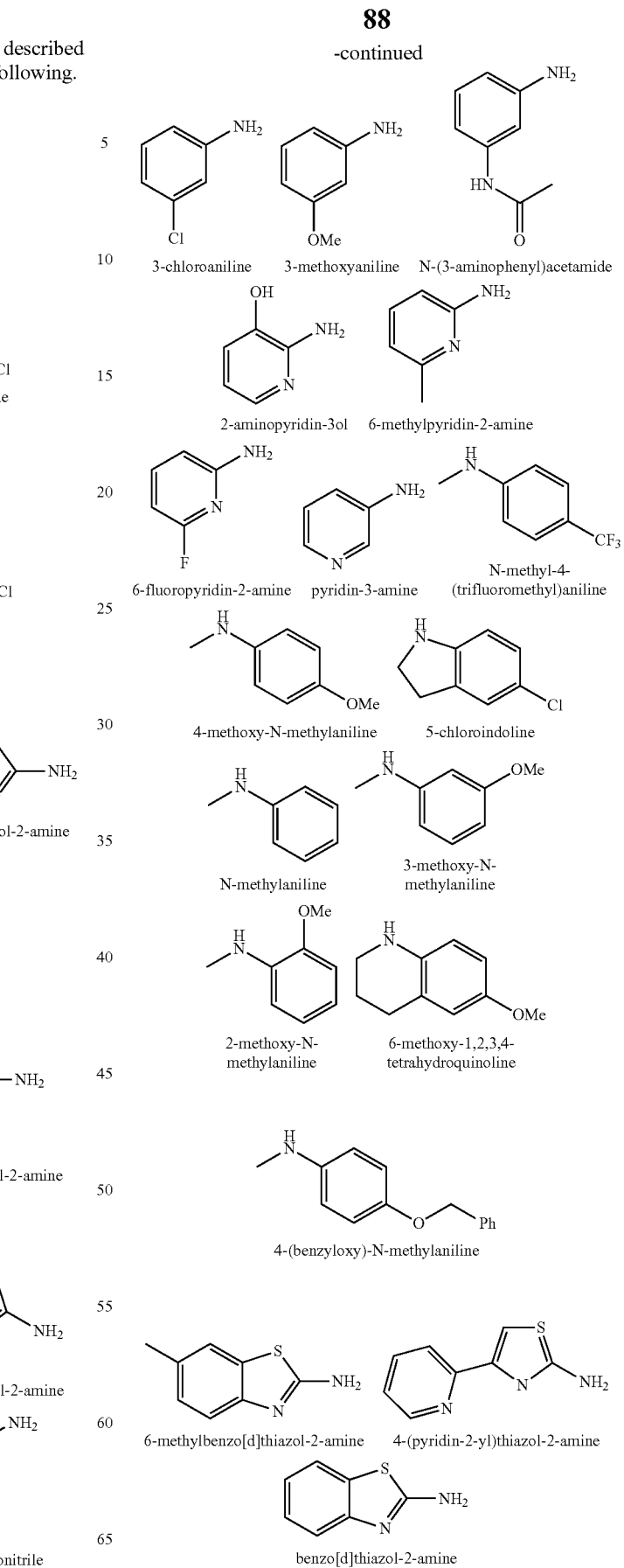

89
-continued

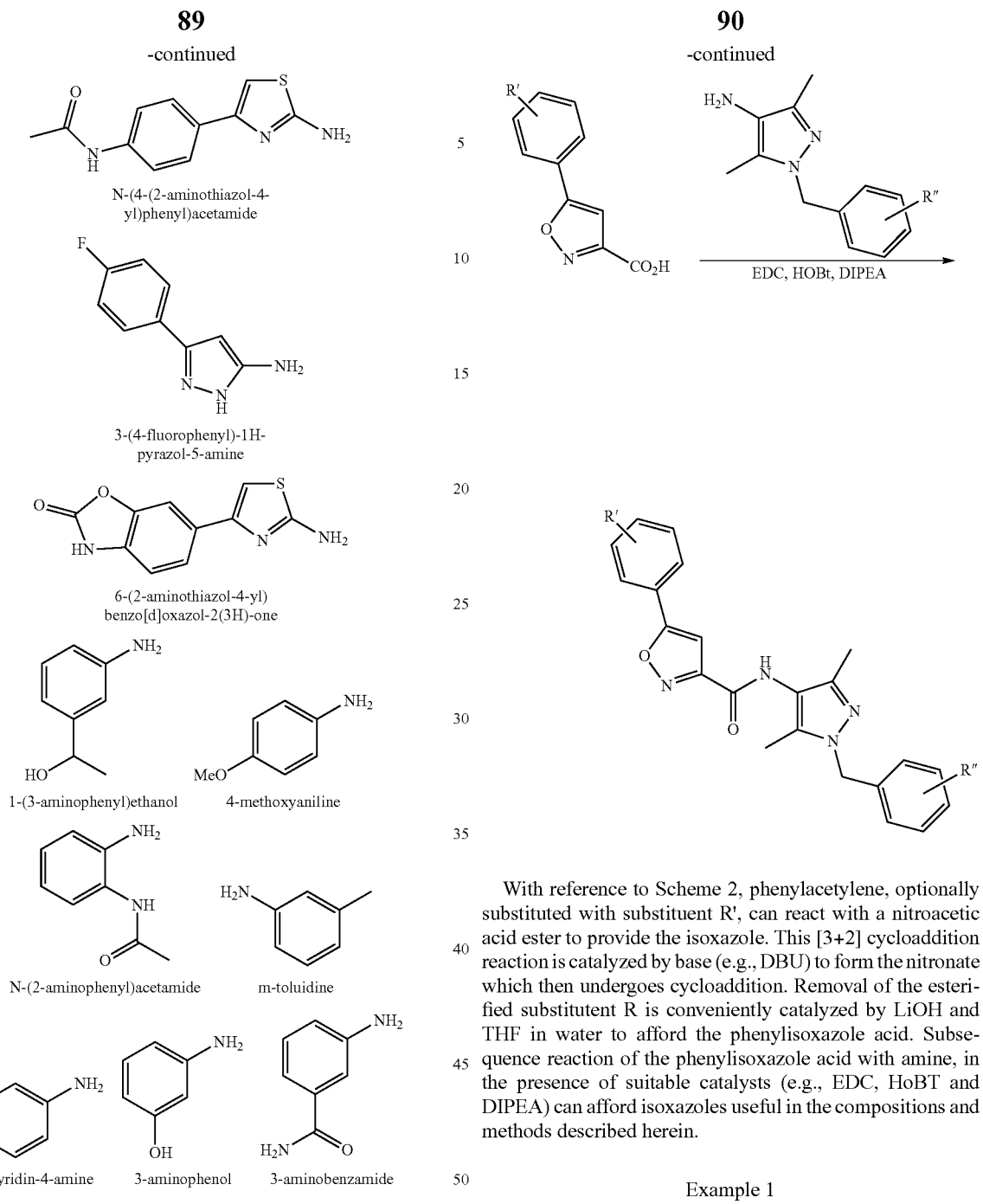

Synthesis of isoxazole containing compounds useful in the compositions and methods described herein can follow synthetic procedures known in the art and/or described herein. An exemplary synthetic pathway is provided in Scheme 2 following.

Scheme 2

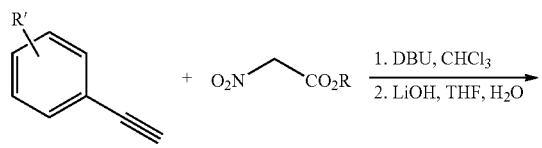

90
-continued

With reference to Scheme 2, phenylacetylene, optionally substituted with substituent R', can react with a nitroacetic acid ester to provide the isoxazole. This [3+2] cycloaddition reaction is catalyzed by base (e.g., DBU) to form the nitronate which then undergoes cycloaddition. Removal of the esterified substituent R is conveniently catalyzed by LiOH and THF in water to afford the phenylisoxazole acid. Subsequence reaction of the phenylisoxazole acid with amine, in the presence of suitable catalysts (e.g., EDC, HoBT and DIPEA) can afford isoxazoles useful in the compositions and methods described herein.

Example 1

4-(3,4-dihydroquinolin-1(2H)-ylsulfonyl)-N-(4-(pyridin-2-yl)thiazol-2-yl)benzamide

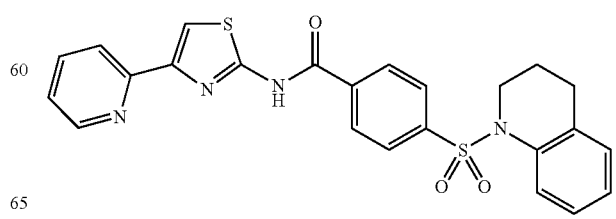

4-(3,4-dihydroquinolin-1(2H)-ylsulfonyl)benzoic acid (1)

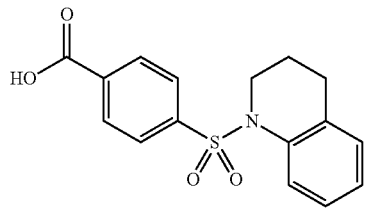 [SMILES: O=C(O)c1ccc(S(=O)(=O)N2CCCc3ccccc32)cc1]

4-(chlorosulfonyl)benzoic acid (0.5 g, 2.27 mmol) was treated with m-toluidine (729 mg, 6.8 mmol) using method A to give 4-(3,4-dihydroquinolin-1(2H)-ylsulfonyl)benzoic acid as an off white solid. Yield: 310 mg (43%). $^1$H-NMR: 8.04 (d, J=8.7 Hz, 2H), 7.70 (d, J=8.7 Hz, 2H), 7.58 (d, J=8.0 Hz, 1H), 7.22-7.15 (m, 1H), 7.12-7.04 (m, 2H), 3.81-3.75 (m, 2H), 2.40 (t, 6.8 Hz, 2H), 1.62-1.53 (m, 2H).

4-(3,4-dihydroquinolin-1(2H)-ylsulfonyl)benzoic acid (1) (400 mg, 1.26 mmol) was treated with 4-(pyridin-2-yl)thiazol-2-amine (290 mg, 1.64 mmol) using method C. The residue was purified using flash chromatography eluting with 50-100% EtOAc in hexanes to give 4-(3,4-dihydroquinolin-1(2H)-ylsulfonyl)-N-(4-(pyridin-2-yl)thiazol-2-yl)benzamide as an off-white solid. Yield: 235 mg (39%). $^1$H-NMR: 8.63-8.60 (m, 1H), 8.21 (d, J=8.5 Hz, 2H), 8.00 (d, J=8.0 Hz, 7.93-7.88 (m, 2H), 7.76 (d, J=8.5 Hz, 2H), 7.61 (d, J=8.0 Hz, 1H), 7.35 (ddd, J=7.5, 5.0, 1.0 Hz, 1H), 7.24-7.19 (m, 1H), 7.14-7.08 (m, 2H), 3.84-3.79 (m, 2H), 2.93 (t, J=8.5 Hz, 2H). 2.45 (t, J=6.5 Hz, 2H), 1.66-1.58 (m, 2H).

Example 2

4-(3,4-dihydroquinolin-1(2H)-ylsulfonyl)-N-(4-p-tolylthiazol-2-yl)benzamide

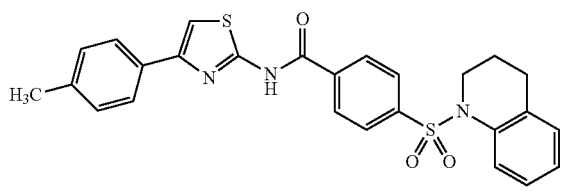 [SMILES: Cc1ccc(-c2csc(NC(=O)c3ccc(S(=O)(=O)N4CCCc5ccccc54)cc3)n2)cc1]

4-(3,4-dihydroquinolin-1(2H)-ylsulfonyl)benzoic acid (1) (100 mg, 0.32 mmol) was treated with 4-p-tolylthiazol-2-amine (50 mg, 0.26 mmol) using method B. The residue was purified using flash chromatography eluting with 0-30% EtOAc in hexanes to give 4-(3,4-dihydroquinolin-1(2H)-ylsulfonyl)-N-(4-p-tolylthiazol-2-yl)benzamide as a yellow solid. Yield: 18 mg (14%). $^1$H-NMR: 8.21 (d, J=8.5 Hz, 2H), 7.83 (d, J=8.0 Hz, 2H), 7.75 (d, J=8.5 Hz, 2H), 7.65 (s, 1H), 7.61 (d, J=8.0 Hz, 1H), 7.27-7.19 (m, 3H), 7.14-7.08 (m, 2H), 3.84-3.80 (m, 2H), 2.45 (t, J=7.0 Hz, 2H), 1.66-1.59 (m, 2H).

Example 3

4-(3,4-dihydroquinolin-1(2H)-ylsulfonyl)-N-(4-phenylthiazol-2-yl)benzamide

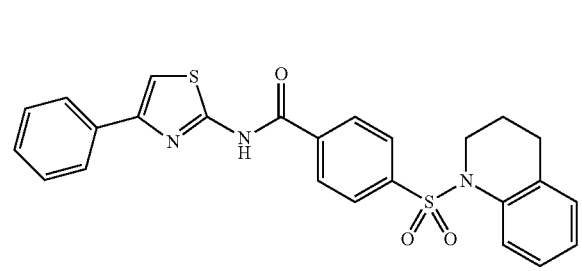 [SMILES: O=C(Nc1nc(-c2ccccc2)cs1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 4-phenylthiazol-2-amine (43 mg, 0.24 mmol) using method B. The residue was purified using flash chromatography eluting with 0-40% EtOAc in hexanes to give 4-(3,4-dihydroquinolin-1(2H)-ylsulfonyl)-N-(4-phenylthiazol-2-yl)benzamide as a white solid. Yield: 43 mg, (37%). $^1$H-NMR: 8.21 (d, J=8.5 Hz, 2H), 7.95 (d, J=8.0 Hz, 2H), 7.78-7.73 (m, 3H), 7.62 (d, J=8.5 Hz, 1H), 7.47-7.42 (t, J=7.5 Hz, 2H), 7.36-7.32 (m, 1H), 7.24-7.08 (m, 3H), 3.84-3.80 (m, 2H), 2.45 (t, J=7.0 Hz, 2H), 1.66-1.59 (m, 2H).

Example 4

4-(3,4-dihydroquinolin-1(2H)-ylsulfonyl)-N-(6-methylbenzo[d]thiazol-2-yl)benzamide

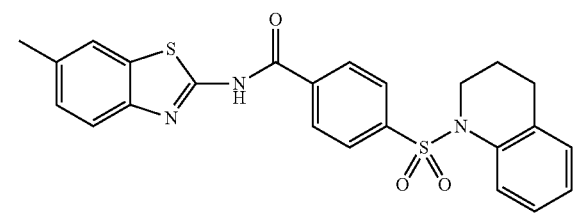 [SMILES: Cc1ccc2nc(NC(=O)c3ccc(S(=O)(=O)N4CCCc5ccccc54)cc3)sc2c1]

4-(3,4-dihydroquinolin-1(2H)-ylsulfonyl)benzoic acid (1) (100 mg, 0.32 mmol) was treated with 6-methylbenzo[d]thiazol-2-amine (43 mg, 0.26 mmol) using method B. The residue was purified using flash chromatography eluting with 0-30% EtOAc in hexanes to give 4-(3,4-dihydroquinolin-1(2H)-ylsulfonyl)-N-(6-methylbenzo[d]thiazol-2-yl)benzamide as a white solid. Yield: 34 mg (28%). $^1$H-NMR: 8.21 (d, J=8.5 Hz, 2H), 7.81 (s, 1H), 7.77 (d, J=8.5 Hz, 2H), 7.68 (br s, 1H), 7.61 (d, J=8.0 Hz, 1H), 7.29 (dd, J=8.0, 1.0 Hz, 1H), 7.24-7.19 (m, 1H), 7.13-7.06 (m, 2H), 3.84-3.80 (m, 2H), 2.47-2.41 (m, 5H), 1.66-1.59 (m, 2H).

Example 5

N-(4-(4-acetamidophenyl)thiazol-2-yl)-4-(3,4-dihydroquinolin-1(2H)-ylsulfonyl)benzamide

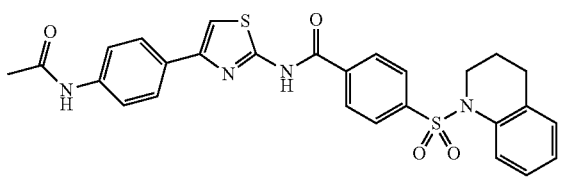 [SMILES: CC(=O)Nc1ccc(-c2csc(NC(=O)c3ccc(S(=O)(=O)N4CCCc5ccccc54)cc3)n2)cc1]

4-(3,4-dihydroquinolin-1(2H)-ylsulfonyl)benzoic acid (1) (100 mg, 0.32 mmol) was treated with N-(4-(2-aminothiazol-4-yl)phenyl)acetamide (57 mg, 0.24 mmol) using method B. The residue was purified using flash chromatography eluting with 0-60% EtOAc in hexanes to give N-(4-(4-acetamidophenyl)thiazol-2-yl)-4-(3,4-dihydroquinolin-1(2H)-ylsulfonyl) benzamide as a white solid. Yield: 28 mg (22%). $^1$H-NMR: 10.02 (s, 1H), 8.20 (d, J=8.5 Hz, 2H), 7.86 (d, J=8.5 Hz, 2H), 7.75 (d, J=8.5 Hz, 2H), 7.67-7.58 (m, 4H), 7.24-7.18 (m, 1H), 7.14-7.08 (m, 2H), 3.84-3.80 (m, 2H), 2.45 (t, J=7.0 Hz, 2H), 2.06 (s, 3H), 1.66-1.59 (m, 2H).

Example 6

3-(3,4-dihydroquinolin-1(2H)-ylsulfonyl)-N-(4-(pyridin-2-yl)thiazol-2-yl)benzamide

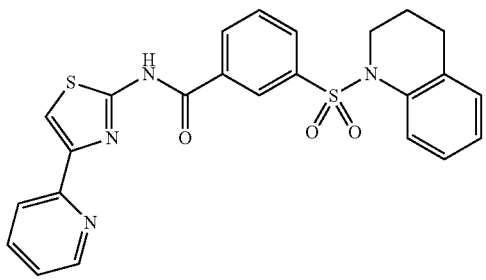 [SMILES: O=C(Nc1nc(-c2ccccn2)cs1)c1cccc(S(=O)(=O)N2CCCc3ccccc32)c1]

3-(3,4-dihydroquinolin-1(2H)-ylsulfonyl)benzoic acid (2)

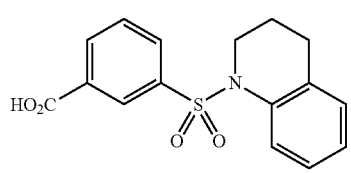 [SMILES: O=C(O)c1cccc(S(=O)(=O)N2CCCc3ccccc32)c1]

3-(chlorosulfonyl)benzoic acid (0.5 g, 2.27 mmol) was treated with 1,2,3,4-tetrahydroquinoline (906 mg, 6.80 mmol) using method A to give 3-(3,4-dihydroquinolin-1(2H)-ylsulfonyl)benzoic acid as an off white solid. Yield: 318 mg (44%). $^1$H-NMR: 8.17 (d, J=8.0 Hz, 1H), 8.06-8.04 (m, 1H), 7.80 (d, J=8.0 Hz, 1H), 7.68 (t, J=8.0 Hz, 1H), 7.61 (d, J=8.0 Hz, 1H), 7.24-7.18 (m, 1H), 7.15-7.05 (m, 2H), 3.80-3.76 (m, 2H), 2.40 (t, J=6.5 Hz, 2H), 1.61-1.54 (m, 2H).

3-(3,4-dihydroquinolin-1(2H)-ylsulfonyl)benzoic acid (2) (100 mg, 0.32 mmol) was treated with 4-(pyridin-2-yl)thiazol-2-amine (47 mg, 0.26 mmol) using method C. The residue was purified using flash chromatography eluting with 75-100% EtOAc in hexanes. The resulting solid was triturated with diethyl ether to give 3-(3,4-dihydroquinolin-1(2H)-ylsulfonyl)-N-(4-(pyridin-2-yl)thiazol-2-yl)benzamide as an off white solid. Yield: 36 mg (29%). $^1$H-NMR: 8.65-8.61 (m, 1H), 8.50 (s, 1H), 8.42-8.35 (m, 1H), 8.03 (d, J=7.5 Hz, 1H), 7.95-7.88 (m, 2H), 7.75-7.68 (m, 2H), 7.64 (d, J=8.5 Hz, 1H) 7.39-7.32 (m, 1H), 7.25-7.18 (m, 1H), 7.12-7.05 (m, 2H), 3.88-3.81 (m, 2H), 2.44 (t, J=7.0 Hz, 2H), 1.68-1.60 (m, 2H).

Example 7

3-(indolin-1-ylsulfonyl)-N-(4-(pyridin-2-yl)thiazol-2-yl)benzamide

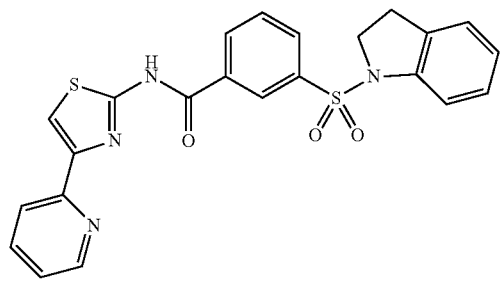 [SMILES: O=C(Nc1nc(-c2ccccn2)cs1)c1cccc(S(=O)(=O)N2CCc3ccccc32)c1]

3-(indolin-1-ylsulfonyl)benzoic acid (3)

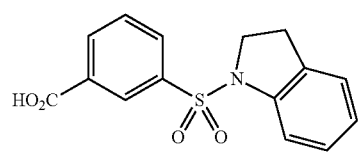 [SMILES: O=C(O)c1cccc(S(=O)(=O)N2CCc3ccccc32)c1]

3-(chlorosulfonyl)benzoic acid (2.0 g, 9.1 mmol) was treated with was treated with indoline (2.7 g, 22.7 mmol) using method A to give 3-(indolin-1-ylsulfonyl)benzoic acid as a light purple solid. Yield: 1.6 g (58%). $^1$H-NMR: 8.23 (t, J=1.5 Hz, 1H), 8.19 (dt, J=8.0, 1.5, 1.5 Hz, 1H), 8.04 (ddd, J=8.0, 2.0, 1.0 Hz, 1H), 7.71 (t, J=8.0 Hz, 1H), 7.49 (d, J=8.0 Hz, 1H), 7.21 (t, J=8.0 Hz, 1H), 7.16 (d, J=7.5 Hz, 1H), 6.99 (dt, J=7.5, 7.5, 1.0 Hz, 1H), 3.92 (t, J=8.5 Hz, 2H), 2.90 (t, J=8.5 Hz, 2H)

3-(indolin-1-ylsulfonyl)benzoic acid (3) (100 mg, 0.33 mmol) was treated with 4-(pyridin-2-yl)thiazol-2-amine (49 mg, 0.28 mmol) using method C. The residue was purified using flash chromatography eluting with 75-100% EtOAc in hexanes. The resulting solid was triturated with diethyl ether to give 3-(indolin-1-ylsulfonyl)-N-(4-(pyridin-2-yl)thiazol-2-yl)benzamide as a white solid. Yield: 17 mg (13%). $^1$H-NMR: 8.65-8.61 (m, 1H), 8.60-8.58 (m, 1H), 8.38 (dt, J=8.0, 1.0, 1.0 Hz, 1H), 8.05-7.99 (m, 2H), 7.95-7.88 (m, 2H), 7.74 (t, J=8.0 Hz, 1H), 7.53 (d, J=8.5 Hz, 1H), 7.38-7.33 (m, 1H), 7.22 (t, J=8.0 Hz, 1H), 7.16 (d, J=7.5 Hz, 1H) 6.99 (dt, J=7.5, 7.5, 1.0 Hz, 1H), 4.03 (t, J=8.5 Hz, 2H), 2.93 (t, J=8.5 Hz, 2H).

Example 8

4-(3,4-dihydroquinolin-1(2H)-ylsulfonyl)-N-(3-methoxyphenyl)benzamide

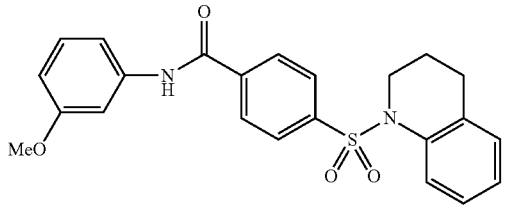 [SMILES: COc1cccc(NC(=O)c2ccc(S(=O)(=O)N3CCCc4ccccc43)cc2)c1]

4-(3,4-dihydroquinolin-1(2H)-ylsulfonyl)benzoic acid (1) (100 mg, 0.32 mmol) was treated with 3-methoxyaniline (30 mg, 0.24 mmol) using method B. The residue was purified using flash chromatography eluting with 0-30% EtOAc in hexanes. The resulting solid was triturated with dichloromethane/hexanes to give 4-(3,4-dihydroquinolin-1(2H)-ylsulfonyl)-N-(3-methoxyphenyl)benzamide as a white solid. Yield: 13 mg (13%). $^1$H-NMR: 10.41 (s, 1H), 8.04 (d, J=8.5 Hz, 2H), 7.74 (d, J=8.5 Hz, 2H), 7.63 (d, J=8.5 Hz, 1H), 7.43-7.41 (m, 1H), 7.34 (d, J=8.5 Hz, 1H), 7.27 (d, J=8.0 Hz, 1H), 7.24-7.18 (m, 1H), 7.12-7.08 (m, 2H), 6.70 (ddd, J=8.0, 2.5, 1.0 Hz, 1H), 3.85-3.79 (m, 2H), 2.45 (t, J=7.0 Hz, 2H), 1.67-1.59 (m, 2H).

Example 9

4-(3,4-dihydroquinolin-1(2H)-ylsulfonyl)-N-(3-(1-hydroxyethyl)phenyl)benzamide

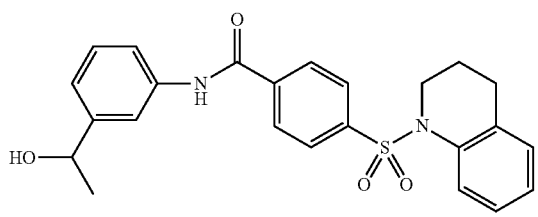 [SMILES: CC(O)c1cccc(NC(=O)c2ccc(S(=O)(=O)N3CCCc4ccccc43)cc2)c1]

4-(3,4-dihydroquinolin-1(2H)-ylsulfonyl)benzoic acid (1) (100 mg, 0.32 mmol) was treated with 1-(3-aminophenyl)ethanol (33 mg, 0.24 mmol) using method B. The residue was purified using flash chromatography eluting with 0-40% EtOAc in hexanes. The resulting solid was triturated with dichloromethane/hexanes to give 4-(3,4-dihydroquinolin-1(2H)-ylsulfonyl)-N-(3-(1-hydroxyethyl)phenyl)benzamide as a white solid. Yield: 38 mg (36%). $^1$H-NMR: 10.42 (br s, 1H), 8.06 (d, J=8.5 Hz, 2H), 7.77-7.71 (m, 3H), 7.63 (d, J=8.0 Hz, 2H), 7.28 (t, J=8.0 Hz, 1H), 7.24-7.18 (m, 1H), 7.12-7.06 (m, 2H), 5.19 (d, J=4.0 Hz, 1H), 4.74-4.66 (m, 1H), 3.84-3.80 (m, 2H), 2.46 (t, J=7.5 Hz, 2H), 1.67-1.59 (m, 2H), 1.31 (d, J=6.5 Hz, 3H).

Example 10

4-(3,4-dihydroquinolin-1(2H)-ylsulfonyl)-N-(pyridin-4-yl)benzamide

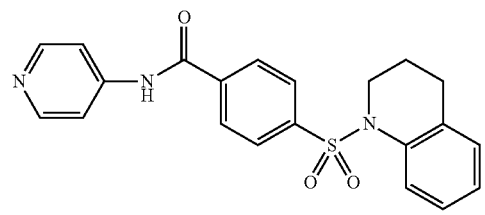 [SMILES: O=C(Nc1ccncc1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 4-aminopyridine (25 mg, 0.26 mmol) using method C. The residue was purified using flash chromatography eluting with 10-50 EtOAc in dichloromethane. The resulting solid was triturated with dichloromethane/hexanes to give 4-(3,4-dihydroquinolin-1(2H)-ylsulfonyl)-N-(pyridin-4-yl)benzamide as a white solid. Yield: 41 mg (40%). $^1$H-NMR: 10.79 (s, 1H), 8.50-8.47 (m, 2H), 8.06 (d, J=8.5 Hz, 2H), 7.79-7.73 (m, 4H), 7.63 (d, J=8.0 Hz, 1H), 7.23-7.08 (m, 3H) 3.85-3.81 (m, 2H), 2.45 (t, J=7.0, 2H), 1.67-1.59 (m, 2H).

Example 11

4-(N-(4-fluorophenyl)-N-methylsulfamoyl)-N-(4-(pyridin-2-yl)thiazol-2-yl)benzamide

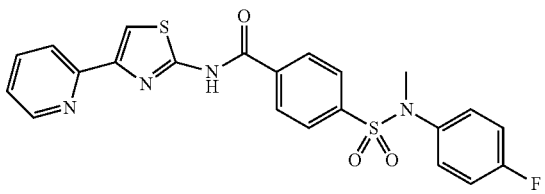 [SMILES: CN(c1ccc(F)cc1)S(=O)(=O)c1ccc(C(=O)Nc2nc(-c3ccccn3)cs2)cc1]

4-(N-(4-fluorophenyl)-N-methylsulfamoyl)benzoic acid (4)

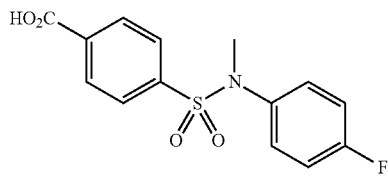 [SMILES: CN(c1ccc(F)cc1)S(=O)(=O)c1ccc(C(=O)O)cc1]

4-(chlorosulfonyl)benzoic acid (0.5 g, 2.27 mmol) was treated with 4-fluoro-N-methylaniline (851 mg, 6.80 mmol) using method A to give 4-(N-(4-fluorophenyl)-N-methylsulfamoyl)benzoic acid as a white solid. Yield: 534 mg (76%). $^1$H-NMR: 8.10 (d, J=8.5 Hz, 2H), 7.62 (d, J=8.5 Hz, 2H), 7.23-7.11 (m, 4H), 3.15 (s, 3H).

4-(N-(4-fluorophenyl)-N-methylsulfamoyl)benzoic acid (4) (100 mg, 0.32 mmol) was treated with 4-(pyridin-2-yl)thiazol-2-amine (48 mg, 0.27 mmol) using method C. The residue was purified using flash chromatography eluting with EtOAc. The resulting solid was triturated with diethyl ether to give 4-(N-(4-fluorophenyl)-N-methylsulfamoyl)-N-(4-(pyridin-2-yl)thiazol-2-yl)benzamide as a yellow solid. Yield: 34 mg (27%). $^1$H-NMR: 8.61 (d, J=4.5 Hz, 1H), 8.29 (d, J=8.5 Hz, 2H), 8.02 (d, J=8.5 Hz, 1H), 7.93-7.83 (m, 2H), 7.65 (d, J=8.5 Hz, 2H), 7.36-7.31 (m, 1H), 7.24-7.12 (m, 4H), 3.17 (s, 3H).

Example 12

4-(N-(4-chlorophenyl)-N-methylsulfamoyl)-N-(4-(pyridin-2-yl)thiazol-2-yl)benzamide

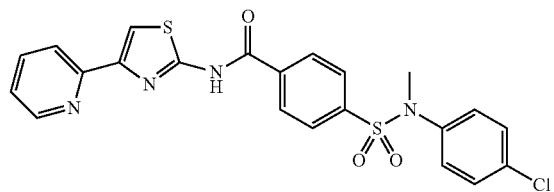 [SMILES: CN(c1ccc(Cl)cc1)S(=O)(=O)c1ccc(C(=O)Nc2nc(-c3ccccn3)cs2)cc1]

4-(N-(4-chlorophenyl)-N-methylsulfamoyl)benzoic acid (5)

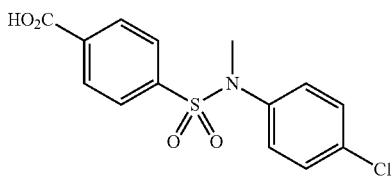

4-(chlorosulfonyl)benzoic acid (0.5 g, 2.27 mmol) was treated with 4-chloro-N-methylaniline (963 mg, 6.80 mmol) using method A to give 4-(N-(4-chlorophenyl)-N-methylsulfamoyl)benzoic acid as a white solid. Yield: 406 mg (55%). $^1$H-NMR: 8.11 (d, J=8.5 Hz, 2H), 7.63 (d, J=8.5 Hz, 2H), 7.42 (d, J=8.5 Hz, 2H), 7.14 (d, J=8.5 Hz, 2H), 3.15 (s, 3H).

4-(N-(4-chlorophenyl)-N-methylsulfamoyl)benzoic acid (5) (100 mg, 0.31 mmol) was treated with 4-(pyridin-2-yl)thiazol-2-amine (45 mg, 0.26 mmol) using method C. The residue was purified using flash chromatography eluting with EtOAc. The resulting solid was triturated with diethyl ether to give 4-(N-(4-chlorophenyl)-N-methylsulfamoyl)-N-(4-(pyridin-2-yl)thiazol-2-yl)benzamide as a yellow solid. Yield: 18 mg (15%). $^1$H-NMR: 8.64-8.61 (m, 1H), 8.29 (d, J=8.5 Hz, 2H), 8.02 (d, J=8.0 Hz, 1H), 7.95-7.87 (m, 2H), 7.68 (d, J=8.5 Hz, 2H), 7.46-7.41 (m, 2H), 7.35 (ddd, J=7.5, 5.0, 1.0 Hz, 1H), 7.19-7.14 (m, 2H), 3.19 (s, 3H).

Example 13

4-(N-methyl-N-(4-(trifluoromethyl)phenyl)sulfamoyl)-N-(4-(pyridin-2-yl)thiazol-2-yl)benzamide

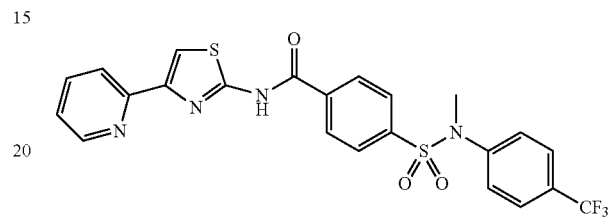

4-(N-methyl-N-(4-(trifluoromethyl)phenyl)sulfamoyl)benzoic acid (6)

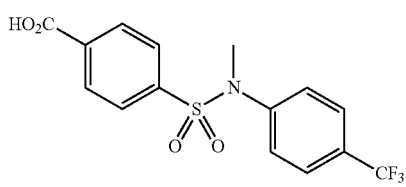 [SMILES: CN(c1ccc(C(F)(F)F)cc1)S(=O)(=O)c1ccc(C(=O)O)cc1]

4-(chlorosulfonyl)benzoic acid (0.5 g, 2.27 mmol) was treated with N-methyl-4-(trifluoromethyl)aniline (1191 mg, 6.80 mmol) using method A to give 4-(N-methyl-N-(4-(trifluoromethyl)phenyl)sulfamoyl)benzoic acid as a white solid. Yield: 385 mg (47%). $^1$H-NMR: 8.11 (d, J=8.5 Hz, 2H), 7.74 (d, J=8.5 Hz, 2H), 7.66 (d, J=8.5 Hz, 2H), 7.39 (d, J=8.5 Hz, 2H), 3.21 (s, 3H).

4-(N-methyl-N-(4-(trifluoromethyl)phenyl)sulfamoyl)benzoic acid (6) (100 mg, 0.28 mmol) was treated with 4-(pyridin-2-yl)thiazol-2-amine (41 mg, 0.23 mmol) using method C. The residue was purified using flash chromatography eluting with EtOAc. The resulting solid was triturated with diethyl ether to give 4-(N-methyl-N-(4-(trifluoromethyl)phenyl)sulfamoyl)-N-(4-(pyridin-2-yl)thiazol-2-yl)benzamide as a yellow solid. Yield: 42 mg (35%). $^1$H-NMR: 8.60 (d, J=4.0 Hz, 1H), 8.28 (d, J=8.5 Hz, 2H), 8.02 (d, J=7.5 Hz, 1H), 7.89 (dt, J=7.5, 7.5, 1.5 Hz, 1H), 7.84 (s, 1H), 7.75 (d, J=8.5

Hz, 2H), 7.68 (d, J=8.5 Hz, 2H), 7.41 (d, J=8.5 Hz, 2H), 7.33 (dd, J=7.0, 5.0 Hz, 1H), 3.25 (s, 1H).

Example 14

4-(N-(4-methoxyphenyl)-N-methylsulfamoyl)-N-(4-(pyridin-2-yl)thiazol-2-yl)benzamide

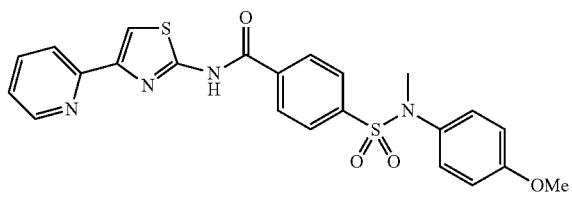 [SMILES: COc1ccc(N(C)S(=O)(=O)c2ccc(C(=O)Nc3nc(-c4ccccn4)cs3)cc2)cc1]

4-(N-(4-methoxyphenyl)-N-methylsulfamoyl)benzoic acid (7)

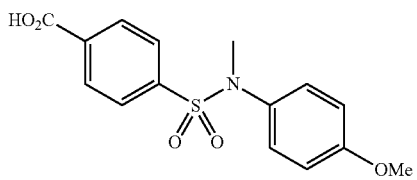 [SMILES: COc1ccc(N(C)S(=O)(=O)c2ccc(C(=O)O)cc2)cc1]

4-(chlorosulfonyl)benzoic acid (0.5 g, 2.27 mmol) was treated with 4-methoxy-N-methylaniline (933 mg, 6.80 mmol) using method A to give 4-(N-(4-methoxyphenyl)-N-methylsulfamoyl)benzoic acid as a yellow solid. Yield: 617 mg (85%). $^1$H-NMR: 8.10 (d, J=8.5 Hz, 2H), 7.63 (d, J=8.5 Hz, 2H), 6.98 (d, J=8.5 Hz, 2H), 6.88 (d, J=8.5 Hz, 2H), 3.74 (s, 3H), 3.13 (s, 3H).

4-(N-(4-methoxyphenyl)-N-methylsulfamoyl)benzoic acid (7) (100 mg, 0.31 mmol) was treated with 4-(pyridin-2-yl)thiazol-2-amine (46 mg, 0.26 mmol) using method C. The residue was purified using flash chromatography eluting with EtOAc. The resulting solid was triturated with diethyl ether to give 4-(N-(4-methoxyphenyl)-N-methylsulfamoyl)-N-(4-(pyridin-2-yl)thiazol-2-yl)benzamide as a yellow solid. Yield: 39 mg (31%). $^1$H-NMR: 8.64-8.61 (m, 1H), 8.28 (d, J=8.5 Hz, 2H), 8.02 (d, J=8.0 Hz, 1H), 7.94-7.88 (m, 2H), 7.67 (d, J=8.5 Hz, 2H), 7.35 (ddd, J=7.5, 5.0, 1.0 Hz, 1H), 7.03-6.99 (m, 2H), 6.91-6.88 (m, 2H), 3.75, s, 3H), 3.16 (s, 3H).

Example 15

4-(5-chloroindolin-1-ylsulfonyl)-N-(4-(pyridin-2-yl)thiazol-2-yl)benzamide

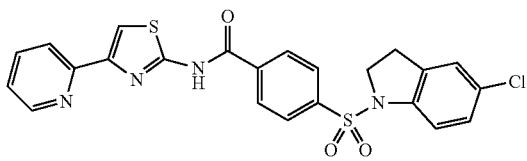 [SMILES: O=C(Nc1nc(-c2ccccn2)cs1)c1ccc(S(=O)(=O)N2CCc3cc(Cl)ccc32)cc1]

4-(5-chloroindolin-1-ylsulfonyl)benzoic acid (8)

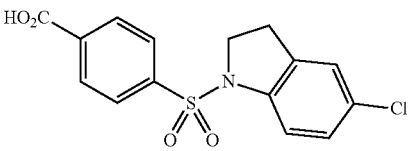 [SMILES: O=C(O)c1ccc(S(=O)(=O)N2CCc3cc(Cl)ccc32)cc1]

3-(chlorosulfonyl)benzoic acid (1.0 g, 4.53 mmol) was treated with 5-chloroindoline (2.08 g, 13.60 mmol) using method A to give 3-(5-chloroindolin-1-ylsulfonyl)benzoic acid as an off white solid. Yield: 720 mg (47%). $^1$H-NMR: 8.09 (d, J=8.5 Hz, 2H), 7.93 (d, J=8.5 Hz, 2H), 7.48-7.43 (m, 1H), 7.27-7.23 (m, 2H), 3.97 (t, J=8.5 Hz, 2H) 2.91 (t, J=8.5 Hz, 2H).

3-(5-chloroindolin-1-ylsulfonyl)benzoic acid (8) (100 mg, 0.30 mmol) was treated with 4-(pyridin-2-yl)thiazol-2-amine (44 mg, 0.25 mmol) in DMF (2 mL) using method C. The residue was purified using flash chromatography eluting with EtOAc. The resulting solid was triturated with diethyl ether to give 4-(5-chloroindolin-1-ylsulfonyl)-N-(4-(pyridin-2-yl)thiazol-2-yl)benzamide as an off white solid. Yield: 53 mg (43%). $^1$H-NMR: 8.63-8.59 (m, 1H), 8.25 (d, J=8.5 Hz, 2H), 8.02-7.86 (m, 5H), 7.49 (d, J=8.5 Hz, 1H), 7.34 (ddd, J=7.5, 5.0, 1.0 Hz, 1H), 7.29-7.24 (m, 2H), 4.00 (t, J=8.5 Hz, 2H), 2.94 (t, J=8.5 Hz, 2H)

Example 16

4-(5-chloroindolin-1-ylsulfonyl)-N-(6-methoxybenzo[d]thiazol-2-yl)benzamide

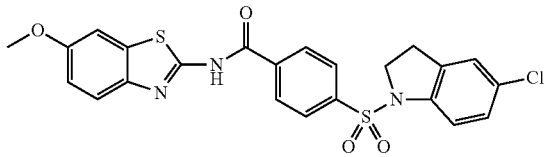 [SMILES: COc1ccc2nc(NC(=O)c3ccc(S(=O)(=O)N4CCc5cc(Cl)ccc54)cc3)sc2c1]

3-(5-chloroindolin-1-ylsulfonyl)benzoic acid (8) (100 mg, 0.30 mmol) was treated with 4-(pyridin-2-yl)thiazol-2-amine (44 mg, 0.25 mmol) using method C. The residue was purified using flash chromatography eluting with 0-50% EtOAc in hexanes. The resulting solid was triturated with diethyl ether to give 4-(5-chloroindolin-1-ylsulfonyl)-N-(6-methoxybenzo[d]thiazol-2-yl)benzamide as an off white solid. Yield: 29 mg (24%). $^1$H-NMR: 8.24 (d, J=8.5 Hz, 2H), 7.98 (d, J=8.5 Hz, 2H), 7.68 (d, J=8.5 Hz, 1H), 7.61 (d, J=2.5 Hz, 1H), 7.49

(d, J=8.5 Hz, 1H), 7.29-7.24 (m, 2H), 7.06 (dd, J=8.5, 2.5 Hz, 1H), 4.04-3.96 (m, 2H), 3.82 (s, 3H), 2.94 (t, J=8.5 Hz, 2H).

Example 17

4-(3,4-dihydroquinolin-1(2H)-ylsulfonyl)-2-fluoro-N-(4-(pyridin-2-yl)thiazol-2-yl)benzamide

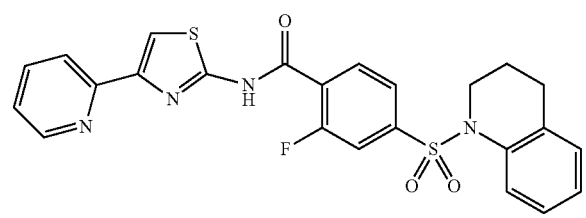 [SMILES: O=C(Nc1nc(-c2ccccn2)cs1)c1ccc(S(=O)(=O)N2CCCc3ccccc32)cc1F]

4-(3,4-dihydroquinolin-1(2H)-ylsulfonyl)-2-fluorobenzoic acid (9) (160 mg, 0.48 mmol) was treated with 4-(pyridin-2-yl)thiazol-2-amine (70 mg, 0.40 mmol) using method C. The residue was purified using flash chromatography eluting with EtOAc. The resulting solid was triturated with diethyl ether to give 4-(3,4-dihydroquinolin-1(2H)-ylsulfonyl)-2-fluoro-N-(4-(pyridin-2-yl)thiazol-2-yl)benzamide as an off white solid. Yield: 38 mg (19%). $^1$H-NMR: 8.63-8.60 (m, 1H), 7.98-7.85 (m, 4H), 7.61 (d, J=8.5 Hz, 2H), 7.52 (dd, J=8.5, 2.0 Hz, 1H), 7.35 (ddd, J=7.5, 5.0, 1.0 Hz, 1H), 7.26-7.20 (m, 1H), 7.15-7.12 (m, 2H), 3.87-3.82 (m, 2H), 2.51-2.47 (m, 2H), 1.71-1.63 (m, 2H).

Example 18

4-(3,4-dihydroquinolin-1(2H)-ylsulfonyl)-N-(3-(4-fluorophenyl)-1H-pyrazol-5-yl)benzamide

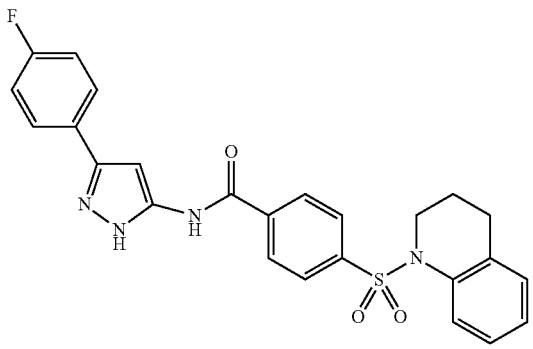 [SMILES: O=C(Nc1cc(-c2ccc(F)cc2)n[nH]1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 3-(4-fluorophenyl)-1H-pyrazol-5-amine (43 mg, 0.24 mmol) using method B. The residue was purified using flash chromatography eluting with 0-8% MeOH in EtOAc. The resulting solid was triturated with dichloromethane/hexanes to give 4-(3,4-dihydroquinolin-1(2H)-ylsulfonyl)-N-(3-(4-fluorophenyl)-1H-pyrazol-5-yl)benzamide as an off white solid. Yield: 36 mg (31%). $^1$H-NMR: 11.11 (s, 1H), 8.10 (d, J=8.5 Hz, 2H), 7.80 (dd, J=8.5, 5.5 Hz, 2H), 7.71 (d, J=8.0 Hz, 2H), 7.62 (d, J=8.5 Hz, 1H), 7.33-7.08 (m, 5H), 7.01 (br s, 1H), 3.83-3.79 (m, 2H), 2.45 (t, J=7.0 Hz, 2H), 1.66-1.58 (m, 2H).

Example 19

4-(N-(4-methoxyphenyl)sulfamoyl)-N-(4-(pyridin-2-yl)thiazol-2-yl)benzamide

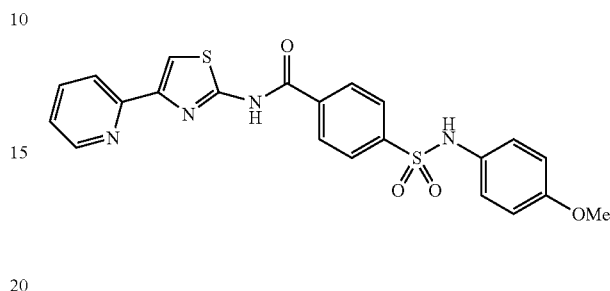

4-(N-(4-methoxyphenyl)sulfamoyl)benzoic acid (10)

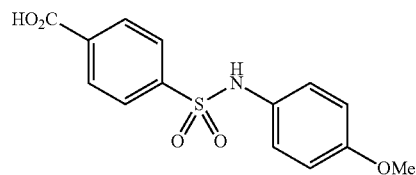 [SMILES: COc1ccc(NS(=O)(=O)c2ccc(C(=O)O)cc2)cc1]

4-(chlorosulfonyl)benzoic acid (573 mg, 2.60 mmol) was treated with 4-methoxyaniline (800 mg, 6.5 mmol) using method A to give 4-(N-(4-methoxyphenyl)sulfamoyl)benzoic acid as an off white solid. Yield: 528 mg (66%). $^1$H-NMR: 10.05 (s, 1H), 6.96 (d, J=8.5 Hz, 2H), 6.80 (d, J=8.5 Hz, 2H), 6.96 (d, J=9.0 Hz, 2H), 6.80 (d, J=9.0 Hz, 2H), 3.67 (s, 3H).

4-(N-(4-methoxyphenyl)sulfamoyl)benzoic acid (10) (104 mg, 0.34 mmol) was treated with 4-(pyridin-2-yl)thiazol-2-amine (50 mg, 0.28 mmol) using method C. The residue was purified using flash chromatography eluting with EtOAc. The resulting solid was triturated with diethyl ether to give 4-(N-(4-methoxyphenyl)sulfamoyl)-N-(4-(pyridin-2-yl)thiazol-2-yl)benzamide as a yellow solid. Yield: 29 mg (25%). $^1$H-NMR: 10.08 (s, 1H), 8.63-8.60 (m, 1H), 8.21 (d, J=8.5 Hz, 2H), 8.04-7.87 (m, 3H), 7.82 (d, J=8.5 Hz, 2H), 7.34 (ddd, J=7.5, 5.0, 1.0 Hz, 1H), 7.01-6.90 (m, 3H), 6.82 (d, J=9.0 Hz, 2H), 3.66 (s, 3H).

Example 20

4-(N-(3-chlorophenyl)sulfamoyl)-N-(4-(pyridin-2-yl)thiazol-2-yl)benzamide

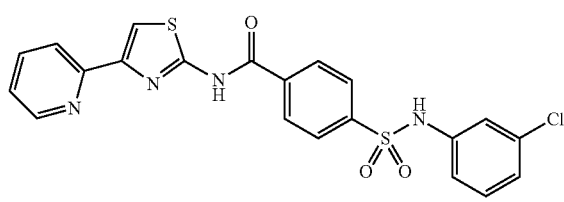 [SMILES: O=C(Nc1nc(-c2ccccn2)cs1)c1ccc(S(=O)(=O)Nc2cccc(Cl)c2)cc1]

4-(N-(3-chlorophenyl)sulfamoyl)benzoic acid (11)

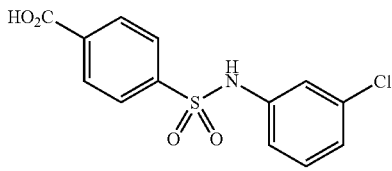 [SMILES: O=C(O)c1ccc(S(=O)(=O)Nc2cccc(Cl)c2)cc1]

4-(chlorosulfonyl)benzoic acid (22) (553 mg, 2.60 mmol) was treated with 3-chloroaniline (800 mg, 6.3 mmol) using method A to give 4-(N-(3-chlorophenyl)sulfamoyl)benzoic acid as an off white solid. Yield: 382 mg (49%). $^1$H-NMR: 10.73 (s, 1H), 8.09 (d, J=8.5 Hz, 2H), 7.88 (d, J=8.5 Hz, 2H), 7.27 (t, J=8.5 Hz, 1H), 7.13-7.04 (m, 3H).

4-(N-(3-chlorophenyl)sulfamoyl)benzoic acid (11) (106 mg, 0.34 mmol) was treated with 4-(pyridin-2-yl)thiazol-2-amine (50 mg, 0.28 mmol) using method C. The residue was purified using flash chromatography eluting with 50-100% EtOAc in hexanes. The resulting solid was triturated with diethyl ether to give 4-(N-(3-chlorophenyl)sulfamoyl)-N-(4-(pyridin-2-yl)thiazol-2-yl)benzamide as a yellow solid. Yield: 49 mg (37%). $^1$H-NMR: 10.77 (s, 1H), 8.63-8.61 (m, 1H), 8.25 (d, J=8.5 Hz, 2H), 8.00 (d, J=8.0 Hz, 1H), 7.95-7.88 (m, 4H), 7.35 (ddd, J=7.5, 5.0, 1.0 Hz, 1H), 7.30 (t, J=8.0 Hz, 1H), 7.15 (t, J=2 Hz, 1H), 7.13-7.08 (m, 2H), 3.32 (s, 3H).

Example 21

4-(N-(3-methoxyphenyl)-N-methylsulfamoyl)-N-(4-(pyridin-2-yl)thiazol-2-yl)benzamide

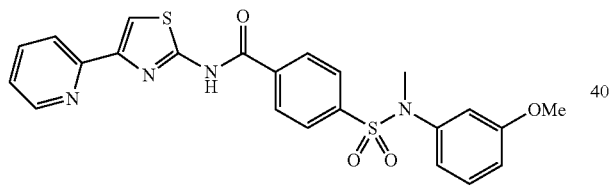

4-(N-(3-methoxyphenyl)-N-methylsulfamoyl)benzoic acid (12)

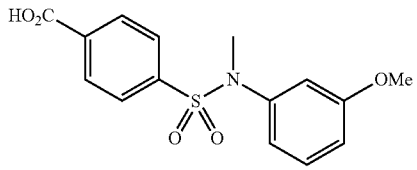 [SMILES: COc1cccc(N(C)S(=O)(=O)c2ccc(C(=O)O)cc2)c1]

4-(chlorosulfonyl)benzoic acid (500 mg, 2.27 mmol) was treated with 3-methoxy-N-methylaniline (933 mg, 6.8 mmol) using method A to give 4-(N-(3-methoxyphenyl)-N-methylsulfamoyl)benzoic acid as an off white solid. Yield: 398 mg (55%). $^1$H-NMR: 8.10 (d, J=8.5 Hz, 2H), 7.66 (d, J=8.5 Hz, 2H), 7.25 (t, J=8.0 Hz, 1H), 6.88 (ddd, J=8.5, 2.5, 1.0 Hz, 1H), 6.67-6.64 (m, 2H), 3.69 (s, 3H), 3.16 (s, 3H).

4-(N-(3-methoxyphenyl)-N-methylsulfamoyl)benzoic acid (12) (100 mg, 0.31 mmol) was treated with 4-(pyridin-2-yl)thiazol-2-amine (50 mg, 0.28 mmol) using method C. The residue was purified using flash chromatography eluting with 50-100% EtOAc in hexanes. The resulting solid was triturated with diethyl ether to give 4-(N-(3-methoxyphenyl)-N-methylsulfamoyl)-N-(4-(pyridin-2-yl)thiazol-2-yl)benzamide as a yellow solid. Yield: 56 mg (41%). $^1$H-NMR: 8.64-8.61 (m, 1H), 8.28 (d, J=8.5 Hz, 2H), 8.02 (d, J=8.0 Hz, 1H), 7.94-7.88 (m, 3H), 7.71 (d, J=8.5 Hz, 2H), 7.36 (ddd, 7.5, 5.0, 1.0 Hz, 1H), 7.27 (t, J=8.0 Hz, 1H), 6.92-6.88 (m, 1H), 6.71-6.67 (m, 2H), 3.70 (s, 3H), 3.20 (s, 3H).

Example 22

4-(N-(2-methoxyphenyl)-N-methylsulfamoyl)-N-(4-(pyridin-2-yl)thiazol-2-yl)benzamide

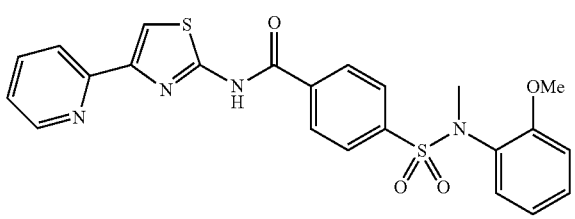 [SMILES: COc1ccccc1N(C)S(=O)(=O)c1ccc(C(=O)Nc2nc(-c3ccccn3)cs2)cc1]

4-(N-(2-methoxyphenyl)-N-methylsulfamoyl)benzoic acid (13)

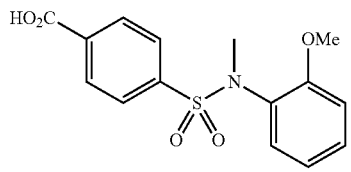 [SMILES: COc1ccccc1N(C)S(=O)(=O)c1ccc(C(=O)O)cc1]

4-(chlorosulfonyl)benzoic acid (500 mg, 2.27 mmol) was treated with 2-methoxy-N-methylaniline (933 mg, 6.8 mmol) using method A to give 4-(N-(2-methoxyphenyl)-N-methylsulfamoyl)benzoic acid as an off white solid. Yield: 515 mg (71%). $^1$H-NMR: 8.11 (d, J=8.5 Hz, 2H), 7.73 (d, J=8.5 Hz, 2H), 7.33 (ddd, J=8.5, 7.5, 1.5 Hz, 1H), 7.17 (dd, J=7.5, 1.5 Hz, 1H), 7.00-6.92 (m, 2H), 3.33 (s, 3H), 3.14 (s, 3H).

4-(N-(2-methoxyphenyl)-N-methylsulfamoyl)benzoic acid (13) (109 mg, 0.34 mmol) was treated with 4-(pyridin-2-yl)thiazol-2-amine (50 mg, 0.28 mmol) using method C. The residue was purified using flash chromatography eluting with 50-100% EtOAc in hexanes. The resulting solid was triturated with diethyl ether to give 4-(N-(2-methoxyphenyl)-N-methylsulfamoyl)-N-(4-(pyridin-2-yl)thiazol-2-yl)benzamide as an off white solid. Yield: 46 mg (34%). $^1$H-NMR: 8.65-8.62 (m, 1H), 8.27 (d, J=8.5 Hz, 2H), 8.03 (d, J=7.5 Hz, 1H), 7.95-7.89 (m, 2H), 7.77 (d, J=8.5 Hz, 2H), 7.38-7.32 (m, 2H), 7.22 (dd, J=7.5, 1.5 Hz, 1H), 7.01-6.94 (m, 2H), 3.34 (s, 3H), 3.18 (s, 3H).

Example 23

N-(4-(pyridin-2-yl)thiazol-2-yl)-4-(N-m-tolylsulfamoyl)benzamide

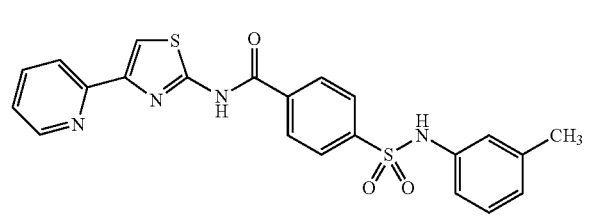 [SMILES: Cc1cccc(NS(=O)(=O)c2ccc(C(=O)Nc3nc(-c4ccccn4)cs3)cc2)c1]

4-(N-m-tolylsulfamoyl)benzoic acid (14)

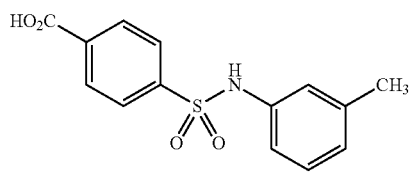 [SMILES: Cc1cccc(NS(=O)(=O)c2ccc(C(=O)O)cc2)c1]

4-(chlorosulfonyl)benzoic acid (500 mg, 2.27 mmol) was treated with m-toluidine (729 mg, 6.8 mmol) using method A to give 4-(N-m-tolylsulfamoyl)benzoic acid as an off white solid. Yield: 463 mg (70%). $^1$H-NMR: 8.10 (d, J=8.5 Hz, 2H), 7.64 (d, J=8.5 Hz, 2H), 7.22 (t, J=8.0 Hz, 1H), 7.12 (d, J=8.0 Hz, 1H), 6.95 (s, 1H), 6.85 (d, J=8.0 Hz, 1H), 3.14 (s, 3H), 2.26 (s, 3H).

4-(N-m-tolylsulfamoyl)benzoic acid (14) (99 mg, 0.34 mmol) was treated with 4-(pyridin-2-yl)thiazol-2-amine (50 mg, 0.28 mmol) using method C. The residue was purified using flash chromatography eluting with 75-100% EtOAc in hexanes. The resulting solid was triturated with dichloromethane/hexanes to give N-(4-(pyridin-2-yl)thiazol-2-yl)-4-(N-m-tolylsulfamoyl)benzamide as an off white solid. Yield: 24 mg (19%). $^1$H-NMR: 8.64-8.62 (m, 1H), 8.28 (d, J=8.5 Hz, 2H), 8.02 (d, J=8.0 Hz, 1H), 7.95-7.89 (m, 2H), 7.69 (d, J=8.5 Hz, 2H), 7.36 (ddd, J=7.5, 5.0, 1.0 Hz, 1H), 7.24 (t, J=8.0 Hz, 1H), 7.13 (d, J=7.5 Hz, 1H), 6.98-6.96 (m, 1H), 6.88 (d, J=8.0 Hz, 1H), 3.18 (s, 3H).

Example 24

4-(N-(4-methoxyphenyl)-N-methylsulfamoyl)-N-(6-methylbenzo[d]thiazol-2-yl)benzamide

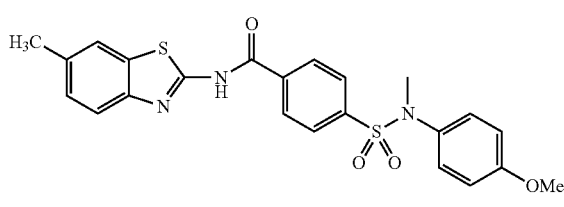 [SMILES: COc1ccc(N(C)S(=O)(=O)c2ccc(C(=O)Nc3nc4ccc(C)cc4s3)cc2)cc1]

4-(N-(4-methoxyphenyl)-N-methylsulfamoyl)benzoic acid (7) (100 mg, 0.31 mmol) was treated with 6-methylbenzo[d]thiazol-2-amine (43 mg, 0.26 mmol) using method C. The residue was purified using flash chromatography eluting with 0-30% EtOAc in hexanes. The resulting solid was triturated with dichloromethane/hexanes to give 4-(N-(4-methoxyphenyl)-N-methylsulfamoyl)-N-(6-methylbenzo[d]thiazol-2-yl)benzamide as an off white solid. Yield: 57 mg (47%). $^1$H-NMR: 8.28 (d, J=8.5 Hz, 2H), 7.83 (s, 1H), 7.74-7.63 (m, 3H), 7.30 (dd, J=8.0, 1.5 Hz, 1H), 7.00 (d, J=8.5 Hz, 1H), 6.90 (d, J=8.5 Hz, 2H), 3.75 (s, 3H), 3.16 (s, 3H), 2.44 (s, 3H).

Example 25

N-(6-methoxybenzo[d]thiazol-2-yl)-4-(N-(4-methoxyphenyl)-N-methylsulfamoyl)benzamide

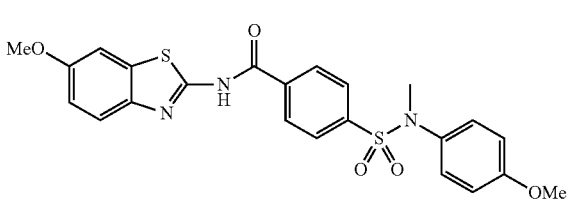 [SMILES: COc1ccc(N(C)S(=O)(=O)c2ccc(C(=O)Nc3nc4ccc(OC)cc4s3)cc2)cc1]

4-(N-(4-methoxyphenyl)-N-methylsulfamoyl)benzoic acid (7) (100 mg, 0.31 mmol) was treated with 6-methoxybenzo[d]thiazol-2-amine (47 mg, 0.26 mmol) using method C. The residue was purified using flash chromatography eluting with 0-40% EtOAc in hexanes. The resulting solid was triturated with dichloromethane/hexanes to give N-(6-methoxybenzo[d]thiazol-2-yl)-4-(N-(4-methoxyphenyl)-N-methylsulfamoyl)benzamide as a yellow solid. Yield: 26 mg (21%). $^1$H-NMR: 8.28 (d, J=8.5 Hz, 2H), 7.74-7.61 (m, 4H), 7.08 (dd, J=9.0, 2.5 Hz, 1H), 7.00 (d, J=8.5 Hz, 2H), 6.91-6.88 (m, 2H), 3.83 (s, 3H), 3.74 (s, 3H), 3.16 (s, 3H).

Example 26

N-(4-(4-acetamidophenyl)thiazol-2-yl)-4-(N-(4-methoxyphenyl)-N-methylsulfamoyl)benzamide

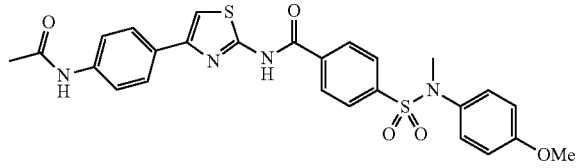 [SMILES: COc1ccc(N(C)S(=O)(=O)c2ccc(C(=O)Nc3nc(-c4ccc(NC(C)=O)cc4)cs3)cc2)cc1]

4-(N-(4-methoxyphenyl)-N-methylsulfamoyl)benzoic acid (7) (100 mg, 0.31 mmol) was treated with N-(4-(2-aminothiazol-4-yl)phenyl)acetamide (61 mg, 0.26 mmol) using method C. The residue was purified using flash chromatography eluting with 30-90% EtOAc in hexanes. The resulting solid was triturated with dichloromethane/hexanes to give N-(4-(4-acetamidophenyl)thiazol-2-yl)-4-(N-(4-methoxyphenyl)-N-methylsulfamoyl)benzamide as a yellow solid. Yield: 68 mg (49%). $^1$H-NMR: 10.03 (s, 1H), 8.27 (d, J=9.0 Hz, 2H), 7.86 (d, J=8.5 Hz, 2H), 7.68-7.63 (m, 4H), 7.60 (s, 1H), 7.01 (d, J=9.0 Hz, 2H), 6.89 (d, J=9.0 Hz, 2H), 3.75 (s, 3H), 3.16 (s, 3H).

Example 27

4-(N-(4-methoxyphenyl)-N-methylsulfamoyl)-N-(pyridin-4-yl)benzamide

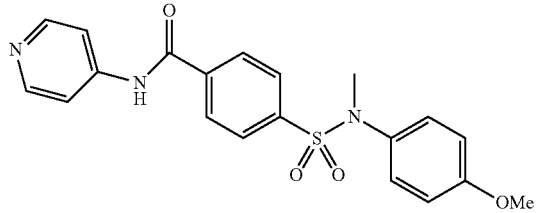 [SMILES: COc1ccc(N(C)S(=O)(=O)c2ccc(C(=O)Nc3ccncc3)cc2)cc1]

4-(N-(4-methoxyphenyl)-N-methylsulfamoyl)benzoic acid (7) (100 mg, 0.31 mmol) was treated with 4-aminopyridine (24 mg, 0.26 mmol) using method C. The residue was purified using flash chromatography eluting with 0-70% EtOAc in hexanes. The resulting solid was triturated with dichloromethane/hexanes to give 4-(N-(4-methoxyphenyl)-N-methylsulfamoyl)-N-(pyridin-4-yl)benzamide as an off white solid. Yield: 67 mg (65%). $^1$H-NMR: 10.82 (s, 1H), 8.51 (d, J=6.0 Hz, 2H), 8.12 (d, J=8.5 Hz, 2H), 7.78 (d, J=6.0 Hz, 2H), 7.69 (d, J=8.5 Hz, 2H), 7.01 (d, J=8.5 Hz, 2H), 6.90 (d, J=8.5 Hz, 2H), 3.75 (s, 3H), 3.15 (s, 3H).

Example 28

N-(3-(1-hydroxyethyl)phenyl)-4-(N-(4-methoxyphenyl)-N-methylsulfamoyl)benzamide

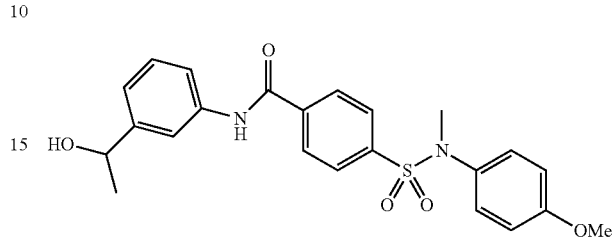

4-(N-(4-methoxyphenyl)-N-methylsulfamoyl)benzoic acid (7) (100 mg, 0.31 mmol) was treated with 1-(3-aminophenyl)ethanol (36 mg, 0.26 mmol) using method C. The residue was purified using flash chromatography eluting with 0-40% EtOAc in hexanes. The resulting solid was triturated with dichloromethane/hexanes to give N-(3-(1-hydroxyethyl)phenyl)-4-(N-(4-methoxyphenyl)-N-methylsulfamoyl)benzamide as an off white solid. Yield: 52 mg (46%). $^1$H-NMR: 10.45 (s, 1H), 8.12 (d, J=8.5 Hz, 2H), 7.75-7.74 (m, 1H), 7.68-7.64 (m, 3H), 7.30 (t, J=8.0 Hz, 1H), 7.10 (d, J=8.0 Hz, 1H), 7.01 (d, J=8.0 Hz, 2H), 6.90 (d, J=8.0 Hz, 2H), 5.19 (d, J=4.5 Hz, 1H), 4.75-4.68 (m, 1H), 3.75 (s, 3H), 3.15 (s, 3H), 1.33 (d, J=6.5 Hz, 3H).

Example 29

N-(4-(4-acetamidophenyl)thiazol-2-yl)-3-(indolin-1-ylsulfonyl)benzamide

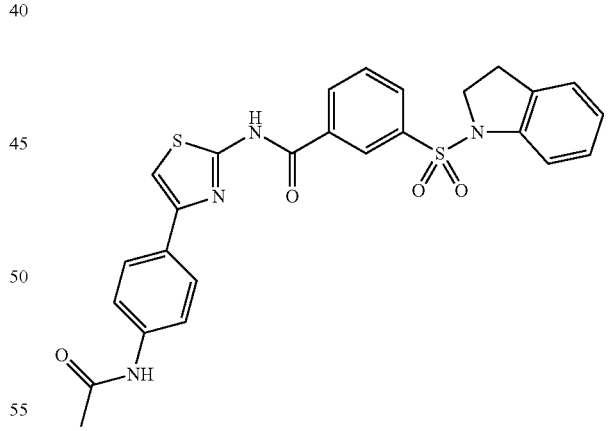

3-(indolin-1-ylsulfonyl)benzoic acid (3) (200 mg, 0.66 mmol) and amine (128 mg, 0.55 mmol) using method C. The residue was purified using flash chromatography eluting with 30-90% EtOAc in hexanes. The resulting solid was triturated with dichloromethane/hexanes to give N-(4-(4-acetamidophenyl)thiazol-2-yl)-3-(indolin-1-ylsulfonyl)benzamide as an off white solid. Yield: 78 mg (27%). $^1$H-NMR: 10.02 (s, 1H), 8.58 (s, 1H), 8.37 (d, J=8.0 Hz, 1H), 8.00 (d, J=8.0 Hz, 1H), 7.88 (d, J=8.5 Hz, 2H), 7.74 (t, J=8.0 Hz, 1H), 7.65 (d, J=8.0 Hz, 2H), 7.60 (s, 1H), 7.53 (d, J=8.0 Hz, 1H), 7.22 t, J=8.0 Hz, 1H), 7.16 (d, J=8.0 Hz, 1H), 6.99 (dt, J=7.5, 7.5, 1.0 Hz, 1H), 4.03 (t, J=8.5 Hz, 1H), 2.93 (t, J=8.5 Hz, 1H), 2.06 (s, 3H).

Example 30

N-(3-(4-fluorophenyl)-1H-pyrazol-5-yl)-3-(indolin-1-ylsulfonyl)benzamide

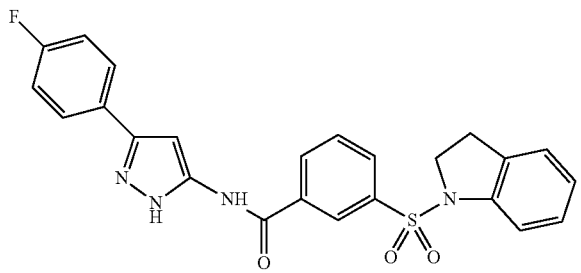 [SMILES: O=C(Nc1cc(-c2ccc(F)cc2)n[nH]1)c1cccc(S(=O)(=O)N2CCc3ccccc32)c1]

3-(indolin-1-ylsulfonyl)benzoic acid (3) (200 mg, 0.66 mmol) and amine (97 mg, 0.55 mmol) using method C. The residue was purified using flash chromatography eluting with 0-30% EtOAc in hexanes. The resulting solid was triturated with dichloromethane/hexanes to give N-(3-(4-fluorophenyl)-1H-pyrazol-5-yl)-3-(indolin-1-ylsulfonyl)benzamide as a yellow solid. Yield: 49 mg (19%). $^1$H-NMR: 8.58 (t, J=2.0 Hz, 1H), 8.31 (ddd, J=8.0, 1.0, 1.0 Hz, 1H), 8.02 (ddd, J=8.0, 2.0, 1.0 Hz, 1H), 7.79-7.71 (m, 3H), 7.53-7.47 (m, 3H), 7.20-7.14 (m, 1H), 6.99 (dt, J=7.5, 7.5, 1.0 Hz, 1H), 6.93 (s, 2H), 5.92 (s, 1H), 3.97 (s, 3H), 2.93 (t, J=8.5 Hz, 2H).

Example 31

4-(N-(4-(benzyloxy)phenyl)-N-methylsulfamoyl)-N-(4-(pyridin-2-yl)thiazol-2-yl)benzamide

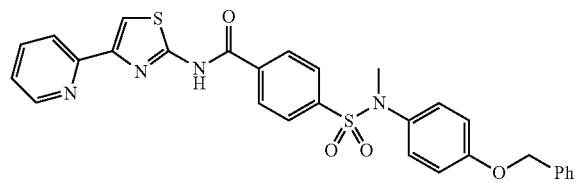 [SMILES: CN(c1ccc(OCc2ccccc2)cc1)S(=O)(=O)c1ccc(C(=O)Nc2nc(-c3ccccn3)cs2)cc1]

4-(N-(4-(benzyloxy)phenyl)-N-methylsulfamoyl) benzoic acid (15)

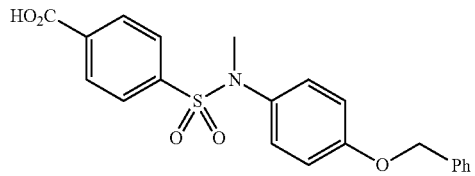 [SMILES: CN(c1ccc(OCc2ccccc2)cc1)S(=O)(=O)c1ccc(C(=O)O)cc1]

4-(chlorosulfonyl)benzoic acid (1.0 g, 4.53 mmol) was treated with 4-(benzyloxy)-N-methylaniline (1.45 g, 6.8 mmol) and DIPEA (0.59 g, 4.53 mmol) using method A to give 4-(N-(4-(benzyloxy)phenyl)-N-methylsulfamoyl)benzoic acid as an off white solid. Yield: 716 mg (40%). $^1$H-NMR: 8.10 (d, J=8.5 Hz, 2H), 7.62 (d, J=8.5 Hz, 2H), 7.46-7.30 (m, 5H), 7.01-6.94 (m, 4H), 5.08 (s, 2H), 3.13 (s, 3H).

4-(N-(4-(benzyloxy)phenyl)sulfamoyl)benzoic acid (15) (493 mg, 1.24 mmol) was treated with 4-(pyridin-2-yl)thiazol-2-amine (200 mg, 1.13 mmol) using method C. The residue was purified using flash chromatography eluting with 0-8% MeOH in dichloromethane. The resulting solid was triturated with diethyl ether to give 4-(N-(4-(benzyloxy)phenyl)-N-methylsulfamoyl)-N-(4-(pyridin-2-yl)thiazol-2-yl) benzamide as an off white solid. Yield: 289 mg (46%). $^1$H-NMR: 8.62 (d, J=5.0 Hz, 1H), 8.29 (d, J=8.5 Hz, 2H), 8.02 (d, J=8.0 Hz, 1H), 7.94-7.88 (m, 2H), 7.67 (d, J=8.5 Hz, 2H), 7.46-7.31 (m, 6H), 7.04-6.96 (m, 4H), 5.10 (s, 2H), 3.16 (s, 3H).

Example 32

4-(N-methyl-N-phenylsulfamoyl)-N-(4-(pyridin-2-yl)thiazol-2-yl)benzamide

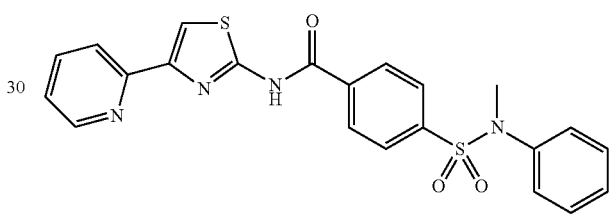

4-(N-methyl-N-phenylsulfamoyl)benzoic acid (16)

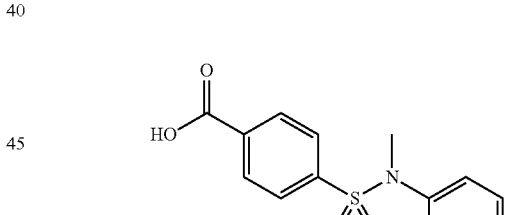

4-(chlorosulfonyl)benzoic acid (500 mg, 2.27 mmol) was treated with N-methylaniline (729 mg, 6.8 mmol) using method A to give 4-(N-methyl-N-phenylsulfamoyl)benzoic acid as an off-white solid. Yield: 374 mg (57%). $^1$H-NMR: 8.09 (d, J=8.5 Hz, 2H), 7.62 (d, J=8.5 Hz, 2H), 7.38-7.28 (m, 3H), 7.13-7.08 (m, 2H), 3.17 (s, 3H).

4-(N-methyl-N-phenylsulfamoyl)benzoic acid (16) (100 mg, 0.31 mmol) was treated with 4-(pyridin-2-yl)thiazol-2-amine (50 mg, 0.28 mmol) using method C. The residue was purified using flash chromatography eluting with 50-100% EtOAc in hexanes. The resulting solid was triturated with diethyl ether to give 4-(N-methyl-N-phenylsulfamoyl)-N-(4-(pyridin-2-yl)thiazol-2-yl)benzamide as an orange solid. Yield: 31 mg (24%). $^1$H-NMR: 8.63-8.61 (m, 1H), 8.28 (d, J=8.5 Hz, 2H), 8.02 (d, J=8.0 Hz, 1H), 7.94-7.88 (m, 2H), 7.68 (d, J=8.5 Hz, 2H), 7.40-7.30 (m, 4H), 7.13 (d, J=7.0 Hz, 2H), 3.20 (s, 3H).

Example 33

4-(6-methoxy-3,4-dihydroquinolin-1(2H)-ylsulfonyl)-N-(4-(pyridin-2-yl)thiazol-2-yl)benzamide

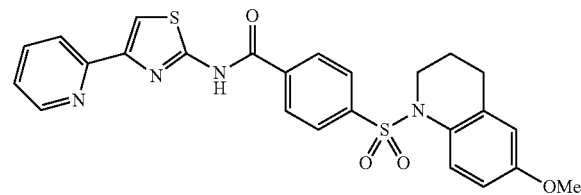 [SMILES: COc1ccc2c(c1)CCCN2S(=O)(=O)c1ccc(C(=O)Nc2nc(-c3ccccn3)cs2)cc1]

4-(6-methoxy-3,4-dihydroquinolin-1(2H)-ylsulfonyl)benzoic acid (17)

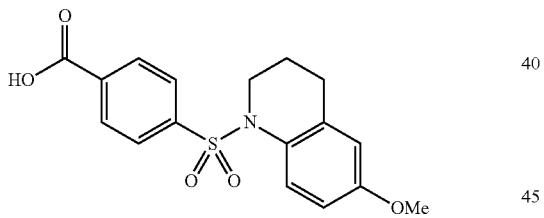

4-(chlorosulfonyl)benzoic acid (500 mg, 2.27 mmol) was treated with 6-methoxy-1,2,3,4-tetrahydroquinoline (1.0 g, 6.13 mmol) using method A to give 4-(6-methoxy-3,4-dihydroquinolin-1(2H)-ylsulfonyl)benzoic acid as an off-white solid. Yield: 358 mg (46%). ¹H-NMR: 8.04 (d, J=8.5 Hz, 2H), 7.64 (d, J=8.5 Hz, 2H), 7.52 (d, J=9.0 Hz, 1H), 6.81 (dd, J=9.0, 3.0 Hz, 1H), 6.65 (d, J=3.0 Hz, 1H), 3.75-3.70 (m, 5H), 2.29 (t, J=7.0 Hz, 2H), 1.53-1.45 (m, 2H).

4-(6-methoxy-3,4-dihydroquinolin-1(2H)-ylsulfonyl)benzoic acid (17) (118 mg, 0.34 mmol) was treated with 4-(pyridin-2-yl)thiazol-2-amine (50 mg, 0.28 mmol) using method C. The residue was purified using flash chromatography eluting with 50-100% EtOAc in hexanes. The resulting solid was triturated with diethyl ether to give 4-(6-methoxy-3,4-dihydroquinolin-1(2H)-ylsulfonyl)-N-(4-(pyridin-2-yl)thiazol-2-yl)benzamide as an off-white solid. Yield: 56 mg (39%). ¹H-NMR: 8.64-8.61 (m, 1H), 8.21 (d, J=8.5 Hz, 2H), 8.01 (d, J=7.5 Hz, 1H), 7.94-7.88 (m, 2H), 7.69 (d, J=8.5 Hz, 2H), 7.58-7.45 (m, 2H), 7.35 (ddd, J=7.5, 5.0, 1.0 Hz, 1H), 6.83 (dd, J=9.0, 3.0 Hz, 1H), 6.67 (d, J=3.0 Hz, 1H), 3.79-3.70 (m, 5H), 2.33 (t, J=7.0, 2H), 1.57-1.48 (m, 2H).

Example 34

N-(benzo[d]thiazol-2-yl)-4-(3,4-dihydroquinolin-1(2H)-ylsulfonyl)benzamide

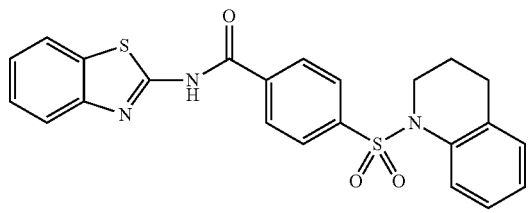 [SMILES: O=C(Nc1nc2ccccc2s1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with benzo[d]thiazol-2-amine (39 mg, 0.26 mmol) using method B. The residue was purified using flash chromatography eluting with 0-20% EtOAc in hexanes to give N-(benzo[d]thiazol-2-yl)-4-(3,4-dihydroquinolin-1(2H)-ylsulfonyl)benzamide as an off-white solid. Yield: 29 mg (25%). ¹H-NMR: 8.22 (d, J=8.5 Hz, 2H), 8.02 (d, J=8.0 Hz, 1H), 7.73 (d, J=8.5 Hz, 2H), 7.62 (d, J=8.0 Hz, 1H), 7.50-7.45 (m, 1H), 7.37-7.32 (m, 1H), 7.24-7.19 (m, 1H), 7.14-7.08 (m, 2H), 3.84-3.80 (m, 2H), 2.44 (t, J=7.0 Hz, 2H), 1.66-1.58 (m, 2H).

Example 35

4-(3,4-dihydroquinolin-1(2H)-ylsulfonyl)-N-(4-methylbenzo[d]thiazol-2-yl)benzamide

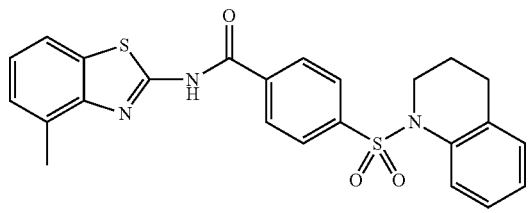 [SMILES: Cc1cccc2sc(NC(=O)c3ccc(S(=O)(=O)N4CCCc5ccccc54)cc3)nc12]

4-(3,4-dihydroquinolin-1(2H)-ylsulfonyl)benzoic acid (1) (100 mg, 0.32 mmol) was treated with 4-methylbenzo[d]thiazol-2-amine (44 mg, 0.24 mmol) using method B. The residue was purified using flash chromatography eluting with 0-30% EtOAc in hexanes to give 4-(3,4-dihydroquinolin-1(2H)-ylsulfonyl)-N-(4-methylbenzo[d]thiazol-2-yl)benzamide as a white solid. Yield: 24 mg (21%). ¹H-NMR: 8.22 (d, J=8.5 Hz, 2H), 7.84 (d, J=8.0 Hz, 1H), 7.76 (d, J=8.5 Hz, 2H), 7.62 (d, J=8.5 h, 1H), 7.31-7.08 (m, 5H), 3.85-3.79 (m, 2H), 2.62 (s, 3H), 2.45 (t, J=7.0 Hz, 2H), 1.66-1.58 (m, 2H).

Example 36

4-(3,4-dihydroquinolin-1(2H)-ylsulfonyl)-N-(6-fluorobenzo[d]thiazol-2-yl)benzamide

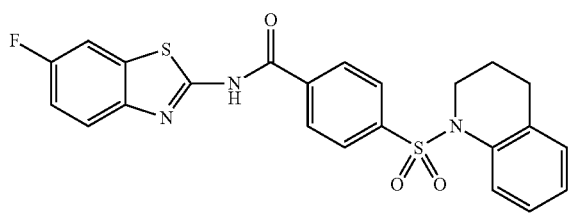 [SMILES: O=C(Nc1nc2ccc(F)cc2s1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 6-fluorobenzo[d]thiazol-2-amine (41 mg, 0.24 mmol) using method B. The residue was purified using flash chromatography eluting with 0-40% EtOAc in hexanes to give 4-(3,4-dihydroquinolin-1(2H)-ylsulfonyl)-N-(6-fluorobenzo[d]thiazol-2-yl)benzamide as an off-white solid. Yield: 22 mg (19%). $^1$H-NMR: 8.22 (d, J=8.5 Hz, 2H), 7.94 (dd, J=8.5, 2.5 Hz, 1H), 7.84-7.75 (m, 3H), 7.61 (d, J=8.5 Hz, 2H), 7.33 (dt, J=9.0, 3.0 Hz, 1H), 7.24-7.19 (m, 1H), 7.14-7.08 (m, 2H), 3.84-3.80 (m, 2H), 2.45 (t, J=7.0 Hz, 2H), 1.66-1.58 (m, 2H).

Example 37

3-(3,4-dihydroquinolin-1(2H)-ylsulfonyl)-N-(6-methoxybenzo[d]thiazol-2-yl)benzamide

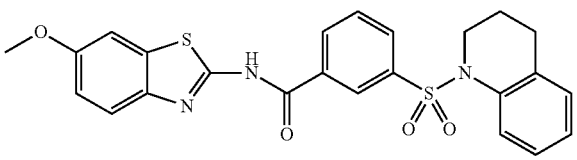 [SMILES: COc1ccc2nc(NC(=O)c3cccc(S(=O)(=O)N4CCCc5ccccc54)c3)sc2c1]

3-(3,4-dihydroquinolin-1(2H)-ylsulfonyl)benzoic acid (18) (100 mg, 0.32 mmol) was treated with 6-methoxybenzo[d]thiazol-2-amine (47 mg, 0.26 mmol) using method C. The residue was purified using flash chromatography eluting with 0-30% EtOAc in hexanes. The resulting solid was triturated with dichloromethane/hexanes to give 3-(3,4-dihydroquinolin-1(2H)-ylsulfonyl)-N-(6-methoxybenzo[d]thiazol-2-yl)benzamide as an off-white solid. Yield: 32 mg (25%). $^1$H-NMR: 8.48 (s, 1H), 8.40-8.35 (m, 1H), 7.77-7.59 (m, 5H), 7.24-7.18 (m, 1H) 7.11-7.05 (m, 3H), 3.87-3.81 (m, 2H), 2.44 (t, J=6.5 Hz, 2H), 1.68-1.59 (m, 2H).

Example 38

N-(3-cyanophenyl)-4-(3,4-dihydroquinolin-1(2H)-ylsulfonyl)benzamide

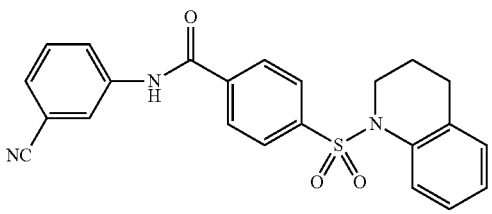 [SMILES: N#Cc1cccc(NC(=O)c2ccc(S(=O)(=O)N3CCCc4ccccc43)cc2)c1]

4-(3,4-dihydroquinolin-1(2H)-ylsulfonyl)benzoic acid (1) (100 mg, 0.32 mmol) was treated with 3-aminobenzonitrile (29 mg, 0.24 mmol) using method B. The residue was purified using flash chromatography eluting with 0-30% EtOAc in hexanes. The resulting solid was triturated with dichloromethane/hexanes to give N-(3-cyanophenyl)-4-(3,4-dihydroquinolin-1(2H)-ylsulfonyl)benzamide as a white solid. Yield: 12 mg (12%). $^1$H-NMR: 10.76 (s, 1H), 8.23-8.20 (m, 1H), 8.07 (d, J=8.5 Hz, 2H), 8.03-7.98 (m, 1H), 7.77 (d, J=8.5 Hz, 2H), 7.63 (d, J=8.5 Hz, 1H), 7.61-7.58 (m, 2H), 7.23-7.18 (m, 1H), 7.11-7.07 (m, 2H), 3.85-3.80 (m, 2H), 2.45 (t, J=7.0 Hz, 2H), 1.68-1.59 (m, 2H).

Example 39

4-(3,4-dihydroquinolin-1(2H)-ylsulfonyl)-N-(3-hydroxypyridin-2-yl)benzamide

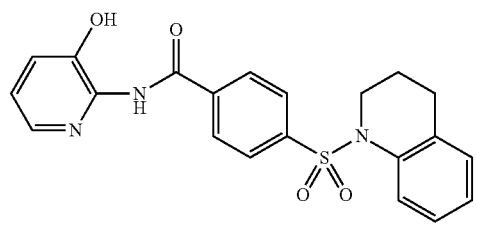 [SMILES: O=C(Nc1ncccc1O)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 2-aminopyridin-3-ol (29 mg, 0.26 mmol) using method C. The residue was purified using flash chromatography eluting with 0-60% EtOAc in hexanes. The resulting solid was triturated with dichloromethane/hexanes to give 4-(3,4-dihydroquinolin-1(2H)-ylsulfonyl)-N-(3-hydroxypyridin-2-yl)benzamide as an off-white solid. Yield: 23 mg (21%). $^1$H-NMR: 8.08 (d, J=8.5 Hz, 2H), 7.93 (dd, J=5.0, 1.5 Hz, 1H), 7.72 (d, J=8.5 Hz, 2H), 7.63

(d, J=8.5 Hz, 1H), 7.31 (dd, J=8.0, 1.5 Hz, 1H), 7.23-7.18 (m, 2H), 7.12-7.08 (m, 2H), 3.84-3.79 (m, 2H), 2.44 (J=7.0 Hz, 2H), 1.66-1.58 (m, 2H).

Example 40

4-(3,4-dihydroquinolin-1(2H)-ylsulfonyl)-N-(6-methylpyridin-2-yl)benzamide

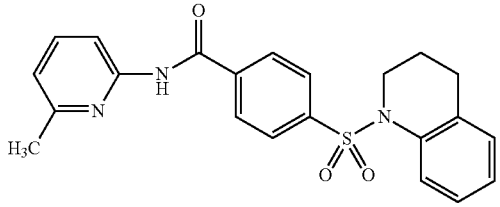 [SMILES: Cc1cccc(NC(=O)c2ccc(S(=O)(=O)N3CCCc4ccccc43)cc2)n1]

4-(3,4-dihydroquinolin-1(2H)-ylsulfonyl)benzoic acid (1) (100 mg, 0.32 mmol) was treated with 6-methylpyridin-2-amine (28 mg, 0.26 mmol) using method C. The residue was purified using flash chromatography eluting with 0-30% EtOAc in hexanes. The resulting solid was triturated with dichloromethane/hexanes to give 4-(3,4-dihydroquinolin-1(2H)-ylsulfonyl)-N-(6-methylpyridin-2-yl)benzamide as a white solid. Yield: 14 mg (13%). $^1$H-NMR: 10.95 (s, 1H), 8.08 (d, J=8.5 Hz, 2H), 7.96 (d, J=8.5 Hz, 1H), 7.73 (t, J=8.0 Hz, 1H), 7.69 (d, J=8.5 Hz, 2H), 7.62 (d, J=8.5 Hz, 1H), 7.24-7.18 (m, 1H), 7.12-7.07 (m, 2H), 7.04 (d, J=7.5 Hz, 1H), 3.82-3.78 (m, 2H), 2.47-2.42 (m, 5H), 1.65-1.57 (m, 2H).

Example 41

4-(3,4-dihydroquinolin-1(2H)-ylsulfonyl)-N-(5-fluoropyridin-2-yl)benzamide

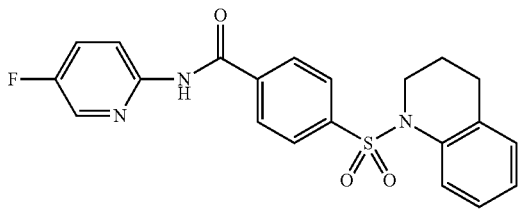 [SMILES: O=C(Nc1ccc(F)cn1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 6-fluoropyridin-2-amine (29 mg, 0.26 mmol) using method C. The residue was purified using flash chromatography eluting with 0-5 EtOAc in dichloromethane. The resulting solid was triturated with dichloromethane/hexanes to give 4-(3,4-dihydroquinolin-1(2H)-ylsulfonyl)-N-(5-fluoropyridin-2-yl)benzamide as an off-white solid. Yield: 16 mg (15%). $^1$H-NMR: 11.15 (s, 1H), 8.41 (d, J=3.5 Hz, 1H), 8.18 (dd, J=9.0, 4.0 Hz, 1H), 8.08 (d, J=8.5 Hz, 2H), 7.81 ddd, J=9.0, 8.0, 3.0 Hz, 1H), 7.71 (d, J=8.5 Hz, 2H), 7.61 (d, J=8.5 Hz, 1H), 7.23-7.08 (m, 3H), 3.83-3.78 (m, 2H), 2.45 (t, J=7.0, 2H), 1.66-1.58 (m, 2H).

Example 42

4-(3,4-dihydroquinolin-1(2H)-ylsulfonyl)-N-(pyridin-3-yl)benzamide

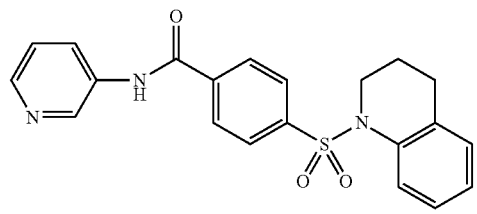 [SMILES: O=C(Nc1cccnc1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 3-aminopyridine (25 mg, 0.26 mmol) using method C. The residue was purified using flash chromatography eluting with 10-50 EtOAc in dichloromethane. The resulting solid was triturated with dichloromethane/hexanes to give 4-(3,4-dihydroquinolin-1(2H)-ylsulfonyl)-N-(pyridin-3-yl)benzamide as a white solid. Yield: 48 mg (47%). $^1$H-NMR: 10.66 (s, 1H), 8.89 (d, J=2.5 Hz, 1H) 8.33 (dd, J=4.5, 1.5 Hz, 1H), 8.15 (ddd, J=8.0, 2.5, 1.5 Hz, 1H) 8.08 (d, J=8.5 Hz, 2H), 7.77 (d, J=8.5 Hz, 2H), 7.64 (d, J=8.5 Hz, 1H), 7.41 (ddd, J=8.5, 4.5, 0.5 Hz, 1H), 7.24-7.08 (m, 3H), 3.85-3.81 (m, 2H), 2.45 (t, J=7.0, 2H), 1.67-1.59 (m, 2H).

Example 43

3-(indolin-1-ylsulfonyl)-N-(6-methylbenzo[d]thiazol-2-yl)benzamide

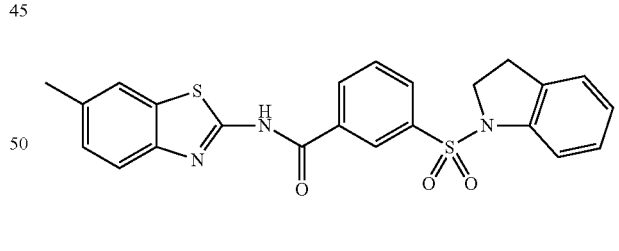

3-(indolin-1-ylsulfonyl)benzoic acid (3) (200 mg, 0.66 mmol) and 6-methylbenzo[d]thiazol-2-amine (90 mg, 0.55 mmol) in DMF (4 mL) was added DIPEA (213 mg, 1.65 mmol) and pybop (429 mg, 0.82 mmol). using method C. The residue was purified using flash chromatography eluting with 0-30% EtOAc in hexanes. The resulting solid was triturated with dichloromethane/hexanes to give 3-(indolin-1-ylsulfonyl)-N-(6-methylbenzo[d]thiazol-2-yl)benzamide as a white solid. Yield: 78 mg (32%). $^1$H-NMR: 8.58 (s, 1H), 8.38 (d, J=8 Hz, 1H), 8.02 (d, J=8.0 Hz, 1H), 7.82 (s, 1H), 7.77-7.65 (m, 3H), 7.53 (d, J=8.5 Hz, 1H), 7.30 (dd, J=8.5, 1.0 Hz, 1H), 7.22 (t, J=8.0 Hz, 1H), 7.16 (d, J=7.0 Hz, 1H), 6.99 (dt, J=7.5, 7.5, 1.0 Hz, 1H), 4.02 (t, J=8.5 Hz, 2H), 2.92 (t, J=8.5 Hz, 2H), 2.43 (s, 3H).

Example 44

3-(indolin-1-ylsulfonyl)-N-(6-methoxybenzo[d]thiazol-2-yl)benzamide

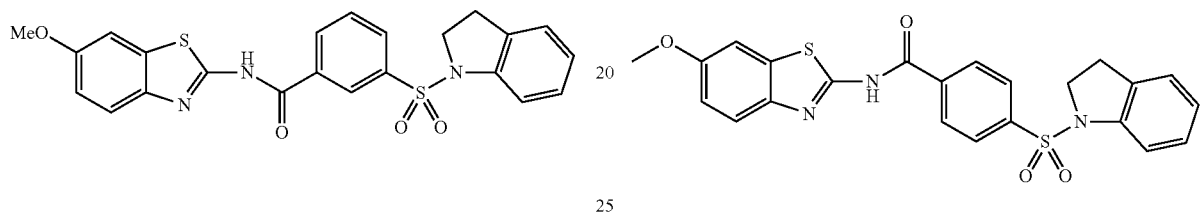

3-(indolin-1-ylsulfonyl)benzoic acid (3) (200 mg, 0.66 mmol) and 6-methoxybenzo[d]thiazol-2-amine (99 mg, 0.55 mmol) using method C. The residue was purified using flash chromatography eluting with 0-40% EtOAc in hexanes. The resulting solid was triturated with dichloromethane/hexanes to give 3-(indolin-1-ylsulfonyl)-N-(6-methoxybenzo[d]thiazol-2-yl)benzamide as an off-white solid. Yield: 89 mg (35%). ¹H-NMR: 8.57 (s, 1H), 8.37 (d, J=8 Hz, 1H), 8.01 (d, J=8.0 Hz, 1H), 7.77-7.66 (m, 2H), 7.63 (d, J=2.5 Hz, 1H), 7.53 (d, J=8.5 Hz, 1H), 7.22 (t, J=7.5 Hz, 1H), 7.16 (d, J=7.5 Hz, 1H), 7.07 (dd, J=8.5, 2.5, 1H), 6.99 (dt, J=7.5, 7.5, 1.0 Hz, 1H), 4.02 (t, J=8.5 Hz, 2H), 3.83 (s, 3H), 2.92 (t, J=8.5 Hz, 2H).

Example 45

4-(indolin-1-ylsulfonyl)-N-(4-(pyridin-2-yl)thiazol-2-yl)benzamide

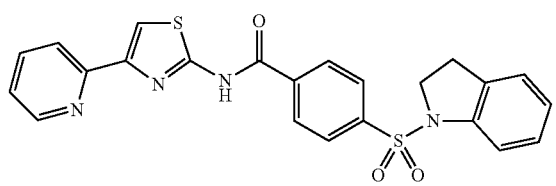 [SMILES: O=C(Nc1nc(-c2ccccn2)cs1)c1ccc(S(=O)(=O)N2CCc3ccccc32)cc1]

4-(indolin-1-ylsulfonyl)benzoic acid (8) (100 mg, 0.33 mmol) was treated with 4-(pyridin-2-yl)thiazol-2-amine (49 mg, 0.28 mmol) using method C. The residue was purified using flash chromatography eluting with 50-100% EtOAc in hexanes to give 4-(indolin-1-ylsulfonyl)-N-(4-(pyridin-2-yl)thiazol-2-yl)benzamide as an off-white solid. Yield: 61 mg (48%). ¹H-NMR: 8.63-8.59 (m, 1H), 8.23 (d, J=8.5 Hz, 2H), 8.02-7.95 (m, 3H), 7.93-7.87 (m, 2H), 7.51 (d, 8.5 Hz, 1H), 7.37-7.32 (m, 1H), 7.26-7.15 (m, 2H), 7.01 (ddd, J=7.5, 7.5, 1.0 Hz, 1H), 4.01-3.95 (t, J=8.5 Hz, 2H), 2.93 (t, J=8.5 Hz, 2H).

Example 46

4-(indolin-1-ylsulfonyl)-N-(6-methoxybenzo[d]thiazol-2-yl)benzamide 4-(indolin-1-ylsulfonyl)benzoic acid (8) (100 mg, 0.33 mmol) was treated with 6-methoxybenzo[d]thiazol-2-amine (50 mg, 0.28 mmol) using method C. The residue was purified using flash chromatography eluting with 0-30% EtOAc in hexanes to give 4-(indolin-1-ylsulfonyl)-N-(6-methoxybenzo[d]thiazol-2-yl)benzamide as a white solid. Yield: 24 mg (19%). ¹H-NMR: 8.23 (d, J=8.5 Hz, 2H), 7.98 (d, J=8.5 Hz, 2H), 7.72-7.64 (m, 1H), 7.61 (d, J=3.0 Hz, 1H), 7.50 (d, J=8.0 Hz, 1H), 7.22 (t, J=8.0 Hz, 1H), 7.17 (d, J=7.5 Hz, 1H), 7.06 (dd, J=8.5, 3.0 Hz, 1H), 7.01 (dt, J=7.5, 1.0 Hz, 1H), 3.99 (t, J=8.5 Hz, 2H), 2.93 (t, J=8.5 Hz, 2H)

Example 47

3-(indolin-1-ylsulfonyl)-N-(6-methoxybenzo[d]thiazol-2-yl)benzamide

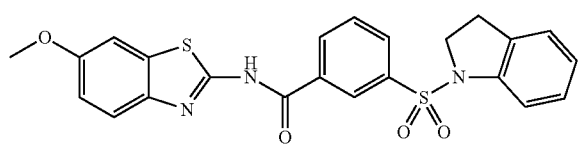 [SMILES: COc1ccc2nc(NC(=O)c3cccc(S(=O)(=O)N4CCc5ccccc54)c3)sc2c1]

3-(indolin-1-ylsulfonyl)benzoic acid (3) (100 mg, 0.33 mmol) was treated with 6-methoxybenzo[d]thiazol-2-amine (46 mg, 0.25 mmol) using method C. The residue was purified using flash chromatography eluting with 0-30% EtOAc in hexanes. The resulting solid was triturated with dichloromethane/hexanes to give 3-(indolin-1-ylsulfonyl)-N-(6-methoxybenzo[d]thiazol-2-yl)benzamide as a white solid. Yield: 30 mg (25%). ¹H-NMR: 8.58 (s, 1H), 8.37 (d, J=8.0 Hz, 1H), 8.01 (d, J=8.0 Hz, 1H), 7.77-7.59 (m, 3H), 7.53 (d, J=8.0 Hz, 1H), 7.22 (t, J=8.0 Hz, 1H), 7.16 (d, J=7.5 Hz, 1H), 7.08 (dd, J=9.0, 2.5 Hz, 1H), 6.99 (dt, J=7.5, 7.5, 1.0 Hz, 1H), 4.02 (t, J=8.0 Hz, 2H), 2.93 (t, J=8.0 Hz, 2H).

Example 48

4-(3,4-dihydroquinolin-1(2H)-ylsulfonyl)-N-(2-methoxyphenyl)benzamide

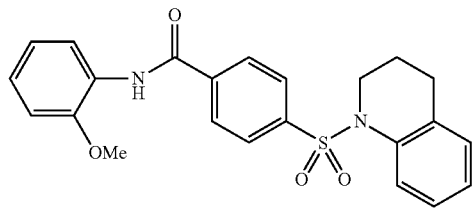 [SMILES: COc1ccccc1NC(=O)c1ccc(S(=O)(=O)N2CCCc3ccccc32)cc1]

4-(3,4-dihydroquinolin-1(2H)-ylsulfonyl)benzoic acid (20) (100 mg, 0.32 mmol) was treated with 2-methoxyaniline (30 mg, 0.24 mmol) using method B. The residue was purified using flash chromatography eluting with 0-20% EtOAc in hexanes. The resulting solid was triturated with dichloromethane/hexanes to give 4-(3,4-dihydroquinolin-1(2H)-ylsulfonyl)-N-(2-methoxyphenyl)benzamide as a white solid. Yield: 39 mg (38%). $^1$H-NMR: 9.75 (s, 1H), 8.05 (d, J=8.5 Hz, 2H), 7.73 (d, J=8.5 Hz, 2H), 7.69-7.61 (m, 2H), 7.24-7.07 (m, 5H), 6.96 (dt, J=7.5, 7.5, 1.0 Hz, 1H), 3.85-3.79 (m, 2H), 2.46 (t, J=7.0 Hz, 2H), 1.67-1.59 (m, 2H).

Example 49

4-(3,4-dihydroquinolin-1(2H)-ylsulfonyl)-N-(2-hydroxyphenyl)benzamide

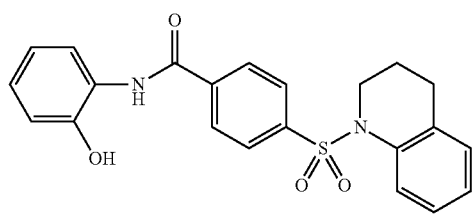 [SMILES: O=C(Nc1ccccc1O)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 2-aminophenol (27 mg, 0.24 mmol) using method B. The residue was purified using flash chromatography eluting with 0-30% EtOAc in hexanes. The resulting solid was triturated with dichloromethane/hexanes to give 4-(3,4-dihydroquinolin-1(2H)-ylsulfonyl)-N-(2-hydroxyphenyl)benzamide as an off-white solid. Yield: 23 mg (23%). $^1$H-NMR: 9.72 (br s, 1H), 8.07 (d, J=8.5 Hz, 2H), 7.73 (d, J=8.5 Hz, 2H), 7.63 (d, J=8.5 Hz, 1H), 7.56 (d, J=8.5 Hz, 1H), 7.24-7.02 (m, 4H), 6.91 (dd, J=8.0, 1.0 Hz, 1H), 6.81 (dt, J=8.0, 8.0, 1.0 Hz, 1H), 3.85-3.79 (m, 2H), 2.45 (t, J=7.0 Hz, 2H), 1.66-1.59 (m, 2H).

Example 50

4-(3,4-dihydroquinolin-1(2H)-ylsulfonyl)-N-(4-methoxyphenyl)benzamide

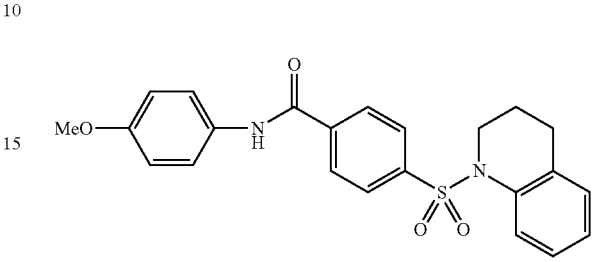

4-(3,4-dihydroquinolin-1(2H)-ylsulfonyl)benzoic acid (1) (100 mg, 0.32 mmol) was treated with 4-methoxyaniline (30 mg, 0.24 mmol) using method B. The residue was purified using flash chromatography eluting with 0-40% EtOAc in hexanes. The resulting solid was triturated with dichloromethane/hexanes to give 4-(3,4-dihydroquinolin-1(2H)-ylsulfonyl)-N-(4-methoxyphenyl)benzamide as a white solid. Yield: 47 mg (46%). $^1$H-NMR: 10.33 (s, 1H), 8.04 (d, J=8.5 Hz, 2H), 7.73 (d, J=8.5 Hz, 2H), 7.66-7.61 (m, 3H), 7.24-7.18 (m, 1H), 7.11-7.08 (m, 2H), 6.93 (d, J=9.0, 2 Hz, 2H), 3.84-3.80 (m, 2H), 2.45 (t, J=6.5 Hz, 2H), 1.66-1.58 (m, 2H).

Example 51

N-(2-acetamidophenyl)-4-(3,4-dihydroquinolin-1(2H)-ylsulfonyl)benzamide

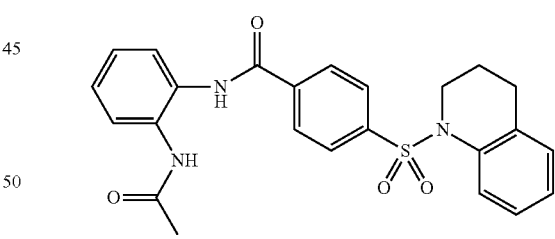

4-(3,4-dihydroquinolin-1(2H)-ylsulfonyl)benzoic acid (1) (100 mg, 0.32 mmol) was treated with N-(2-aminophenyl)acetamide (36 mg, 0.24 mmol) using method B. The residue was purified using flash chromatography eluting with 0-40% EtOAc in hexanes. The resulting solid was triturated with dichloromethane/hexanes to give N-(2-acetamidophenyl)-4-(3,4-dihydroquinolin-1(2H)-ylsulfonyl)benzamide as an off-white solid. Yield: 26 mg (24%). $^1$H-NMR: 10.01 (s, 1H), 9.60 (s, 1H), 8.07 (d, J=8.5 Hz, 2H), 7.77 (d, J=8.5 Hz, 2H), 7.63 (d, J=8.5 Hz, 1H), 7.58 (d, J=8.5 Hz, 2H), 7.24-7.16 (m, 3H), 7.11-7.08 (m, 2H), 3.85-3.80 (m, 2H), 2.47 (d, J=7.0 Hz, 2H), 2.06 (s, 3H), 1.69-1.60 (m, 2H).

Example 52

N-(3-acetamidophenyl)-4-(3,4-dihydroquinolin-1(2H)-ylsulfonyl)benzamide

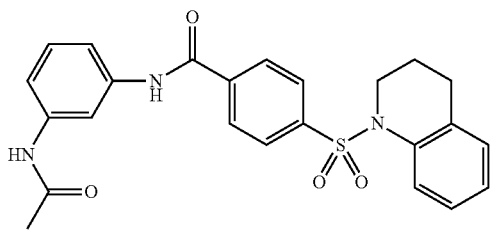 [SMILES: CC(=O)Nc1cccc(NC(=O)c2ccc(S(=O)(=O)N3CCCc4ccccc43)cc2)c1]

4-(3,4-dihydroquinolin-1(2H)-ylsulfonyl)benzoic acid (1) (100 mg, 0.32 mmol) was treated with N-(3-aminophenyl)acetamide (36 mg, 0.24 mmol) using method B. The residue was purified using flash chromatography eluting with 0-60% EtOAc in hexanes. The resulting solid was triturated with dichloromethane/hexanes to give N-(3-acetamidophenyl)-4-(3,4-dihydroquinolin-1(2H)-ylsulfonyl)benzamide as a white solid. Yield: 44 mg (40%). $^1$H-NMR: 10.46 (s, 1H), 9.97 (s, 1H), 8.08 (m, 1H), 8.04 (d, J=8.5 Hz, 2H), 7.74 (d, J=8.5 Hz, 2H), 7.63 (d, J=8.0 Hz, 1H), 7.40 (d, J=8.5 Hz, 1H), 7.33 (d, J=8.5 Hz, 1H), 7.25 (d, J=8.0 Hz, 1H), 7.23-7.18 (m, 1H), 7.11-7.08 (m, 2H), 3.84-3.80 (m, 2H), 2.46 (t, J=7.0 Hz, 2H), 2.04 (s, 3H), 1.67-1.59 (m, 2H).

Example 53

4-(3,4-dihydroquinolin-1(2H)-ylsulfonyl)-N-(5-methyl-4-phenylthiazol-2-yl)benzamide

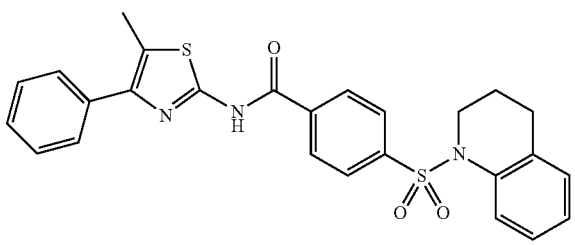 [SMILES: Cc1sc(NC(=O)c2ccc(S(=O)(=O)N3CCCc4ccccc43)cc2)nc1-c1ccccc1]

4-(3,4-dihydroquinolin-1(2H)-ylsulfonyl)benzoic acid (1) (100 mg, 0.32 mmol) was treated with 5-methyl-4-phenylthiazol-2-amine (46 mg, 0.24 mmol) using method B. The residue was purified using flash chromatography eluting with 0-30% EtOAc in hexanes to give 4-(3,4-dihydroquinolin-1(2H)-ylsulfonyl)-N-(5-methyl-4-phenylthiazol-2-yl)benzamide as an off-white solid. Yield: 54 mg (46%). $^1$H-NMR: 8.19 (d, J=8.5 Hz, 2H), 7.74 (d, J=8.0 Hz, 2H), 7.68 (d, J=7.5 Hz, 2H), 7.61 (d, J=8.5 Hz, 1H) 7.50-7.34 (m, 3H), 7.24-7.08 (m, 3H), 3.84-3.78 (m, 2H), 2.52 (s, 3H), 2.45 (t, J=7.0 Hz, 2H), 1.66-1.57 (m, 2H).

Example 54

N-(3-chlorophenyl)-4-(3,4-dihydroquinolin-1(2H)-ylsulfonyl)benzamide

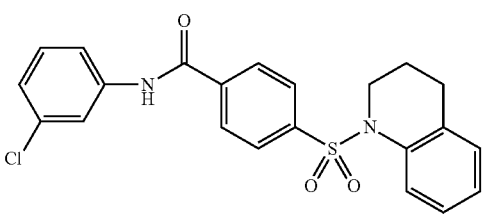 [SMILES: O=C(Nc1cccc(Cl)c1)c1ccc(S(=O)(=O)N2CCCc3ccccc32)cc1]

4-(3,4-dihydroquinolin-1(2H)-ylsulfonyl)benzoic acid (1) (100 mg, 0.32 mmol) was treated with 3-chloroaniline (31 mg, 0.24 mmol) using method B. The residue was purified using flash chromatography eluting with 0-20% EtOAc in hexanes. The resulting solid was triturated with dichloromethane/hexanes to give N-(3-chlorophenyl)-4-(3,4-dihydroquinolin-1(2H)-ylsulfonyl)benzamide as a white solid. Yield: 24 mg (23%). $^1$H-NMR: 10.60 (s, 1H), 8.05 (d, J=8.5 Hz, 2H), 7.93 (t, J=2.0 Hz, 1H), 7.76 (d, J=8.5 Hz, 2H), 7.66 (ddd, J=8.5, 2.0, 1.0 Hz, 1H), 7.63 (d, J=8.5 Hz, 1H), 7.39 (t, J=8.0 Hz, 1H), 7.24-7.16 (m, 2H), 7.12-7.07 (m, 2H), 3.86-3.80 (m, 2H), 2.45 (t, J=7.0 Hz, 2H), 1.67-1.59 (m, 2H).

Example 55

4-(3,4-dihydroquinolin-1(2H)-ylsulfonyl)-N-(3-hydroxyphenyl)benzamide

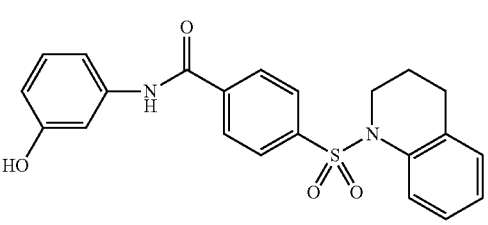

4-(3,4-dihydroquinolin-1(2H)-ylsulfonyl)benzoic acid (1) (100 mg, 0.32 mmol) was treated with 3-aminophenol (29 mg, 0.26 mmol) using method C. The residue was purified using flash chromatography eluting with 0-50 EtOAc in hexanes. The resulting solid was triturated with dichloromethane/hexanes to give 4-(3,4-dihydroquinolin-1(2H)-ylsulfonyl)-N-(3-hydroxyphenyl)benzamide as an off-white solid. Yield: 38 mg (35%). $^1$H-NMR: 8.21 (d, J=8.5 Hz, 2H), 7.80 (d, J=8.5 Hz, 2H), 7.61 (d, J=8.0 Hz, 1H), 7.24-7.08 (m, 3H), 7.06 (t, J=8.0 Hz, 1H), 6.48 (ddd, J=8.0, 2.0, 1.0 Hz, 1H), 6.41 (t, J=2.0 Hz, 1H), 6.36 (ddd, J=8.0, 2.0, 1.0 Hz, 1H), 3.84-3.80 (m, 2H), 2.45 (t, J=7.0, 2H), 1.67-1.59 (m, 2H).

Example 56

N-(3-carbamoylphenyl)-4-(3,4-dihydroquinolin-1 (2H)-ylsulfonyl)benzamide

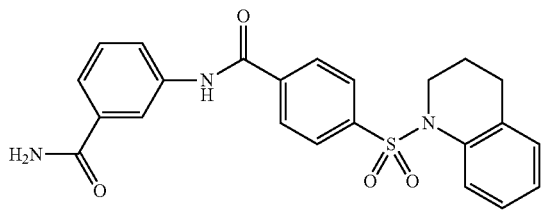 [SMILES: NC(=O)c1cccc(NC(=O)c2ccc(S(=O)(=O)N3CCCc4ccccc43)cc2)c1]

4-(3,4-dihydroquinolin-1(2H)-ylsulfonyl)benzoic acid (1) (100 mg, 0.32 mmol) was treated with 3-aminobenzamide (36 mg, 0.26 mmol) using method C. The residue was purified using flash chromatography eluting with 10-50 EtOAc in dichloromethane. The resulting solid was triturated with dichloromethane/hexanes to give N-(3-carbamoylphenyl)-4-(3,4-dihydroquinolin-1(2H)-ylsulfonyl)benzamide as a white solid. Yield: 35 mg (31%). $^1$H-NMR: 10.58 (s, 1H), 8.22-8.20 (m, 1H), 8.08 (d, J=8.5 Hz, 2H), 7.95 (s, 1H), 7.92-7.88 (m, 1H), 7.75 (d, J=8.5 Hz, 2H), 7.62 (t, J=8.0 Hz, 2H), 7.43 (t, J=7.5 Hz, 1H), 7.35 (s, 1H), 7.24-7.08 (m, 3H), 3.84-3.80 (m, 2H), 2.46 (t, J=7.0, 2H), 1.67-1.59 (m, 2H).

Example 57

3-(indolin-1-ylsulfonyl)-N-(3-methoxyphenyl)benzamide

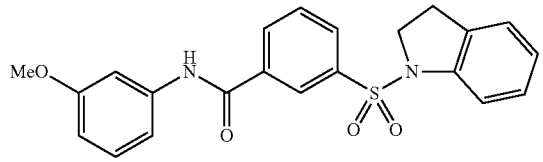 [SMILES: COc1cccc(NC(=O)c2cccc(S(=O)(=O)N3CCc4ccccc43)c2)c1]

3-(indolin-1-ylsulfonyl)benzoic acid (3) (200 mg, 0.66 mmol) and 3-methoxyaniline (68 mg, 0.55 mmol) using method C. The residue was purified using flash chromatography eluting with 0-30% EtOAc in hexanes. The resulting solid was triturated with dichloromethane/hexanes to give 3-(indolin-1-ylsulfonyl)-N-(3-methoxyphenyl)benzamide as an off-white solid. Yield: 94 mg (42%). $^1$H-NMR: 8.34 (s, 1H), 8.22 (d, J=8.0 Hz, 1H), 7.99 (d, J=8.0 Hz, 1H), 7.72 (t, J=8.0 Hz, 1H), 7.51 (d, J=8.0 Hz, 1H), 7.42 (t, J=2.0 Hz, 1H), 7.32 (d, J=8.5 Hz, 1H), 7.27 (t, J=8.0 Hz, 1H), 7.21 (t, J=8.0 Hz, 1H), 7.16 (d, J=7.5 Hz, 1H), 6.99 (dt, J=7.5, 7.5, 1.0 Hz, 1H), 6.71 (ddd, J=8.0, 2.5, 1.0 Hz, 1H), 3.98 (t, J=8.5 Hz, 2H), 3.32 (s, 3H), 2.92 (t, J=8.5 Hz, 2H)

Example 58

3-(indolin-1-ylsulfonyl)-N-(pyridin-4-yl)benzamide

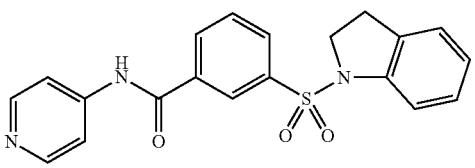 [SMILES: O=C(Nc1ccncc1)c1cccc(S(=O)(=O)N2CCc3ccccc32)c1]

3-(indolin-1-ylsulfonyl)benzoic acid (3) (200 mg, 0.66 mmol) and 4-aminopyridine (52 mg, 0.55 mmol) using method C. The residue was purified using flash chromatography eluting with 30-90 EtOAc in hexanes. The resulting solid was triturated with dichloromethane/hexanes to give 3-(indolin-1-ylsulfonyl)-N-(pyridin-4-yl)benzamide as an off-white solid. Yield: 86 mg (43%). $^1$H-NMR: 10.81 (s, 1H), 8.50 (d, J=6.0 Hz, 2H), 8.35 (t, J=1.5 Hz, 1H), 8.24 (dt, J=8.0, 1.0, 1.0, 1H), 8.01 (dt, J=8.0, 1.0, 1.0, 1H), 7.77-7.72 (m, 3H), 7.50 (d, J=8.0 Hz, 1H), 7.21 (t, J=7.5 Hz, 1H), 7.16 (d, J=7.0 Hz, 1H), 6.99 (dt, J=7.5, 7.5, 1.0 Hz, 1H), 3.98 (t, J=8.5 Hz, 2H), 2.91 (t, J=8.5 Hz, 2H).

Example 59

N-(3-(1-hydroxyethyl)phenyl)-3-(indolin-1-ylsulfonyl)benzamide

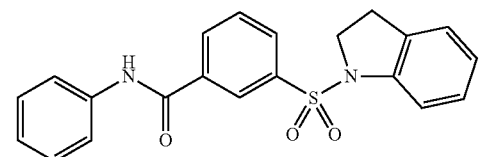

3-(indolin-1-ylsulfonyl)benzoic acid (3) (200 mg, 0.66 mmol) and 1-(3-aminophenyl)ethanol (75 mg, 0.55 mmol) using method C. The residue was purified using flash chromatography eluting with 0-50% EtOAc in hexanes. The resulting solid was triturated with dichloromethane/hexanes to give N-(3-(1-hydroxyethyl)phenyl)-3-(indolin-1-ylsulfonyl)benzamide as an off-white solid. Yield: 93 mg (40%). $^1$H-NMR: 10.46 (s, 1H), 8.37 (s, 1H), 8.25 (d, J=8.0 Hz, 1H), 7.98 (d, J=8.0 Hz, 1H), 7.74-7.69 (m, 2H), 7.64 (d, J=8.5 Hz, 1H), 7.51 (d, J=8.0 Hz, 1H), 7.29 (t, J=8.0 Hz, 1H), 7.21 (t, J=8.0 Hz, 1H), 7.16 (d, J=7.5 Hz, 1H), 7.09 (d, J=8.0 Hz, 1H), 6.99 (dt, J=7.5, 7.5, 1.0 Hz, 1H), 5.19 (d, J=4.0 Hz, 1H), 4.75-4.68 (m, 1H), 3.98 (t, J=8.5 Hz, 2H), 2.93 (t, J=8.5 Hz, 2H), 1.32 (d, J=6.0 Hz, 3H).

Example 60

4-(3,4-dihydroquinolin-1(2H)-ylsulfonyl)-N-(4-(2-oxo-2,3-dihydrobenzo[d]oxazol-6-yl)thiazol-2-yl)benzamide

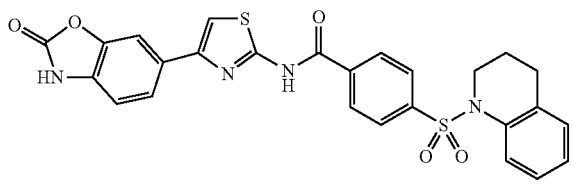 [SMILES: O=C(Nc1nc(-c2ccc3[nH]c(=O)oc3c2)cs1)c1ccc(S(=O)(=O)N2CCCc3ccccc32)cc1]

4-(3,4-dihydroquinolin-1(2H)-ylsulfonyl)benzoic acid (1) (200 mg, 0.63 mmol) was treated with 6-(2-aminothiazol-4-yl)benzo[d]oxazol-2(3H)-one (198 mg, 0.55 mmol) using method C. The residue was purified using flash chromatography eluting with 0-70% EtOAc in hexanes. The resulting solid was triturated with dichloromethane/hexanes to give 4-(3,4-dihydroquinolin-1(2H)-ylsulfonyl)-N-(4-(2-oxo-2,3-dihydrobenzo[d]oxazol-6-yl)thiazol-2-yl)benzamide as a yellow solid. Yield: 73 mg (22%). $^1$H-NMR: 8.21 (d, J=8.5 Hz, 2H), 7.84-7.74 (m, 4H), 7.69 (s, 1H), 7.62 (d, J=8.5 Hz, 1H), 7.24-7.19 (m, 1H), 7.15 (d, J=8.5 Hz, 1H), 7.13-7.07 (m, 2H), 3.85-3.78 (m, 2H), 2.45 (t, J=7.0 Hz, 2H), 1.67-1.58 (m, 2H).

Example 61

N-(3-methoxyphenyl)-4-(N-(4-methoxyphenyl)-N-methylsulfamoyl)benzamide

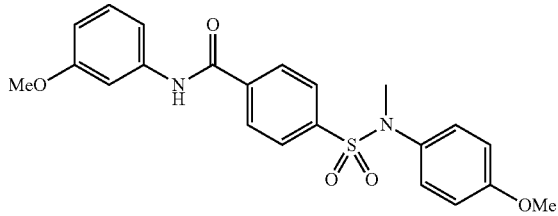 [SMILES: COc1ccc(N(C)S(=O)(=O)c2ccc(C(=O)Nc3cccc(OC)c3)cc2)cc1]

4-(N-(4-methoxyphenyl)-N-methylsulfamoyl)benzoic acid (7) (100 mg, 0.31 mmol) was treated with 3-methoxyaniline (32 mg, 0.26 mmol) using method C. The residue was purified using flash chromatography eluting with 0-30% EtOAc in hexanes. The resulting solid was triturated with dichloromethane/hexanes to give N-(3-methoxyphenyl)-4-(N-(4-methoxyphenyl)-N-methylsulfamoyl)benzamide as a white solid. Yield: 70 mg (63%). $^1$H-NMR: 10.44 (s, 1H), 8.10 (d, J=8.5 Hz, 2H), 7.66 (d, J=8.5 Hz, 2H), 7.45 (t, J=2.0 Hz, 1H), 7.37 (d, J=8.0 Hz, 1H), 7.27 (t, J=7.5 Hz, 1H), 7.00 (d, J=9.0 Hz, 2H), 6.90 (d, J=8.5 Hz, 2H), 6.72 (ddd, J=8.0, 2.5, 1.0 Hz, 1H), 3.76 (s, 3H), 3.75 (s, 3H), 3.15 (s, 3H).

Example 62

Commercially Available Compounds

Compounds useful in the compositions and methods described herein may include the following.

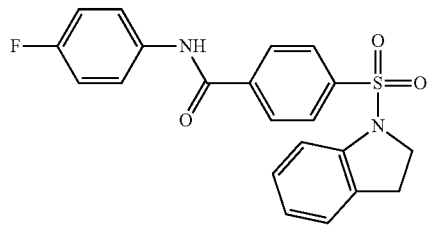

ChemDiv ID# 3338-5689

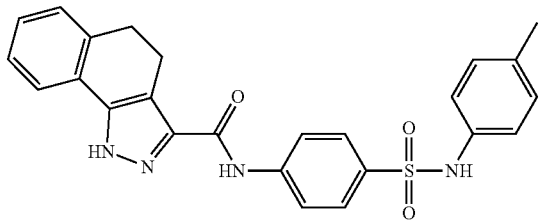

ChemDiv ID# G365-0141

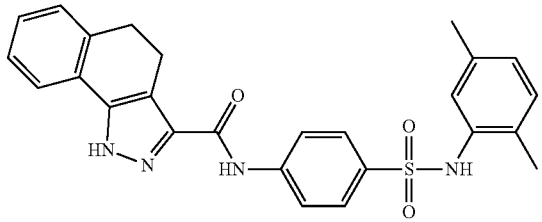

ChemDiv ID# G365-0142

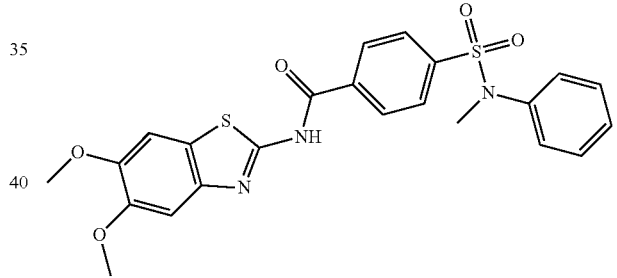

ChemDiv ID# G786-0926

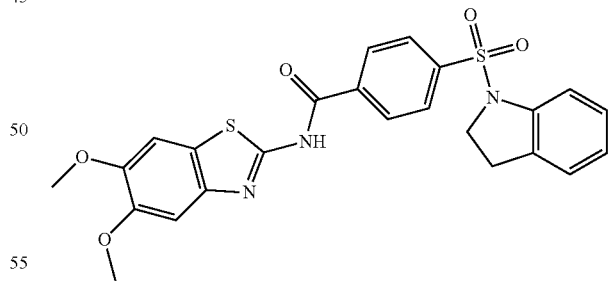

ChemDiv ID# G786-0928

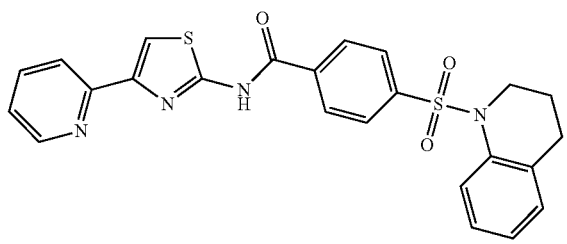

ChemDiv ID# G786-1090

-continued

ChemDiv ID# G856-2339

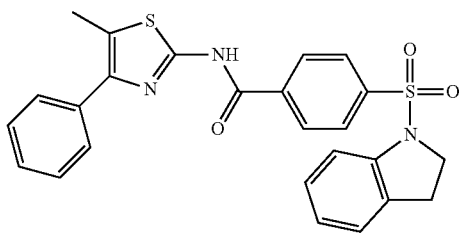

ChemDiv ID# K838-0117

Example 63

Screening Procedures

Drug stocks and dilutions. Compounds are prepared as 10 mM stocks for each compound in DMSO. Dilutions are prepared in a 96-well plate in DMSO. The stock dilutions are as follows: 10 mM, 3 mM, 1 mM, 300 µM, 100 µM, 30 µM, 10 µM, 3 µM, 1 µM, 300 nM, 100 nM, and 30 nM. Plates are then sealed and stored at −20 C.

Screening with STF293 and SW480STF. HEK STF293 cells are seeded at approximately 25,000-30,000 cells/well in a 96-well (100 uL volume). On the first day, Wnt3a-conditioned media (1:1) will be added along with diluted compounds (1:100). For example, for 100 ul of STF293 cells, 100 ul of Wnt3a-conditioned media and 2 ul of drug will be added to each well. The final concentrations should therefore be 100 µM, 30 µM, 10 µM, 3 µM, 1 µM, 300 nM, 100 nM, 30 nM, 10 nM, 3 nM, 1 nM, and 0.3 nM. On the second day, the media is removed and 75 ul of Passive Lysis Buffer (Promega) is added to each well. The plate will be shaken at 130 rpm for 15 minutes. For the Steady Glo assay, 45 ul of the lysis is removed and added to a white 96-well plate containing 45 uL/well of Steady Glo solution (Promega). For the Cell Titer assay, 25 ul of the lysis is transferred to a white 96-well plate containing 25 ul/well of Cell Titer solution (Promega). Both Steady Glo and Cell Titer assays will be read with a luminescence plate reader. When determining $EC_{50}$, the Steady Glo values will be divided by the Cell Titer values to normalize for cell number and the resulting values plotted in a dose-response curve.

Example 64

Activity in Reporter Assays

Experimental. All compounds were tested using the human cell line HEK STF293. This cell line carries a Wnt reporter (TCF/LEF1 promoter), which drives expression of the firefly luciferase protein. The level of Wnt activity is directly correlated with the level of luciferase activity (determined using a simple assay). Compounds that inhibit Wnt signaling by reducing luciferase activity in these two cell lines are further tested biochemically. Biochemical confirmation that compounds inhibit Wnt signaling is obtained by immunoblotting for beta-catenin in HEK STF293 cells and demonstrating that its levels are reduced.

Compounds were prepared as 10 mM stocks for each compound in DMSO. Dilutions were prepared in a 96-well plate in DMSO. The stock dilutions are as follows: 10 mM, 1 mM, 100 µM M, 10 µM, 100 nM, and 10 nM. Plates were sealed and stored at −20 C.

HEK STF293 cells were seeded at approximately 25,000-30,000 cells/well in a 96-well (100 uL volume). On the first day, Wnt3a-conditioned media (1:1) were added along with diluted compounds (1:100). For example, for 100 ul of STF293 cells, 100 ul of Wnt3a-conditioned media and 2 ul of drug was added to each well. The final concentrations should therefore be 100 uM, 10 uM, 1 uM, 100 nM, 10 nM, and 1 nM. On the second day, the media is removed and 75 ul of Passive Lysis Buffer (Promega) is added to each well. The plate is shaken at 130 rpm for 15 minutes. For the Steady Glo assay, 45 ul of the lysis is removed and added to a white 96-well plate containing 45 uL/well of Steady Glo solution (Promega). For the Cell Titer assay, 25 ul of the lysis is transferred to a white 96-well plate containing 25 ul/well of Cell Titer solution (Promega). Both Steady Glo and Cell Titer assays were read with a luminescence plate reader. When determining EC50, the Steady Glo values were divided by the Cell Titer values to normalize for cell number.

The control CMV driven cell line assay was performed as recited above for the STF293 assay except that no Wnt3a-conditioned media was added to the plated cells and 1 ul of diluted compound was added instead of 2 ul.

Three concentrations were chosen based on the EC50 curves from the STF293 assay. From the original 10 mM stocks, the following dilutions were prepared in DMSO and stored at −20 C: 100 uM, 50 uM, and 10 uM.

HEK293 cells were seeded in a 6-well plate at approximately $8.0 \times 10^5$ cells (2 mL per well). On the first day, Wnt3a-conditioned media (1:1) and compounds (1:100) were added to the plated cells. The final concentrations of compounds were 1 uM, 500 nM, and 100 nM. Vehicle (DMSO) and a Wnt3a-conditioned media plus Vehicle samples were also prepared as controls. Lysates were collected (with non-denaturing lysis buffer) after 24 hours incubation, and protein concentrations determined by Bradford Assay. Immunoblotting with an anti-beta-catenin antibody (equivalent amounts of protein/lane for each condition) were subsequently performed to determine beta-catenin levels.

Results. Included in Tables 1 and 2 below are compounds that showed inhibitory activity in the HEK STF293 assay disclosed above.

TABLE 1

| Structure | EC$_{50}$ |
|---|---|
| (7-(trifluoromethyl)-5-phenyl-4,5,6,7-tetrahydropyrazolo[1,5-a]pyrimidine-2-carboxylic acid (1-benzyl-3,5-dimethyl-1H-pyrazol-4-yl)amide) | ++ |
| 5-(4-fluorophenyl)-isoxazole-3-carboxylic acid [1-(4-fluorobenzyl)-3,5-dimethyl-1H-pyrazol-4-yl]amide | + |
| 5-(4-bromophenyl)-isoxazole-3-carboxylic acid (1-benzyl-3,5-dimethyl-1H-pyrazol-4-yl)amide | ++ |
| 5-(2-methoxyphenyl)-isoxazole-3-carboxylic acid [1-(4-fluorobenzyl)-3,5-dimethyl-1H-pyrazol-4-yl]amide | + |

TABLE 1-continued

| Structure | EC$_{50}$ |
|---|---|
| (4-fluorophenyl)-[4-(2,3-dihydroindol-1-ylsulfonyl)phenyl]carboxamide | + |
| 4,5-dihydro-1H-benz[g]indazole-3-carboxylic acid [4-(4-methylphenylsulfamoyl)phenyl]amide | + |
| 4,5-dihydro-1H-benz[g]indazole-3-carboxylic acid [4-(2,5-dimethylphenylsulfamoyl)phenyl]amide | + |
| 5,6-dimethoxybenzothiazol-2-yl 4-[N-methyl-N-phenylsulfamoyl]benzamide | + |
| 5,6-dimethoxybenzothiazol-2-yl 4-(2,3-dihydroindol-1-ylsulfonyl)benzamide | + |

TABLE 1-continued
| Structure | EC$_{50}$ |
|---|---|
| (pyridin-2-yl-thiazol-2-yl)-benzamide-sulfonyl-tetrahydroquinoline | ++ |
| (pyridin-2-yl-methylthiazol-2-yl)-benzamide-sulfonyl-indoline | + |
| 2-carbamoylphenyl-benzamide-sulfonanilide | + |
++ indicates an EC50 equal to or below 100 nM
+ indicates an EC50 above 100 nM
TABLE 2
| Compound | Cmpd Name |
|---|---|
| 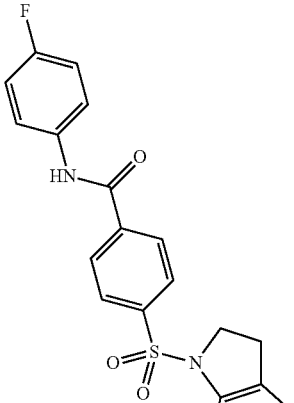 | N-(4-fluorophenyl)-4-(indolin-1-ylsulfonyl)benzamide |

TABLE 2-continued
| Compound | Cmpd Name |
|---|---|
| 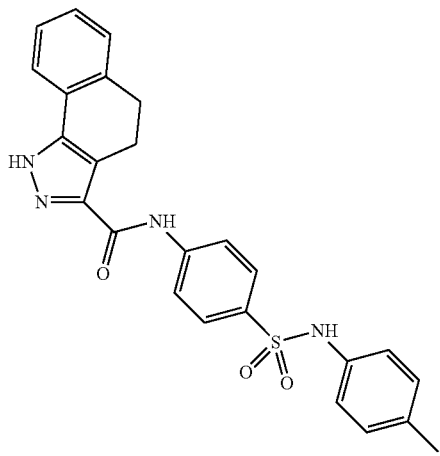 [SMILES: Cc1ccc(NS(=O)(=O)c2ccc(NC(=O)c3n[nH]c4c3CCc3ccccc3-4)cc2)cc1] | N-(4-(N-p-tolylsulfamoyl)phenyl)-4,5-dihydro-1H-benzo[g]indazole-3-carboxamide |
| 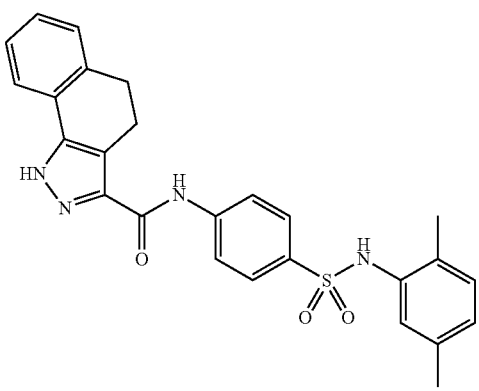 [SMILES: Cc1ccc(C)c(NS(=O)(=O)c2ccc(NC(=O)c3n[nH]c4c3CCc3ccccc3-4)cc2)c1] | N-(4-(N-(2,5-dimethylphenylsulfamoyl)phenyl)-4,5-dihydro-1H-benzo[g]indazole-3-carboxamide |
| 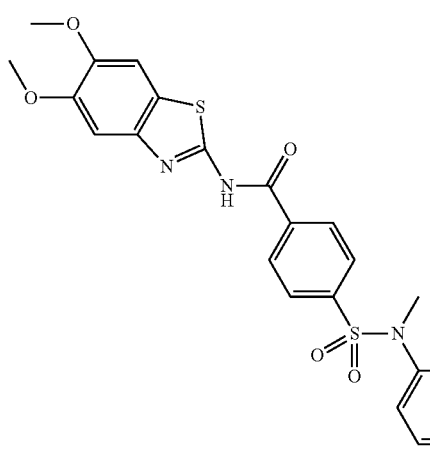 | N-(5,6-dimethoxybenzo[d]thiazol-2-yl)-4-(N-methyl-N-phenyl sulfamoyl)benzamide |

TABLE 2-continued
| Compound | Cmpd Name |
|---|---|
| 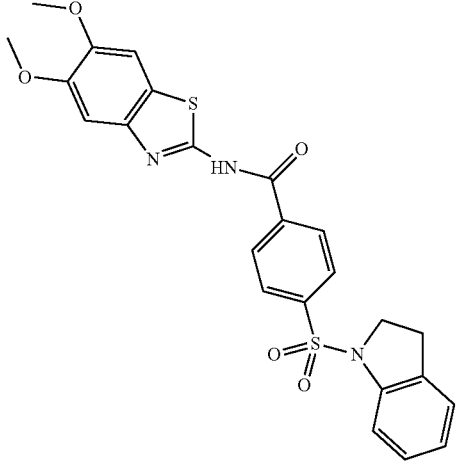 [SMILES: COc1cc2nc(NC(=O)c3ccc(S(=O)(=O)N4CCc5ccccc54)cc3)sc2cc1OC] | N-(5,6-dimethoxybenzo[d]thiazol-2-yl)-4-(indolin-1-ylsulfonyl)benzamide |
| 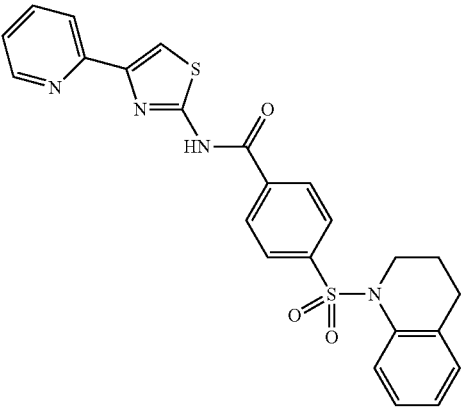 [SMILES: O=C(Nc1nc(-c2ccccn2)cs1)c1ccc(S(=O)(=O)N2CCCc3ccccc32)cc1] | 4-(3,4-dihydroquinolin-1(2H)-ylsulfonyl)-N-(4-(pyridin-2-yl)thiazol-2-yl)benzamide |
| 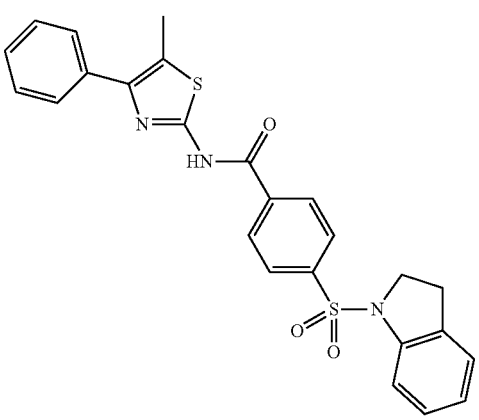 [SMILES: Cc1sc(NC(=O)c2ccc(S(=O)(=O)N3CCc4ccccc43)cc2)nc1-c1ccccc1] | 4-(indolin-1-ylsulfonyl)-N-(5-methyl-4-phenylthiazol-2-yl)benzamide |

TABLE 2-continued

| Compound | Cmpd Name |
|---|---|
| | N-(2-carbamoylphenyl)-3-(N-phenylsulfamoyl)benzamide |
| | 4-(3,4-dihydroquinolin-1(2H)-ylsulfonyl)-N-(4-p-tolylthiazol-2-yl)benzamide |
| | 4-(3,4-dihydroquinolin-1(2H)-ylsulfonyl)-N-(4-phenylthiazol-2-yl)benzamide |

| Compound | Cmpd Name |
|---|---|
| | 4-(3,4-dihydroquinolin-1(2H)-ylsulfonyl)-N-(6-methylbenzo[d]thiazol-2-yl)benzamide |
| | N-(4-(4-acetamidophenyl)thiazol-2-yl)-4-(3,4-dihydroquinolin-1(2H)-ylsulfonyl)benzamide |
| | 3-(3,4-dihydroquinolin-1(2H)-ylsulfonyl)-N-(4-(pyridin-2-yl)thiazol-2-yl)benzamid |

TABLE 2-continued

| Compound | Cmpd Name |
|---|---|
| | 3-(indolin-1-ylsulfonyl)-N-(4-(pyridin-2-yl)thiazol-2-yl)benzamide |
| | 4-(3,4-dihydroquinolin-1(2H)-ylsulfonyl)-N-(3-methoxyphenyl)benzamide |
| | 4-(3,4-dihydroquinolin-1(2H)-ylsulfonyl)-N-(3-(1-hydroxyethyl)phenyl)benzamide |
| | 4-(3,4-dihydroquinolin-1(2H)-ylsulfonyl)-N-(pyridin-4-yl)benzamide |

TABLE 2-continued

| Compound | Cmpd Name |
| --- | --- |
|  | 4-(N-(4-fluorophenyl)-N-methylsulfamoyl)-N-(4-(pyridin-2-yl)thiazol-2-yl)benzamide |
|  | 4-(N-(4-chlorophenyl)-N-methylsulfamoyl)-N-(4-(pyridin-2-yl)thiazol-2-yl)benzamide |
|  | 4-(N-methyl-N-(4-(trifluoromethyl)phenyl)sulfamoyl)-N-(4-(pyridin-2-yl)thiazol-2-yl)benzamide |

| Compound | Cmpd Name |
|---|---|
| | 4-(N-(4-methoxyphenyl)-N-methylsulfamoyl)-N-(4-(pyridin-2-yl)thiazol-2-yl)benzamide |
| | 4-(5-chloroindolin-1-ylsulfonyl)-N-(4-(pyridin-2-yl)thiazol-2-yl)benzamide |
| | 4-(5-chloroindolin-1-ylsulfonyl)-N-(6-methoxybenzo[d]thiazol-2-yl)benzamide |

| Compound | Cmpd Name |
|---|---|
| | 4-(3,4-dihydroquinolin-1(2H)-ylsulfonyl)-2-fluoro-N-(4-(pyridin-2-yl)thiazol-2-yl)benzamide |
| | 4-(3,4-dihydroquinolin-1(2H)-ylsulfonyl)-N-(3-(4-fluorophenyl)-1H-pyrazol-5-yl)benzamide |
| | 4-(N-(4-methoxyphenyl)sulfamoyl)-N-(4-(pyridin-2-yl)thiazol-2-yl)benzamide |

TABLE 2-continued

| Compound | Cmpd Name |
|---|---|
| | 4-(N-(3-chlorophenyl)sulfamoyl)-N-(4-(pyridin-2-yl)thiazol-2-yl)benzamide |
| | 4-(N-(3-methoxyphenyl)-N-methylsulfamoyl)-N-(4-(pyridin-2-yl)thiazol-2-yl)benzamide |
| | 4-(N-(2-methoxyphenyl)-N-methylsulfamoyl)-N-(4-(pyridin-2-yl)thiazol-2-yl)benzamide |

TABLE 2-continued

| Compound | Cmpd Name |
|---|---|
|  | N-(4-(pyridin-2-yl)thiazol-2-yl)-4-(N-m-tolylsulfamoyl)benzamide |
|  | 4-(N-(4-methoxyphenyl)-N-methylsulfamoyl)-N-(6-methylbenzo[d]thiazol-2-yl)benzamide |
|  | N-(6-methoxybenzo[d]thiazol-2-yl)-4-(N-(4-methoxyphenyl)-N-methylsulfamoyl)benzamide |

TABLE 2-continued

| Compound | Cmpd Name |
| --- | --- |
|  | N-(4-(4-acetamidophenyl)thiazol-2-yl)-4-(N-(4-methoxyphenyl)-N-methylsulfamoyl)benzamide |
|  | 4-(N-(4-methoxyphenyl)-N-methylsulfamoyl)-N-(pyridin-4-yl)benzamide |
|  | N-(3-(1-hydroxyethyl)phenyl)-4-(N-(4-methoxyphenyl)-N-methylsulfamoyl)benzamide |

TABLE 2-continued

| Compound | Cmpd Name |
| --- | --- |
| (structure) | N-(4-(4-acetamidophenyl)thiazol-2-yl)-3-(indolin-1-ylsulfonyl)benzamide |
| (structure) | N-(3-(4-fluorophenyl)-1H-pyrazol-5-yl)-3-(indolin-1-ylsulfonyl)benzamide |
| (structure) | 4-(N-(4-(benzyloxy)phenyl)-N-methylsulfamoyl)-N-(4-(pyridin-2-yl)thiazol-2-yl)benzamide |

Example 65

Functional (Cell Proliferation) Assay

Experimental: Viability of colorectal (CRC) cells (SW480 cells, DLD-1 cells, HCT116 cells, and SW620 cells) in the presence of compounds was performed using the CellTiter-Glo® assay (Promega) according to manufacturer's instructions. This luminescence-based assay is sensitive (can measure down to 15 cells/well) and allows for multi-well formats. The assay measures the amount of ATP, which is proportional to the number of cells present in the culture. Briefly, cells are plated onto 96-well plates at low density in the presence of normal growth media and increasing concentration of compounds. The number of viable cells is then determined 48 and 72 hours later and compared with the vehicle treated controls.

Results. Certain compounds of the present invention showed anti-proliferation activity.

What is claimed is:

1. A compound having the formula:

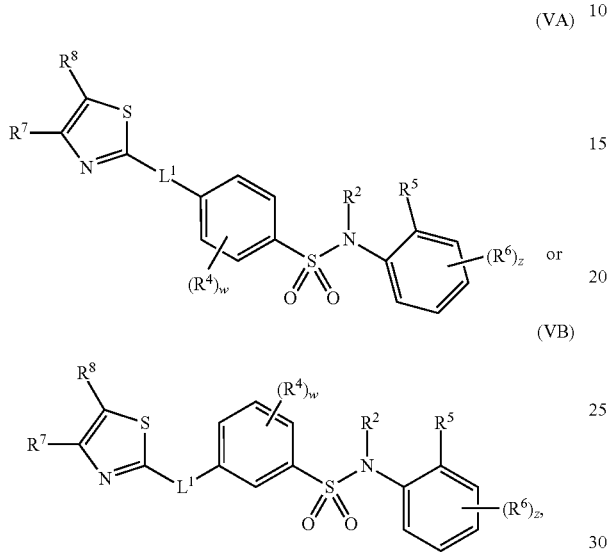

wherein,

R$^2$ is hydrogen, halogen, —CN, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is independently halogen, —CN, —CF$_3$ —NR$^{4A}$—C(O)R$^{4B}$, —NR$^{4A}$—C(O)—OR$^{4B}$, —C(O)NR$^{4A}$R$^{4B}$, —NR$^{4A}$S(O)$_2$R$^{4B}$, —S(O)$_2$N(R$^{4B}$), —SR$^{4A}$,—S(O)$_2$R$^{4B}$, —NR$^{4A}$R$^{4B}$, —OR$^{4A}$, —C(O)R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —CN, —CF$_3$—NR$^{5A}$—C(O)R$^{5B}$, —NR$^{5A}$—C(O)—OR$^{5B}$, —C(O)NR$^{5A}$R$^{5B}$, —NR$^{5A}$S(O)$_2$R$^{5B}$, —S(O)$_2$N(R$^{5A}$)(R$^{5B}$), —SR$^{5A}$, —S(O)R$^{5B}$, —S(O)$_2$R$^{5B}$, —NR$^{5A}$R$^{5B}$, —OR$^{5A}$, —C(O)R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^2$ and R$^5$ are optionally joined together to form a substituted or unsubstituted heterocycloalkyl or substituted or unsubstituted heteroaryl;

R$^6$ is independently halogen, —CN, —CF$_3$, —NR$^{6A}$—C(O)R$^{6B}$, —NR$^{6A}$—C(O)—OR$^{6B}$, —C(O)NR$^{6A}$R$^{6B}$, —NR$^{6A}$S(O)$_2$R$^{6B}$,—S(O)$_2$N(R$^{6A}$)(R$^{6B}$), —SR$^{6A}$, —S(O)R$^{6B}$, —S(O)$_2$R$^{6B}$, —NR$^{6A}$R$^{6B}$, —OR$^{6A}$, —C(O)R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CN, —CF$_3$, —NR$^{7A}$—C(O)R$^{7B}$, —NR$^{7A}$—C(O)—OR$^{7B}$,—C(O)NR$^{7A}$R$^{7B}$, —NR$^{7A}$S(O)$_2$R$^{7B}$, —S(O)$_2$N(R$^{7A}$)(R$^{7B}$), —SR$^{7A}$, —S(O)R$^{7B}$, —S(O)$_2$R$^{7B}$, —NR$^{7A}$R$^{7B}$, —OR$^{7A}$, —C(O)R$^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, CN, —NR$^{8A}$—C(O)R$^{8B}$, —NR$^{8A}$—C(O)—OR$^{8B}$, —C(O)NR$^{8A}$R$^{8B}$, —NR$^{8A}$S(O)$_2$R$^{8B}$, —S(O)$_2$N(R$^{8A}$)(R$^{8B}$), —SR$^{8A}$, —S(O)R$^{8B}$, —S(O)$_2$R$^{8B}$, —NR$^{8A}$R$^{8B}$, —OR$^{8A}$, —C(O)R$^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^7$ and R$^8$ are optionally joined together to form a substituted or unsubstituted cycloalkyl, substituted or unsubstituted heterocycloalkyl, substituted or unsubstituted aryl, or substituted or unsubstituted heteroaryl;

R$^{4A}$, R$^{4B}$, R$^{5A}$, R$^{5B}$, R$^{6A}$, R$^{6B}$, R$^{7A}$, R$^{7B}$, R$^{8A}$, R$^{8B}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;

L$^1$ is —NH—C(O)—or —C(O)—NH—;

z is an integer from 0 to 4; and w is an integer from 0 to 4.

2. The compound of claim 1, wherein said compound has the formula:

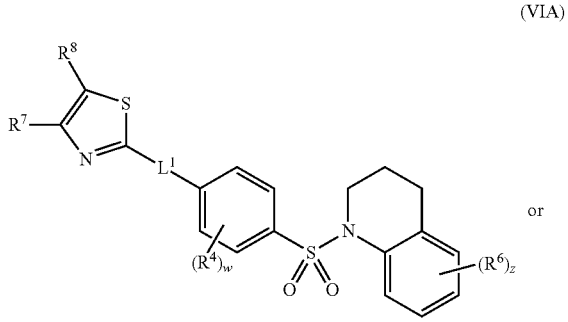

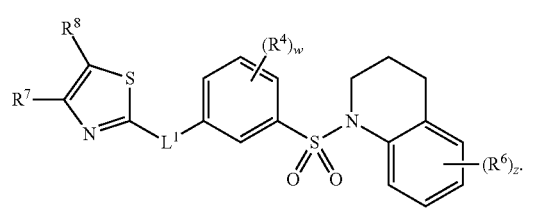

3. The compound of claim 1, wherein said compound has the formula:

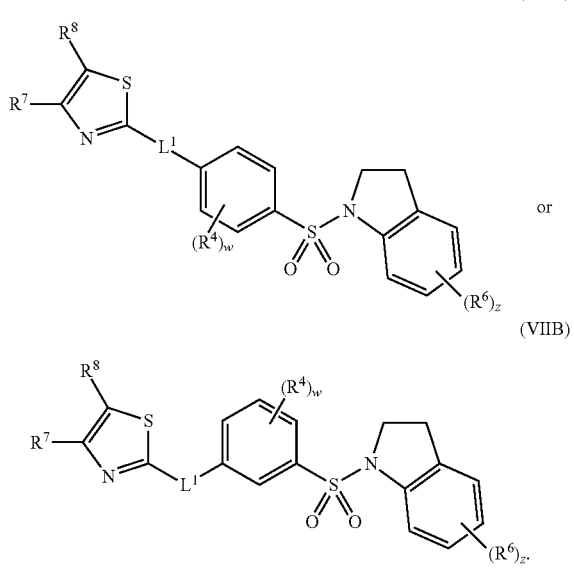

(VIIA)

or (VIIB)

4. The compound of claim 1, wherein $R^2$ and $R^5$ are not joined together to form a substituted or unsubstituted heterocycloalkyl or substituted or unsubstituted heteroaryl.

5. The compound of claim 1, wherein said compound has the formula:

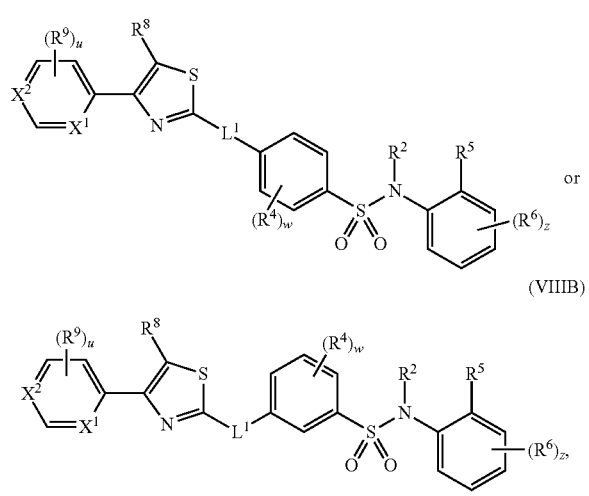

(VIIIA)

or (VIIIB)

wherein, $X^1$ and $X^2$ are independently carbon or nitrogen;

$R^9$ is independently halogen, —CN, —CF$_3$, —NR$^{9A}$-C(O)R$^{9B}$, —NR$^{9A}$—C(O)—OR$^{9B}$, —C(O)NR$^{9A}$R$^{9B}$, —NR$^{9A}$S(O)$_2$R$^{9B}$, —S(O)$_2$N(R$^{9A}$)(R$^{9B}$), —SR$^{9A}$, —S(O)R$^{9B}$, —S(O)$_2$R$^{9B}$, —NR$^{9A}$R$^{9B}$, —OR$^{9A}$, —C(O)R$^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{9A}$ and $R^{9B}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl; and u is an integer from 0 to 5.

6. The compound of claim 5, wherein said compound has the formula:

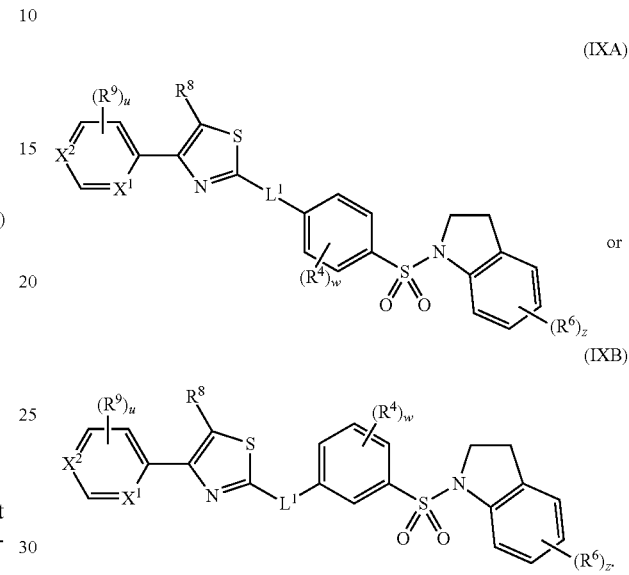

(IXA)

or (IXB)

7. The compound of claim 5, wherein said compound has the formula:

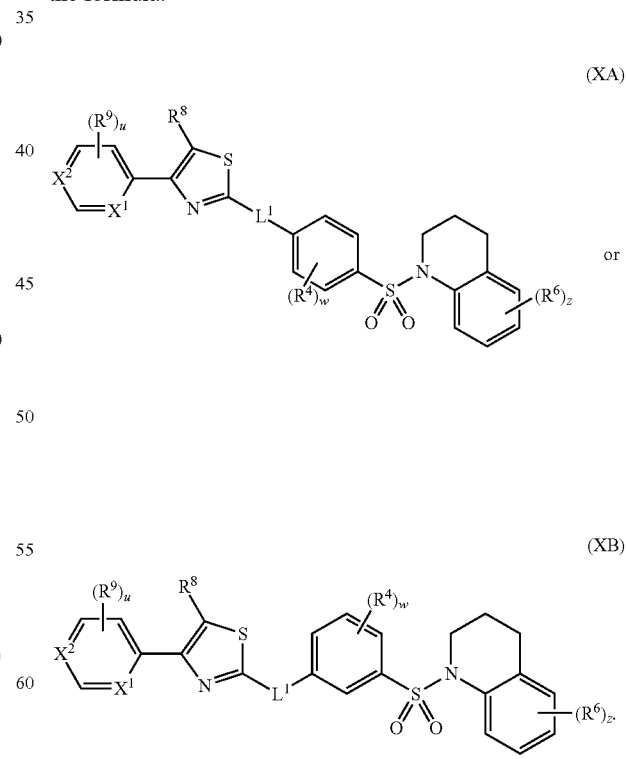

(XA)

or (XB)

8. The compound of claim 5, wherein $R^2$ and $R^5$ are not joined together to form a substituted or unsubstituted heterocycloalkyl or substituted or unsubstituted heteroaryl.

9. The compound of claim 1 having the formula:

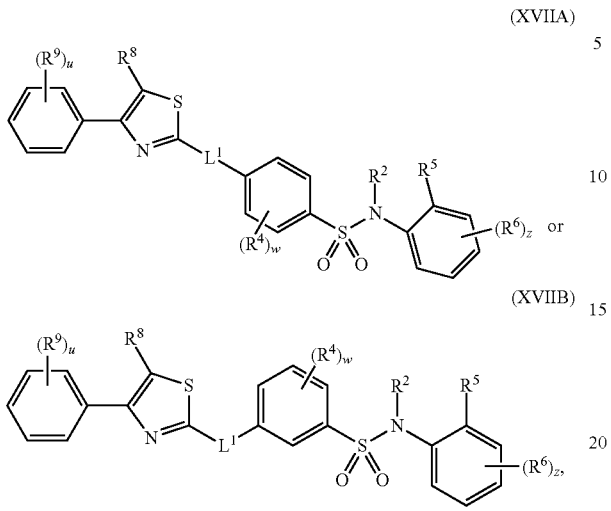

(XVIIA)

(XVIIB)

wherein,
$R^9$ is independently halogen, —CN, —$CF_3$, —$NR^{9A}$-C(O)$R^{9B}$, —$NR^{9A}$—C(O)—$OR^{9B}$, —C(O)$NR^{9A}R^{9B}$, —$NR^{9A}$S(O)$_2R^{9B}$, —S(O)$_2$N($R^{9A}$)($R^{9B}$), —$SR^{9A}$, —S(O)$R^{9B}$, —S(O)$_2R^{9B}$, —$NR^{9A}R^{9B}$, —$OR^{9A}$, -C(O)$R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{9A}$ and $R^{9B}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;
and
u is an integer from 0 to 5.

10. The compound of claim 9, wherein said compound has the formula:

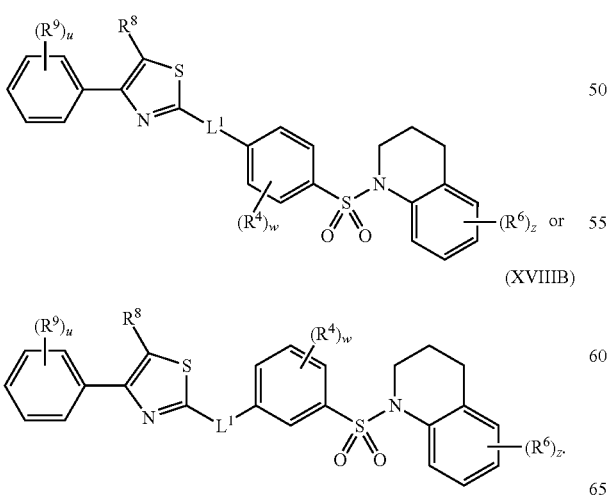

(XVIIIA)

(XVIIIB)

11. The compound of claim 1 having the formula:

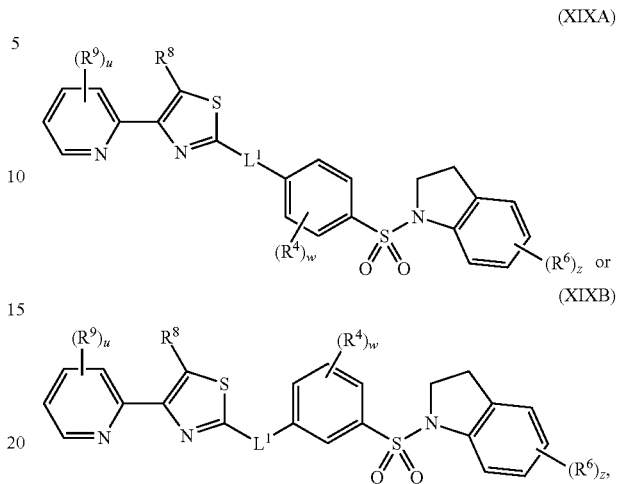

(XIXA)

(XIXB)

wherein,
$R^9$ is independently halogen, —CN, —$CF_3$, —$NR^{9A}$—C(O)$R^{9B}$, —$NR^{9A}$—C(O)—$OR^{9B}$, —C(O)$NR^{9A}R^{9B}$, —$NR^{9A}$S(O)$_2R^{9B}$, —S(O)$_2$N($R^{9A}$)($R^{9B}$), —$SR^{9A}$, —S(O)$R^{9B}$, —S(O)$_2R^{9B}$, —$NR^{9A}R^{9B}$, —$OR^{9A}$, —C(O)$R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{9A}$ and $R^{9B}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;
and
u is an integer from 0 to 5.

12. The compound of claim 1 having the formula:

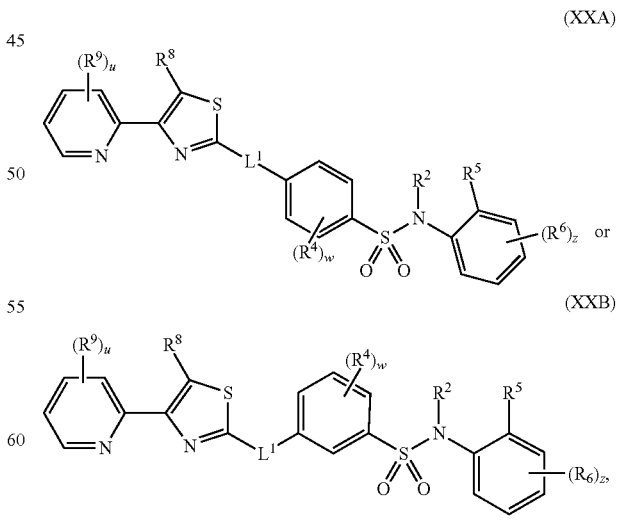

(XXA)

(XXB)

wherein,
$R^9$ is independently halogen, —CN, —$CF_3$, —$NR^{9A}$—C(O)$R^{9B}$, —$NR^{9A}$—C(O)—$OR^{9B}$, —C(O)$NR^{9A}R^{9B}$, —NR⁹ᴬS(O)₂R⁹ᴮ,—S(O)₂N R⁹ᴬ)(R⁹ᵇ), —SR⁹ᴬ, —S(O)R⁹ᴮ, —S(O)₂R⁹ᴮ, —NR⁹ᴬR⁹ᴮ, —OR⁹ᴬ, —C(O)R⁹ᴮ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ᴬ and R⁹ᴮ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl; and u is an integer from 0 to 5.

13. The compound of claim 1 having the formula:

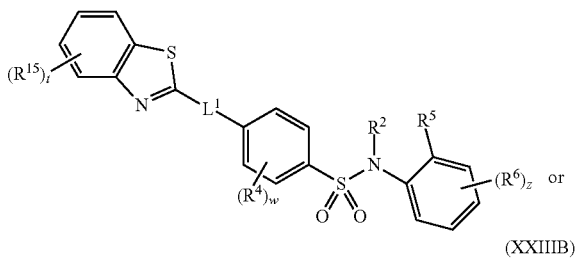

(XXIIIA)

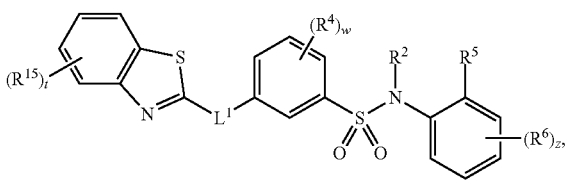

(XXIIIB)

wherein,

R¹⁵ is independently halogen, —CN, —CF₃, —NR¹⁵ᴬ—C(O)R¹⁵ᴮ, —NR¹⁵ᴬ—C(O)—OR¹⁵ᴮ, —C(O)NR¹⁵ᴬR¹⁵ᴮ, —NR¹⁵ᴬS(O)₂R¹⁵ᴮ, —S(O)₂N(R¹⁵ᴬ)(R¹⁵ᴮ), —SR¹⁵ᴬ, —S(O)R¹⁵ᴮ, —S(O)₂R¹⁵ᴮ, —NR¹⁵ᴬR¹⁵ᴮ, —OR¹⁵ᴬ, —C(O)R¹⁵ᴮ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹⁵ᴬ and R¹⁵ᴮ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl; and t is an integer from 0 to 4.

14. A pharmaceutical composition comprising a pharmaceutical acceptable excipient and the compound of one of claims 1-8, 9-12 or 13.

15. A method of reducing a Wnt-mediated effect on a cell, said method comprising contacting said cell with an effective amount of the compound of one of claim 1-8, 9-12 or 13.

16. The method of claim 15, wherein said Wnt-mediated effect is an increase in degradation of Pygopus, an increase in degradation of beta-Catenin, a decrease in degradation of Axin, a decrease in activity of Myc, a decrease in activity of CD44, a decrease in activity of Axin2, a decrease in activity of Bcl-9, or a decrease in activity of cyclin D.

17. The method of claim 15, wherein R² is hydrogen or unsubstituted alkyl.

18. A method of treating cancer in a subject in need thereof, said method comprising administering to said subject an effective amount of the compound of one of claim 1-8, 9-12 or 13 or a pharmaceutically acceptable salt thereof.

19. The method of claim 18, wherein said cancer is colon cancer, breast cancer, gastric cancer, brain cancer, head and neck cancer, liver cancer, lung cancer, lymphoma, melanoma, pancreatic cancer or prostate cancer.

* * * * *